(12) United States Patent
Xiang et al.

(10) Patent No.: US 10,889,572 B2
(45) Date of Patent: Jan. 12, 2021

(54) REACTIVE OXYGEN SPECIES SCAVENGERS AND USE FOR TREATING DISEASES

(71) Applicant: XW LABORATORIES INC., Grand Cayman (KY)

(72) Inventors: Jia-Ning Xiang, Wuhan (CN); Zude Qi, Wuhan (CN); Dezheng Ning, Wuhan (CN); Xianbo Liu, Wuhan (CN)

(73) Assignee: XW LABORATORIES INC., Grand Cayman (KY)

( * ) Notice: Subject to any disclaimer, the term of this patent is extended or adjusted under 35 U.S.C. 154(b) by 0 days.

(21) Appl. No.: 16/801,286

(22) Filed: Feb. 26, 2020

(65) Prior Publication Data

US 2020/0199108 A1 Jun. 25, 2020

Related U.S. Application Data

(63) Continuation of application No. PCT/CN2017/100431, filed on Sep. 4, 2017.

(51) Int. Cl.
*C07D 403/12* (2006.01)
*C07D 403/14* (2006.01)

(52) U.S. Cl.
CPC ........ *C07D 403/12* (2013.01); *C07D 403/14* (2013.01)

(58) Field of Classification Search
None
See application file for complete search history.

(56) References Cited

U.S. PATENT DOCUMENTS

| 5,798,377 A | 8/1998 | Lumma et al. |
| 9,650,352 B2 | 5/2017 | Wainer et al. |

FOREIGN PATENT DOCUMENTS

| CN | 104395283 | 3/2015 |
| CN | 106866784 | 6/2017 |
| WO | 97/07750 | 3/1997 |
| WO | 97/15190 A1 | 5/1997 |
| WO | 2004/045601 | 6/2004 |
| WO | 2011/052950 A2 | 5/2011 |
| WO | 2012/068081 A | 5/2012 |

OTHER PUBLICATIONS

Mahalakshmi, The Use of D-Amino Acids in Peptide Design Chapter 5.9, In: D-Amino Acids: A New Frontier in Amino Acid and Protein Research © 2006 Nova Science Publishers, Inc., pp. 415-430. (Year: 2006).*
Hong, et al, Effect of D-Amino Acid Substitution on the Stability, the Secondary Structure, and the Activity of Membrane-Active Peptide, Biochemical Pharmacology, vol. 58, pp. 1775-1780, 1999. (Year: 1999).*
Tugyi, et al, Partial D-amino acid substitution: Improved enzymatic stability and preserved Ab recognition of a MUC2 epitope peptide, PNAS Jan. 11, 2005 vol. 102 No. 2 413-418. (Year: 2005).*
International Search Report and Written Opinion for PCT Application No. PCT/CN2017/097805, dated May 29, 2018, 8 pages.
International Search Report and Written Opinion for PCT Application No. PCT/CN2017/100431, dated Jun. 4, 2018, 12 pages.
International Search Report and Written Opinion for PCT Application No. PCT/CN2019/070912, dated Mar. 27, 2019, 11 pages.
Registry RN 1430202-54-2, Oct. 21, 2013.
Jiang et al., "Structural Requirements for Optimized Delivery, Inhibition of Oxidative Stress, and Antiapoptotic Activity of Targeted Nitroxides", The Journal of Pharmacology and Experimental Therapeutics, Dec. 2007, vol. 320, No. 3, p. 1050-1060.
Krainz et al., "A Mitochondrial-Targeted Nitroxide is a Potent Inhibitor of Ferroptosis", ACS Central Science, Sep. 2016, vol. 2, p. 653-659.
Wipf et al., "Mitochondrial Targeting of Selective Electron Scavengers: Synthesis and Biological Analysis of Hemigramicidin-TEMPO Conjugates", Journal American Chemical Society, Aug. 2005, vol. 127, p. 12460-12461.

* cited by examiner

*Primary Examiner* — Thomas S Heard

(57) ABSTRACT

A compound of Formula (I), pharmaceutically acceptable salts thereof, and individual enantiomers or diastereomers thereof. Compositions and methods useful for treatment or suppression of diseases, developmental delays and symptoms related to oxidative stress.

Formula (I)

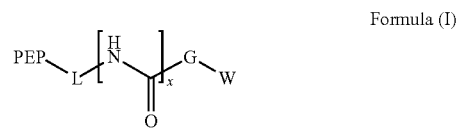

25 Claims, No Drawings

REACTIVE OXYGEN SPECIES SCAVENGERS AND USE FOR TREATING DISEASES

This application claims the benefit under 35 U.S.C. § 111(a) of PCT International Application No. PCT/CN2017/1004313 filed on Sep. 4, 2017, which is incorporated by reference in its entirety.

FIELD OF THE INVENTION

The present invention provides compositions and methods useful for treatment or suppression of diseases, developmental delays and symptoms related to oxidative stress. More specifically, the compositions and methods comprise administrating an effective amount of a compound that is a ferroptosis and apoptosis modulator.

BACKGROUND OF INVENTION

While localized ROS (reactive oxygen species) are critical to the eukaryotic cell's biological metabolism and development, excessive flux of unrestrained ROS leads to cellular dysfunctions and/or death.

Since its introduction in 2012, ferroptosis has emerged as a key mechanistic pathway for excess ROS flux (especially in the mitochondria) which ultimately leads to non-apototic cell death. As the key element in ferroptosis, the loss of glutathione peroxidase 4 (GPx4) activity allows for a lethal excess of ROS which then leads to cellular destruction by oxidative stress (e.g., peroxidation of the membrane's polyunsaturated phospholipids). Since GPx4 uses glutathione (GSH) as the key co-factor for scavenging ROS, GSH production deficit can arise from blocked induction (e.g., via known small compounds such as erastin and excess glutamates) of its 'up-stream' Xc$^-$ system (a glutamate/cystine anti-transporter). On the other hand, inducing excess ROS flux via ferroptosis can kill certain cancer cells.

Based on the above reviews as well as references about some other inhibitors attributable to their anti-ferroptotic mechanisms of action (e.g., ferrostatins: patent applications—US 2016/0297748 and WO 2013/152039, quinones such as MitoQ), small peptides such as SS-31: patent publication WO 2004070054 (A2)); nitroxides such as XJB-5-131 and JP4-039 analogs: patent publication WO 2012112851 (A2)). XJB-5-131 has also been applied in the application of inhibition of ferroptosis, wherein it plays a critical role of intramitochondrial lipid peroxidation in ferroptosis. Also, the reference compound ferrostatin-1 and XJB-5-131 may share similar mechanisms of action or that both compounds operate on the same signaling pathway. Ferroptosis can be linked to a variety of well-known diseases broadly grouped as involving the non-central nervous system (non-CNS) or CNS.

Non-CNS: cardiovascular (e.g., atherosclerosis, hypertensive cardiomyopathy, congestive heart failure, stroke, etc.), metabolic (e.g., diabetes and its related complications such as neuropathy, hyperlipidemia, etc.), urinary (e.g., acute kidney injury (AKI)), age related diseases (e.g., skeletal muscle atrophy, and dry aged macular degeneration (Dry-AMD) and trauma (e.g., radiation injury, inducing rhabdomyolysis, traumatic brain injury, major surgery, etc.). In the case of AKI, US FDA today has yet to approve a drug to specifically cure this disease which especially affects ~30% of US patients hospitalized in intensive care units. When AKI unfortunately progresses to the late/chronic stages, hemo-dialysis and ultimately kidney replacement become the major remaining treatment options.

CNS: neuro-motor (e.g., Parkinson's, Huntington's, amyotrophic lateral sclerosis, epilepsy, etc.) and cognitive (e.g., Alzheimer's). In the case of epilepsy which affects over 50 million people globally, a significant minority (20-30%) of patients are/become resistant to more than 20 currently approved drugs. Undoubtedly, ongoing research will likely link more diseases due to and more inhibitors of ferroptosis since its 2012 introduction. Thus, as exemplified by AKI and epilepsy some other diseases to be linked to ferroptosis in the future also urgently need better (likely novel) drugs.

SUMMARY OF THE INVENTION

The following is only an overview of some aspects of the present invention but is not limited thereto. All references of this specification are incorporated herein by reference in their entirety. When the disclosure of this specification is different with citations, the disclosure of this specification shall prevail. The present invention provides compounds and pharmaceutical compositions, which modulates ferroptosis in a subject; include certain TEMPO derivatives, their preparation, and the corresponding pharmaceutical compositions. The compounds and/or pharmaceutical compositions of the present invention can be potentially used in the manufacture of a medicament for preventing, treating, ameliorating certain disorder or a disease in a patient.

One aspect of the present invention is a compound of Formula (I), pharmaceutically acceptable salts thereof, and individual enantiomers or diastereomers thereof:

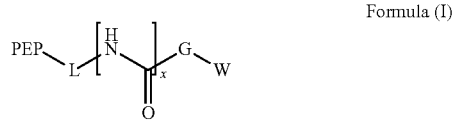

Formula (I)

wherein, x is 0 or 1;

G is absent, O, NH or CH$_2$;

W is:

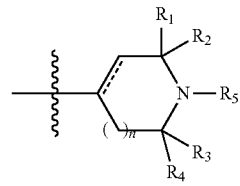

wherein,

R$_1$, R$_2$, R$_3$, or R$_4$ is C$_1$-C$_6$ alkyl, R$_5$ is OH, or O, n is 0, 1, 2 or 3, L is absent, or selected from a group consisting of: C$_1$-C$_{10}$ alkyl, C$_1$-C$_{10}$ alkoxyl, cycloalkyl, C$_1$-C$_{10}$ alkylcycloalkyl, heterocycloalkyl, C$_1$-C$_{10}$ alkylheterocycloalkyl, aryl, C$_1$-C$_{10}$ alkylaryl, heteroaryl, and C$_1$-C$_{10}$ alkylheteroaryl, wherein said cycloalkyl, or heterocycloalkyl has about 3 to about 7 ring carbons, and said aryl or heteroaryl has about 5 to about 10 ring carbons;

PEP is a peptidyl moiety having the following structure:

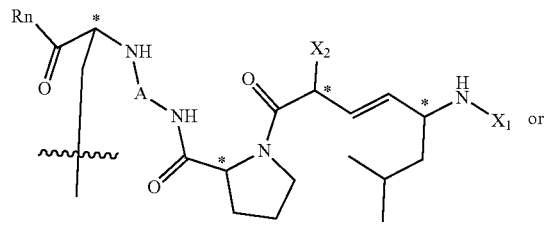

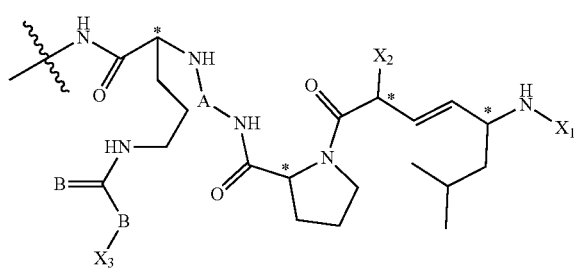

wherein a * mark denotes a chiral center in either an (S) or (R) configuration;

B is absent, N, NH, or O;

$X_1$ is selected from a group consisting of H, —(C=O)—O—$R_m$, —(SO)—O—$R_m$, —(SO)—O—$R_m$, —(SO$_2$)—N—($R_m$)$_2$, and —(C=O)—N—($R_m$)$_2$, wherein $R_m$ is $C_1$-$C_6$ alkyl, $C_1$-$C_6$ alkoxyl, $C_1$-$C_6$ alkenyl, $C_1$-$C_6$ haloalkyl, cycloalkyl, $C_1$-$C_6$ alkylcycloalkyl, heterocycloalkyl, $C_1$-$C_6$ alkylheterocycloalkyl, aryl, $C_1$-$C_6$ alkylaryl, heteroaryl, or $C_1$-$C_6$ alkylheteroaryl, wherein said cycloalkyl or heterocycloalkyl has about 3 to about 7 ring carbons, and said aryl or heteroaryl has about 5 to about 10 ring carbons;

Rn is selected from —O—$X_3$, —S—$X_3$, —NH—$X_3$, or —N—$X_{4a}(X_{4b})$;

$X_2$ or $X_3$ is selected from a group consisting of H, $C_1$-$C_{10}$ alkyl, $C_1$-$C_{10}$ alkenyl, aryl, $C_1$-$C_6$ alkylaryl, heteroaryl, and $C_1$-$C_6$ alkylheteroaryl, wherein said aryl or heteroaryl having from 5 to 6 ring carbons;

$X_{4a}$ and $X_{4b}$ are independently selected from $C_1$-$C_6$ alkyl, substituted-$C_1$-$C_6$ alkyl; $X_{4a}$ and $X_{4b}$ can, optionally, together form $C_3$-$C_8$ heterocycloalkyl, substituted-$C_3$-$C_8$ heterocycloalkyl.

A is absent or selected from a group consisting of: Alanine, Leucine, Isoleucine, Phenylalanine, Methionine, Proline, Glycine, Tryptophan, Serine, Threonine, Cysteine, Tyrosine, Asparagine, Glutamine, Histidine, Lysine, Arginine, Aspartic acid, Glutamic acid, and Valine, each of which can be in either a D or L configuration; the amino residue is either unprotected, or protected by a protecting group selected from a group consisting of Cbz and Fmoc;

with the proviso that PEP is not one of the following:

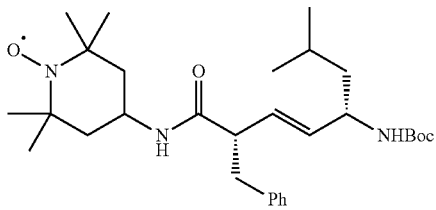

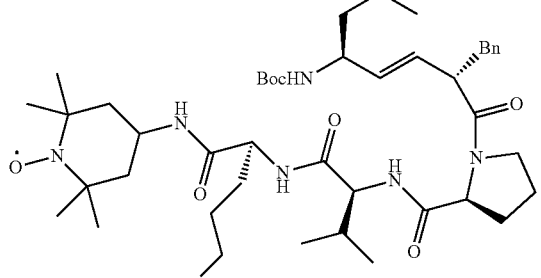

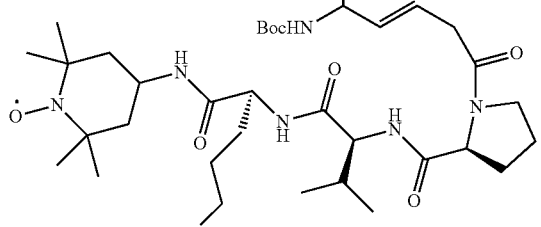

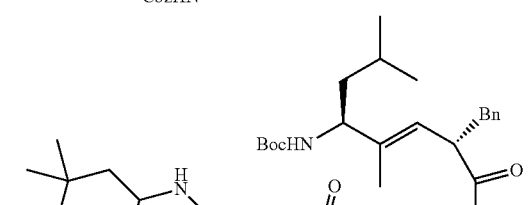

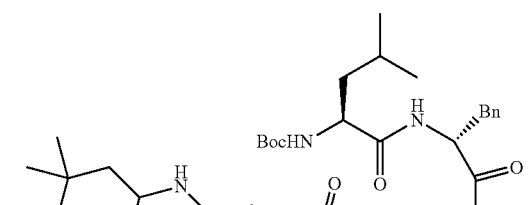

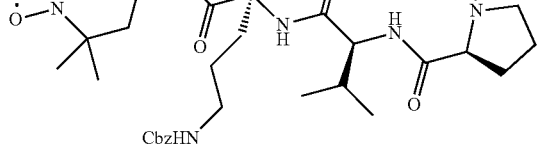

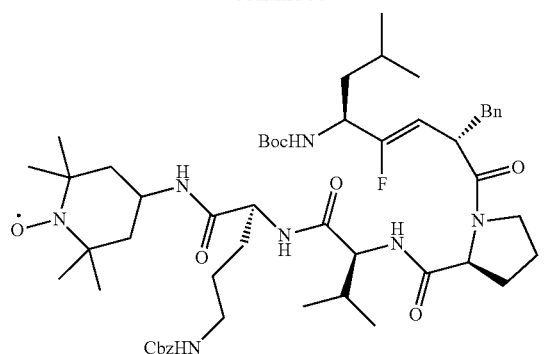
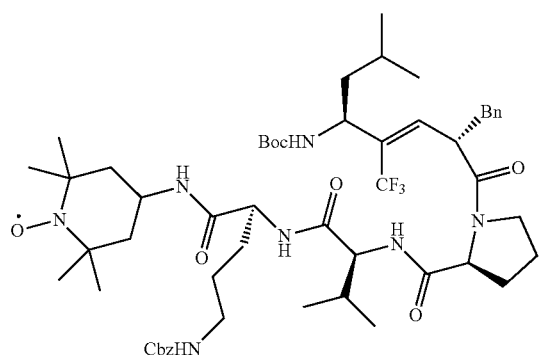
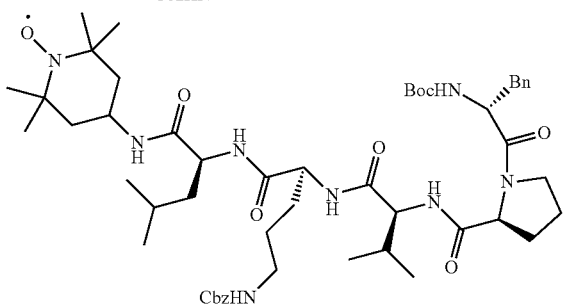
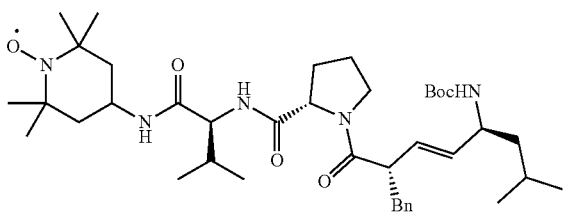
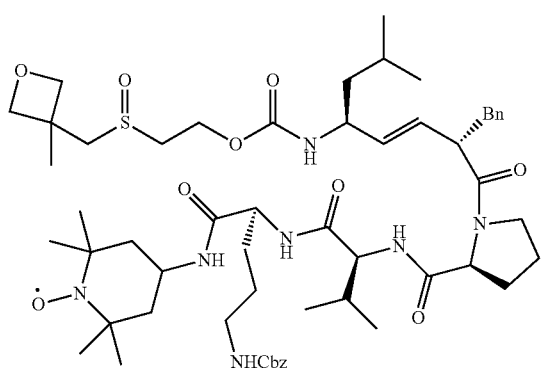
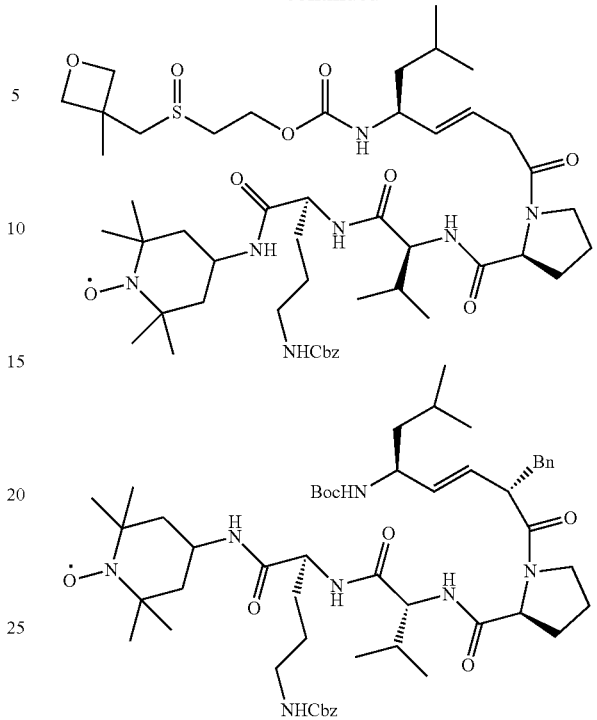

In another aspect, the invention relates to pharmaceutical compositions each comprising an effective amount of at least one compound of Formula (I) or a pharmaceutically acceptable salt of a compound of Formula (I), and individual enantiomers and diastereomers thereof. Pharmaceutical compositions according to the invention may further comprise at least one pharmaceutically acceptable excipient, carrier, adjuvant, solvent, support or a combination thereof and may further comprise therapeutically effective amounts of one or more, optional, adjunctive active ingredients.

In a further aspect of the present invention, the compounds of Formula (I) or a pharmaceutically acceptable salt of a compound of Formula (I), and individual enantiomers and diastereomers thereof, are useful as ferroptosis modulators. Thus, the invention is directed to the use of an effective amount of at least one aforementioned compound of Formula (I) or a pharmaceutically acceptable salt of a compound of Formula (I), and individual enantiomers and diastereomers thereof in the manufacture of a medicament to be used in a method for reducing reactive oxygen species (ROS) in a cell comprising contacting a cell with an effective amount of said compound as a ferroptosis modulator.

In still another aspect of the present invention, there is directed to a method for modulating ferroptosis in a subject, comprising exposing the subject to an effective amount of at least one compound of Formula (I), or a pharmaceutically acceptable salt of a compound of Formula (I), and individual enantiomers and diastereomers thereof, and at least one pharmaceutically acceptable excipient, carrier, adjuvant, solvent, support or a combination thereof, and further therapeutically effective amounts of one or more, optional, adjunctive active ingredients.

Another aspect of the present invention concerns the use of pharmaceutical compositions each comprising an effective amount of at least one compound of Formula (I) or a pharmaceutically acceptable salt of a compound of Formula (I), and individual enantiomers and diastereomers thereof, and at least one pharmaceutically acceptable excipient, carrier, adjuvant, solvent, support or a combination thereof, and further therapeutically effective amounts of one or more, optional, adjunctive active ingredients, in the manufacture of a medicament for preventing, treating or lessening an oxidative stress related disorder or disease in a patient by administering therapeutically effective amounts of said compound or said pharmaceutical composition as a ferroptosis modulator.

In yet another aspect, the invention is directed to a method for preventing, treating or lessening an oxidative stress related disorder or disease in a patient by modulating certain ferroptosis process in said patient by administering to the patient a therapeutically effective amount of the aforementioned pharmaceutical compositions each comprising an effective amount of at least one compound of Formula (I) or a pharmaceutically acceptable salt of a compound of Formula (I), and individual enantiomers and diastereomers thereof, and at least one pharmaceutically acceptable excipient, carrier, adjuvant, solvent, support or a combination thereof, and further therapeutically effective amounts of one or more, optional, adjunctive active ingredients.

In yet another aspect, the present invention is directed to methods of making compounds of Formula (I) and pharmaceutically acceptable salts thereof.

In certain embodiments of the compounds, pharmaceutical compositions, and methods of the invention, the compound of Formula (I) is a compound selected from those species described or exemplified in the detailed description below or is a pharmaceutically acceptable salt of such a compound.

Another preferred embodiment, the present invention is directed to methods of preparing pharmaceutical compositions each comprising an effective amount of at least one compound of Formula (I), or a pharmaceutically acceptable salt of a compound of Formula (I), and further individual enantiomers and diastereomers thereof. As aforementioned, pharmaceutical compositions according to the invention may further comprise at least one pharmaceutically acceptable excipient, carrier, adjuvant, solvent, support or a combination thereof and further comprise therapeutically effective amounts of one or more, optional, adjunctive active ingredients.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (*J. Cell Sci.*, (1995) 108, 2897). The compounds of the invention may also be administered sequentially with known anticancer or cytotoxic agents when a combination formulation is inappropriate. In any combination treatment, the invention is not limited in the sequence of administration; compounds of Formula (I) may be administered either prior to or after administration of the known anticancer or cytotoxic agent. For example, the cytotoxic activity of the cyclin-dependent kinase inhibitor flavopiridol is affected by the sequence of administration with anticancer agents (*Cancer Research*, (1997) 57, 3375). Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, beads, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (Ed.), *Remington's Pharmaceutical Sciences*, $18^{th}$ Ed., (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or via an eye drop or an intravitreous injection Preferably, the pharmaceutical preparation is in a unit dosage form. In such form, the preparation is subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and additional embodiments, features, and advantages of the invention will be apparent from the following detailed description and through practice of the invention.

DETAILED DESCRIPTION AND PARTICULAR EMBODIMENTS

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

Definitions and General Terminology

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing" and "comprising" are used in their open, non-limiting sense.

As used herein, the singular forms "a", "an" and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical Definitions

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylamino" as used herein denotes an amino group as defined herein wherein one hydrogen atom of the amino group is replaced by an alkyl group as defined herein. Aminoalkyl groups can be defined by the following general formula —NH-alkyl. This general formula includes groups of the following general formulae: —NH—$C_1$-$C_{10}$ alkyl and —NH—$C_1$-$C_6$ alkyl. Examples of aminoalkyl groups include, but are not limited to aminomethyl, aminoethyl, aminopropyl, aminobutyl.

The term "alkoxy" as used herein includes —O—(alkyl), wherein alkyl is defined above.

As used herein, "alkoxyalkyl" means —(alkylenyl)-O—(alkyl), wherein each "alkyl" is independently an alkyl group defined above.

The term "amine" as used herein refers to an —$NH_2$ group.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

"Aryloxy" as used herein refers to an —O—(aryl) group, wherein aryl is defined as above.

"Arylalkyl" as used herein refers to an —(alkylenyl)—(aryl) group, wherein alkylenyl and aryl are as defined above. Non-limiting examples of arylalkyls comprise a lower alkyl group. Non-limiting examples of suitable arylalkyl groups include benzyl, 2-phenethyl, and naphthalenylmethyl.

"Arylalkoxy" as used herein refers to an —O—(alkylenyl)-aryl group wherein alkylenyl and aryl are as defined above.

The term "deuterium," and "deuterated" as used herein means being, being substituted with, a stable isotope of hydrogen having one proton and one neutron.

The term "halogen" as used herein refers to fluorine, chlorine, bromine, or iodine. The term "halo" represents chloro, fluoro, bromo, or iodo.

The term "haloalkyl" denotes an alkyl group as defined above wherein one or more, for example one, two, or three of the hydrogen atoms of the alkyl group are replaced by a halogen atom, for example fluoro, bromo, or chloro, in particular fluoro. Examples of haloalkyl include, but are not limited to, monofluoro-, difluoro-, or trifluoro-methyl, -ethyl or -propyl, for example, 3,3,3-trifluoropropyl, 2-fluoroethyl, 2,2,2-trifluoroethyl, fluoromethyl, difluoromethyl, or trifluoromethyl, or bromoethyl or chloroethyl. Similarly, the term "fluoroalkyl" refers to an alkyl group as defined above substituted with one or more, for example one, two, or three fluorine atoms.

The term "haloalkoxy" as used herein refers to an —O—(haloalkyl) group wherein haloalkyl is defined as above. Exemplary haloalkoxy groups are bromoethoxy, chloroethoxy, trifluoromethoxy and 2,2,2-trifluoroethoxy.

The term "hydroxy" means an —OH group.

The term "hydroxyalkyl" denotes an alkyl group that is substituted by at least one hydroxy group, for example, one, two or three hydroxy group(s). The alkyl portion of the hydroxyalkyl group provides the connection point to the remainder of a molecule. Examples of hydroxyalkyl groups include, but are not limited to, hydroxymethyl, hydroxyethyl, 1-hydroxypropyl, 2-hydroxyisopropyl, 1,4-dihydroxybutyl, and the like.

The term "oxo" means an =O group and may be attached to a carbon atom or a sulfur atom. The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 12 ring carbon atoms. A non-limiting category of cycloalkyl groups are saturated or partially saturated, monocyclic carbocycles having from 3 to 6 carbon atoms. Illustrative examples of cycloalkyl groups include, but are not limited to, the following moieties:

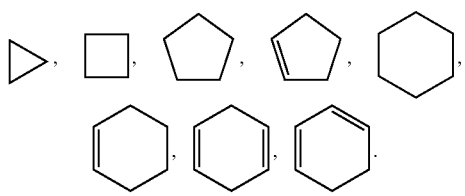

The term "cycloalkoxy" refers to a —O—(cycloalkyl) group.

The term "heterocycloalkyl" as used herein refers to cycloalkl, as defined in this application, provided that one or more of the ring carbons indicated, are replaced by a moiety selected from —O—, —N=, —C(O)—, —S—.

As used herein, the term "heteroaryl" refers to a monocyclic, or fused polycyclic, aromatic heterocycle having from three to 15 ring atoms that are selected from carbon, oxygen, nitrogen, selenium and sulfur. Suitable heteroaryl groups do not include ring systems that must be charged to be aromatic, such as pyrylium. Some suitable 5-membered heteroaryl rings (as a monocyclic heteroaryl or as part of a polycyclic heteroaryl) have one oxygen, sulfur, or nitrogen atom, or one nitrogen plus one oxygen or sulfur, or 2, 3, or 4 nitrogen atoms. Some suitable 6-membered heteroaryl rings (as a monocyclic heteroaryl or as part of a polycyclic heteroaryl) have 1, 2, or 3 nitrogen atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Those skilled in the art will recognize that the species of heteroaryl, and cycloalkyl groups listed or illustrated above are not exhaustive, and that additional species within the scope of these defined terms may also be selected.

As described herein, compounds disclosed herein may optionally be substituted with one or more substituents, or as exemplified by particular classes, subclasses, and species of the invention.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl, alkylenyl, heteroaryl, $R_1$, $R_2$, or $R_a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4, while a range expressed as "10-20%" includes 10%, 11%, 12%, 13%, 14%, 15%, 16%, 17%, 18%, 19% and 20%. Similarly, numerical ranges are also intended to include sequential fractional integers. For example, a range expressed as "1-2%" would include 1.0%, 1.1%, 1.2%, 1.3%, 1.4%, 1.5%, 1.6%, 1.7%, 1.8%, 1.9% and 2.0%.

When a multifunctional moiety is shown, the point of attachment to the core is indicated by a line or hyphen. For example, aryloxy- refers to a moiety in which an oxygen atom is the point of attachment to the core molecule while aryl is attached to the oxygen atom.

Additional Definitions

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given protein, receptor and/or ion channels.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein, the terms "administration of" and "administering a" compound should be understood to mean providing a compound of the invention, pharmaceutical composition comprising a compound or a prodrug of a compound of the invention to an individual in need thereof. It is recognized that one skilled in the non-limiting art can treat a patient presently afflicted with related diseases or disorders or by prophylactically treat a patient afflicted with the diseases or disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the other types of reactions or interactions such as to cause the dissociation of one or more of the ingredients. Accordingly, the pharmaceutical compositions of the present invention encompass any composition made by mixing a compound of the present invention and a pharmaceutically acceptable carrier.

Additional Chemical Descriptions

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

"Stereoisomer" refers to compounds which have identical chemical constitution but differ with regard to the arrangement of the atoms or groups in space. Stereoisomers include enantiomer, diastereomers, conformer (rotamer), geometric (cis/trans) isomer, atropisomer etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be in racemic or enantiomerically enriched, for example the (R)-, (S)—or (R,S)— configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)—configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)—isomers may be prepared using chiral synthons or chiral reagents or resolved using conventional techniques. If the compound contains a double bond, the substituent may be E or Z configuration. If the compound contains a disubstituted cycloalkyl, a cycloalkyl substituent may have a cis- or trans- configuration relative to another substituent of the same cycloalkyl frame.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al. Enantiomers, Racemates and Resolutions (Wiley Interscience, New York, 1981); Principles of Asymmetric Synthesis (2nd Ed. Robert E. Gawley, Jeffrey Aube, Elsevier, Oxford, UK, 2012); Eliel, E. L. Stereochemistry of Carbon Compounds (McGraw-Hill, NY, 1962); Wilen, S. H. Tables of Resolving Agents and Optical Resolutions, p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column.

The compounds of the invention can form pharmaceutically acceptable salts, which are also within the scope of this invention. A "pharmaceutically acceptable salt" refers to a salt of a free acid or base of a compound of Formula (I) that is non-toxic, is physiologically tolerable, is compatible with the pharmaceutical composition in which it is formulated and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al., Camille G. (eds.) Handbook of Pharmaceutical Salts. Properties, Selection and Use. (2002) Zurich: Wiley-VCH; S. Berge et al., *Journal of Pharmaceutical Sciences* (1977) 66(1) 1-19; P. Gould, International J. of Pharmaceutics (1986) 33 201-217; Anderson et al., The Practice of Medicinal Chemistry (1996), Academic Press, New York; and in The Orange Book (Food & Drug Administration, Md., available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., *J. Pharmaceutical Sci.*, 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al., AAPS PharmSciTech., 5(1), article 12 (2004); and A. L. Bingham et al, Chem. Commun., 603-604 (2001). A typical, non-limiting process involves dissolving the compound of the invention in a suitable amount of the solvent (organic solvent or water or a mixture thereof) at a higher than ambient temperature and cooling the solution at a rate sufficient to form crystals which are then isolated by standard methods. Analytical techniques such as, for example, infrared spectroscopy, show the presence of the solvent (or water) in the crystals as a solvate (or hydrate).

The present invention also relates to pharmaceutically active metabolites of compounds of Formula (I)a or (I)b and uses of such metabolites in the methods of the invention. A "pharmaceutically active metabolite" means a pharmacologically active product of metabolism in the body of a compound of Formula (I)a or (I)b or salt thereof. Active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, *Design of Prodrugs* (Elsevier Press, 1985); and Larsen, *Design and Application of Prodrugs, Drug Design and Development* (Krogsgaard-Larsen et al., eds., *Harwood Academic Publishers*, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^{2}H$ or $^{3}H$), detection or imaging techniques such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The use of the terms "salt", "solvate", "polymorph", and the like, with respect to the compounds described herein is intended to apply equally to the salt, solvate, and polymorph forms of enantiomers, stereoisomers, rotamers, tautomers, atropisomers, and racemates of the compounds of the invention. Abbreviation:

| | | | |
|---|---|---|---|
| EA | Ethyl Acetate; | DCM | Dichloromethane; |
| THF | Tetrahydrofuran; | PE | Petroleum Ether; |
| i-PrOH | Isopropanol; | t-Bu | tert-Butyl; |
| iPr | Isopropyl; | PivCl | Pivaloyl Chloride; |
| TEA | Triethylamine; | DIPEA | N-Ethyldiisopropylamine; |
| n-BuLi | n-Butyllithium; | $(Boc)_2O$ | Di-tert-butyl decarbonate; |
| HMDS | Hexamethyldisilazide; | CAN | Ammonium ceric nitrate; |
| BnBr | Benzyl bromide; | TFA | Trifluoracetic acid; |
| Bn | Benzyl; | DMF | N,N'-dimethylformamide; |
| Vc | L-ascorbic acid; | Boc | tert-Butyloxy carbonyl; |
| m-CPBA | m-Chloroperbenzoic acid; | DIAD | Diisopropyl azodicarboxylate; |
| NaHMDS | Sodium bis(trimethylsilyl)amide; | TBAF | Tetrabutylammonium Fluoride; |
| CbzCl | Benzyl Chloroformate; | MTBE | Methyl Tert-butyl Ether; |
| DMSO | Dimethyl Sulphoxide; | Fmoc | 9-Fluorenylmethoxycarbonyl; |
| Cbz | Carbobenzyl; | DMAP | 4-(dimethylamino)pyridine; |
| HATU | O-(7-azabenzotriazol-1-yl)uronium hexafluoro-phosphate; | | |
| 4-AT | (2,2,6,6-Tetramethyl-1-oxy-4-piperidinyl)amine; | | |
| TEMPO | 2,2,6,6-Tetramethylpiperidinooxy; | | |
| $T_3P$ | 2,4,6-tripropyl-1,3,5,2,4,6-trioxatriphosphorinane-2,4,6-trioxide; | | |
| DBU | 1,8-Diazabicyclo[5.4.0]undec-7-ene; | | |

Description of Compounds of the Invention

The present invention relates to particular molecules and pharmaceutically acceptable salts or isomers thereof. The invention further relates to molecules which are useful in modulating dysfunctional glutamate transmission and pharmaceutically acceptable salts, solvates, esters, or isomers thereof.

The invention is directed to compounds as described herein and pharmaceutically acceptable salts, solvates, esters, or isomers thereof, and pharmaceutical compositions comprising one or more compounds as described herein and pharmaceutically acceptable salts or isomers thereof.

One aspect of this invention is the compounds, compositions, kits, and antidotes for modulating glutamate transmission in mammals having a compound of Formula (I), pharmaceutically acceptable salts thereof, and individual enantiomers or diastereomers thereof:

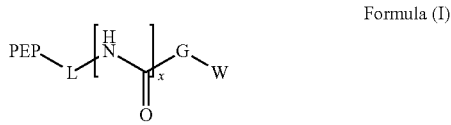

Formula (I)

wherein, x is 0 or 1;

G is absent, O, NH or $CH_2$;

W is:

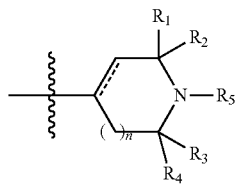

wherein, $R_1$, $R_2$, $R_3$, or $R_4$ is $C_1$-$C_6$ alkyl, $R_5$ is OH, or O, n is 0, 1, 2 or 3, L is absent, or selected from a group consisting of $C_1$-$C_{10}$ alkyl, $C_1$-$C_{10}$ alkoxyl, cycloalkyl, $C_1$-$C_{10}$ alkylcycloalkyl, heterocycloalkyl, $C_1$-$C_{10}$ alkylheterocycloalkyl, aryl, $C_1$-$C_{10}$ alkylaryl, heteroaryl, and $C_1$-$C_{10}$ alkylheteroaryl, wherein said cycloalkyl, or heterocycloalkyl has about 3 to about 7 ring carbons, and said aryl or heteroaryl has about 5 to about 10 ring carbons;

PEP is a peptidyl moiety having the following structure:

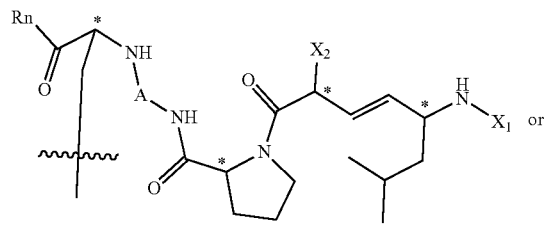 or

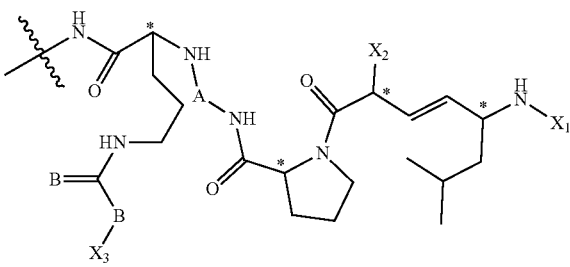

wherein a * mark denotes a chiral center in either an (S) or (R) configuration;

B is absent, N, NH, or O;

$X_1$ is selected from a group consisting of H, —(C=O)—O—$R_m$, —(SO)—O—$R_m$, —($SO_2$)—O—$R_m$, —($SO_2$)—N—$(R_m)_2$ and —(C=O)—N—$(R_m)_2$, wherein $R_m$ is $C_1$-$C_6$ alkyl, $C_1$-$C_6$ alkoxyl, $C_1$-$C_6$ alkenyl, $C_1$-$C_6$ haloalkyl, cycloalkyl, $C_1$-$C_6$ alkylcycloalkyl, heterocycloalkyl, $C_1$-$C_6$ alkylheterocycloalkyl, aryl, $C_1$-$C_6$ alkylaryl, heteroaryl, or $C_1$-$C_6$ alkylheteroaryl, wherein said cycloalkyl or heterocycloalkyl has about 3 to about 7 ring carbons, and said aryl or heteroaryl has about 5 to about 10 ring carbons;

Rn is selected from —O—$X_3$, —S—$X_3$, —NH—$X_3$, or —N—$X_{4a}(X_{4b})$;

$X_2$ or $X_3$ is selected from a group consisting of H, $C_1$-$C_{10}$ alkyl, $C_1$-$C_{10}$ alkenyl, aryl, $C_1$-$C_6$ alkylaryl, heteroaryl, and $C_1$-$C_6$ alkylheteroaryl, wherein said aryl or heteroaryl having from 5 to 6 ring carbons;

$X_{4a}$ and $X_{4b}$ are independently selected from $C_1$-$C_6$ alkyl, substituted-$C_1$-$C_6$ alkyl; $X_{4a}$ and $X_{4b}$ can, optionally, together form $C_3$-$C_8$ heterocycloalkyl, substituted-$C_3$-$C_8$ heterocycloalkyl.

A is absent or selected from a group consisting of: Alanine, Leucine, Isoleucine, Phenylalanine, Methionine, Proline, Glycine, Tryptophan, Serine, Threonine, Cysteine, Tyrosine, Asparagine, Glutamine, Histidine, Lysine, Arginine, Aspartic acid, Glutamic acid, and Valine, each of which can be in either a D or L configuration; the amino residue is either unprotected, or protected by a protecting group selected from a group consisting of Cbz and Fmoc;

with the proviso that PEP is not one of the following:

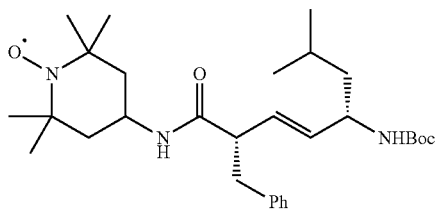

21
-continued
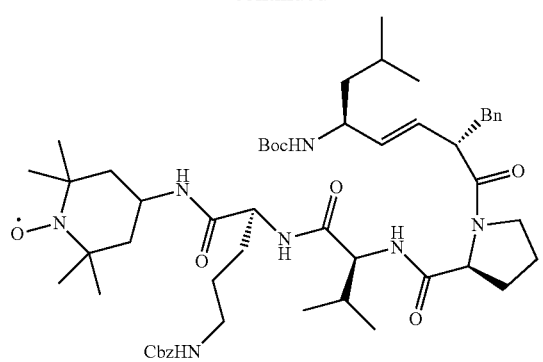
22
-continued
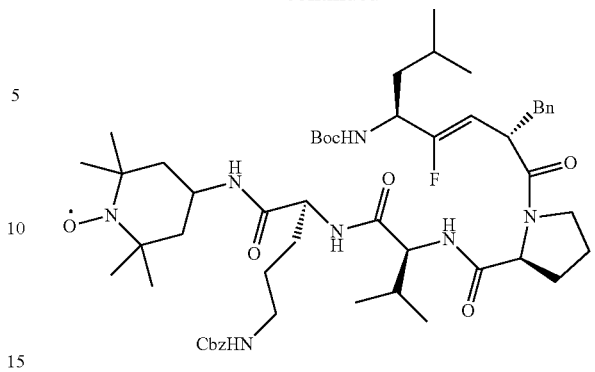
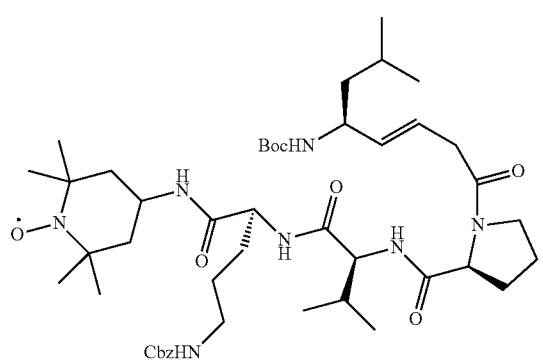
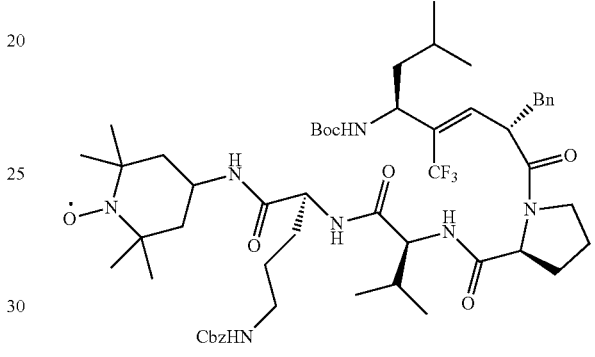
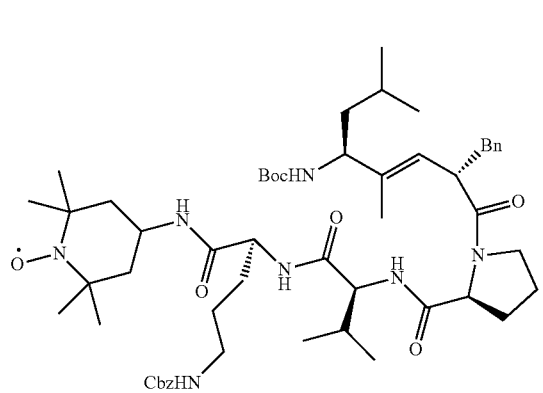
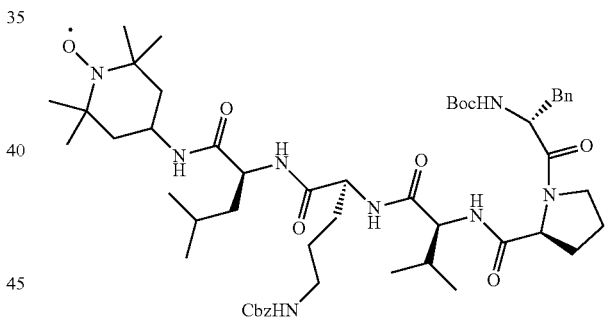
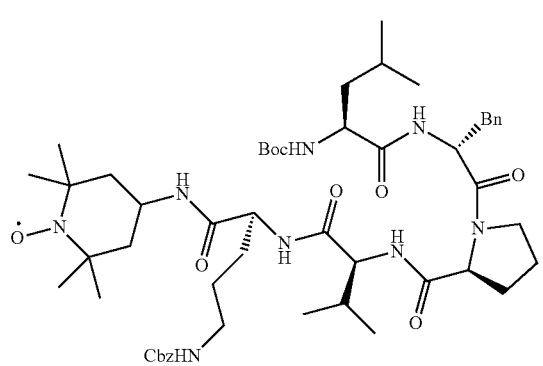
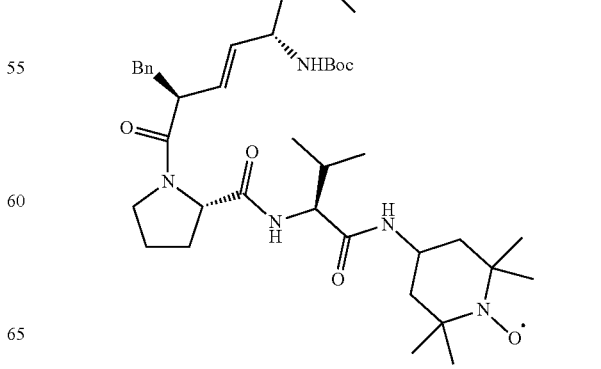

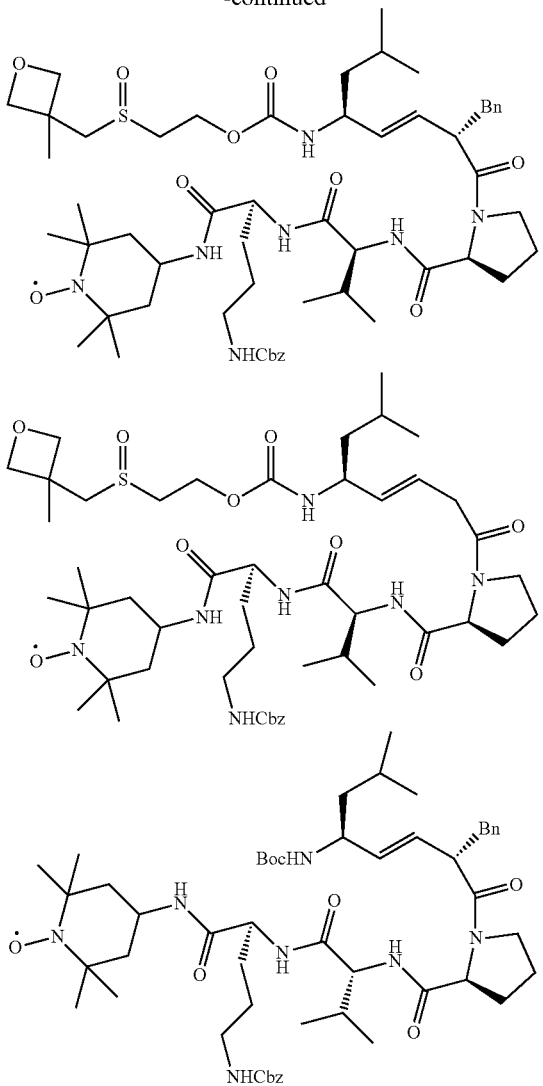

In some embodiments, in which compounds have the general Formula (I), wherein G is O.

In some other embodiments, in which compounds have the general Formula (I), wherein x is 1.

In still other embodiments, in which compounds have the general Formula (I), wherein L is $C_1$-$C_6$ alkyl, preferably $C_3$-$C_4$ alkyl.

Another embodiment of the invention is the provision of compounds having the general Formula (I), wherein PEP is:

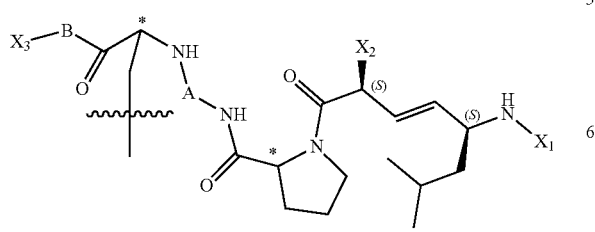

Yet another embodiment of the invention is the provision of a compound, wherein A is absent or Valine.

Yet another embodiment of the invention is the provision of a compound, wherein B is O, or NH.

Yet another embodiment of the invention is the provision of a compound, wherein $R_m$ is $C_1$-$C_6$ alkyl, $C_1$-$C_6$ alkoxyl.

Yet another embodiment of the invention is the provision of a compound, wherein $X_2$ is $C_1$-$C_6$ alkylaryl, $C_1$-$C_6$ alkoxylaryl, $C_1$-$C_{10}$ heteroaryl, $C_1$-$C_{10}$ heterocyclicalkyl.

Yet another embodiment of the invention is the provision of a compound, wherein $X_3$ is $C_1$-$C_6$ alkyl, $C_1$-$C_6$ cyclicalkyl.

Yet another embodiment of the invention is the provision of a compound, wherein $X4_a$ and $X4_b$ are independently selected from $C_1$-$C_6$ alkyl, substituted-$C_1$-$C_6$ alkyl; $X_{4a}$ and $X_{4b}$ can, optionally, together form $C_3$-$C_8$ heterocycloalkyl, substituted-$C_3$-$C_8$ heterocycloalkyl.

Yet another embodiment of the invention is the provision of a compound, wherein $R_m$ is t-Bu-, $X_2$ is Ph-$CH_2$— and $X_3$ is t-Bu-.

Yet another embodiment of the invention is the provision of a compound, wherein $R_m$ is t-Bu-, $X_2$ is Ph-$CH_2$— and $X_3$ is i-Propyl-.

Yet another embodiment of the invention is the provision of a compound, wherein $R_m$ is t-Bu-, $X_2$ is Ph-$CH_2$— and $X_3$ is cyclohexyl.

Yet another embodiment of the invention is the provision of a compound, wherein $R_m$ is t-Bu-, $X_2$ is Ph-$CH_2$— and $X_3$ is cyclopropyl.

Yet another embodiment of the invention is the provision of a compound, wherein $R_m$ is t-Bu-, $X_2$ is Ph-$CH_2$— and $X_3$ is diethylamine.

Yet another embodiment of the invention is the provision of a compound, wherein $R_m$ is t-Bu-, $X_2$ is Ph-$CH_2$— and $X_3$ is piperidine.

In certain embodiments, the compound of Formula (I) is further illustrated by the following compound group consisting of:

I

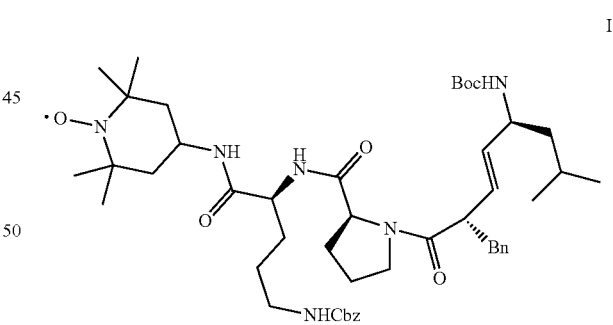

II

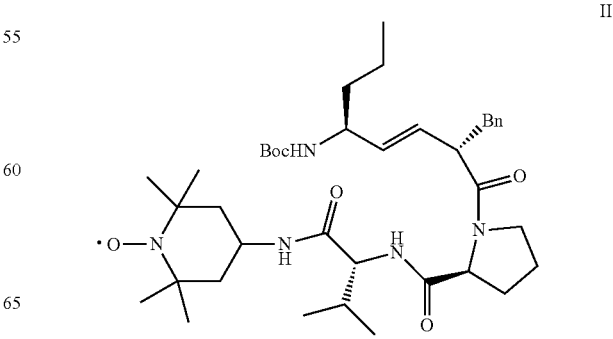

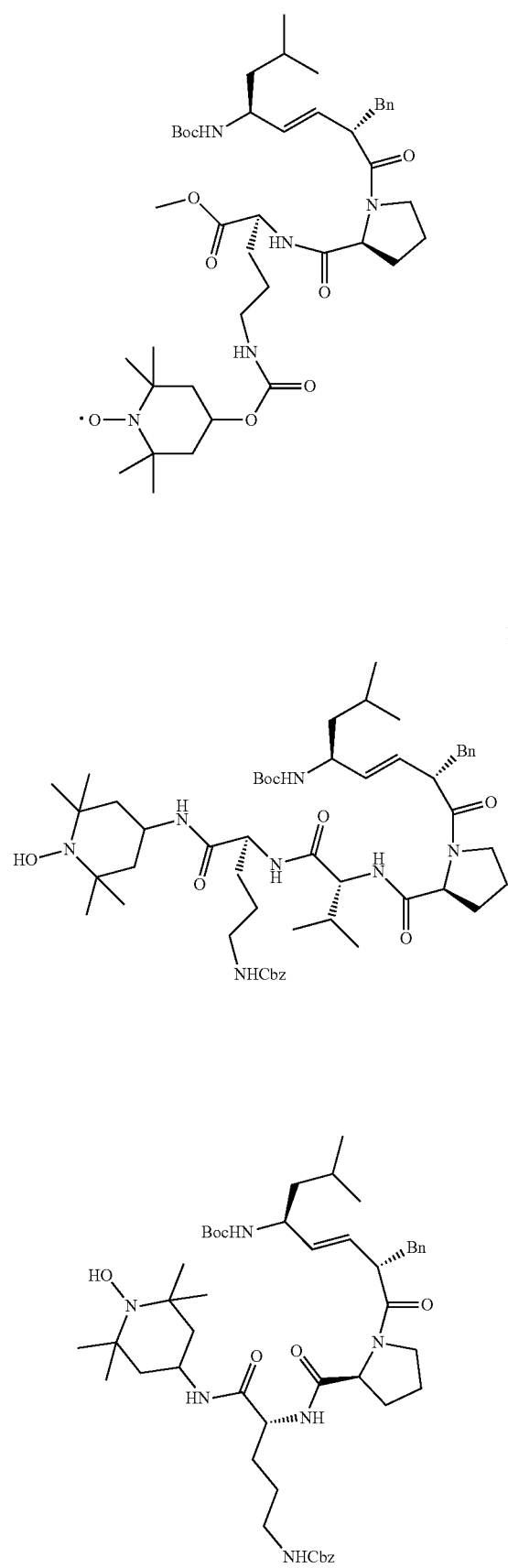

X
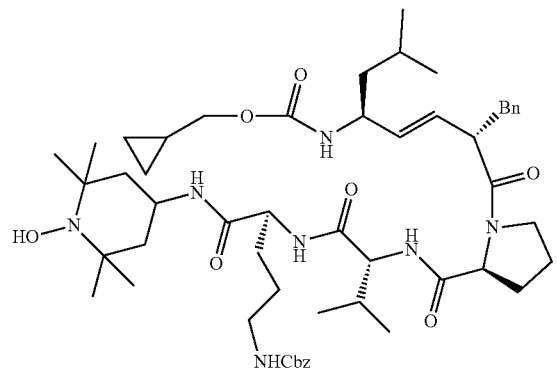
XI
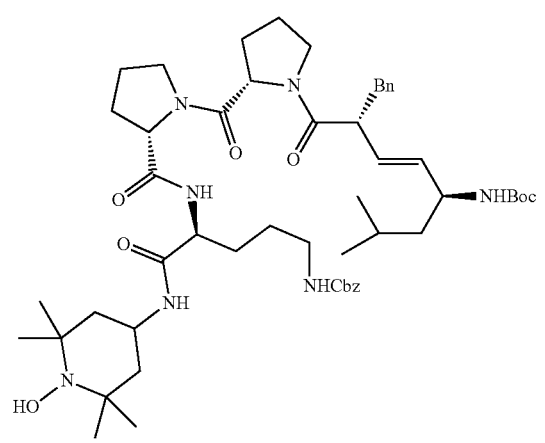
XII
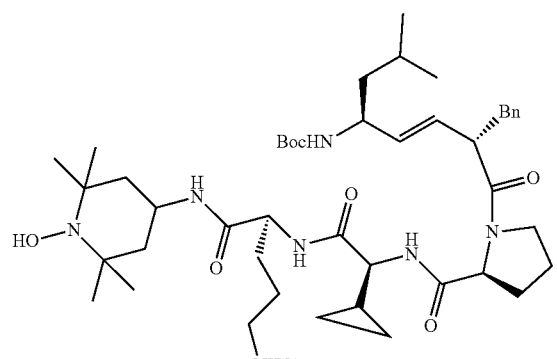
XIII
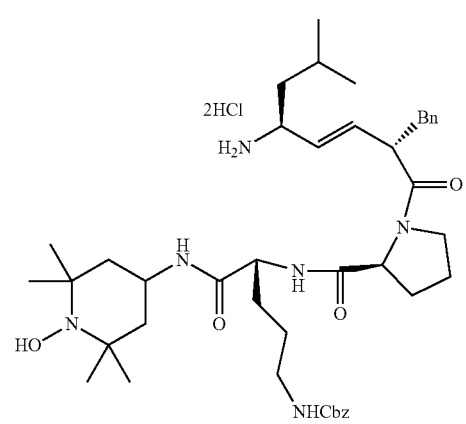
XIV
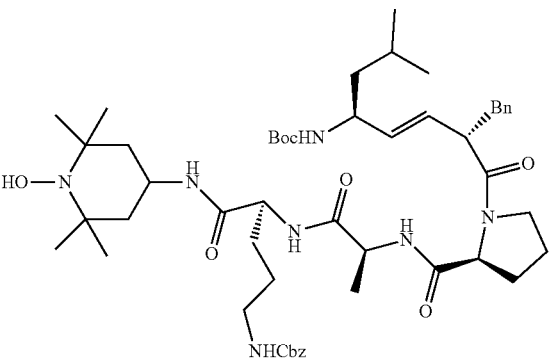
XV
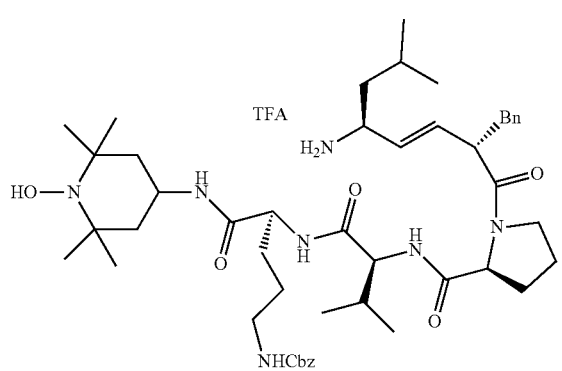
XVI
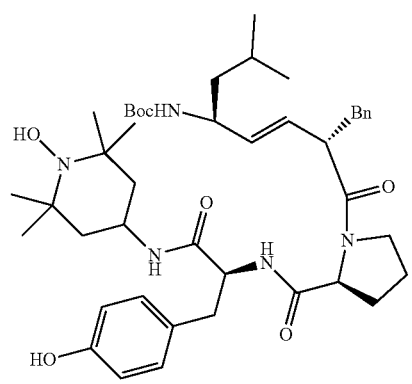
XVII XVIII
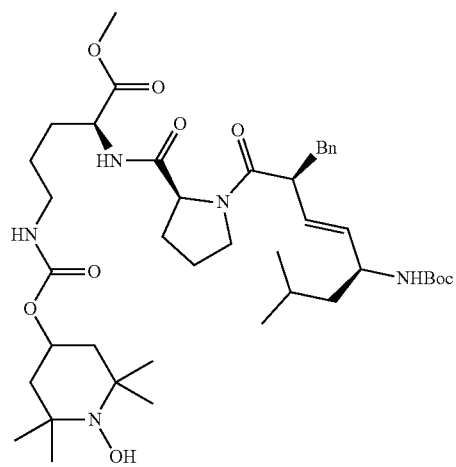
XX
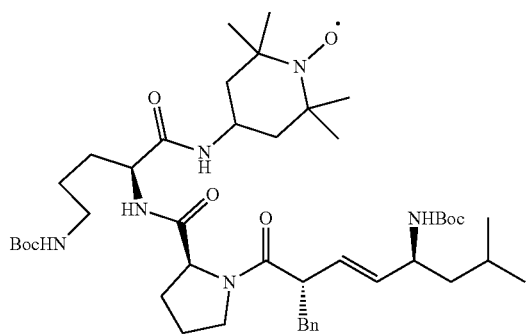
XXI
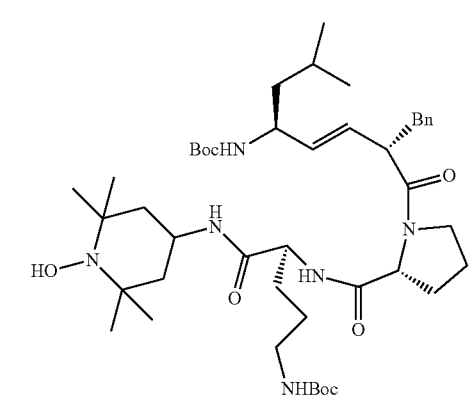
XXII
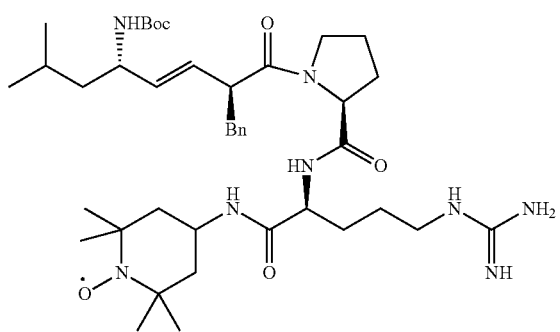
XXIII
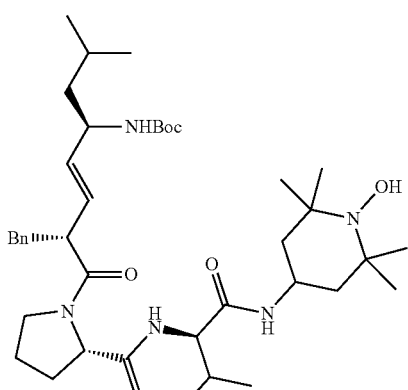
XXIV
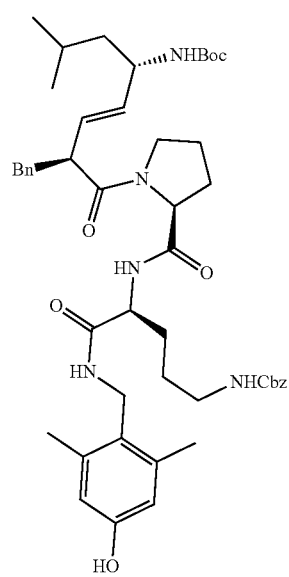
XXV
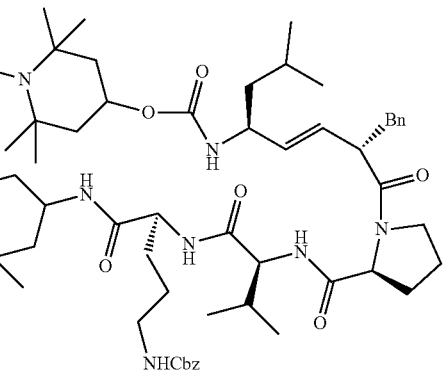

-continued
XXVI
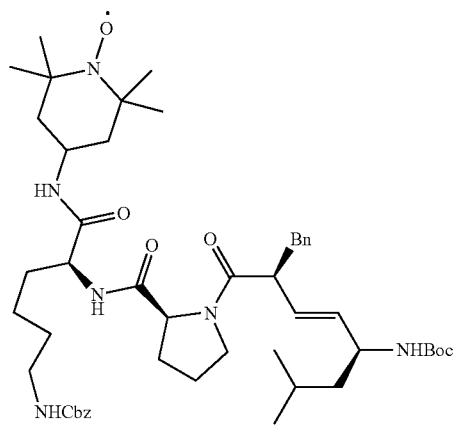
XXIX
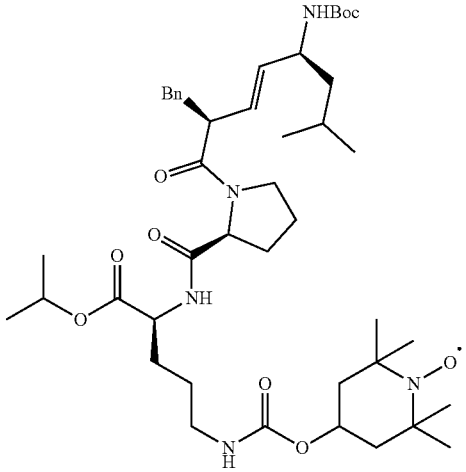
XXVII
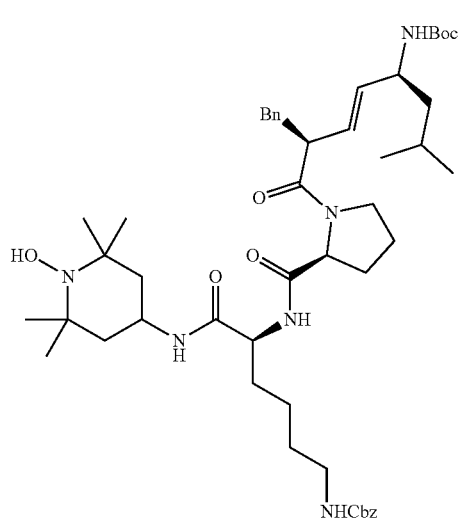
XXX
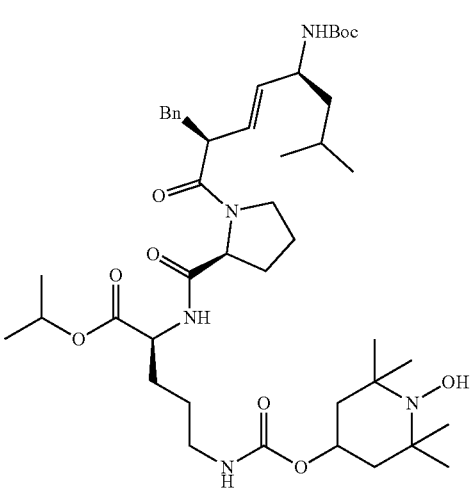
XXVIII
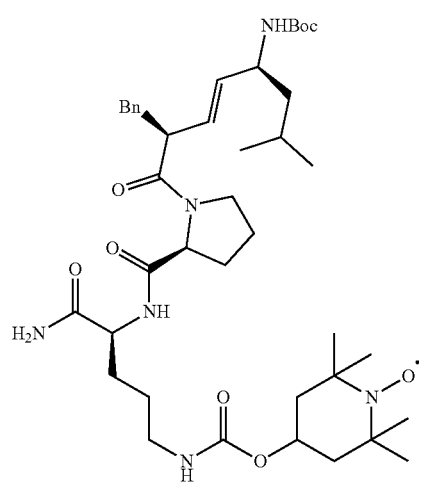
XXXI
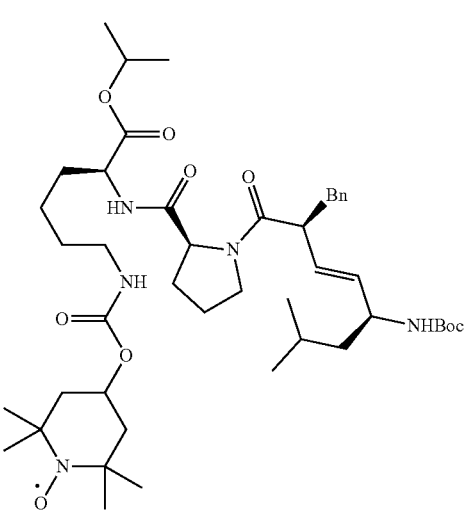

XXXII
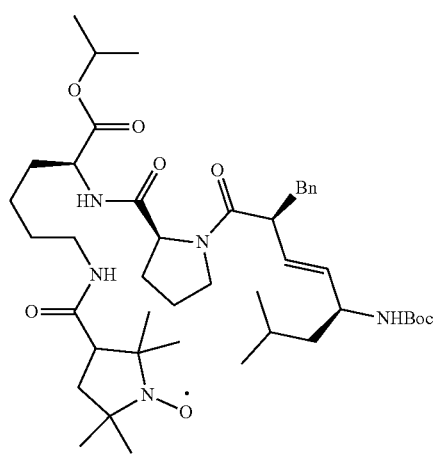
XXXV
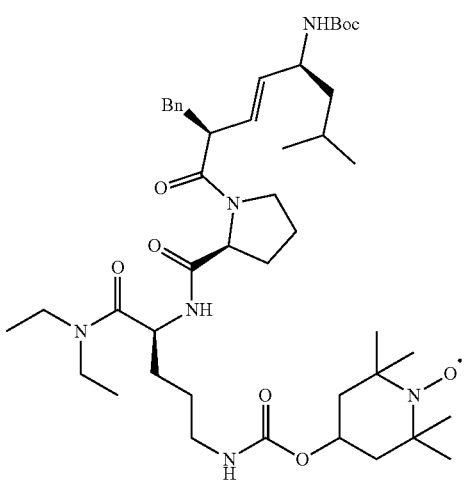
XXXIII
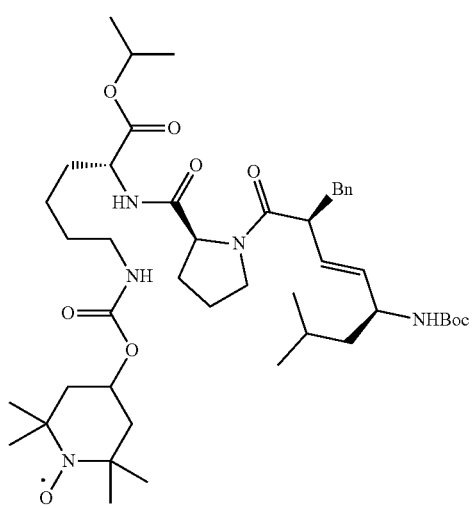
XXXVI
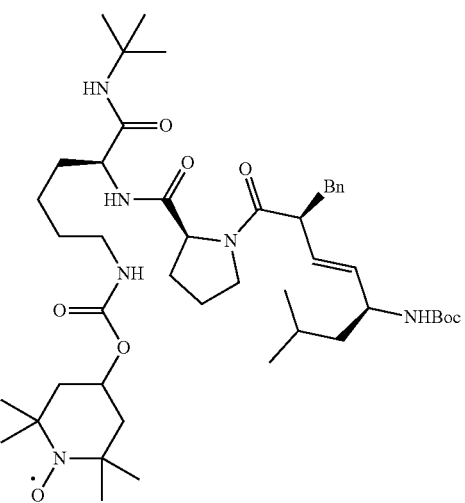
XXXIV
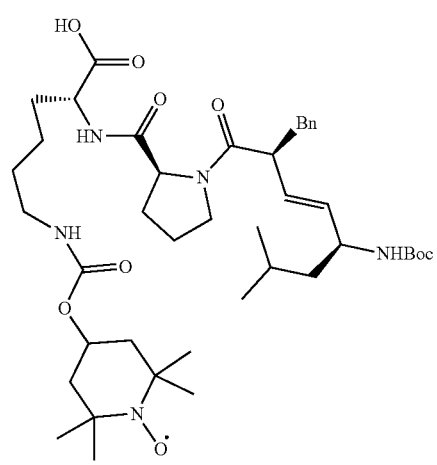
XXXVII
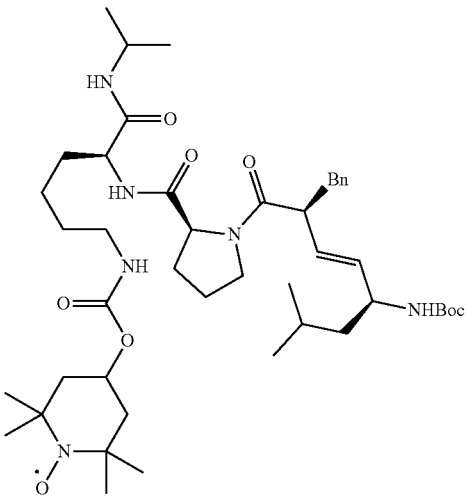

35
-continued
XXXVIII
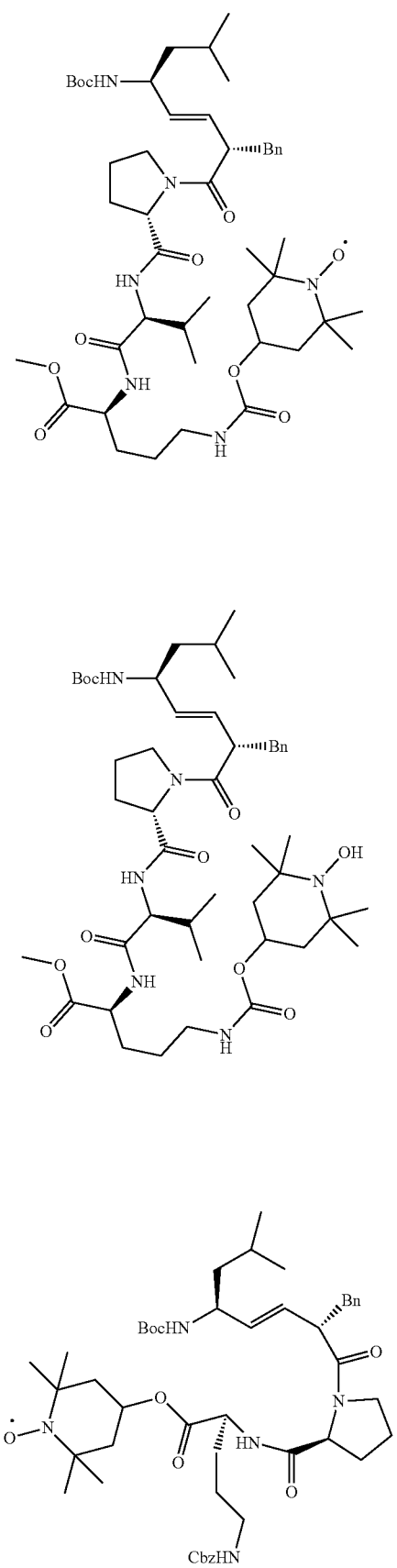
XXXIX
XXXX
36
-continued
XXXXI
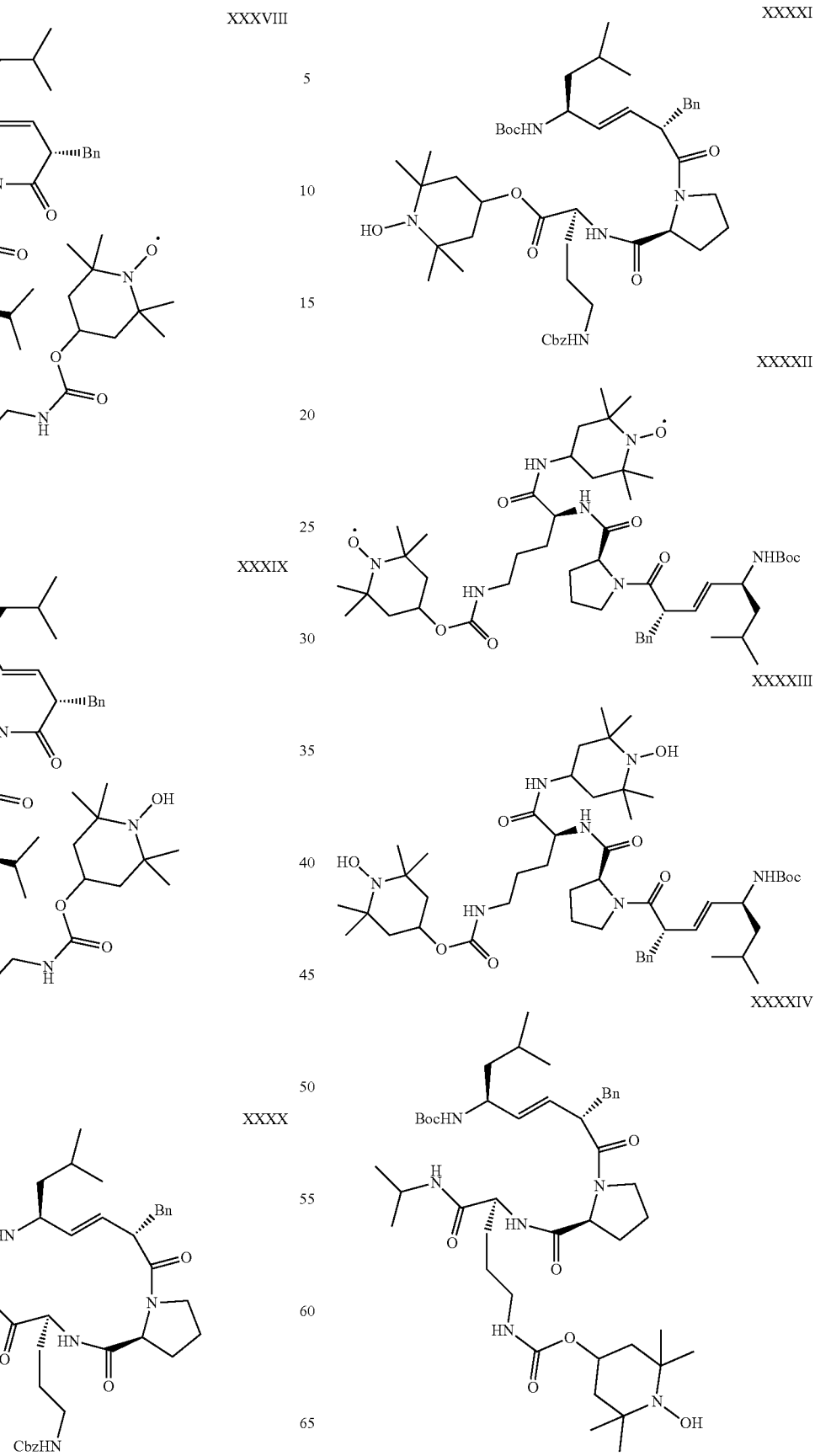
XXXXII
XXXXIII
XXXXIV

XXXXV

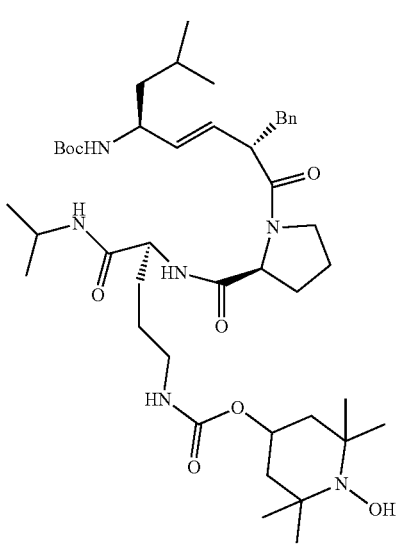

XXXXVI

XXXXVII

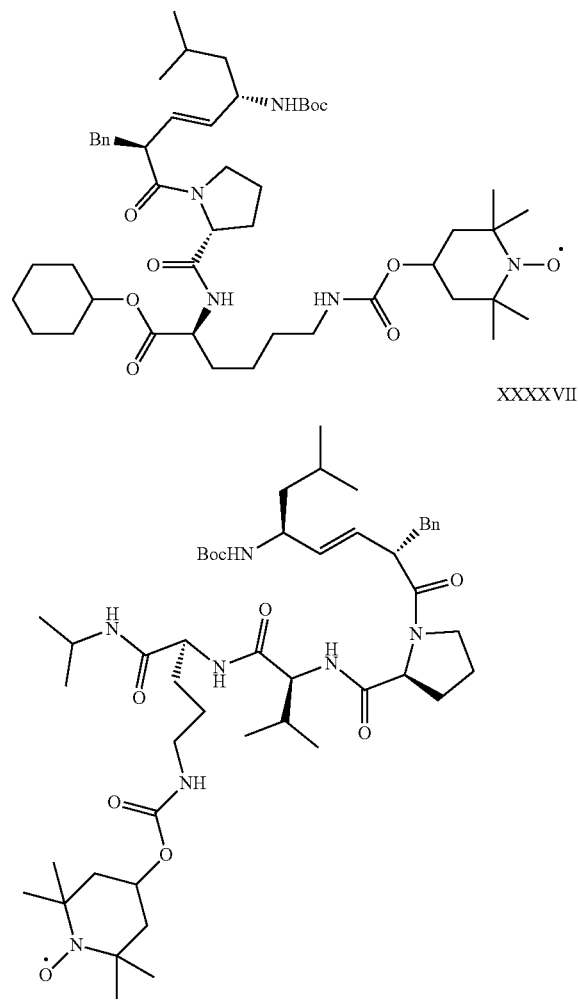

and pharmaceutically acceptable salts thereof.

An aspect of the present invention concerns compounds disclosed herein.

An aspect of the present invention concerns compounds which are or can be modulators of ferroptosis.

An aspect of the present invention concerns the use of compounds disclosed herein for the preparation of a medicament used in the treatment, prevention, inhibition or elimination of an oxidative stress related disorder or disease in a patient.

An aspect of the present invention concerns the use of compounds disclosed herein as a modulator of ferroptosis for the preparation of a medicament used in the treatment, prevention, inhibition or elimination of a disorder or disease or medical condition in a patient by modulating ferroptosis in said patient.

The present invention also describes one or more methods of synthesizing the compounds of the present invention.

The invention also describes one or more uses of the compounds of the present invention.

The invention also describes one or more uses of the compounds of the present invention with an adjunctive agent.

The present invention also describes one or more methods of preparing various pharmaceutical compositions comprising the compounds of the present invention.

The invention also describes one or more uses of the various pharmaceutical compositions of the present invention for the preparation of a medicament used in the treatment, prevention, inhibition or elimination of an oxidative stress related disorder or disease in a patient or medical condition in a patient by modulating ferroptosis in said patient.

Pharmaceutical Composition of the Compound of the Invention and Preparations and Administration The present invention provides a pharmaceutical composition comprising compounds of the present invention, e.g., example compounds. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a pharmaceutical composition containing compounds of the invention with, optionally, one or more adjunctive therapeutic active agents. The amount of the compound of the pharmaceutical composition disclosed herein refers to an amount which can be effectively detected to modulate ferroptosis in biological samples and in a patient. The active ingredient may be administered to subjects in need of such treatment in dosage that will provide optimal pharmaceutical efficacy, which is not limited to the desired therapeutic effects, on the route of administration, and on the duration of the treatment. The dosage will vary from patient to patient depending upon the nature and severity of disease, the patient's weight, special diet then being followed by a patient, concurrent medication, and other factors which those skilled in the art will recognize.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof provide, directly or indirectly, a compound as otherwise described herein, or a therapeutically effective metabolite or residue thereof.

The pharmaceutical compositions of the invention may be prepared and packaged in bulk form wherein a safe and effective amount of a compound of Formula (I) disclosed herein can be extracted and then given to the patient, such as with powders or syrups. Generally, dosage levels of between 0.0001 to 10 mg/kg of body weight daily are administered to the patient to obtain effective modulation of dysfunctional glutamate transmission. Alternatively, the pharmaceutical compositions of the invention may be prepared and packaged in unit dosage form wherein each physically discrete unit contains a safe and effective amount of a compound of Formula (I) disclosed herein.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient in the combination should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are resources that are available to the skilled artisan that describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared for example at normal ambient temperature and pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and ascorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy, supra*).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a sterile vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a D50 value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of Formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research*, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminum stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered via one or more applications per day to the affected area; over skin areas occlusive dressings may advantageously be used. Continuous or prolonged delivery may be achieved via an adhesive reservoir system.

Uses of the Compounds and Compositions of the Invention

Compounds or pharmaceutical compositions of the invention disclosed herein can be used in an amount which can be effectively detected to modulate ferroptosis in biological samples, or a related disorder or disease in a subject. Such uses may include in the manufacture of a medicament for treating, preventing, ameliorating or mitigating a disorder or disease in a subject, as well as other medicaments for modulating ferroptosis, and the compounds of this invention have superior pharmacokinetic and pharmacodynamic properties, fewer toxic side-effect.

Specifically, the amount of the compound of compositions of the present invention may be shown to effectively and detectably modulate ferroptosis in biological samples, or a related disorder or disease in a subject. The compounds or pharmaceutical compositions of the invention may be used for preventing, treating or alleviating diseases relating to ferroptosis in patients.

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal and is typically by injection or infusion. Parenteral administration includes intravenous, intramuscular, and subcutaneous injection or infusion. Topical administration includes application to the skin as well as intraocular, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasal.

In one embodiment, the compound of the invention or the pharmaceutical composition thereof may be administered once or according to a dosing regimen wherein multiple doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as its absorption, distribution, and half-lives of metabolism and elimination, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's tolerance to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties can be correlated with in vitro and in vivo tests using advantageously mammals, e.g., mice, rats, dogs, non-human primates, such as monkeys or isolated organs, tissues and preparations thereof. The compounds of the present invention can be applied in vitro in the form of solutions, e.g., preferably aqueous solutions, and in vivo via topically, inhalingly, enterally or parenterally, advantageously intravenously, e.g., as a suspension or in aqueous solution.

In one embodiment, a therapeutically effective dosage of the compound disclosed herein from about 0.1 mg to about 1,000 mg per day. The pharmaceutical compositions should provide a dosage of from about 0.1 mg to about 1,000 mg of the compound. In a special embodiment, pharmaceutical dosage unit forms are prepared to provide from about 1 mg to about 1,000 mg, about 10 mg to about 500 mg, about 20 mg to about 200 mg, about 25 mg to about 100 mg, or about 30 mg to about 60 mg of the active ingredient or a combination of essential ingredients per dosage unit form. In a special embodiment, pharmaceutical dosage unit forms are prepared to provide about 1 mg, 5 mg, 10 mg, 20 mg, 25 mg, 50 mg, 100 mg, 250 mg, 500 mg, 1000 mg of the active ingredient.

Preferred Embodiment of the Invention

General Synthetic Procedures

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (I) above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. For example, the synthesis of non-exemplified compounds according to the invention may be successfully performed by modifications apparent to those skilled in the art, by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed here.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated.

Preparation of Compounds

Compounds of the present invention, including salts, esters, hydrates, or solvates thereof, can be prepared using any known organic synthesis techniques and can be synthesized according to any of numerous possible synthetic routes.

The reactions for preparing compounds of the present invention can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and atmospheric pressure column chromatography using silica gel. HPLC, High performance liquid chromatography; J. coupling constant (in NMR); min, minute(s); h, hour(s); NMR, nuclear magnetic resonance; prep, preparative.

Compounds of the present invention can be synthesized using the methods described below, together with synthetic methods known in the art of synthetic organic chemistry, or variations thereon as appreciated by those skilled in the art. Preferred methods include but are not limited to those methods described below. Specifically, the compounds of the present invention of Formula (I) can be synthesized by following the steps outlined in the exemplary general synthetic schemes listed below, and the abbreviations for the reactants or for the chemical groups of the reactants included in the synthetic schemes are defined in the Examples.

Scheme 1: The following reaction sequence is used to synthesize compounds of structure A.

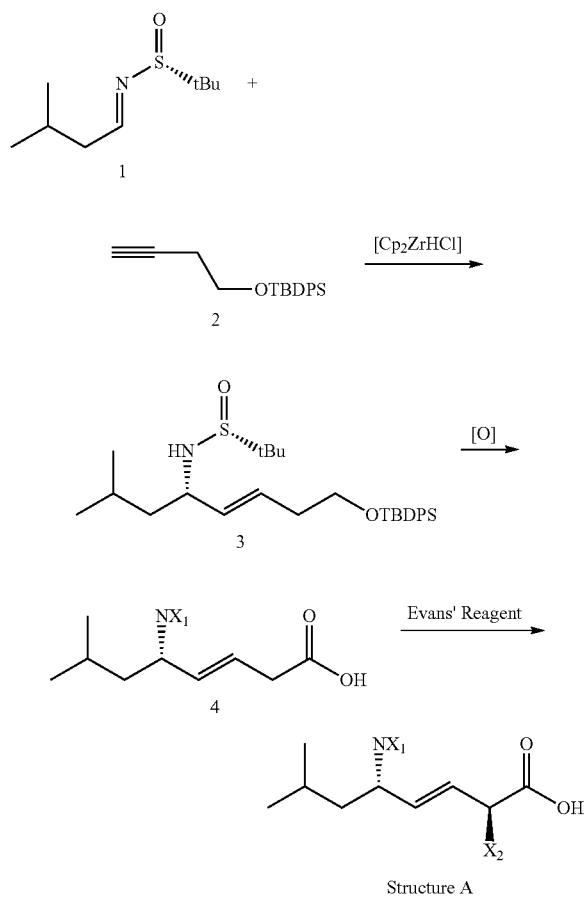

The synthesis towards structure A can be conducted according to the relevant procedures disclosed in references (1, *Journal of the American Chemical Society*, 2005, 127, 12460-12461; 2, *Organic Letter,* 2011, 13, 2318-2321; *Journal of Organic Chemistry,* 2010, 75, 941-944), but is not limited to these disclosed procedures. Sulfonamide derivatives 1 condensed with compound 2 at the presence of $Cp_2ZrHCl$ to give the enantiomer compound 3, which is further removed the protecting group and oxidized to acid compound 4. With the help of Evans chiral auxiliary, another chiral center was added onto the compound 4 to furnish structure A.

Scheme 2: The following reaction sequence is used to synthesize compounds of structure B.

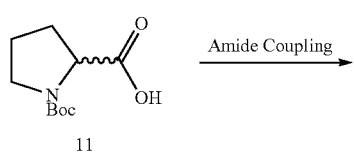

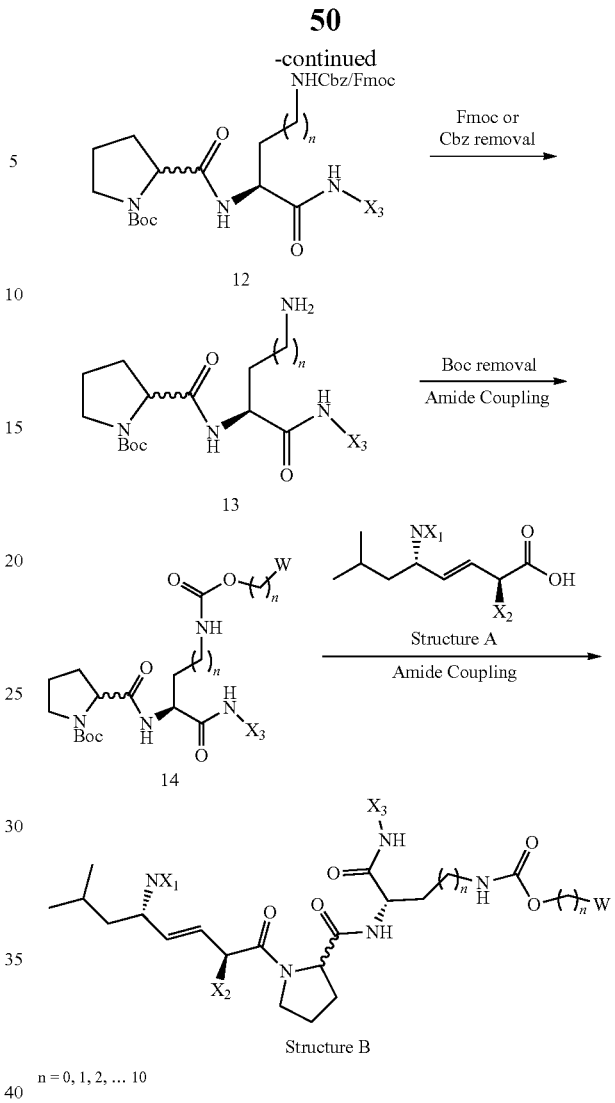

The synthesis towards structure B can be conducted according to the relevant procedures disclosed in references (*Bulletin of the Chemical Society of Japan,* 1993, 66, 3113-3115; U.S. Pat. No. 7,528,174B2), but is not limited to these disclosed procedures.

Scheme 3: The following reaction sequence is used to synthesize compounds of structure C.

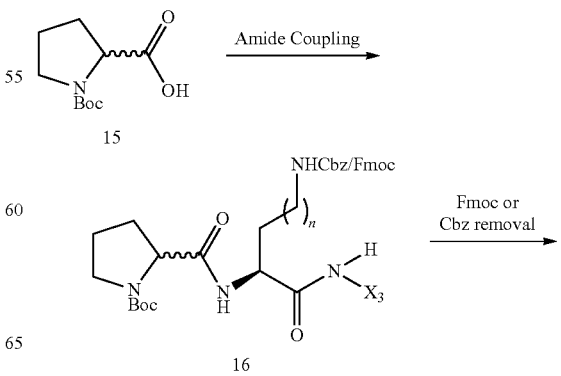

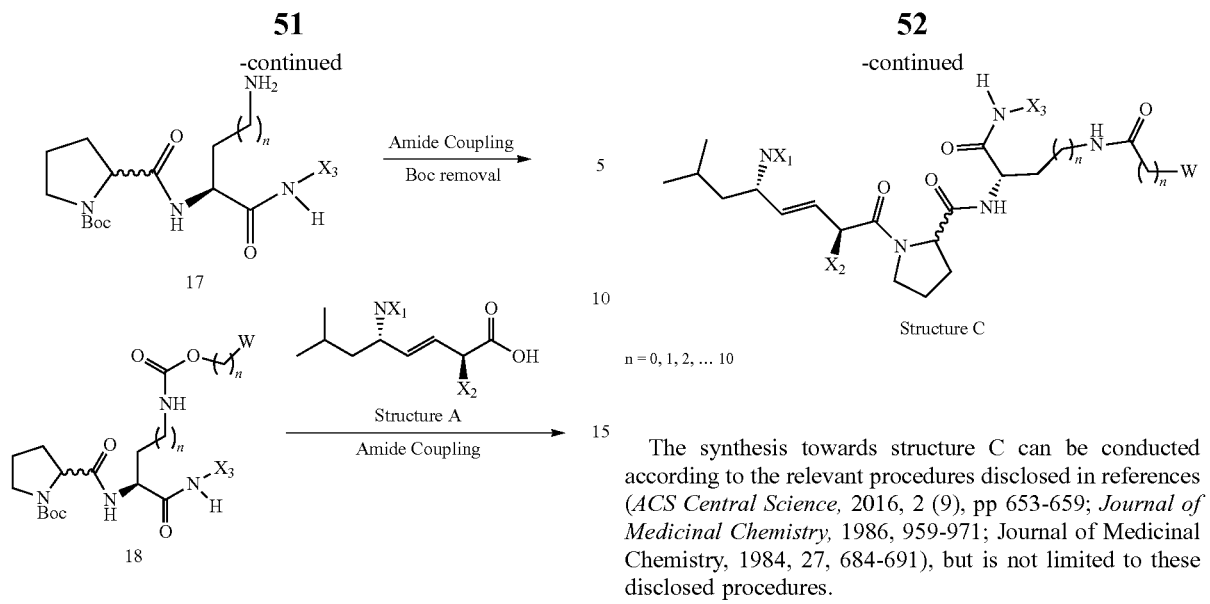
n = 0, 1, 2, ... 10
The synthesis towards structure C can be conducted according to the relevant procedures disclosed in references (*ACS Central Science*, 2016, 2 (9), pp 653-659; *Journal of Medicinal Chemistry*, 1986, 959-971; Journal of Medicinal Chemistry, 1984, 27, 684-691), but is not limited to these disclosed procedures.
Scheme 4: The following reaction sequence is used to synthesize compounds of structure D.
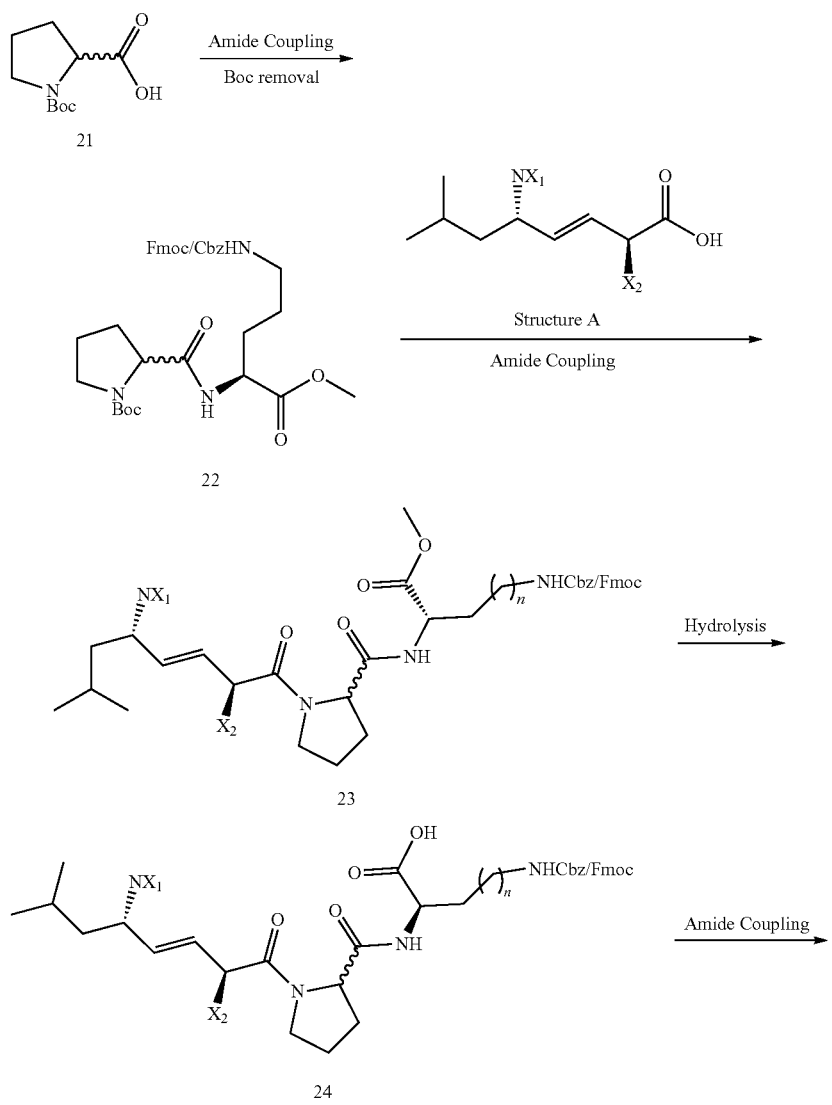

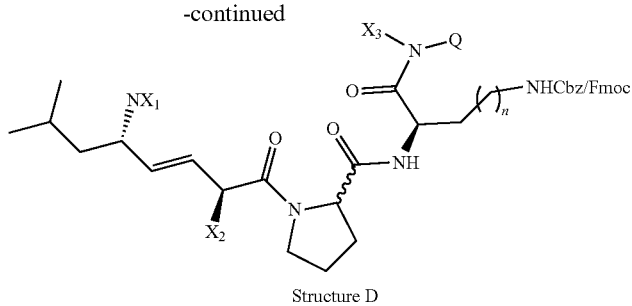

Structure D n = 0, 1, 2, ... 10

The synthesis towards structure D can be conducted according to the relevant procedures disclosed in references (US2007161573A1; US2009042808A1; *Journal of Medicinal Chemistry,* 1984, 27, 1351-1354), but is not limited to these disclosed procedures.

Scheme 5: The following reaction sequence is used to synthesize compounds of structure E.

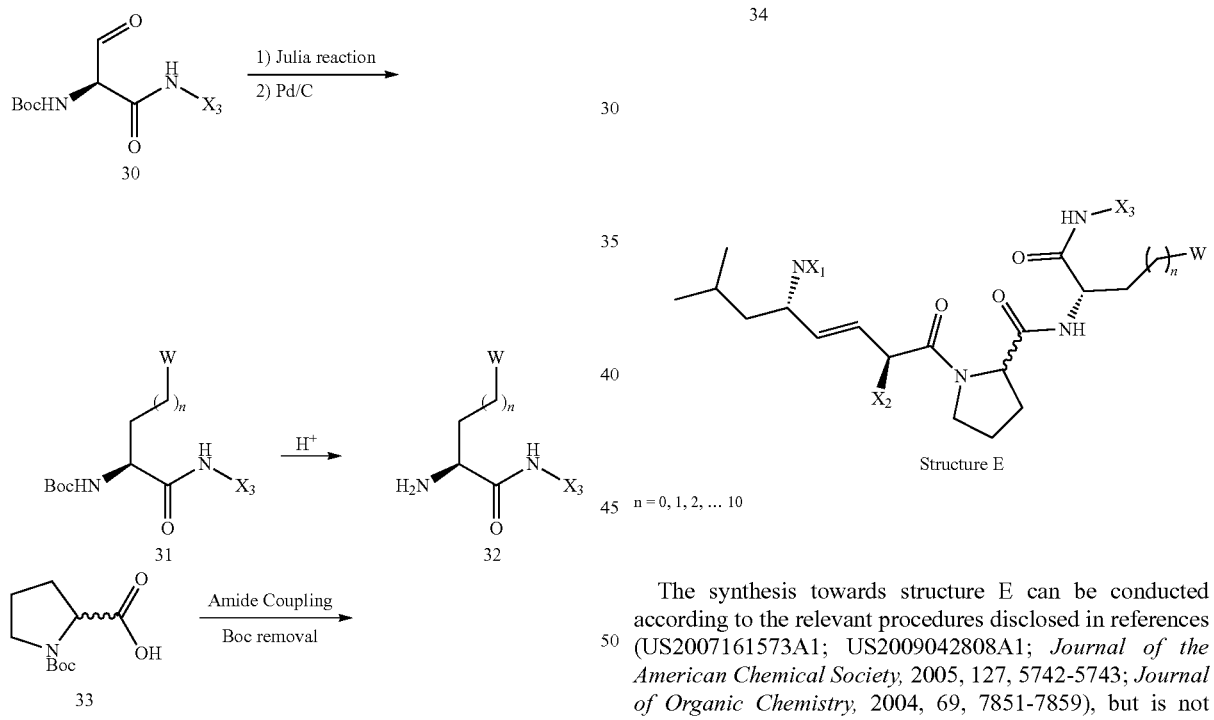

Structure E n = 0, 1, 2, ... 10

The synthesis towards structure E can be conducted according to the relevant procedures disclosed in references (US2007161573A1; US2009042808A1; *Journal of the American Chemical Society,* 2005, 127, 5742-5743; *Journal of Organic Chemistry,* 2004, 69, 7851-7859), but is not limited to these disclosed procedures.

Scheme 6: When PEP (see definition) of A is Valine, the following reaction sequence is used to synthesize compounds of structure F.

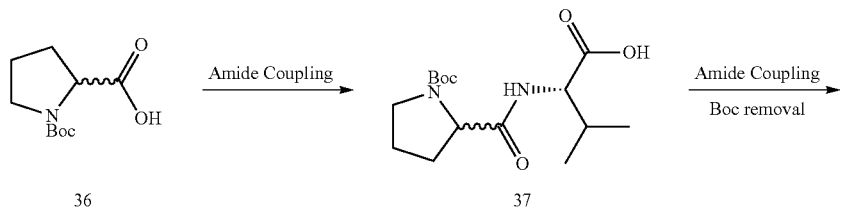

-continued

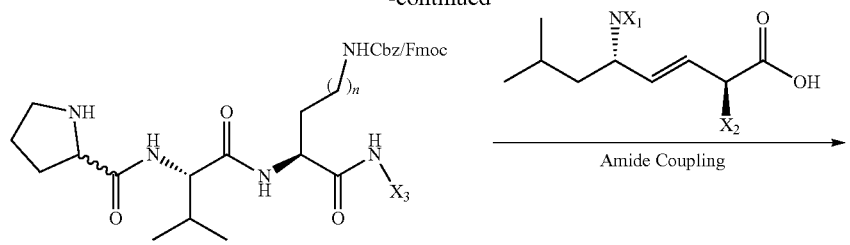

38

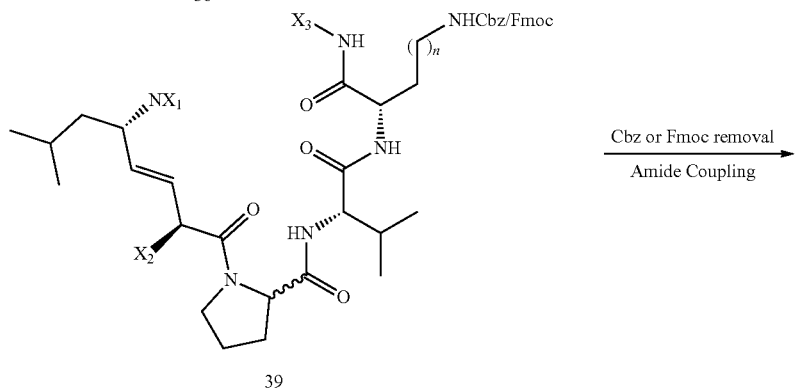

39

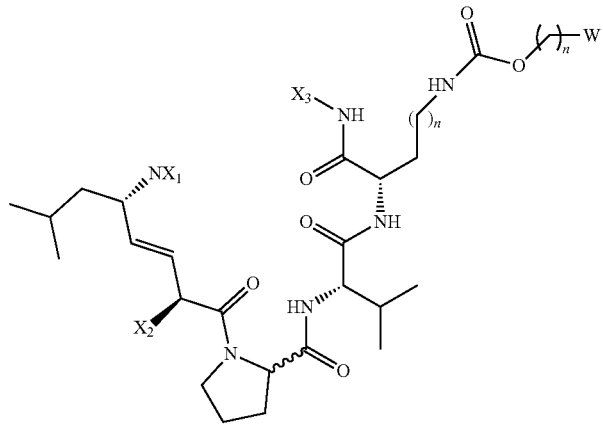

Structure F n = 0, 1, 2, ... 10

The synthesis towards structure F can be conducted according to the relevant procedures disclosed in references (US 2007161573A1; *Journal of the American Chemical Society*, 2005, 127, 5742-5743; *International Journal of Peptide and Protein Research*, 1996; 47, 460-466), but is not limited to these disclosed procedures.

Scheme 7: When PEP of A is Valine, the following reaction sequence is used to synthesize compounds of structure H.

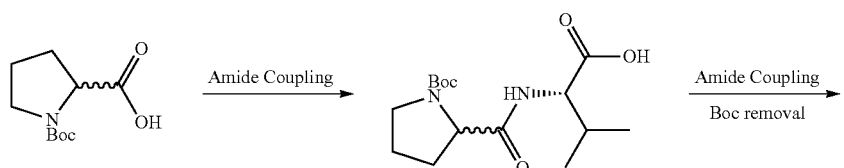

41                    42

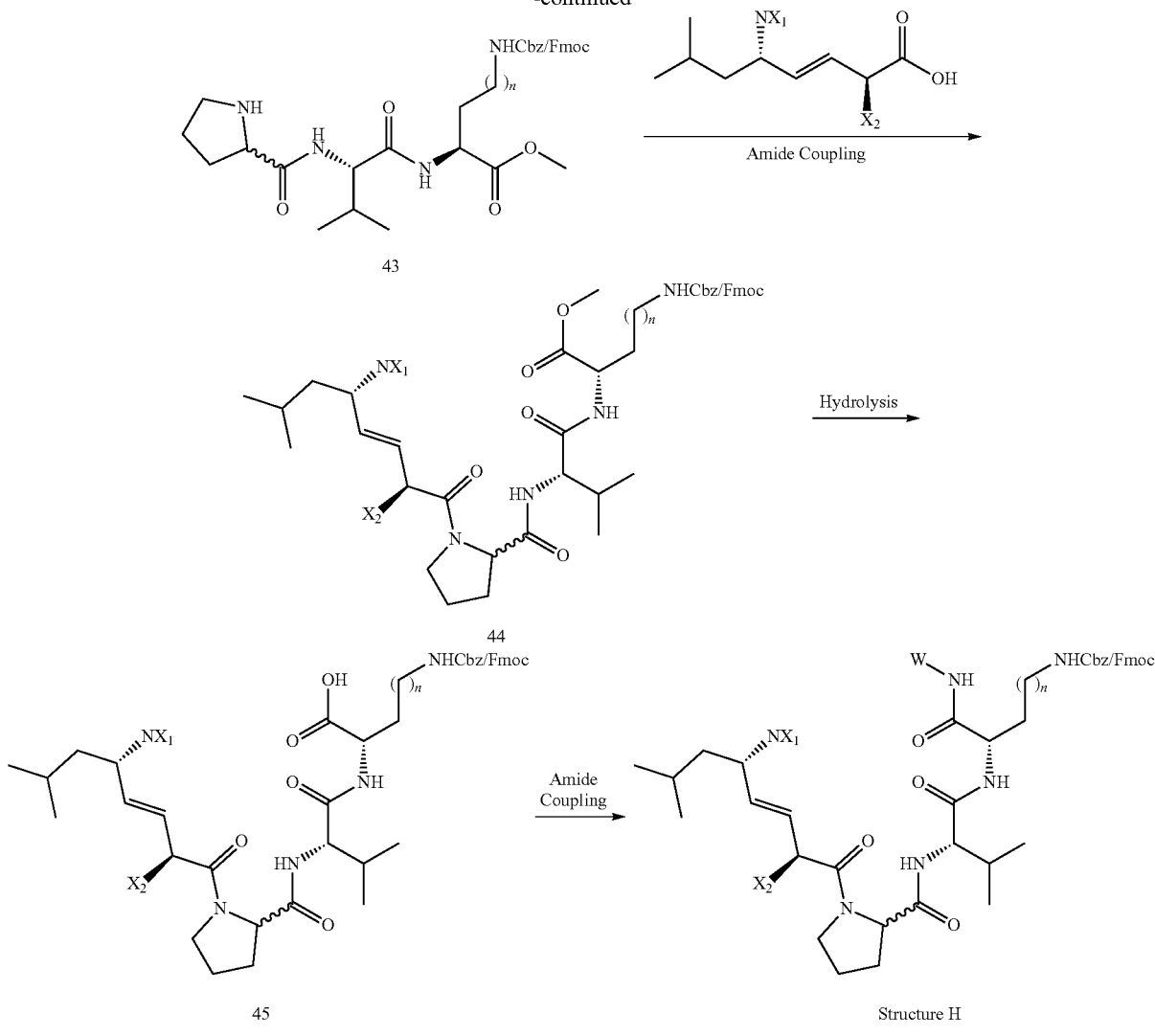

n = 0, 1, 2, ... 10

The synthesis towards structure H can be conducted according to the relevant procedures disclosed in references (US2007161573A1; Journal of Pharmacology and Experimental Therapeutics, 2007, 320, 1050-1060), but is not limited to these disclosed procedures.

Preparation and Characterization of Exemplary Compounds

Compounds encompassed in the present disclosure may be prepared via different schemes. Detailed preparation processes of those exemplary compounds via various schemes are described below and the characterization results are listed as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodeca-molybdophosphoric acid in ethanol and subsequent heating. Column chromatography was performed using silica gel (200-400 mesh) from commercial suppliers. $^1$H NMR spectra were recorded on an Agilent 400-MR NMR spectrometer (400.00 MHz for 1H) at room temperature. Solvent signal was used as reference for $^1$H NMR (CDCl$_3$, 7.26 ppm; CD$_3$OD, 3.31 ppm; DMSO-d6, 2.50 ppm; D$_2$O, 4.79 ppm). The following NMR acronyms and abbreviations were used to explain the multiplicities: s=singlet, d=doublet, t=triplet, q=quartet, br. s.=broad singlet, dd=double doublet, td=triple doublet, dt=double triplet, dq=double quartet, m=multiplet.

EXAMPLES

It should be noted that embodiments of the present invention described in detail below are exemplary for explaining the present invention only, and not be construed as limiting the present scope of invention. Examples without a specific technology or condition can be implemented according to technology or condition in the documentation of the art or according to the product instructions. The reagents or instruments without manufacturers are available through conventional purchase. Those having skill in the art will recognize that the starting materials may be varied and additional steps employed to produce compounds encompassed by the present inventions, as demonstrated by the following examples.

Example I

Benzyl N-[(4S)—4-{[(2S)-1-[(2S,3E,5S)-2-Benzyl-5-{[(Tert-Butoxy)Carbonyl]Amino}-7-Methyloct-3-Enoyl]Pyrrolidin-2-Yl]Formamido}-4-[(1-Oxyl-2,2,6,6-Tetramethylpiperidin-4-Yl)Carbamoyl]Butyl] Carbamate (I)

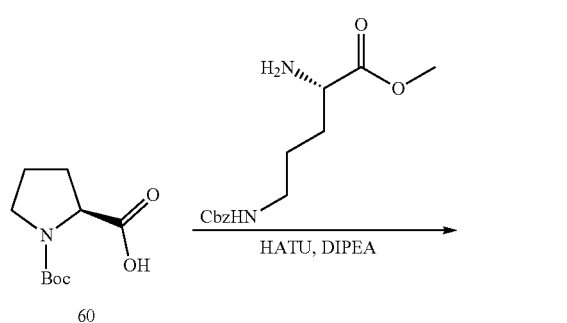

60

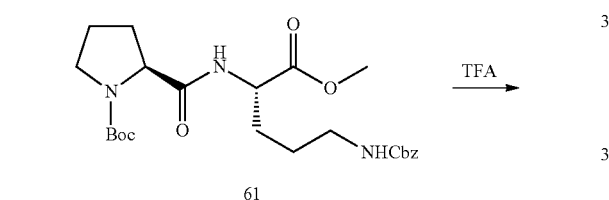

61

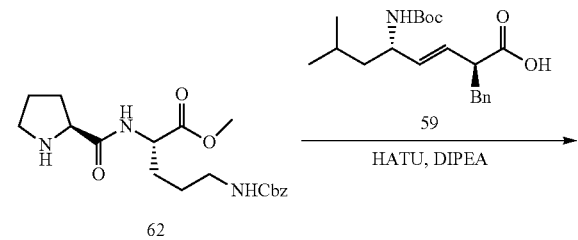

62

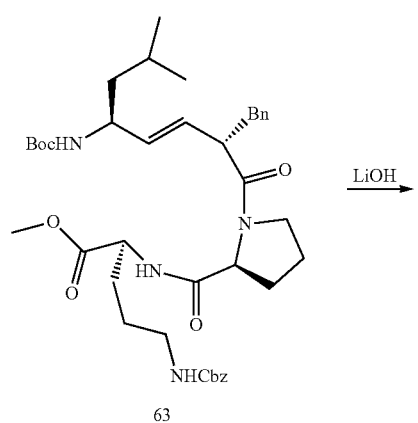

63

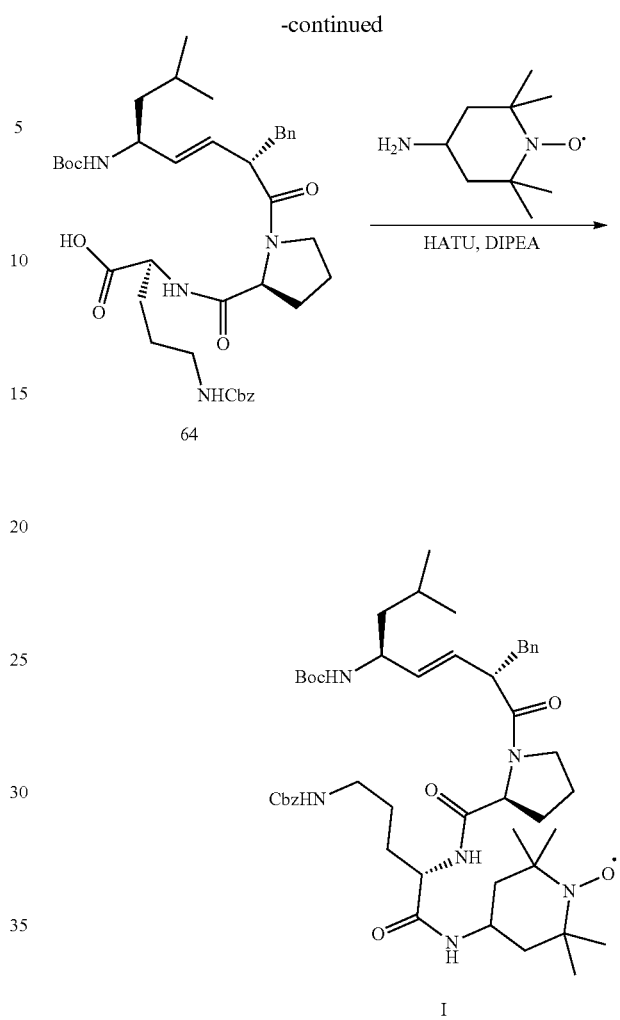

Step 1: Synthesis of (S)-tert-butyl 2-(((S)-5-(((benzyloxy)carbonyl)amino)-1-methoxy-1-oxopentan-2-yl)carbamoyl)pyrrolidine-1-carboxylate (61).

To a solution of compound 60 (1.5 g, 6.97 mmol) and (S)-methyl 2-amino-5-(((benzyloxy)carbonyl)amino)pentanoate (2.6 g, 8.37 mmol) in CH$_2$Cl$_2$ (20 mL) at 0° C. was added DIPEA (2.7 g, 20.91 mmol) and HATU (3.4 mL, 9.06 mmol). The reaction mixture was allowed to warm to 25° C. and stirred for 3 h. The reaction mixture was quenched with saturated NH$_4$Cl solution (20 mL), washed with saturated aqueous brine solution (3×10 mL), dried over MgSO$_4$ and concentrated. The residue was purified by column chromatography on silica gel (petroleum ether/EtOAc=5:1 to 1:1) to give product 61 (1.5 g, 56%) as a white foam. $^1$H NMR: (400 MHz, CDCl$_3$) δ 7.35-7.29 (m, 5H), 5.08 (s, 2H), 4.56 (s, 1H), 4.26 (s, 1H), 3.73 (s, 3H), 3.45 (s, 2H), 3.21-3.20 (d, J=4.0 Hz, 2H), 2.80 (s, 2H), 1.93-1.86 (m, 2H), 1.68-1.63 (m, 2H), 1.53 (m, 2H), 1.44 (m, 9H).

Step 2: Synthesis of (S)-methyl 5-(((benzyloxy)carbonyl)amino)-2-((S)—pyrrolidine-2-carboxamido)pentanoate (62).

To a solution of compound 61 (1.4 g, 2.93 mmol) in CH$_2$Cl$_2$ (10 mL) at 0° C. was added TFA (3.0 mL). The resulting solution was stirred for 10 min at 0° C., and 3 h at 25° C. The solvent was concentrated in vacuum, and CH₂Cl₂ (10 mL) and 5% aqueous Na₂CO₃ solution were added until pH 8-9. The aqueous layer was extracted with CH₂Cl₂ (3×20 mL). The combined organic phase was dried over Na₂SO₄ and concentrated in vacuum to give product 62 (980 mg, 91%) as an oil product.

Step 3: Synthesis of (S)-methyl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (63).

To a solution of compound 62 (250 mg, 0.66 mmol) and compound 59 (200 mg, 0.55 mmol, the procedure was according to the references: 1, Journal of the American Chemical Society, 2005, 127, 12460-12461; 2, Organic Letter, 2011, 13, 2318-2321) in CH₂Cl₂ (50 mL) at 0° C. was added DIPEA (142 mg, 1.10 mmol) and HATU (272 mg, 0.72 mmol). The reaction mixture was allowed to warm to 25° C. and stirred for 3 h. The reaction mixture was quenched with saturated aqueous NH₄Cl solution (20 mL), washed with saturated aqueous brine solution (3×10 mL), dried over MgSO₄ and concentrated to give crude product 63 (426 mg, 100%, crude) as a white foam which was used for the next step without further purification. MS (ESI): [M+H⁺]= 721.9.

Step 4: Synthesis of (S)-2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoic acid (64)

A solution of compound 63 (426 mg, 0.55 mmol) in THF/MeOH (4.0/1.0 mL) was treated with LiOH.H₂O (46 mg, 1.10 mmol). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over Na₂SO₄, and concentrated in vacuo to afford product 64 (395 mg, 100%), which was carried on for next step without purification. MS (ESI): [M+H⁺]=707.9.

Step 4: Synthesis of benzyl N-[(4S)—4-{[(2S-1-[(2S,3E,5S)-2-benzyl-5-{[(tert-butoxy)carbonyl]amino}-7-methyl-oct-3-enoyl]pyrrolidin-2-yl]formamido}-4-[(1-oxyl-2,2,6,6-tetramethylpiperidin-4-yl)carbamoyl]butyl]carbamate (65).

A solution of the crude compound 64 (395 mg, 0.55 mmol) in dry CH₂Cl₂ (5 mL) at 0° C. was treated with HATU (274 mg, 0.72 mmol), DIPEA (142 mg, 1.1 mmol), and 4-AT (113 mg, 0.66 mmol). The reaction mixture was stirred at 25° C. for 3 h, then quenched with saturated NH₄Cl solution (20 mL). The aqueous phase was separated and extracted with CH₂Cl₂ (3×20 mL), and the combined organic layers were dried over MgSO₄ and concentrated. The crude material was purified by pre-HPLC (Venusil XBP C18 (5 μm, 30×250 mm), 0.1% HCl in eluant) to give product I (110 mg, 24%) as an orange solid. MS (ESI): [M+H⁺]=860.7.

Example II tert-Butyl ((4S,7S,E)-7-benzyl-8-((S)-2-(((R)-1-((1-oxyl-2,2,6,6-tetramethylpiperidin-4-yl)amino)-3-methyl-1-oxobutan-2-yl)carbamoyl)pyrrolidin-1-yl)-2-methyl-8-oxooct-5-en-4-yl)carbamate (II)

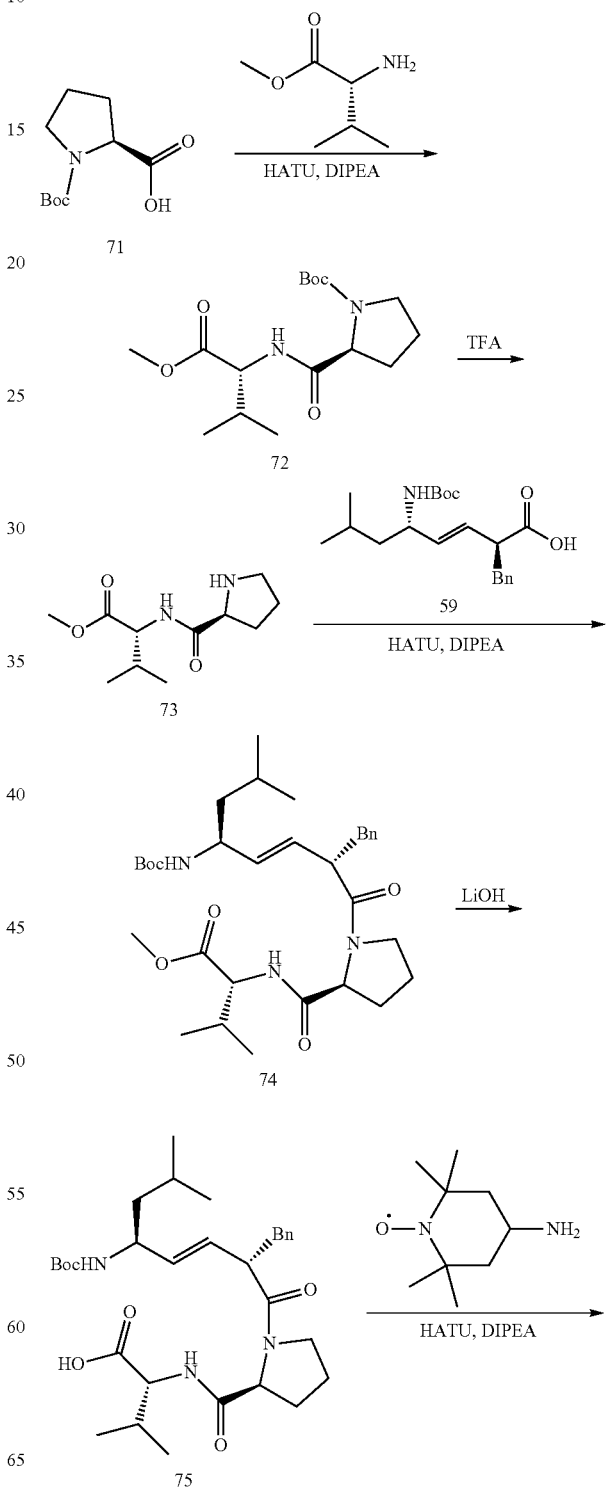

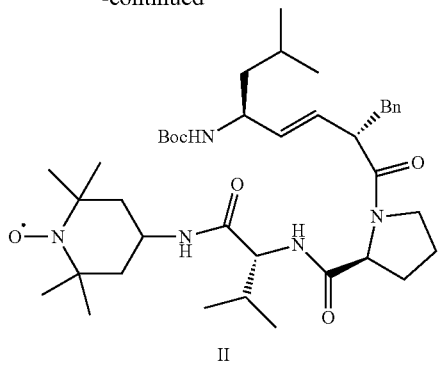

II

Step 1: Synthesis of (S)-tert-butyl 2-(((R)-1-methoxy-3-methyl-1-oxobutan-2-yl)carbamoyl)pyrrolidine-1-carboxylate (72).

To a solution of compound 71 (4.0 g, 18.58 mmol) and (R)-methyl 2-amino-3-methylbutanoate (3.8 g, 22.29 mmol) in CH$_2$Cl$_2$ (40 mL) at 0° C. was added DIPEA (2.8 g, 13 mmol) and HATU (5.6 mL, 33 mmol). The reaction mixture was allowed to warm to 25° C. and stirred for 3 h. The reaction mixture was quenched with saturated aqueous NH$_4$Cl solution (20 mL), washed with saturated aqueous brine solution (3×10 mL), dried over Na$_2$SO$_4$ and concentrated to give product 72 (5.6 g, 92%) as a white foam solid. $^1$H NMR: (400 MHz, CDCl$_3$) δ 4.53 (s, 1H), 4.33 (s, 1H), 3.71 (s, 3H), 3.48 (s, 2H), 2.14-2.20 (m, 3H), 1.89-1.86 (t, J=4.0 Hz, 2H), 1.47 (s, 9H), 0.96-0.94 (d, J=8.0 Hz, 3H), 0.88-0.89 (d, J=4.0 Hz, 3H).

Step 2: Synthesis of (R)-methyl 3-methyl-2-((S)-pyrrolidine-2-carboxamido)butanoate (73).

To a solution of compound 72 (120 mg, 0.37 mmol) in CH$_2$Cl$_2$ (5 mL) at 0° C. was added TFA (1.0 mL). The resulting solution was stirred 10 min at 0° C., and 3 h at 25° C. The solvent was concentrated, and CH$_2$Cl$_2$ (5 mL) and 5% Na$_2$CO$_3$ solution were added until pH 8-9. The layers were separated, and the aqueous layer was extracted with CH$_2$Cl$_2$ (10 mL). The combined organic layers were dried over Na$_2$SO$_4$ and concentrated to give product 73 (72 mg, 86%) as an oil.

Step 3: Synthesis of (R)-methyl 2-((S)-1-((2S,5S,E)-2-benzyl-5-((tert-butoxycarbonyl)amino)-7-methyloct-3-enoyl)pyrrolidine-2-carboxamido)-3-methylbutanoate (74).

To a solution of compound 73 (85 mg, 0.37 mmol) and compound 9 (110 mg, 0.30 mmol) in CH$_2$Cl$_2$ (5 mL) at 0° C. was added DIPEA (80 mg, 0.60 mmol) and HATU (148 mg, 0.39 mmol). The reaction mixture was allowed to warm to 25° C. and stirred for 3 h. The reaction mixture was quenched with saturated NH$_4$Cl solution (20 mL), washed with saturated aqueous brine solution (3×20 mL), dried over MgSO$_4$ and concentrated to give crude product 74 (65 mg, 38%) as a white foam which was used to next step without further purification. MS (ESI): [M+H$^+$]=572.3.

Step 4: Synthesis of (R)-2-((S)-1-((2S, 5S, E)-2-benzyl-5-((tert-butoxycarbonyl)amino)-7-methyloct-3-enoyl)pyrrolidine-2-carboxamido)-3-methylbutanoic acid (75).

A solution of compound 74 (60 mg, 0.11 mmol) in THF/MeOH=4/1 (2/0.5 mL) was treated with LiOH.H$_2$O (6 mg, 0.14 mmol). The reaction mixture was stirred at 25° C. for 2 h, then the solvent was removed under vacuum and the resulting mixture treated with EtOAc (10 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over Na$_2$SO$_4$, and concentrated to afford product 75 (51.0 mg, 84%), which was carried on crude to the coupling reaction.

Step 5: Synthesis of tert-butyl ((4S,7S,E)-7-benzyl-8-((S)-2-(((R)-1-((1-oxyl-2,2,6,6-tetramethylpiperidin-4-yl)amino)-3-methyl-1-oxobutan-2-yl)carbamoyl)pyrrolidin-1-yl)-2-methyl-8-oxooct-5-en-4-yl)carbamate (II).

A solution of the crude compound 75 (50 mg, 0.09 mmol) in dry CH$_2$Cl$_2$ (5 mL) at 0° C. was treated with HATU (45 mg, 0.12 mmol), DIPEA (35.0 mg, 0.27 mmol), and 4-amino-TEMPO (30 mg, 0.18 mmol). The reaction mixture was stirred at 25° C. for 3 h, then quenched with saturated aqueous NH$_4$Cl solution (20 mL). The aqueous phase was separated and extracted with CH$_2$Cl$_2$ (10 mL), and the combined organic layers were dried over MgSO$_4$ and concentrated. The crude material was purified by column chromatography on silica gel (petroleum ether/EtOAc=5:1 to 1:1) to give product II (38 mg, 84%) as an orange solid. MS (ESI): [M+H$^+$]=711.5.

Example III

Methyl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-5-({[(1-oxyl-2,2,6,6-tetramethylpiperidin-4-yl)oxy]carbonyl}amino) pentanoate (III)

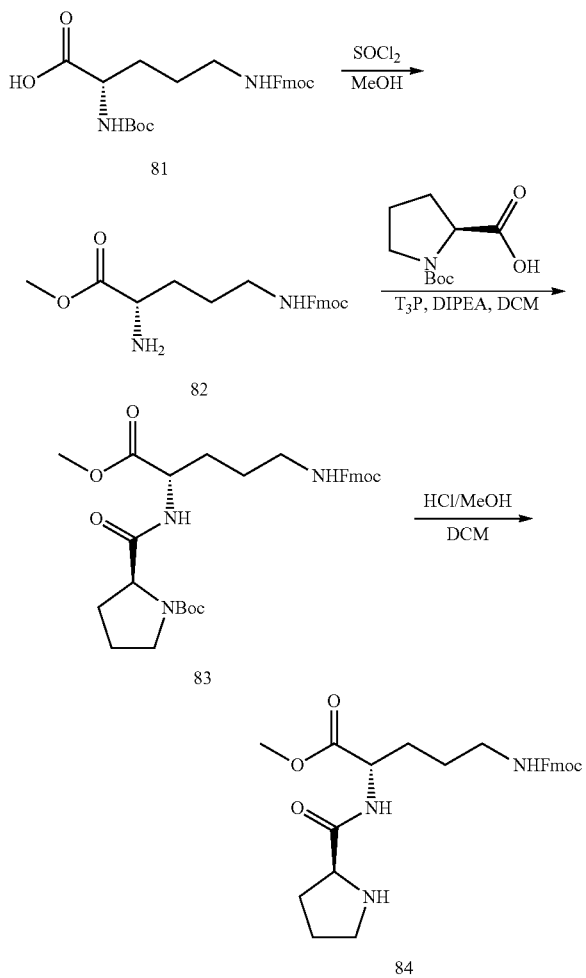

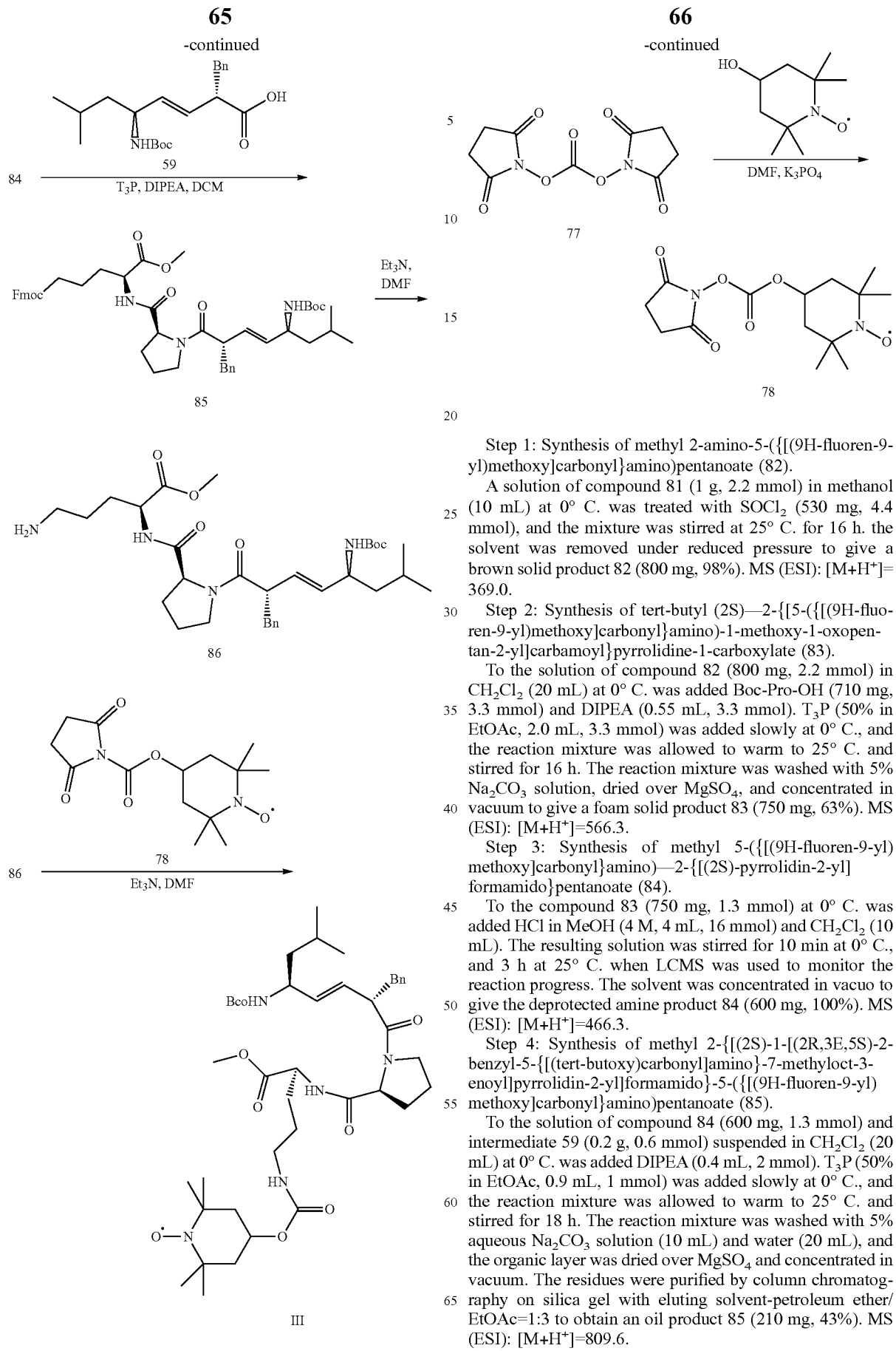

Step 1: Synthesis of methyl 2-amino-5-({[(9H-fluoren-9-yl)methoxy]carbonyl}amino)pentanoate (82).

A solution of compound 81 (1 g, 2.2 mmol) in methanol (10 mL) at 0° C. was treated with $SOCl_2$ (530 mg, 4.4 mmol), and the mixture was stirred at 25° C. for 16 h. the solvent was removed under reduced pressure to give a brown solid product 82 (800 mg, 98%). MS (ESI): [M+H$^+$]= 369.0.

Step 2: Synthesis of tert-butyl (2S)—2-{[5-({[(9H-fluoren-9-yl)methoxy]carbonyl}amino)-1-methoxy-1-oxopentan-2-yl]carbamoyl}pyrrolidine-1-carboxylate (83).

To the solution of compound 82 (800 mg, 2.2 mmol) in $CH_2Cl_2$ (20 mL) at 0° C. was added Boc-Pro-OH (710 mg, 3.3 mmol) and DIPEA (0.55 mL, 3.3 mmol). $T_3P$ (50% in EtOAc, 2.0 mL, 3.3 mmol) was added slowly at 0° C., and the reaction mixture was allowed to warm to 25° C. and stirred for 16 h. The reaction mixture was washed with 5% $Na_2CO_3$ solution, dried over $MgSO_4$, and concentrated in vacuum to give a foam solid product 83 (750 mg, 63%). MS (ESI): [M+H$^+$]=566.3.

Step 3: Synthesis of methyl 5-({[(9H-fluoren-9-yl)methoxy]carbonyl}amino)—2-{[(2S)-pyrrolidin-2-yl]formamido}pentanoate (84).

To the compound 83 (750 mg, 1.3 mmol) at 0° C. was added HCl in MeOH (4 M, 4 mL, 16 mmol) and $CH_2Cl_2$ (10 mL). The resulting solution was stirred for 10 min at 0° C., and 3 h at 25° C. when LCMS was used to monitor the reaction progress. The solvent was concentrated in vacuo to give the deprotected amine product 84 (600 mg, 100%). MS (ESI): [M+H$^+$]=466.3.

Step 4: Synthesis of methyl 2-{[(2S)-1-[(2R,3E,5S)-2-benzyl-5-{[(tert-butoxy)carbonyl]amino}-7-methyloct-3-enoyl]pyrrolidin-2-yl]formamido}-5-({[(9H-fluoren-9-yl)methoxy]carbonyl}amino)pentanoate (85).

To the solution of compound 84 (600 mg, 1.3 mmol) and intermediate 59 (0.2 g, 0.6 mmol) suspended in $CH_2Cl_2$ (20 mL) at 0° C. was added DIPEA (0.4 mL, 2 mmol). $T_3P$ (50% in EtOAc, 0.9 mL, 1 mmol) was added slowly at 0° C., and the reaction mixture was allowed to warm to 25° C. and stirred for 18 h. The reaction mixture was washed with 5% aqueous $Na_2CO_3$ solution (10 mL) and water (20 mL), and the organic layer was dried over $MgSO_4$ and concentrated in vacuum. The residues were purified by column chromatography on silica gel with eluting solvent-petroleum ether/EtOAc=1:3 to obtain an oil product 85 (210 mg, 43%). MS (ESI): [M+H$^+$]=809.6.

Step 5: Synthesis of methyl 5-amino-2-{[(2S)-1-[(2R,3E,5S)-2-benzyl-5-{[(tert-butoxy)carbonyl]amino}-7-methyl-oct-3-enoyl]pyrrolidin-2-yl]formamido}pentanoate (86).

To a solution of compound 85 (210 mg, 0.26 mmol) in 10 mL DMF was added Et₃N (1 mL, 7.5 mmol), the mixture was stirred at 25° C. for 16 h. and the crude product 86 was not purified and used directly for next step. MS (ESI): [M+H⁺]=587.3.

Step 6: Synthesis of methyl (2S)—2-{[(2S)-1-[(2S,3E,5S)-2-benzyl-5-{[(tert-butoxy)carbonyl]amino}-7-methyl-oct-3-enoyl]pyrrolidin-2-yl]formamido}-5-({[(1-oxyl-2,2,6,6-tetramethylpiperidin-4-yl)oxy]carbonyl}amino)pentanoate (87).

A solution of 4-hydroxy-TEMPO (180 mg, 1.04 mmol) in 5 mL of DMF was treated with N,N'-disuccinimidyl carbonate (77) (260 mg, 1.04 mmol) and pyridine (200 μL, 0.2 mmol) and the resulting mixture was heated at 40° C. for 16 hours. The solution was cooled to room temperature and compound 78 was directly used for the next step.

To a solution of 86 (crude from previous step) in 10 mL DMF was added intermediate 78. The mixture was stirred at 25° C. for 16 h, LCMS was used to monitor the reaction progress. The reaction was quenched by water (10 mL) and extracted by EtOAc (2×20 mL), the combined organic phase was washed by water (3×20 mL), saturated aqueous brine solution (3×10 mL) and dried over Na₂SO₄, the solvent was removed under reduce pressure to give a crude residue and purified by prep-HPLC (Venusil XBP C18 (5 μm, 30×250 mm), 0.1% HCl in eluant) give a yellow solid product III (8 mg, 4%, over two steps). MS (ESI): [M+H⁺]=785.6.

Example IV

Benzyl N-[(4S)-4-[(2R)—2-{[(2S)-1-[2S,3E,5S)-2-benzyl-5-{[(tert-butoxy)carbonyl]amino}-7- methyl-oct-3-enoyl]pyrrolidin-2-yl]formamido}-3-methylbutanamido]-4-[(1-hydroxy-2,2,6,6-tetramethylpiperidin-4-yl)carbamoyl]butyl]carbamate (IV)

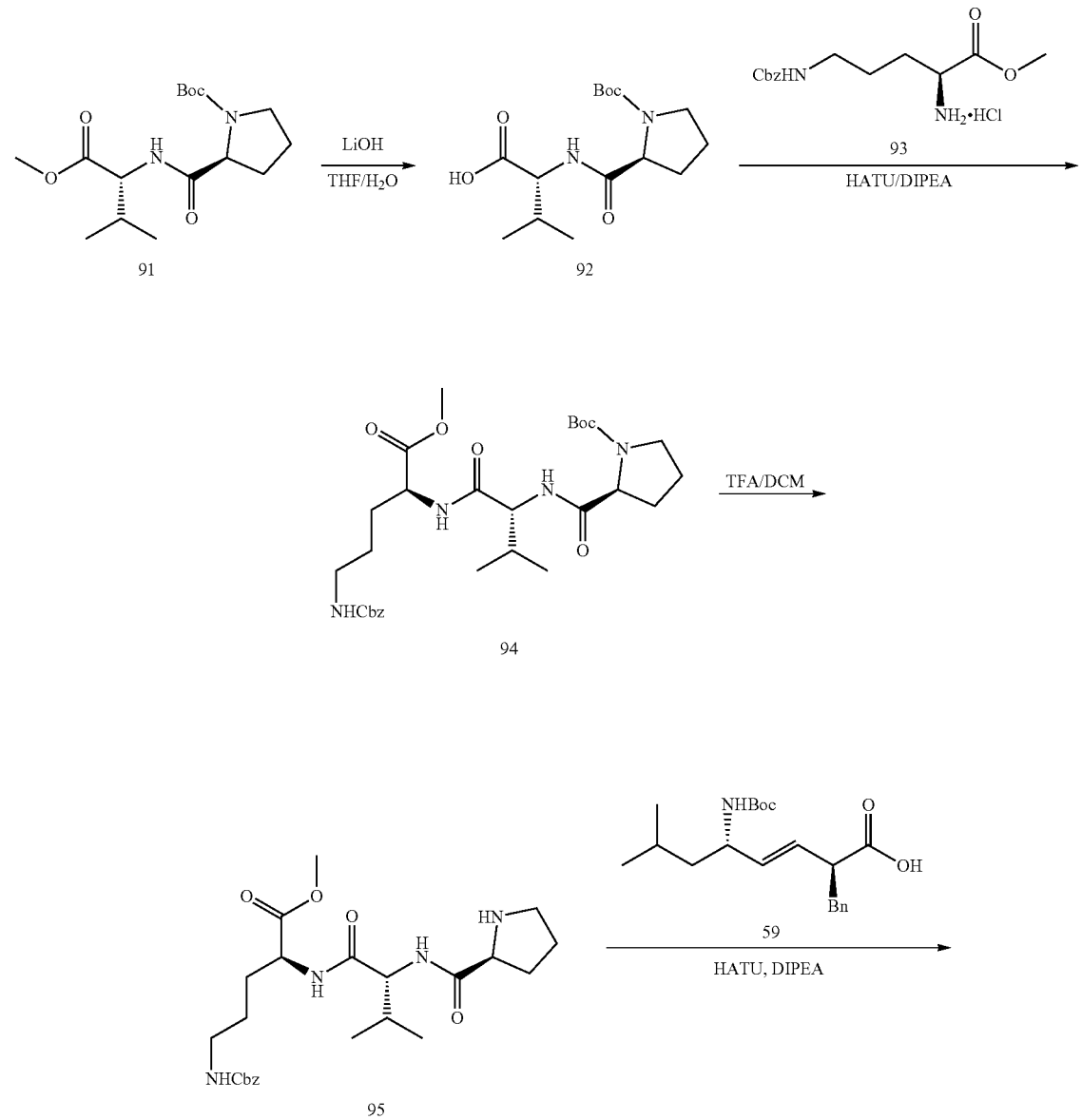

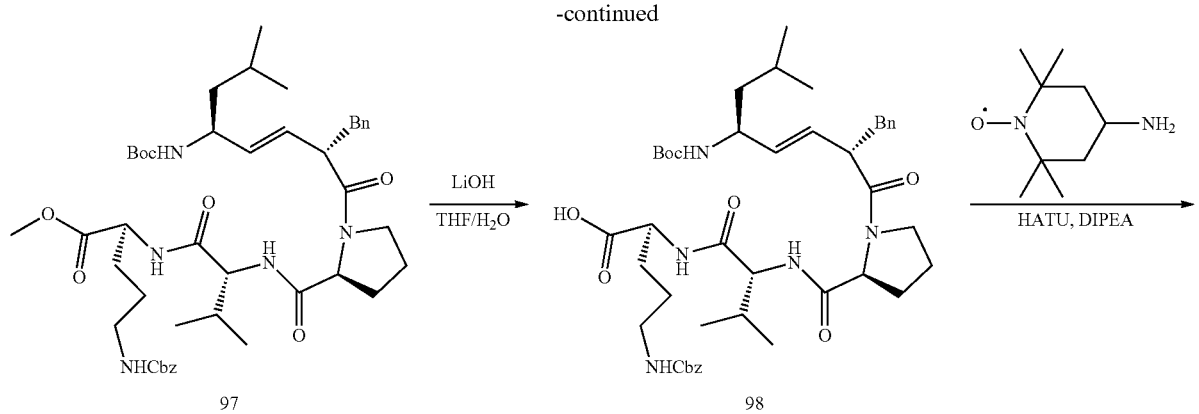

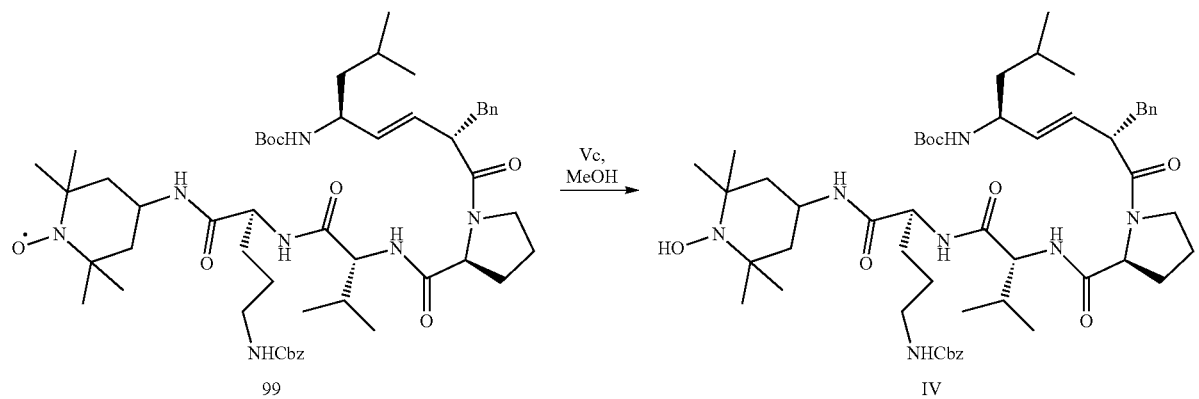

Step 1: Synthesis of (R)-2-((S)-1-(tert-butoxycarbonyl) pyrrolidine-2-carboxamido)-3-methylbutanoic acid (92).

A solution of compound 91 (2.0 g, 6.1 mmol) in THF/MeOH=4:1 (10/2.5 mL) was treated with LiOH.H$_2$O (384 mg, 9.14 mmol). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over Na$_2$SO$_4$, and concentrated to afford product 92 (1.8 g, 95%) as a white foam which was carried on for the next coupling reaction.

Step 2: Synthesis of (S)-tert-butyl 2-(((R)-1-(((S)-5-(((benzyloxy)carbonyl)amino)-1-methoxy-1-oxopentan-2-yl)amino)-3-methyl-1-oxobutan-2-yl)carbamoyl)pyrrolidine-1-carboxylate (94).

To a solution of compound 92 (1.5 g, 4.77 mmol) and compound 93 (1.8 g, 5.73 mmol) in CH$_2$Cl$_2$ (20 mL) at 0° C. was added DIPEA (1.8 g, 14.31 mmol) and HATU (2.4 mL, 6.20 mmol). The reaction mixture was allowed to warm to 25° C. and stirred for 3 h. The reaction mixture was quenched with saturated aqueous NH$_4$Cl solution (20 mL), washed with saturated aqueous brine solution (3×10 mL), dried over MgSO$_4$ and concentrated to give crude 94 (1.2 g, 45%) as a white foam. $^1$H NMR: (400 MHz, CDCl$_3$) δ 7.35-7.30 (m, 5H), 5.08 (s, 3H), 4.55-4.54 (d, J=4.0 Hz, 1H), 4.30-4.26 (t, J=8.0 Hz, 2H), 3.72 (s, 3H), 3.47 (s, 3H), 3.21-3.18 (t, J=4.0 Hz, 2H), 2.80 (s, 1H), 1.89-1.71 (m, 3H), 1.54 (s, 2H), 1.54-1.52 (d, J=8.0 Hz, 2H), 1.45 (s, 9H), 1.27-1.24 (m, 2H), 0.98-0.90 (m, 6H).

Step 3: Synthesis of (S)-methyl 5-(((benzyloxy)carbonyl) amino)-2-((R)-3-methyl-2-((S)-pyrrolidine-2-carboxamido) butanamido)pentanoate (95).

To a solution of compound 94 (1.2 g, 2.08 mmol) in CH$_2$Cl$_2$ (9 mL) at 0° C. was added TFA (3.0 mL). The resulting solution was stirred for 10 min at 0° C., and 3 h at 25° C. The solvent was concentrated in vacuo, and CH$_2$Cl$_2$ (10 mL) and 5% Na$_2$CO$_3$ solution were added until pH 8-9. The aqueous layer was extracted with CH$_2$Cl$_2$ (3×20 mL). The combined organic phase was washed with saturated aqueous brine solution (3×20 mL), dried over Na$_2$SO$_4$ and concentrated in vacuum to give product 95 (970 mg, 98%) as a white foam. MS (ESI): [M+H$^+$]=477.6.

Step 4: Synthesis of (S)-methyl 2-((R)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-(((benzyloxy)carbonyl)amino)pentanoate (97).

To a solution of compound 95 (314 mg, 0.66 mmol) and compound 59 (200 mg, 0.55 mmol) in CH$_2$Cl$_2$ (5 mL) at 0° C. was added DIPEA (142 mg, 1.1 mmol) and HATU (274 mg, 0.72 mmol). The reaction mixture was allowed to warm to 25° C. and stirred for 3 h. The reaction mixture was quenched with saturated NH₄Cl solution (20 mL), washed with saturated aqueous brine solution (3×10 mL), dried over MgSO₄ and concentrated in vacuum. The residues were purified by column chromatography on silica gel with eluting solvent petroleum ether/EtOAc=1:3 to give crude product 97 (106 mg, 50%) as a white foam. MS (ESI): [M+H⁺]= 820.7.

Step 5: Synthesis of (S)-2-((R)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-(((benzyloxy)carbonyl)amino)pentanoic acid (98).

A solution of the compound 97 (465 mg, 0.55 mmol) in THF/MeOH (4.0/1.0 mL) was treated with LiOH·H₂O (462 mg, 1.10 mmol in 0.5 mL water). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over Na₂SO₄, and concentrated in vacuum to afford product 98 (380 mg, 86%), which was carried on for the coupling reaction. MS (ESI): [M+H⁺]=806.6.

Step 6: Synthesis of benzyl N-[(4S)-4-[(2R)—2-{[(2S)-1-[(2S,3E,5S)-2-benzyl-5-{[(tert- butoxy)carbonyl]amino}-7-methyloct-3-enoyl]pyrrolidin-2-yl]formamido}-3-methylbutanamido]-4-[(1-oxyl-2,2,6,6-tetramethylpiperidin-4-yl)carbamoyl]butyl]carbamate (99).

A solution of the crude compound 98 (380 mg, 0.47 mmol) in dry CH₂Cl₂ (5 mL) at 0° C. was treated with HATU (232 mg, 0.61 mmol), DIPEA (121.0 mg, 0.94 mmol), and 4-AT (97 mg, 0.57 mmol). The reaction mixture was stirred at 25° C. for 3 h, then quenched with saturated aqueous NH₄Cl solution (20 mL). The mixture was extracted with CH₂Cl₂ (2×20 mL), and the combined organic layers were washed with saturated aqueous brine solution (2×20 mL), dried over Na₂SO₄ and concentrated in vacuum. The crude material was purified by prep-HPLC (Venusil XBP C18 (5 μm, 30×250 mm), 0.1% HCl in eluant) to give product 99 (83.0 mg, 18%) as an orange solid. MS (ESI): [M+H⁺]=959.7.

Step 7: Synthesis of benzyl N-[(4S)-4-[(2R)—2-{[(2S)-1-[(2S,3E,5S)-2-benzyl-5-{[(tert- butoxy)carbonyl]amino}-7-methyloct-3-enoyl]pyrrolidin-2-yl]formamido}-3-methylbutanamido]-4-[(1-hydroxy-2,2,6,6-tetramethylpiperidin-4-yl)carbamoyl]butyl]carbamate (IV).

To a solution of compound 99 (30 mg, 0.03 mmol) in dry MeOH (3 mL) was added Vc (6 mg, 0.03 mmol). After stirring at 25° C. for 30 min, the solvent was removed under vacuum. The residue was purified by prep-HPLC (Venusil XBP C18 (5 μm, 30×250 mm), 0.1% HCl in eluant) to give product IV (29 mg, 93%) as a white solid. MS (ESI): [M+H⁺]=960.6. ¹H NMR: (400 MHz, CDCl₃) δ 8.12-7.96 (m, 5H), 7.34-7.16 (m, 10H), 5.43-5.32 (m, 3H), 5.00 (s, 3H), 4.30-4.12 (m, 6H), 2.99-2.92 (m, 4H), 2.62-2.50 (m, 3H), 1.97-1.91 (m, 13H), 1.42-1.23 (m, 21H), 0.86-0.71 (m, 14H).

Example V

Benzyl N-[(4R)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl] carbamate (V)

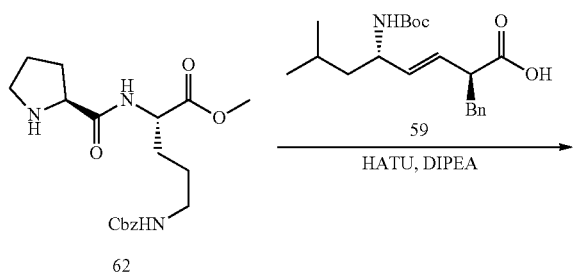

62

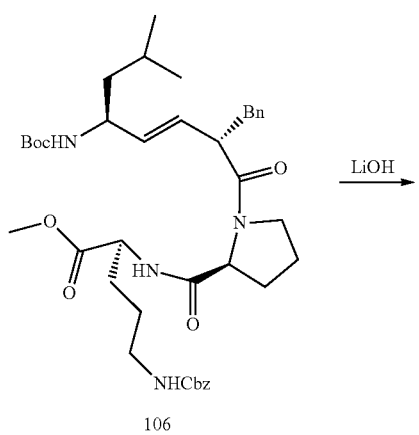

106

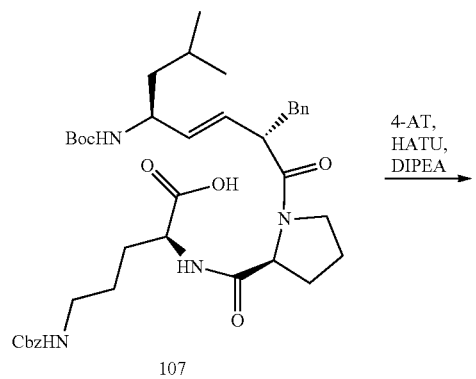

107

-continued

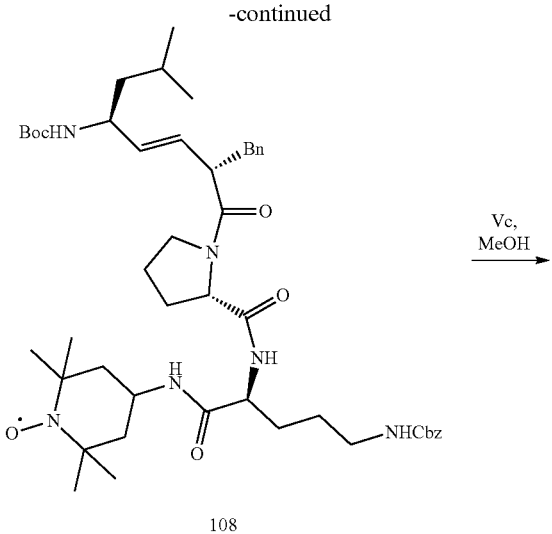

108

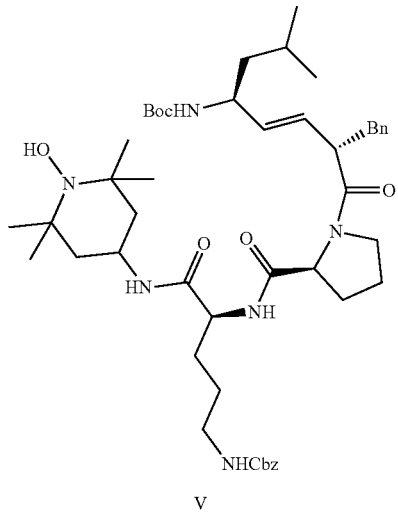

V

Step 1: Synthesis of (R)-methyl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (106).

To a solution of compound 62 (520 mg, 1.38 mmol) and compound 59 (398.0 mg, 1.10 mmol) in $CH_2Cl_2$ (10 mL) at 0° C. was added DIPEA (356 mg, 2.76 mmol) and HATU (682 mg, 1.79 mmol), and stirred for 3 h at 25° C. The reaction mixture was quenched with saturated aqueous $NH_4Cl$ solution (20 mL), washed with saturated aqueous brine solution (3×10 mL), dried over $Na_2SO_4$ and concentrated in vacuum. The residues were purified by column chromatography on silica gel with eluting solvent of petroleum ether/EtOAc=1:3 to give crude product 106 (830 mg crude, 100%) as a white foam. MS (ESI): [M+H$^+$]=721.9.

Step 2: Synthesis of (R)-2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoic acid (107).

A solution of compound 106 (830 mg, 1.10 mmol) in THF/MeOH=(10/2.5 mL) was treated with LiOH.H$_2$O (56 mg, 1.32 mmol in 0.5 mL water). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (3×20 mL), and the combined organic layers were washed with saturated aqueous brine solution (3×20 mL), dried over $Na_2SO_4$, and concentrated in vacuum to afford product 107 (730 mg, 94%), which was carried on crude to the coupling reaction. MS (ESI): [M+H$^+$]=707.0.

Step 3: Synthesis of benzyl N-[(4R)—4-{[(2S)-1-[(2S,3E,5S)-2-benzyl-5-{[(tert-butoxy)carbonyl]amino}-7-methyl-oct-3-enoyl]pyrrolidin-2-yl]formamido}-4-[(1-oxyl-2,2,6,6-tetramethylpiperidin-4-yl)carbamoyl]butyl]carbamate (108).

A solution of the crude compound 107 (730 mg, 1.03 mmol) in dry $CH_2Cl_2$ (5 mL) at 0° C. was treated with HATU (509 mg, 1.34 mmol), DIPEA (266 mg, 2.06 mmol), and 4-AT (212 mg, 1.24 mmol). The reaction mixture was stirred at 25° C. for 3 h, then quenched with saturated aqueous $NH_4Cl$ solution (20 mL). The aqueous phase was separated and extracted with $CH_2Cl_2$ (2×10 mL), and the combined organic layers were dried over $Na_2SO_4$ and concentrated. The crude material was purified by prep-HPLC (Venusil XBP C18 (5 μm, 30×250 mm), 0.1% HCl in eluant) to give product 108 (160 mg, 18%) as an orange solid. MS (ESI): [M+H$^+$]=860.6.

Step 4: Synthesis of benzyl N-[(4R)—4-{[(2S)-1-[(2S,3E,5S)-2-benzyl-5-{[(tert-butoxy)carbonyl]amino}-7-methyl-oct-3-enoyl]pyrrolidin-2-yl]formamido}-4-[(1-hydroxy-2,2,6,6-tetramethylpiperidin-4-yl)carbamoyl]butyl]carbamate (V).

To a solution of compound 108 (152 mg, 0.18 mmol) in dry MeOH (3 mL) was added Vc (32 mg, 0.18 mmol). After stirring at 25° C. for 1 h, the solvent was removed under vacuum and the residue was purified by prep-HPLC (Venusil XBP C18 (5 μm, 30×250 mm), 0.1% HCl in eluant) to give product V (90 mg, 59%) as a white solid. $^1$H NMR: (400 MHz, CDCl$_3$) δ 7.28-7.08 (m, 10H), 5.57-5.52 (m, 1H), 5.41-5.39 (m, 1H), 5.09-5.01 (m, 2H), 4.21 (s, 1H), 4.16 (s, 2H), 4.00 (s, 1H), 3.50 (s, 1H), 3.35 (s, 1H), 3.33-3.12 (m, 3H), 2.67 (s, 1H), 2.15-1.71 (m, 18H), 1.55-1.19 (m, 24H), 0.80-0.79 (d, J=4.0 Hz, 6H). MS (ESI): [M+H$^+$]=861.9.

Example VI tert-Butyl N-[(4S,5E,7S)-7-benzyl-8-[(2R)-2-[(1-hydroxy-2,2,6,6-tetramethylpiperidin-4-yl)carbamoyl]pyrrolidin-1-yl]-2-methyl-8-oxooct-5-en-4-yl]carbamate (VI)

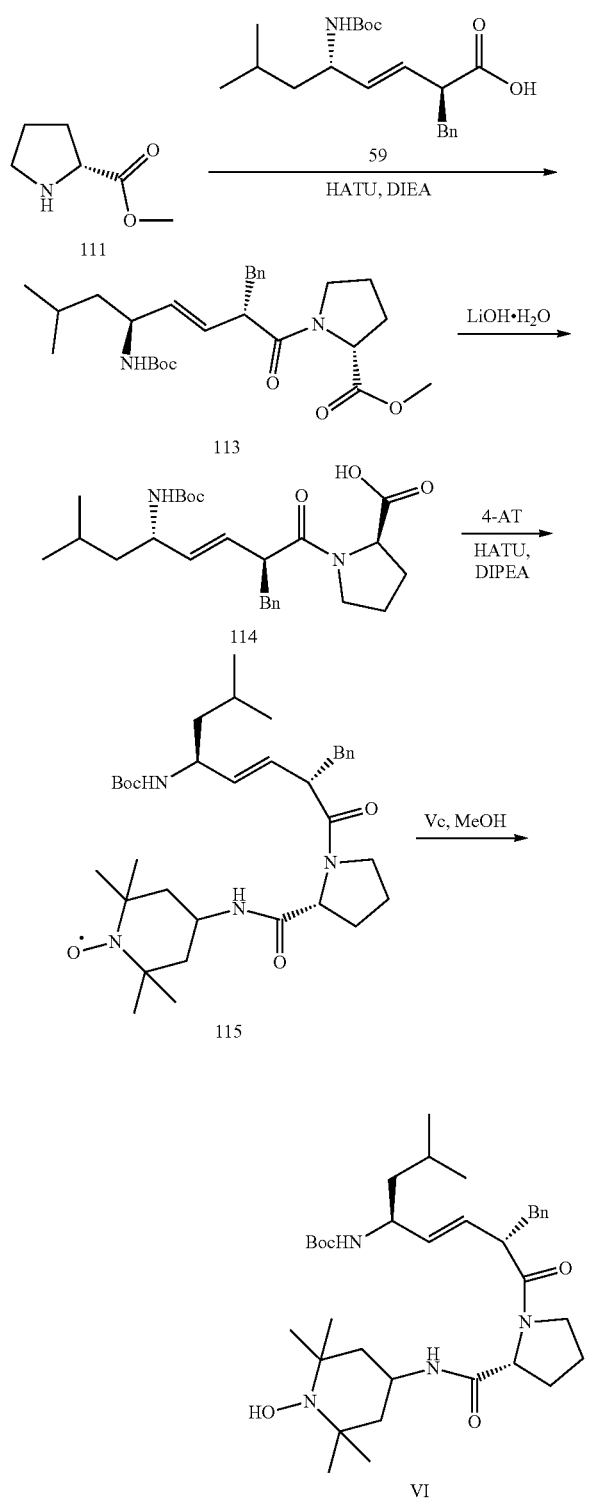

Step 1: Synthesis of (R)-methyl 1-((2S,5S,E)-2-benzyl-5-((tert-butoxycarbonyl)amino)-7-methyloct-3-enoyl)pyrrolidine-2-carboxylate (113).

To a solution of compound 111 (165.0 mg, 1.0 mmol) and compound 59 (300 mg, 0.83 mmol) in $CH_2Cl_2$ (5 mL) at 0° C. was added DIPEA (268 mg, 2.08 mmol) and HATU (410 mL, 1.08 mmol). The reaction mixture was allowed to warm to 25° C. and stirred for 3 h. The reaction mixture was quenched with saturated aqueous $NH_4Cl$ solution (20 mL), washed with saturated aqueous brine solution (3×20 mL), dried over $MgSO_4$ and concentrated in vacuo to give crude product 113 (410 mg, 100%) as a white foam which was used for next step without further purification. MS (ESI): $[M+H^+]$=473.6.

Step 2: Synthesis of (R)-1-((2S,5S,E)-2-benzyl-5-((tert-butoxycarbonyl)amino)-7-methyloct-3-enoyl)pyrrolidine-2-carboxylic acid (114).

A solution of the compound 113 (410 mg, 0.83 mmol) in THF/MeOH (4.0/1.0 mL) was treated with $LiOH \cdot H_2O$ (42 mg, 1.0 mmol, in 0.5 mL water). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over $Na_2SO_4$, and concentrated in vacuum to afford product 114 (390 mg, 100%), which was carried on without purification for the coupling reaction. MS (ESI): $[M+H^+]$=459.

Step 3: Synthesis of tert-butyl N-[(4S,5E,7S)-7-benzyl-8-[(2R)-2-[(1-oxyl-2,2,6,6-tetramethylpiperidin-4-yl)carbamoyl]pyrrolidin-1-yl]-2-methyl-8-oxooct-5-en-4-yl]carbamate (115).

A solution of the crude compound 114 (390 mg, 0.83 mmol) in dry $CH_2Cl_2$ (5 mL) at 0° C. was treated with HATU (410 mg, 1.08 mmol), DIPEA (268 mg, 2.08 mmol), and 4-AT (172 mg, 1.00 mmol). The reaction mixture was stirred at 25° C. for 3 h, then quenched with saturated aqueous $NH_4Cl$ solution (20 mL). The aqueous phase was separated and extracted with $CH_2Cl_2$ (20 mL), and the combined organic layers were dried over $MgSO_4$ and concentrated in vacuum. The crude material was purified by prep-HPLC (Venusil XBP C18 (5 μm, 30×250 mm), 0.1% HCl in eluant) to give product 115 (150 mg, 30%) as an orange solid. MS (ESI): $[M+H^+]$=612.5.

Step 4: Synthesis of tert-butyl N-[(4S,5E,7S)-7-benzyl-8-[(2R)-2-[(1-hydroxy-2,2,6,6-tetramethylpiperidin-4-yl)carbamoyl]pyrrolidin-1-yl]-2-methyl-8-oxooct-5-en-4-yl]carbamate (VI).

To a solution of compound 115 (150 mg, 0.25 mmol) in dry MeOH (3 mL) was added Vc (43 mg, 0.25 mmol). After stirring at 25° C. for 30 min, the solvent was removed under vacuum. The resulting residue was dissolved in $CH_2Cl_2$ (10 mL) and washed with water. The residue was purified by pre-HPLC (Venusil XBP C18 (5 μm, 30×250 mm), 0.1% HCl in eluant) to give VI (91 mg, 60%) as a white solid. $^1$H NMR: (400 MHz, $CDCl_3$) δ 7.30-7.03 (m, 4H), 5.63-5.57 (m, 1H), 5.37-5.32 (m, 1H), 4.50-4.48 (d, J=8.0 Hz, 1H), 4.40 (s, 1H), 4.15-4.14 (m, 2H), 3.50-3.43 (m, 3H), 3.15-2.78 (m, 5H), 2.07 (s, 1H), 2.82 (s, 1H), 1.58-1.25 (m, 30H), 0.88-0.87 (d, J=4.0 Hz, 6H). MS (ESI): $[M+H^+]$=613.6.

Example VII
Benzyl N-[(4S)-4-[(2S)—2-{[(2R)-1-[(2S,3E,5S)-2-benzyl-5-{[(tert-butoxy)carbonyl]amino}-7-methyl-oct-3-enoyl]pyrrolidin-2-yl]formamido}-3-methylbutanamido]-4-[(1-hydroxy-2,2,6,6-tetramethylpiperidin-4-yl)carbamoyl]butyl] carbamate (VII)
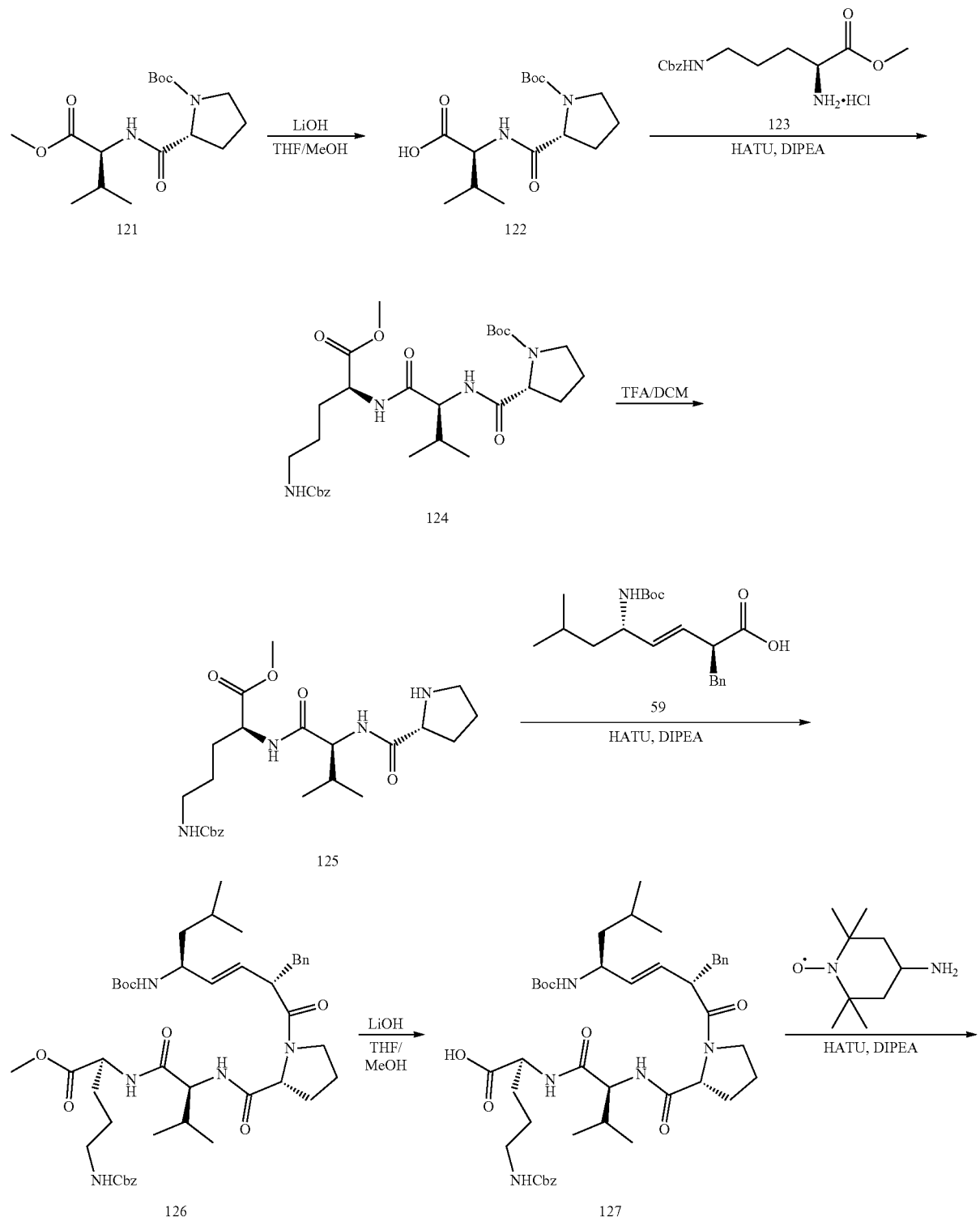

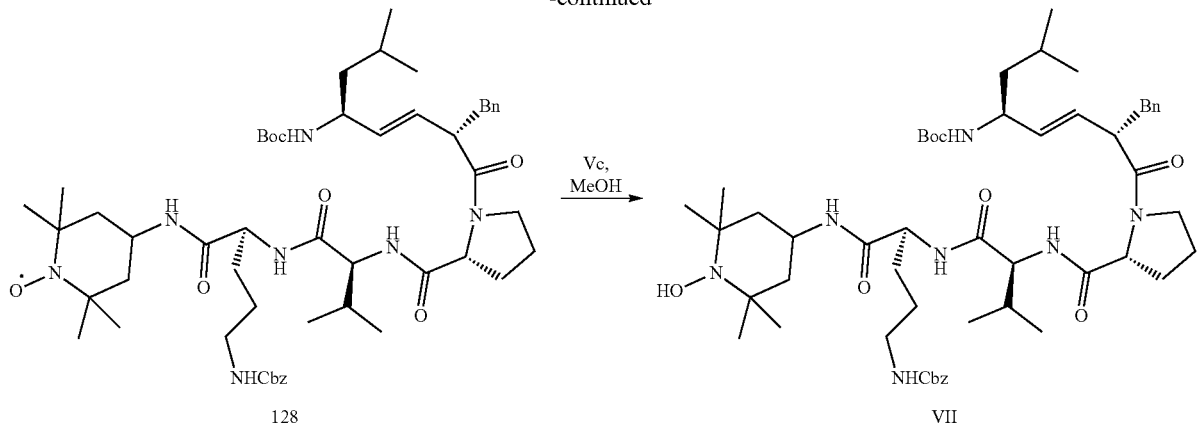

Step 1: Synthesis of (S)-2-((R)-1-(tert-butoxycarbonyl)pyrrolidine-2-carboxamido)-3-methylbutanoic acid (122).

A solution of the compound 121 (6.8 g, 18.58 mmol) in THF/MeOH=4:1 (40 mL) was treated with aqueous LiOH.H$_2$O (940 mg, 22.30 mmol) in water (2 mL). The reaction mixture was stirred at 25° C. for 3 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×10 mL), dried over Na$_2$SO$_4$, and concentrated to afford product 122 (4.6 g, 79%) as a white foam which was carried on for the coupling reaction. MS (ESI): [M+H$^+$]=314.9.

Step 2: Synthesis of (R)-tert-butyl 2-(((S)-1-(((S)-5-(((benzyloxy)carbonyl)amino)-1-methoxy-1-oxopentan-2-yl)amino)-3-methyl-1-oxobutan-2-yl)carbamoyl)pyrrolidine-1-carboxylate (124).

To a solution of compound 122 (2.0 g, 6.37 mmol) and compound 123 (2.4 g, 7.64 mmol) in CH$_2$Cl$_2$ (20 mL) at 0° C. was added DIPEA (2.1 g, 15.93 mmol) and HATU (3.1 mL, 8.28 mmol). The reaction mixture was allowed to warm to 25° C. and stirred for 3 h. The reaction mixture was quenched with saturated aqueous NH$_4$Cl solution (20 mL), washed with saturated aqueous brine solution (3×20 mL), dried over MgSO$_4$ and concentrated in vacuum to give crude product 124 (2.2 g, 61%) as a white foam which was used for next step without further purification. MS (ESI): [M+H$^+$]= 577.7.

Step 3: Synthesis of (S)-methyl 5-(((benzyloxy)carbonyl)amino)-2-((S)-3-methyl-2-((R)-pyrrolidine-2-carboxamido)butanamido)pentanoate (125).

To a solution of compound 124 (2.2 g, 3.82 mmol) in CH$_2$Cl$_2$ (12 mL) at 0° C. was added TFA (3.0 mL). The resulting solution was stirred for 10 min at 0° C., and 3 h at 25° C. The solvent was concentrated in vacuum, and CH$_2$Cl$_2$ (10 mL) and 5% aqueous Na$_2$CO$_3$ solution were added until pH 8-9. The layers were separated, and the aqueous layer was extracted with CH$_2$Cl$_2$ (20 mL). The combined organic layers were dried over Na$_2$SO$_4$ and concentrated to give product 125 (314 mg, 72%) as a white foam. MS (ESI): [M+H$^+$]=477.6.

Step 4: Synthesis of (S)-methyl 2-((S)-2-((R)-1-((2S,5S,E)-2-benzyl-5-((tert-butoxycarbonyl)amino)-7-methyloct-3-enoyl)pyrrolidine-2-carboxamido)-3-methylbutanamido)—5-(((benzyloxy)carbonyl)amino)pentanoate (126).

To a solution of compound 125 (314 mg, 0.66 mmol) and compound 59 (200 mg, 0.55 mmol) in CH$_2$Cl$_2$ (5 mL) at 0° C. was added DIPEA (142 mg, 1.1 mmol) and HATU (274 mg, 0.72 mmol). The reaction mixture was allowed to warm to 25° C. and stirred for 3 h. The reaction mixture was quenched with saturated aqueous NH$_4$Cl solution (20 mL), washed with saturated aqueous brine solution (3×10 mL), dried over MgSO$_4$ and concentrated in vacuum. The residues were purified by silica gel on column chromatography with eluting solvent-petroleum ether/EtOAc=1:3 to give crude product 126 (460 mg, 100%) as a white foam. MS (ESI): [M+H$^+$]=820.7.

Step 5: Synthesis of (S)-2-((S)-2-((R)-1-((2S,5S,E)-2-benzyl-5-((tert-butoxycarbonyl)amino)-7-methyloct-3-enoyl)pyrrolidine-2-carboxamido)-3-methylbutanamido)—5-(((benzyloxy)carbonyl)amino)pentanoic acid (127).

To a solution of the compound 126 (460 mg, 0.55 mmol) in THF/MeOH (4.0/2.0 mL) was treated with LiOH.H$_2$O (56 mg, 1.10 mmol, in 0.5 mL water). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (3×20 mL), dried over Na$_2$SO$_4$, and concentrated to afford product 127 (370 mg, 84%), which was carried on for the next coupling reaction. MS (ESI): [M+H$^+$]=806.6.

Step 6: Synthesis of benzyl N-[(4S)-4-[(2S)—2-{[(2R)-1-[(2S,3E,5S)-2-benzyl-5-{[(tert- butoxy)carbonyl]amino}-7-methyloct-3-enoyl]pyrrolidin-2-yl]formamido}-3-methylbutanamido]-4-[(1-oxyl-2,2,6,6-tetramethylpiperidin-4-yl)carbamoyl]butyl]carbamate (128).

To a solution of the crude compound 127 (370 mg, 0.46 mmol) in dry CH$_2$Cl$_2$ (5 mL) at 0° C. was treated with HATU (227 mg, 0.60 mmol), DIPEA (119 mg, 0.92 mmol), and 4-AT (94 mg, 0.55 mmol). The reaction mixture was stirred at 25° C. for 3 h, then quenched with saturated aqueous NH$_4$Cl solution (10 mL). The aqueous phase was separated and extracted with CH$_2$Cl$_2$ (20 mL), and the combined organic layers were dried over MgSO$_4$ and concentrated in vacuo. The crude material was purified by prep-HPLC (Venusil XBP C18 (5 μm, 30×250 mm), 0.1%

HCl in eluant) to give product 128 (81 mg, 18%) as an orange solid. MS (ESI): [M+H⁺]=959.8.

Step 7: Synthesis of benzyl N-[(4S)-4-[(2S)—2-{[(2R)-1-[(2S,3E,5S)-2-benzyl-5-{[tert-butoxy)carbonyl]amino}-7-methyloct-3-enoyl]pyrrolidin-2-yl]formamido}-3-methylbutanamido]-4-[(1-hydroxy-2,2,6,6-tetramethylpiperidin-4-yl)carbamoyl]butyl]carbamate (VII).

To a solution of compound 128 (76 mg, 0.08 mmol) in dry MeOH (3 mL) was added Vc (14 mg, 0.08 mmol). After stirring at 25° C. for 1 h, the solvent was removed under vacuum. The residue was purified by prep-HPLC (Venusil XBP C18 (5 μm, 30×250 mm), 0.1% HCl in eluant) to give product VII (32 mg, 42%) as a white solid. ¹H NMR: (400 MHz, CDCl₃) δ 7.57-7.03 (m, 8H), 5.74 (m, 2H), 5.09-5.07 (d, J=4.0 Hz, 2H), 4.40-3.08 (m, 14H), 2.75-2.04 (m, 16H), 1.75-1.0 (m, 39H). MS (ESI): [M+H⁺]=960.7.

Example VIII

1-Oxyl-2,2,6,6-tetramethylpiperidin-4-yl N-[(4S,5E,7S)-7-benzyl-8-[(2S)—2-{[(1S)—1-{[(1S)—4-{[(benzyloxy)carbonyl]amino}-1-[(1-oxyl-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl ]carbamate (VIII)

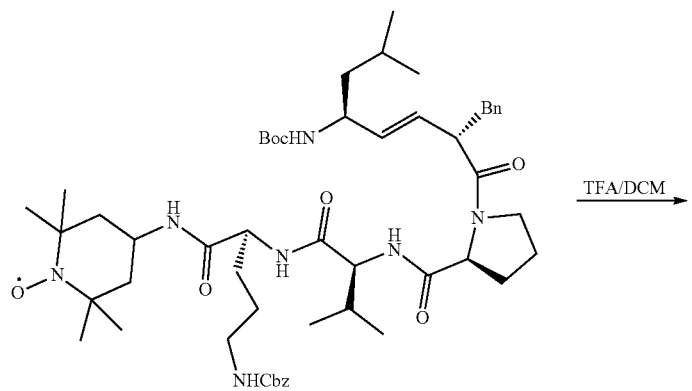

131

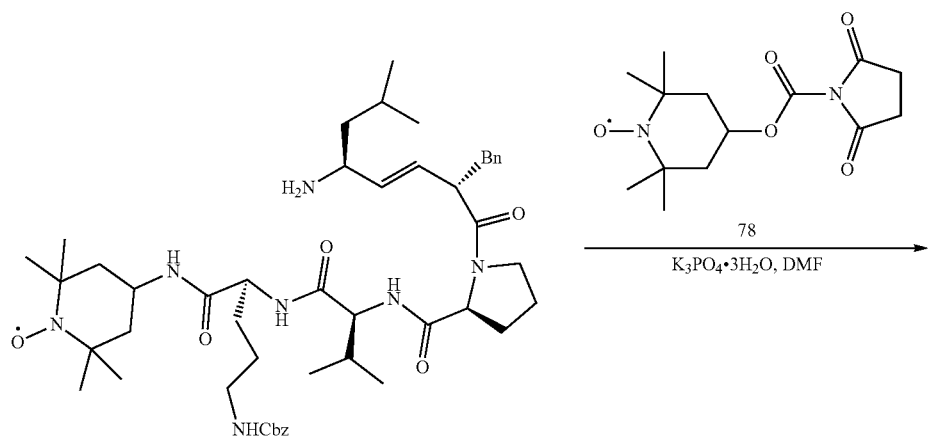

132

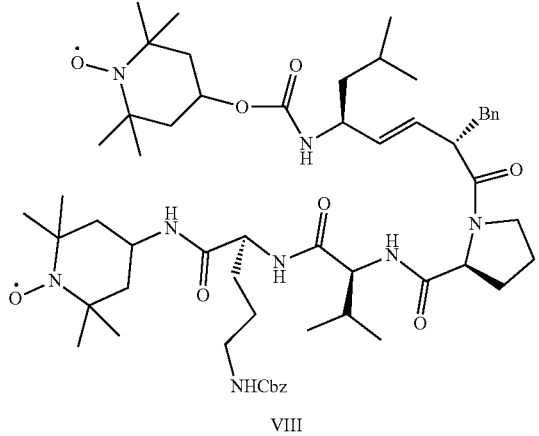

VIII

Step 1: Synthesis of benzyl ((S)-4-((S)-2-((S)-1-((2S,5S,E)-5-amino-2-benzyl-7-methyloct-3-enoyl)pyrrolidine-2-carboxamido)-3-methylbutanamido)—5-((1-oxyl-2,2,6,6-tetramethylpiperidin-4-yl)amino)-5-oxopentyl)carbamate (132).

To a solution of compound 131 (200 mg, 0.21 mmol, the procdure synthesis is according to Journal of the American Chemical Society, 2005, 127, 12460-12461) in CH$_2$Cl$_2$ (5 mL) at 0° C. was added TFA (0.2 mL). The resulting solution was stirred 10 min at 0° C., and 1 h at 25° C. The solvent was concentrated, and CH$_2$Cl$_2$ (5 mL) and 5% aqueous Na$_2$CO$_3$ solution were added until pH 8-9. The layers were separated, and the aqueous layer was extracted with CH$_2$Cl$_2$ (20 mL). The combined organics were dried over Na$_2$SO$_4$ and concentrated in vacuo to give product 132 (176 mg, 97%) as a red oil.

Step 2: Synthesis of 1-oxyl-2,2,6,6-tetramethylpiperidin-4-yl N-[(4S,5E,7S)-7-benzyl-8-[(2S)—2-{[(1S)—1-{[(1S)—4-{[(benzyloxy)carbonyl]amino}-1-[(1-oxyl-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl ]carbamate (VIII).

To a stirred solution of compound 132 (176 mg, 0.2 mmol) and compound 78 (68.5 mg, 0.25 mmol) in DMF (5.0 mL) was added K$_3$PO$_4$.3H$_2$O (66.5 mg, 0.25 mmol). The mixture was then stirred at 25° C. for 16 h. The reaction was quenched with water (10 mL) and extracted with EtOAc (3×20 mL). The organic layer was washed with saturated aqueous brine solution (3×10 mL), dried over Na$_2$SO$_4$ and concentrated in vacuo. The residues were purified by column chromatography on silica gel (petroleum ether/EtOAc=2:1 to 1:10) to give product VIII (106 mg, 50%) as a brownish red solid. MS (ESI): [M+H$^-$]=1058.0.

Example IX

Benzyl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl] carbamate (IX)

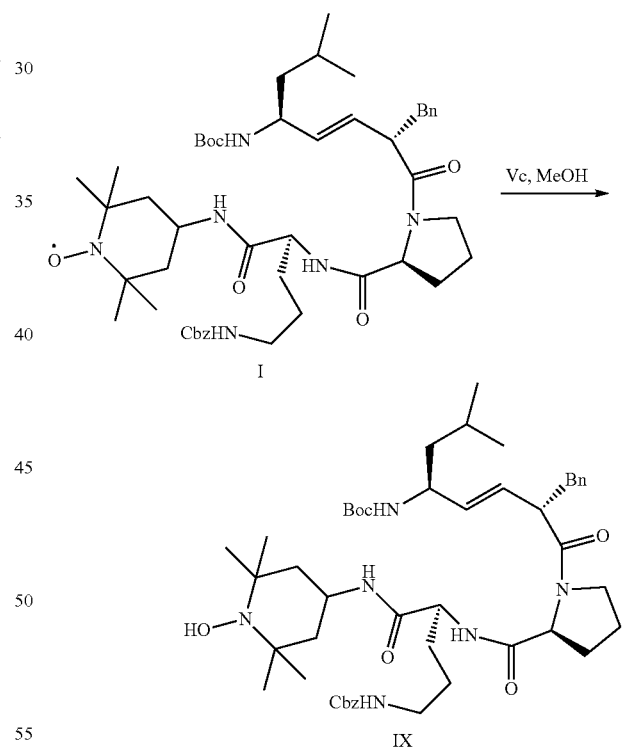

Step 1: Synthesis of benzyl N-[(4S)—4-{[(2S)-1-[(2S,3E,5S)-2-benzyl-5-{[(tert-butoxy)carbonyl]amino}-7-methyl-oct-3-enoyl]pyrrolidin-2-yl]formamido}-4-[(1-hydroxy-2,2,6,6-tetramethylpiperidin-4-yl)carbamoyl]butyl]carbamate (IX).

To a solution of compound I (85 mg, 0.10 mmol) in dry MeOH (3 mL) was added Vc (17 mg, 0.10 mmol). After stirring at 25° C. for 1 h, the solvent was removed under vacuum. The residue was purified by prep-HPLC (Venusil XBP C18 (5 μm, 30×250 mm), 0.1% HCl in eluant) to give product IX (47 mg, 55%) as a white solid. $^1$H NMR: (400 MHz, CDCl$_3$) δ 7.27-7.07 (m, 10H), 5.55-5.46 (m, 1H), 5.35 (s, 1H), 5.25-5.22 (m, 1H), 5.01 (s, 2H), 4.3-4.23 (m, 3H), 3.63 (s, 1H), 3.44 (s, 1H), 3.31 (s, 1H), 3.30 (s, 1H), 3.09-3.06 (m, 4H), 2.47 (s, 1H), 2.10 (s, 8H), 1.94 (s, 2H), 1.84-1.47 (m, 6H), 1.42-1.10 (m, 23H), 0.81-0.75 (m, 6H). MS (ESI): [M+H$^+$]=861.7.
Example X
Cyclopropylmethyl N-[(4S,5E,7S)-7-benzyl-8-[(2S)—2-{[(1R)—1-{[(1S)—4-{[(benzyloxy)carbonyl]amino}-1-[(1-hydroxy-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl]carbamate (X)
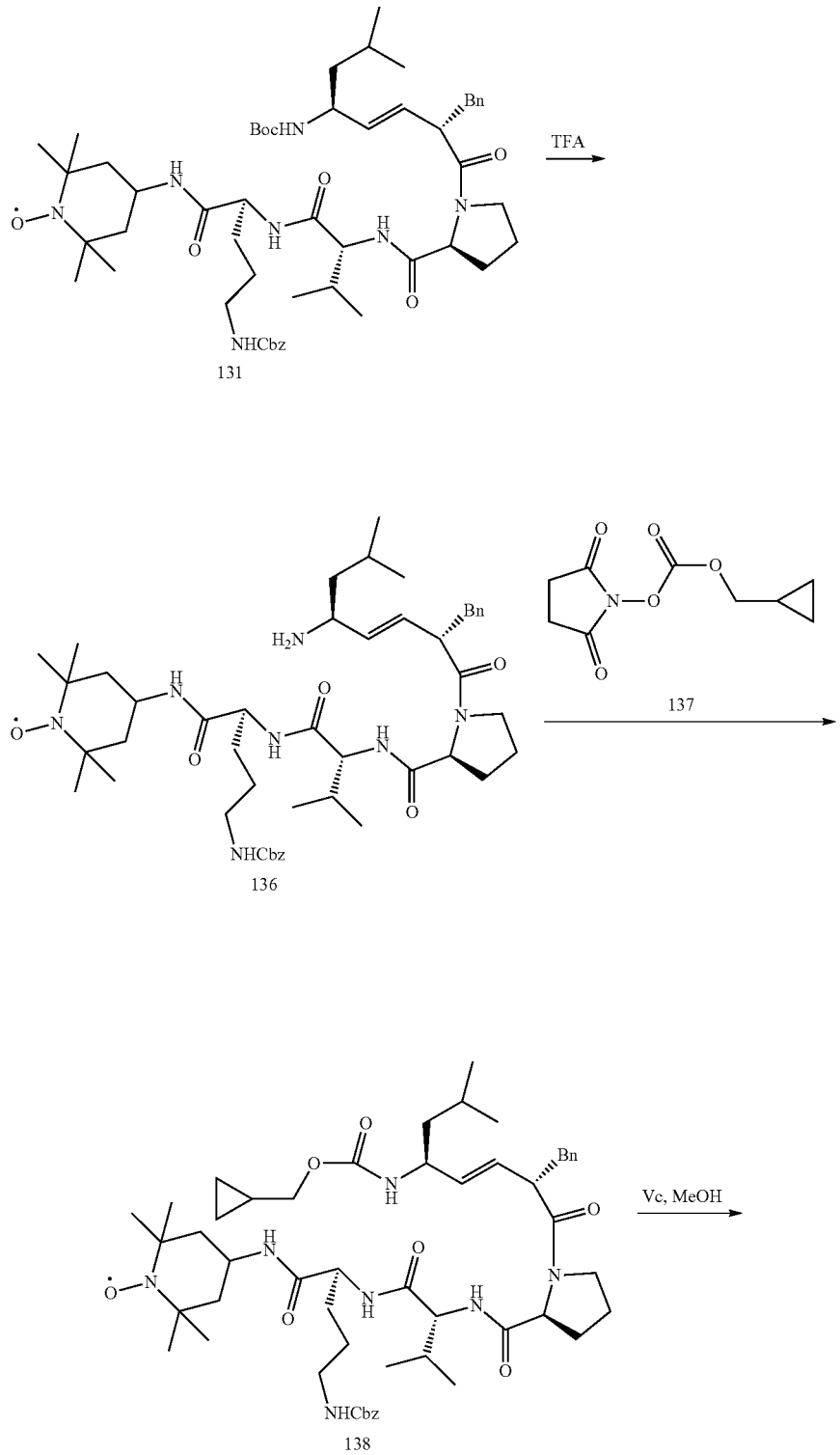

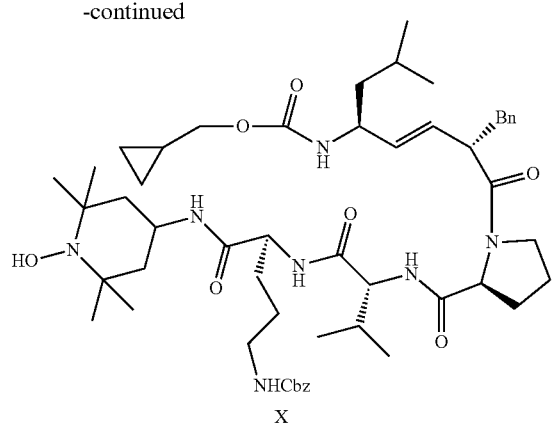

X

Step 1: Synthesis of benzyl ((S)-4-((R)-2-((S)-1-((2S,5S,E)-5-amino-2-benzyl-7-methyloct-3-enoyl)pyrrolidine-2-carboxamido)-3-methylbutanamido)—5-((1-oxyl-2,2,6,6-tetramethylpiperidin-4-yl)amino)-5-oxopentyl)carbamate (132).

To a solution of compound 131 (200 mg, 0.21 mmol) in CH₂Cl₂ (3 mL) at 0° C. was added TFA (1.0 mL). The resulting solution was stirred 10 min at 0° C., and 3 h at 25° C. The solvent was concentrated in vacuum, and CH₂Cl₂ (10 mL) and 5% aqueous Na₂CO₃ solution were added until pH 8-9. The layers were separated, and the aqueous layer was extracted with CH₂Cl₂ (10 mL). The combined organic layer was wash with saturated aqueous brine solution (2×10 mL) dried over Na₂SO₄ and concentrated to give product 136 (171 mg, 95%) as a red foam.

Step 2: Synthesis of cyclopropylmethyl N-[(4S,5E,7S)-7-benzyl-8-[(2S)—2-{[(1R)—1-{(1S)—4-{[(benzyloxy)carbonyl]amino}-1-[(1-oxyl-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl] carbamate (138).

To a solution of compound 136 (171 mg, 0.20 mmol) and compound 137 (51 mg, 0.24 mmol, the procdure synthesis is according to the example of compound 78) in DMF (5.0 mL) at 25° C. was added K₃PO₄.3H₂O (64.0 mg, 0.24 mmol). The reaction mixture was stirred for 16 h at 25° C. The reaction mixture was diluted with EtOAc (10 mL) and water (10 mL). The organic layer was washed with saturated aqueous brine solution (3×20 mL), dried over Na₂SO₄ and concentrated in vacuo. The residue was purified by prep-HPLC (Venusil XBP C18 (5 μm, 30×250 mm), 0.1% HCl in eluant) to give product 138 (76 mg, 40%) as a brownish red foam. MS (ESI): [M+H⁺]=957.9.

Step 3: Synthesis of cyclopropylmethyl N-[(4S,5E,7S)-7-benzyl-8-[(2S)—2-{[(1R)—1-{[1S)—4-{[(benzyloxy)carbonyl]amino}-1-[(1-hydroxy-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl] carbamate (X).

To a solution of compound 138 (74 mg, 0.08 mmol) in dry MeOH (3 mL) was added Vc (14 mg, 0.08 mmol). After stirring at 25° C. for 1 h, the solvent was removed under vacuum. The residue was purified by prep-HPLC (Venusil XBP C18 (5 μm, 30×250 mm), 0.1% HCl in eluant) to give product X (30 mg, 41%) as a white solid. ¹H NMR: (400 MHz, CDCl₃) δ 8.13 (s,1H), 7.32-7.06 (m, 10H), 6.76-6.75 (d, J=4.0 Hz, 1H), 5.47-5.34 (m, 3H), 5.04 (m, 2H), 4.45- 3.78 (m, 8H), 3.38-3.07 (m, 6H), 2.16-1.81 (m, 19H), 1.45-0.54 (m, 25H), 0.61 (s, 2H), 0.26 (s, 2H). MS (ESI): [M+H⁺]=959.3.

Example XI

Benzyl N-[(4S)-4-1-{[(2S)-1-[(2S)-1-[(2R,3E,5S)-2-benzyl-5-{[(tert-butoxy)carbonyl]amino}-7- methyl-oct-3-enoyl]pyrrolidine-2-carbonyl]pyrrolidin-2-yl] formamido}-4-[(1-hydroxy-2,2,6,6-tetramethylpiperidin-4-yl)carbamoyl]butyl] carbamate (XI)

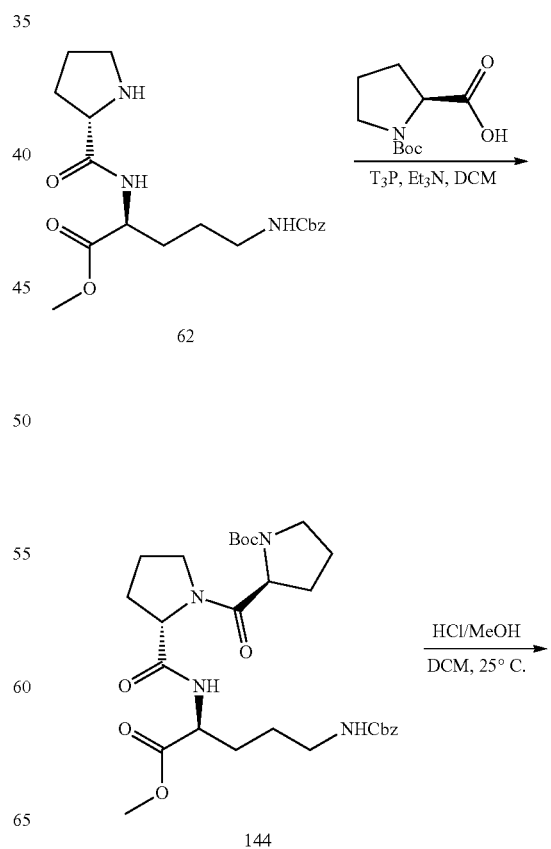

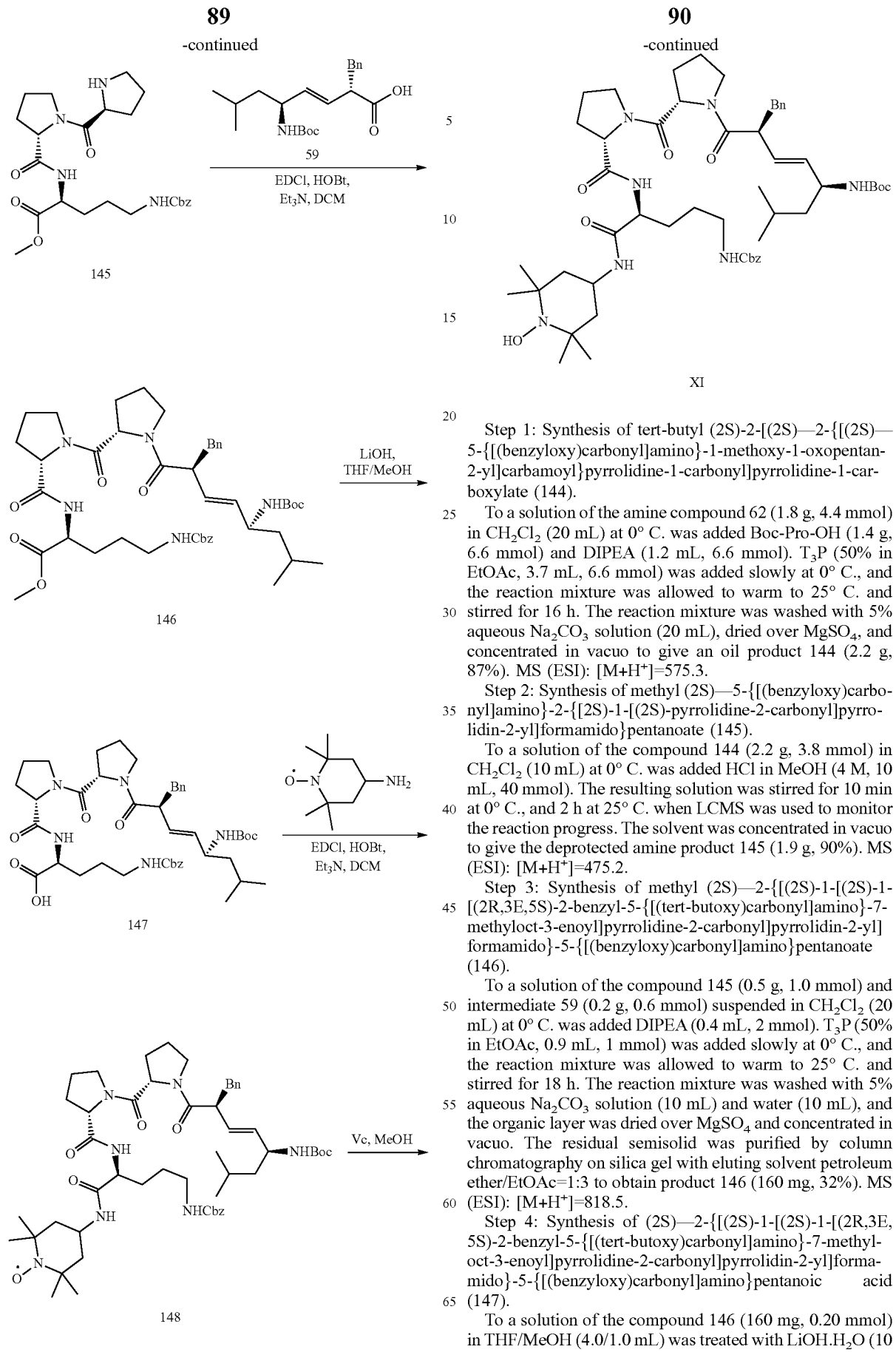

Step 1: Synthesis of tert-butyl (2S)-2-[(2S)—2-{[(2S)—5-{[(benzyloxy)carbonyl]amino}-1-methoxy-1-oxopentan-2-yl]carbamoyl}pyrrolidine-1-carbonyl]pyrrolidine-1-carboxylate (144).

To a solution of the amine compound 62 (1.8 g, 4.4 mmol) in CH$_2$Cl$_2$ (20 mL) at 0° C. was added Boc-Pro-OH (1.4 g, 6.6 mmol) and DIPEA (1.2 mL, 6.6 mmol). T$_3$P (50% in EtOAc, 3.7 mL, 6.6 mmol) was added slowly at 0° C., and the reaction mixture was allowed to warm to 25° C. and stirred for 16 h. The reaction mixture was washed with 5% aqueous Na$_2$CO$_3$ solution (20 mL), dried over MgSO$_4$, and concentrated in vacuo to give an oil product 144 (2.2 g, 87%). MS (ESI): [M+H$^+$]=575.3.

Step 2: Synthesis of methyl (2S)—5-{[(benzyloxy)carbonyl]amino}-2-{[2S)-1-[(2S)-pyrrolidine-2-carbonyl]pyrrolidin-2-yl]formamido}pentanoate (145).

To a solution of the compound 144 (2.2 g, 3.8 mmol) in CH$_2$Cl$_2$ (10 mL) at 0° C. was added HCl in MeOH (4 M, 10 mL, 40 mmol). The resulting solution was stirred for 10 min at 0° C., and 2 h at 25° C. when LCMS was used to monitor the reaction progress. The solvent was concentrated in vacuo to give the deprotected amine product 145 (1.9 g, 90%). MS (ESI): [M+H$^+$]=475.2.

Step 3: Synthesis of methyl (2S)—2-{[(2S)-1-[(2S)-1-[(2R,3E,5S)-2-benzyl-5-{[(tert-butoxy)carbonyl]amino}-7-methyloct-3-enoyl]pyrrolidine-2-carbonyl]pyrrolidin-2-yl]formamido}-5-{[(benzyloxy)carbonyl]amino}pentanoate (146).

To a solution of the compound 145 (0.5 g, 1.0 mmol) and intermediate 59 (0.2 g, 0.6 mmol) suspended in CH$_2$Cl$_2$ (20 mL) at 0° C. was added DIPEA (0.4 mL, 2 mmol). T$_3$P (50% in EtOAc, 0.9 mL, 1 mmol) was added slowly at 0° C., and the reaction mixture was allowed to warm to 25° C. and stirred for 18 h. The reaction mixture was washed with 5% aqueous Na$_2$CO$_3$ solution (10 mL) and water (10 mL), and the organic layer was dried over MgSO$_4$ and concentrated in vacuo. The residual semisolid was purified by column chromatography on silica gel with eluting solvent petroleum ether/EtOAc=1:3 to obtain product 146 (160 mg, 32%). MS (ESI): [M+H$^+$]=818.5.

Step 4: Synthesis of (2S)—2-{[(2S)-1-[(2S)-1-[(2R,3E,5S)-2-benzyl-5-{[(tert-butoxy)carbonyl]amino}-7-methyloct-3-enoyl]pyrrolidine-2-carbonyl]pyrrolidin-2-yl]formamido}-5-{[(benzyloxy)carbonyl]amino}pentanoic acid (147).

To a solution of the compound 146 (160 mg, 0.20 mmol) in THF/MeOH (4.0/1.0 mL) was treated with LiOH.H$_2$O (10 mg, 0.22 mmol, in 0.2 mL water). The reaction mixture was stirred at 25° C. for 4 h, then the solvent was removed under vacuum and the resulting mixture treated with EtOAc (20 mL) and aqueous HCl (1 M) until pH 3-4. The organic phase was separated from water phase. The water phase was extracted with EtOAc (2×20 mL), and the combined organic layers were washed with saturated aqueous brine solution (2×20 mL), dried over $Na_2SO_4$, and concentrated in vacuo to afford the oil product 147 (120 mg, 75%). MS (ESI): $[M+H^+]=804.5$.

Step 5: Synthesis of benzyl N-[(4S)—4-{[(2S)-1-[(2S)-1-[(2R,3E,5S)-2-benzyl-5-{[(tert- butoxy)carbonyl]amino}-7-methyloct-3-enoyl]pyrrolidine-2-carbonyl]pyrrolidin-2-yl]formamido}-4-[(1-Oxyl-2,2,6,6-tetramethylpiperidin-4-yl)carbamoyl]butyl]carbamate (148).

To a solution of the crude compound 147 (120 mg, 0.15 mmol) in dry $CH_2Cl_2$ (5 mL) at 0° C. was treated with HATU (60 mg, 0.15 mmol), DIPEA (25 mg, 0.18 mmol), and 4-AT (30 mg, 0.18 mmol). The reaction mixture was stirred at 25° C. for 16 h, then quenched with saturated aqueous $NH_4Cl$ solution (20 mL). The aqueous phase was separated and extracted with $CH_2Cl_2$ (20 mL). The combined organic layers were dried over $MgSO_4$ and concentrated in vacuo. The crude material was purified by prep-HPLC (Venusil XBP C18 (5 μm, 30×250 mm), 0.1% HCl in eluant) to give product 148 (80 mg, 56%) as an orange solid. MS (ESI): $[M+H^+]=957.7$.

Step 6: Synthesis of benzyl N-[(4S)—4-{[(2S)-1-[(2S)-1-[(2R,3E,5S)-2-benzyl-5-{[(tert- butoxy)carbonyl]amino}-7-methyloct-3-enoyl]pyrrolidine-2-carbonyl]pyrrolidin-2-yl]formamido}-4-[(1-hydroxy-2,2,6,6-tetramethylpiperidin-4-yl)carbamoyl]butyl]carbamate (XI).

To a solution of compound 148 (80 mg, 0.08 mmol) in dry MeOH (3 mL) was added Vc (15 mg, 0.08 mmol). After stirring at 25° C. for 60 min, the solvent was removed under vacuum. The residue was purified by prep-HPLC (Venusil XBP C18 (5° m, 30×250 mm), 0.1% HCl in eluant) to give product XI (15 mg, 19%) as a white solid. $^1$H NMR: (400 MHz, $CDCl_3$) δ 7.35-7.20 (m, 7H), 7.20-7.10 (m, 5H), 5.6-5.30 (m, 2H), 5.1-4.9 (m, 2H), 4.6-4.3 (m, 4H), 3.4-3.2 (m, 6H), 2.4-1.8 (m, 8H), 1.8-1.6 (m, 14H), 1.6-1.2 (m, 22H), 0.8-0.6 (m, 8H). MS (ESI): $[M+H^+]=958.8$.

Example XII

Benzyl N-[(4S)-4-[(2S)—2-{[(2S)-1-[(2R,3E,5S)-2-benzyl-5-{[(tert-butoxy)carbonyl]amino}-7- methyl-oct-3-enoyl]pyrrolidin-2-yl]formamido}-2-cyclopropylacetamido]-4-[(1-hydroxy-2,2,6,6-tetramethylpiperidin-4-yl)carbamoyl]butyl]carbamate (XII)

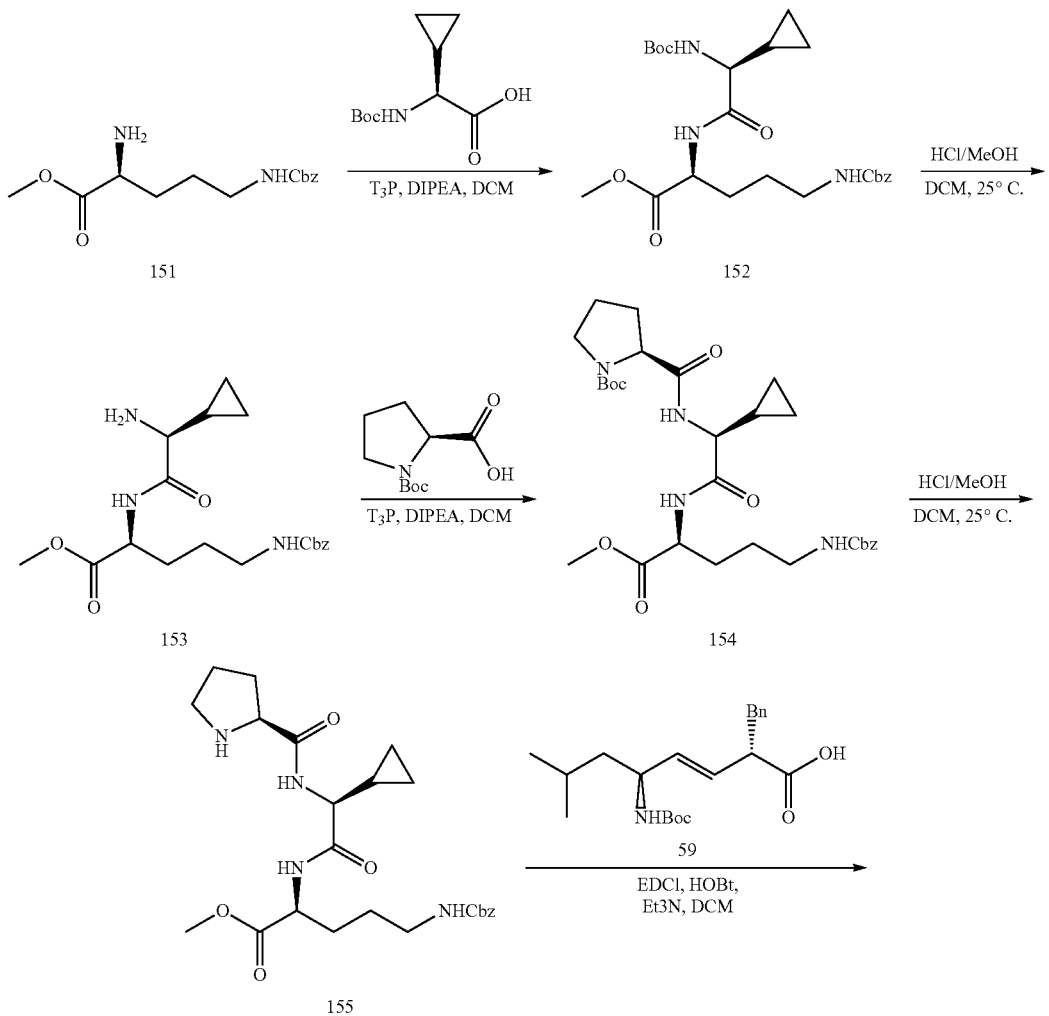

-continued

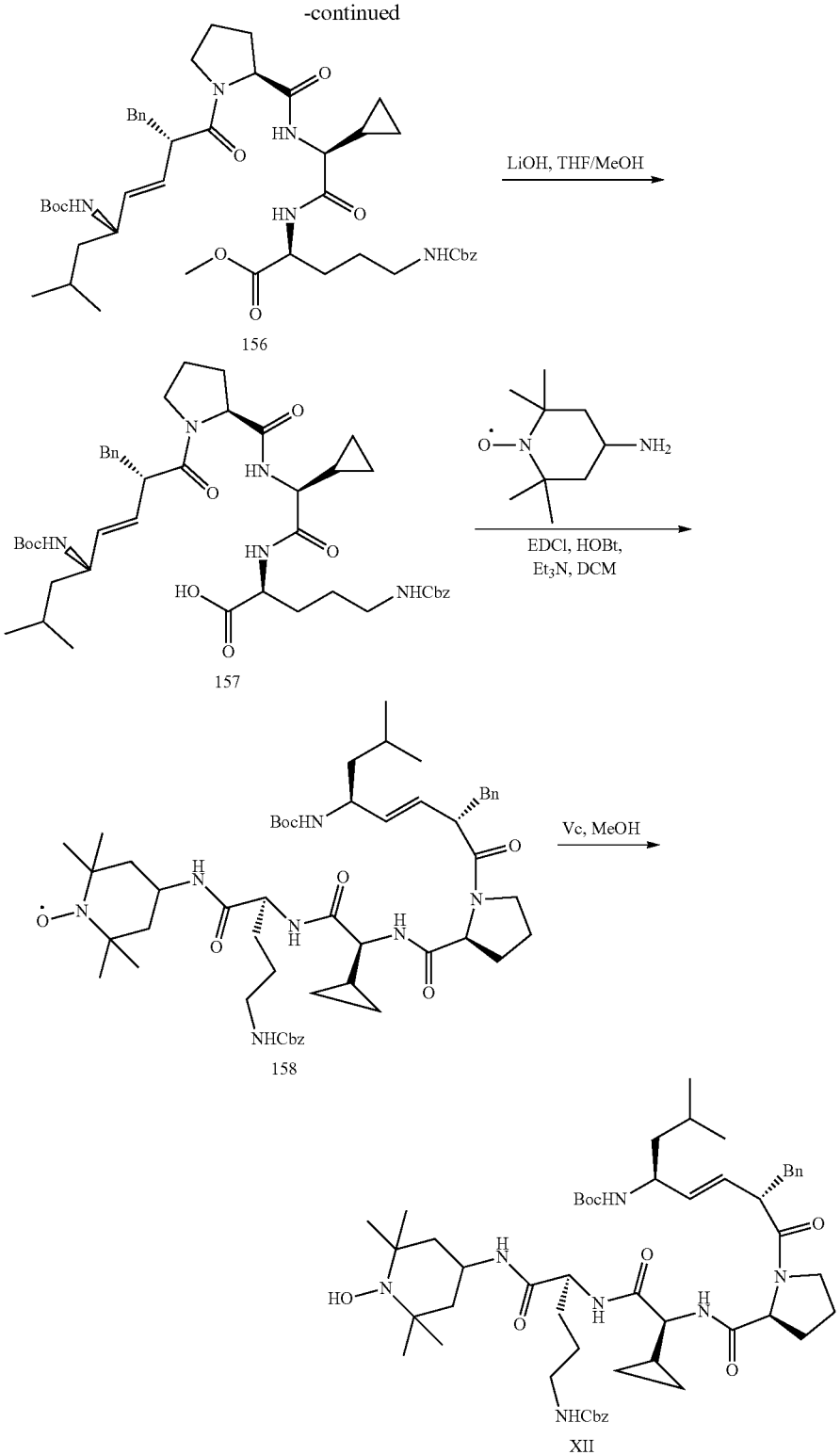

Step 1: Synthesis of methyl (2S)—5-{[(benzyloxy)carbonyl]amino}-2-[(2S)—2-{[(tert-butoxy)carbonyl]amino}-2-cyclopropylacetamido]pentanoate (152).

To a solution of Orn(Z)—OMe (151) (1.5 g, 4.7 mmol) and (S)-2-((tert-butoxycarbonyl)amino)-2-cyclopropylacetic acid (1.0 g, 4.7 mmol) suspended in $CH_2Cl_2$ (20 mL) at 0° C. was added DIPEA (1.0 mL, 6 mmol). $T_3P$ (50% in EtOAc, 4 mL, 6.0 mmol) was added slowly at 0° C., and the reaction mixture was allowed to warm to 25° C. and stirred for 16 h. The reaction mixture was washed with 5% aqueous $Na_2CO_3$ solution (10 mL) and water (2×10 mL), and the organic layer was dried over $MgSO_4$ and concentrated in vacuo. The residual semisolids becomes a dry, cement-like 152 (1.5 g, 68%). MS (ESI): [M+H⁺]=478.1.

Step 2: Synthesis of methyl (2S)-2-[(2S)-2-amino-2-cyclopropylacetamido]-5-{[(benzyloxy)carbonyl]amino}pentanoate (153).

To a solution of compound 152 (1.5 g, 3.0 mmol) in CH₂Cl₂ (10 mL) at 0° C. was added HCl in MeOH (4 M, 5 mL, 20 mmol). The resulting solution was stirred 10 min at 0° C., and 2 h at 25° C. when LCMS was used to monitor the reaction progress. The solvent was concentrated in vacuo to give the deprotected amine product 153 (1.0 g, 83%). MS (ESI): [M+H⁺]=378.0.

Step 3: Synthesis of tert-butyl (2S)—2-{[(5)—{[(2S)—5-{[(benzyloxy)carbonyl]amino}-1-methoxy-1-oxopentan-2-yl]carbamoyl}(cyclopropyl)methyl]carbamoyl}pyrrolidine-1-carboxylate (154).

To a solution of the amine compound 153 (1.0 g, 2.6 mmol) in CH₂Cl₂ (20 mL) at 0° C. was added Boc-Pro-OH (840 mg, 3.9 mmol) and DIPEA (0.64 mL, 3.9 mmol). T₃P (50% in EtOAc, 2.2 mL, 3.9 mmol) was added slowly, and the reaction mixture was allowed to warm to 25° C. and stirred for 16 h. The reaction mixture was washed with 5% aqueous Na₂CO₃ solution (10 mL), dried over MgSO₄, and concentrated in vacuo to give a foam solid product 154 (1.1 g, 90%). MS (ESI): [M+H⁺]=575.3.

Step 4: Synthesis of methyl (2S)—5-{[(benzyloxy)carbonyl]amino}-2-[(2S)-2-cyclopropyl-2-{[(2S)-pyrrolidin-2-yl]formamido}acetamido]pentanoate (155).

To a solution of the compound 154 (1.1 g, 1.9 mmol) in CH₂Cl₂ (10 mL) at 0° C. was added HCl in MeOH (4 M, 5 mL, 20 mmol). The resulting solution was stirred 10 min at 0° C., and 2 h at 25° C. when LCMS was used to monitor the reaction progress. The solvent was concentrated in vacuo to give the deprotected amine product 155 (0.8 g, 89%). MS (ESI): [M+H⁺]=475.3.

Step 5: Synthesis of methyl (2S)-2-[(2S)—2-{[(2S)-1-[(2R,3E,5S)-2-benzyl-5-{[(tert-butoxy)carbonyl]amino}-7-methyloct-3-enoyl]pyrrolidin-2-yl]formamido}-2-cyclopropylacetamido]-5-{[(benzyloxy)carbonyl]amino}pentanoate (156).

To a solution of the compound 155 (0.5 g, 1.0 mmol) and intermediate 59 (0.2 g, 0.6 mmol) suspended in CH₂Cl₂ (20 mL) at 0° C. was added DIPEA (0.4 mL, 2 mmol). T₃P (50% in EtOAc, 0.9 mL, 1 mmol) was added slowly, and the reaction mixture was allowed to warm to 25° C. and stirred for 18 h. The reaction mixture was washed with 5% aqueous Na₂CO₃ solution (10 mL) and water (2×10 mL), and the organic layer was dried over MgSO₄ and concentrated in vacuo. The residue was purified by column chromatography on silica gel with eluting solvent-petroleum ether/EtOAc=1:3, to obtain an oil product 156 (120 mg, 24%). MS (ESI): [M+H⁺]=818.5.

Step 6: Synthesis of (2S)-2-[(2S)—2-{[(2S)-1-[(2R,3E,5S)-2-benzyl-5-{[(tert-butoxy)carbonyl]amino}-7-methyloct-3-enoyl]pyrrolidin-2-yl]formamido}-2-cyclopropylacetamido]-5-{[(benzyloxy)carbonyl]amino}pentanoic acid (157).

To a solution of the compound 156 (120 mg, 0.15 mmol) in THF/MeOH (4.0/1.0 mL) was treated with LiOH.H₂O (10 mg, 0.22 mmol, in 0.2 mL water). The reaction mixture was stirred at 25° C. for 4 h, then the solvent was removed under vacuum and the resulting mixture treated with EtOAc (20 mL) and aqueous HCl (1 M) until pH 3-4. The organic phase was separated from water phase. The water phase was extracted with EtOAc (2×20 mL), and the combined organic layers were washed with saturated aqueous brine solution (3×10 mL), dried over Na₂SO₄, and concentrated in vacuo to afford the oil product 157 (100 mg, 83%). MS (ESI): [M+H⁺]=804.5.

Step 7: Synthesis of benzyl N-[(4S)-4-[(2S)—2-{[(2S)-1-[(2R,3E,5S)-2-benzyl-5-{[(tert-butoxy)carbonyl]amino}-7-methyloct-3-enoyl]pyrrolidin-2-yl]formamido}-2-cyclopropylacetamido]-4-[(1-oxyl-2,2,6,6-tetramethylpiperidin-4-yl)carbamoyl]butyl]carbamate (158).

To a solution of the crude compound 157 (100 mg, 0.12 mmol) in dry CH₂Cl₂ (5 mL) at 0° C. was treated with EDCI (35 mg, 0.18 mmol), HOBt (25 mg, 0.18 mmol), DIEA (25 mg, 0.18 mmol), and 4-AT (30 mg, 0.18 mmol). The reaction mixture was stirred at 25° C. for 16 h, then quenched with saturated aqueous NH₄Cl solution (20 mL). The aqueous phase was separated and extracted with CH₂Cl₂ (20 mL), and the combined organic layers were dried over MgSO₄ and concentrated. The crude material was purified by prep-HPLC (Venusil XBP C18 (5 μm, 30×250 mm), 0.1% HCl in eluant) to give product 158 (30 mg, 26%) as an orange solid. MS (ESI): [M+H⁺]=957.7.

Step 8: Synthesis of benzyl N-[(4S)-4-[(2S)—2-{[(2S)-1-[(2R,3E,5S)-2-benzyl-5-{[(tert-butoxy)carbonyl]amino}-7-methyloct-3-enoyl]pyrrolidin-2-yl]formamido}-2-cyclopropylacetamido]-4-[(1-hydroxy-2,2,6,6-tetramethylpiperidin-4-yl)carbamoyl]butyl]carbamate (XII).

To a solution of the compound 158 (30 mg, 0.03 mmol) in dry MeOH (3 mL) was added Vc (10 mg, 0.05 mmol). After stirring at 25° C. for 60 min, the solvent was removed under vacuum. The residue was purified by pre-HPLC (Venusil XBP C18 (5 μm, 30×250 mm), 0.1% HCl in eluant) to give product XII (4 mg, 13%) as a white solid. ¹H NMR: (400 MHz, CDCl₃) δ 7.35-7.20 (m, 7H), 7.20-7.10 (m, 5H), 5.62-5.30 (m, 2H), 5.15-4.91 (m, 2H), 4.6-4.3 (m, 4H), 3.40-3.2 (m, 6H), 2.41-1.82 (m, 8H), 1.80-1.65 (m, 14H), 1.60-1.20 (m, 22H), 0.88-0.61 (m, 8H). MS (ESI): [M+H⁺]= 958.8.

Example XIII

Benzyl N-[(4R)—4-{[(2S)-1-[(2S,3E,5S)-5-amino-2-benzyl-7-methyloct-3-enoyl]pyrrolidin-2-yl]formamido}-4-[(1-hydroxy-2,2,6,6-tetramethyl-piperidin-4-yl)carbamoyl]butyl]carbamate dihydrochloride (XIII)

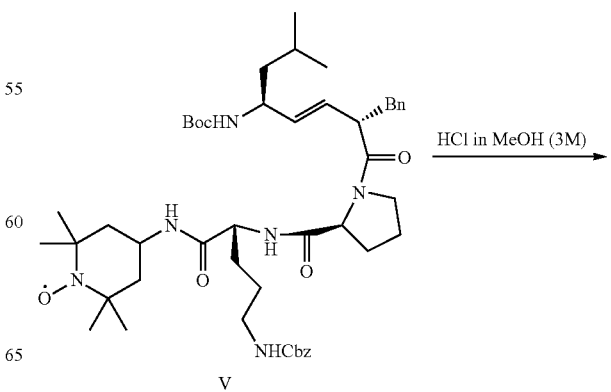

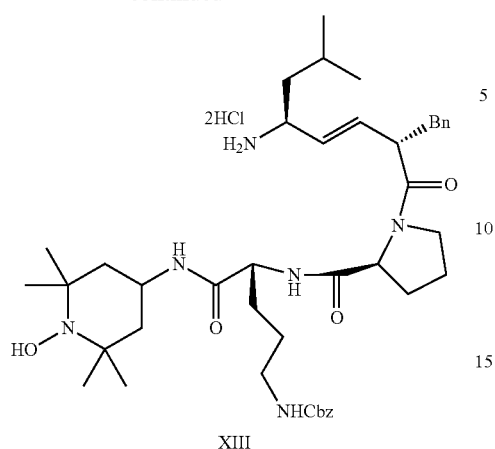

XIII

Step 1: Synthesis of benzyl N-[(4R)—4-{[(2S)-1-[(2S,3E,5S)-5-amino-2-benzyl-7-methyloct-3-enoyl]pyrrolidin-2-yl]formamido}-4-[(1-hydroxy-2,2,6,6-tetramethyl-piperidin-4-yl)carbamoyl]butyl]carbamate dihydrochloride (XIII).

To a solution of the compound V (20 mg, 0.02 mmol) in $CH_2Cl_2$ (5 mL) was added HCl in MeOH (5 mL, 3M) and stirred at 25° C. for 1 h. The solvent was removed and the residue was purified by prep-HPLC (Venusil XBP C18 (5 μm, 30×250 mm), 0.1% HCl in eluant) to give product XIII (4.6 mg, 31%) as a white solid. MS (ESI): [M+H$^+$]=761.6.

Example XIV

Benzyl N-[(4S)-4-[(2S)—2-{[(2S)-1-[(2S,3E,5S)-2-benzyl-5-{[(tert-butoxy)carbonyl]amino}-7- methyl-oct-3-enoyl]pyrrolidin-2-yl]formamido}propanamido]-4-[(1-hydroxy-2,2,6,6-tetramethylpiperidin-4-yl)carbamoyl]butyl]carbamate (XIV)

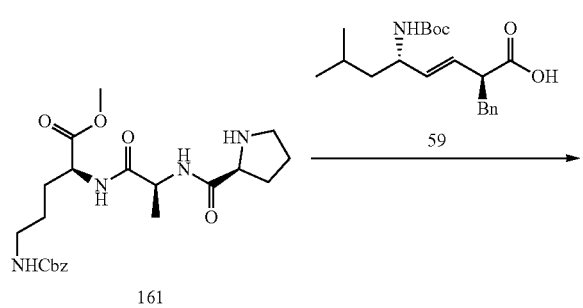

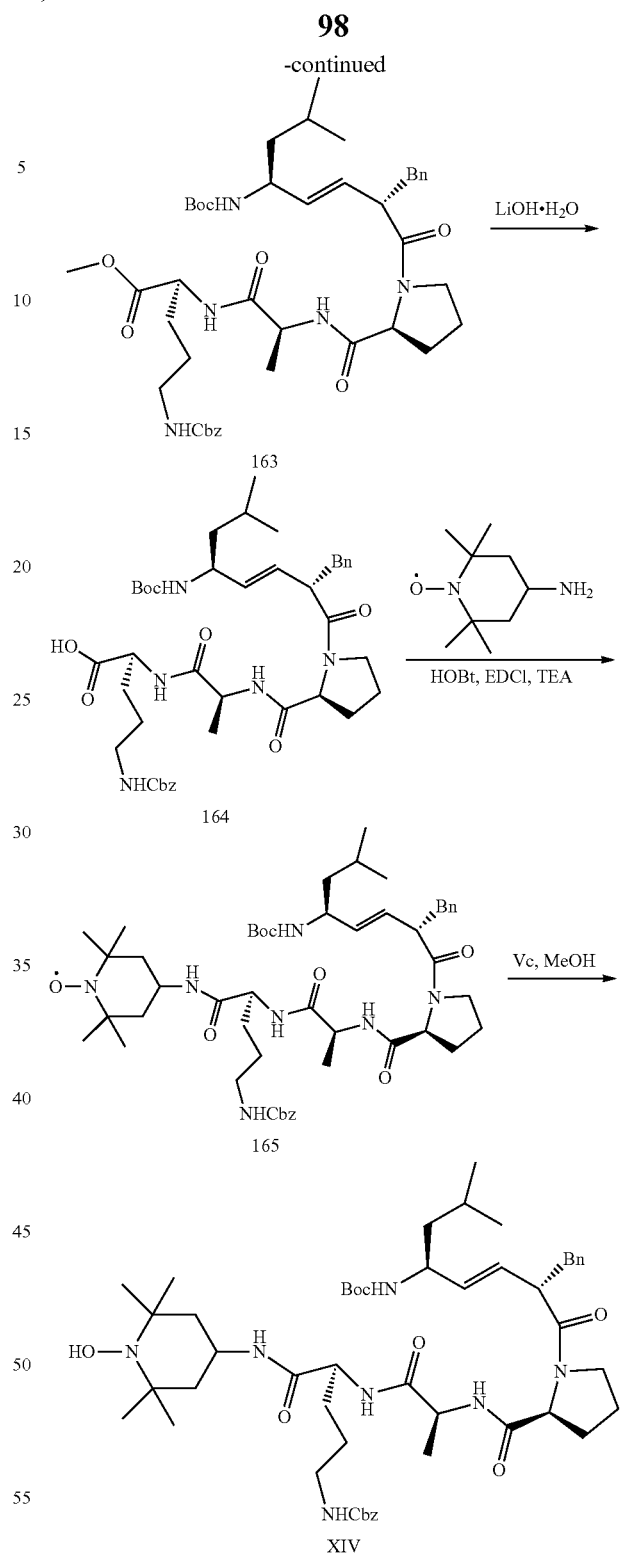

Step 1: Synthesis of methyl (2S)-2-[(2S)—2-{[(2S)-1-[(2S,3E,5S)-2-benzyl-5-{[(tert-butoxy)carbonyl]amino}-7-methyloct-3-enoyl]pyrrolidin-2-yl]formamido}propanamido]-5-{[(benzyloxy)carbonyl]amino}pentanoate (163).

To a solution of compound 161 (465 mg, 0.96 mmol, the procedure was according to *Journal of the American Chemical Society*, 2005, 127, 12460-12461) and compound 59 (290 mg, 0.80 mmol) in $CH_2Cl_2$ (5 mL) at 0° C. was added HOBt (130.0 mg), EDCI (185.0 mg, 0.96 mmol) and TEA (242.0 mg, 0.96 mmol). The reaction mixture was allowed to warm to 25° C. and stirred for 16 h. The reaction mixture was quenched with aqueous HCl (1M, 5 mL), washed with saturated aqueous brine solution (3×20 mL), dried over $Na_2SO_4$ and concentrated in vacuo. The residue was purified via a column chromatography (silica gel, petroleum ether/ EtOAc=3:1 to 1:1) to give product 163 (210 mg, 28%) as a white foam. MS (ESI): $[M+H^+]$=792.6.

Step 2: Synthesis of (2S)-2-[(2S)—2-{[(2S)-1-[(2S,3E,5S)-2-benzyl-5-{[(tert-butoxy)carbonyl]amino}-7-methyloct-3-enoyl]pyrrolidin-2-yl]formamido}propanamido]-5-{[(benzyloxy)carbonyl]amino}pentanoic acid (164).

To a solution of compound 163 (210 mg, 0.26 mmol) in THF/MeOH (4.0/1.0 mL) was treated with $LiOH \cdot H_2O$ (33 mg, 0.80 mmol in 0.2 mL water). The reaction mixture was stirred at 25° C. for 2 h, then the solvent was removed under vacuum. The resulting mixture was treated with EtOAc (10 mL) and aqueous HCl (1 M) until pH 3. The organic phase was separated from water phase. The water phase was extracted with EtOAc (2×20 mL), and the combined organic layers were washed with saturated aqueous brine solution (2×20 mL), dried over $Na_2SO_4$, and concentrated to afford product 164 (170 mg, 84%) as a white foam, which was carried on for the next coupling reaction. MS (ESI): $[M+H^+]$= 778.4.

Step 3: Synthesis of benzyl N-[(4S)-4-[(2S)—2-{[(2S)-1-[(2S,3E,5S)-2-benzyl-5-{[(tert- butoxy)carbonyl]amino}-7-methyloct-3-enoyl]pyrrolidin-2-yl]formamido}pro- panamido]-4-[(1-oxyl-2,2,6,6-tetramethylpiperidin-4-yl)carbamoyl]butyl]carbamate (165).

To a solution of the crude compound 164 (170 mg, 0.22 mmol) in dry $CH_2Cl_2$ (5 mL) at 0° C. was treated with HOBt (39.0 mg, 0.29 mmol), EDCI (55.0 mg, 0.29 mmol), TEA (44.0 mg, 0.44 mmol), and 4-AT (44.0 mg, 0.26 mmol). The reaction mixture was stirred at 25° C. for 16 h, then the reaction mixture was washed with 5% aqueous $NaHCO_3$ solution (10 mL) and then aqueous HCl (10 mL, 1M). The aqueous phase was separated and extracted with $CH_2Cl_2$ (10 mL), and the combined organic layers were dried over $Na_2SO_4$ and concentrated in vacuo to give crude product 165 (230 mg, crude) as a brownish red solid. MS (ESI): $[M+H^+]$= 931.8.

Step 4: Synthesis of benzyl N-[(4S)-4-[(2S)—2-{[(2S)-1-[(2S,3E,5S)-2-benzyl-5-{[(tert- butoxy)carbonyl]amino}-7-methyloct-3-enoyl]pyrrolidin-2-yl]formamido}propanamido]-4-[(1-hydroxy-2,2,6,6-tetramethylpiperidin-4-yl)carbamoyl]butyl]carbamate (XIV).

To a solution of compound 165 (230 mg, 0.25 mmol) in dry MeOH (3 mL) was added Vc (44 mg, 0.08 mmol). After stirring at 25° C. for 1 h, the solvent was removed under vacuum. The residue was purified by pre-HPLC (Venusil XBP C18 (5 μm, 30×250 mm), 0.1% HCl in eluant) to give product XIV (16 mg 42%) as a white solid. MS (ESI): $[M+H^+]$=932.8.

Example XV

Benzyl N-[(4S)-4-[(2S)—2-{[(2S)-1-[(2S,3E,5S)-5-amino-2-benzyl-7-methyloct-3-enoyl]pyrrolidin-2-yl]formamido}-3-methylbutanamido]-4-[(1-hydroxy-2,2,6,6-tetramethylpiperidin-4-yl)carbamoyl]butyl]carbamate trifluoroacetic acid salt (XV)

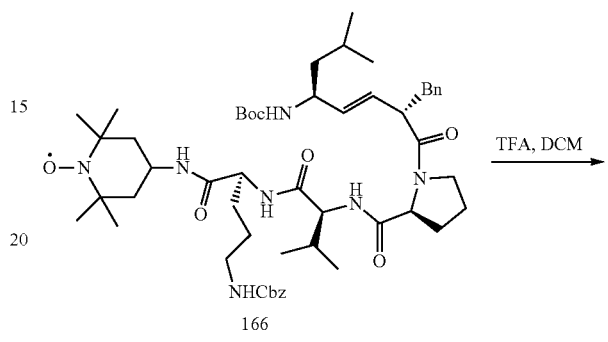

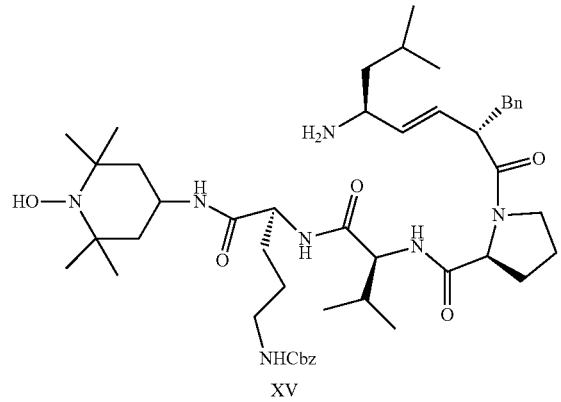

Step 1: Synthesis of benzyl N-[(4S)-4-[(2S)—2-{[(2S)-1-[(2S,3E,5S)-5-amino-2-benzyl-7-methyloct-3-enoyl]pyrrolidin-2-yl]formamido}-3-methylbutanamido]-4-[(1-hydroxy-2,2,6,6-tetramethylpiperidin-4-yl)carbamoyl]butyl] carbamate trifluoroacetic acid salt (XV).

To a solution of compound 166 (50 mg, 0.05 mmol, the procedure was according to Journal of the American Chemical Society, 2005, 127, 12460-12461) in $CH_2Cl_2$ (5 mL) at 0° C. was added TFA (0.2 mL). The resulting solution was stirred at 0° C. for 2 h. The solvent was concentrated in vacuo and the residue was purified by prep-HPLC (Venusil XBP C18 (5 μm, 30×250 mm), 0.1% HCl in eluant) to give product XV (16 mg, 36%) as a white solid. MS (ESI): $[M+H^+]$=859.7.

Example XVI tert-Butyl N-[(4S,5E,7S)-7-benzyl-8-[(2S)—2-{[(1S)-1-[(1-hydroxy-2,2,6,6-tetramethylpiperidin-4-yl)carbamoyl]-2-(4-hydroxyphenyl)ethyl]carbamoyl}pyrrolidin-1-yl]-2-methyl-8-oxooct-5-en-4-yl]carbamate (XVI)

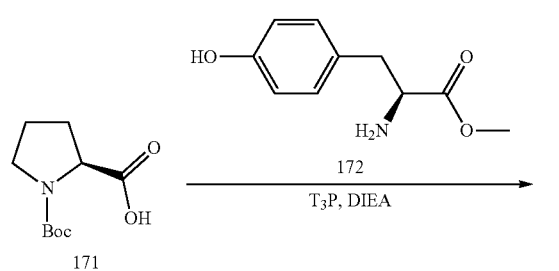

171 + 172 →(T₃P, DIEA)

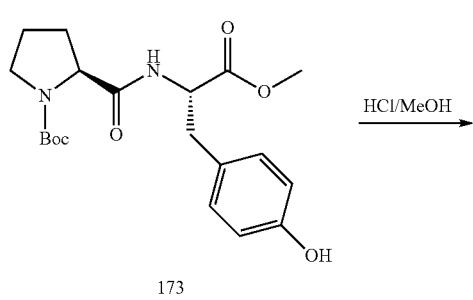

173 →(HCl/MeOH)

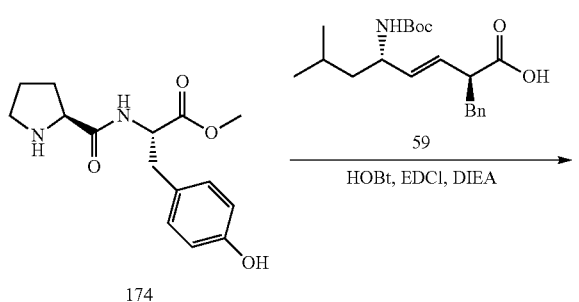

174 + 59 →(HOBt, EDCl, DIEA)

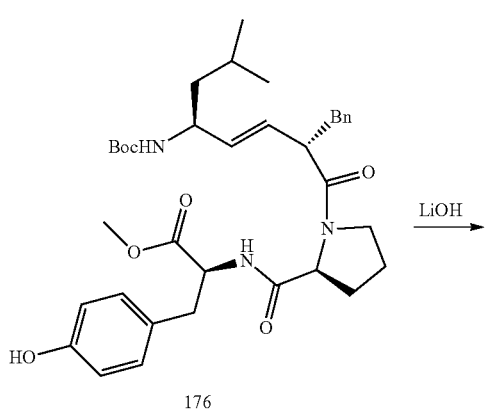

176 →(LiOH)

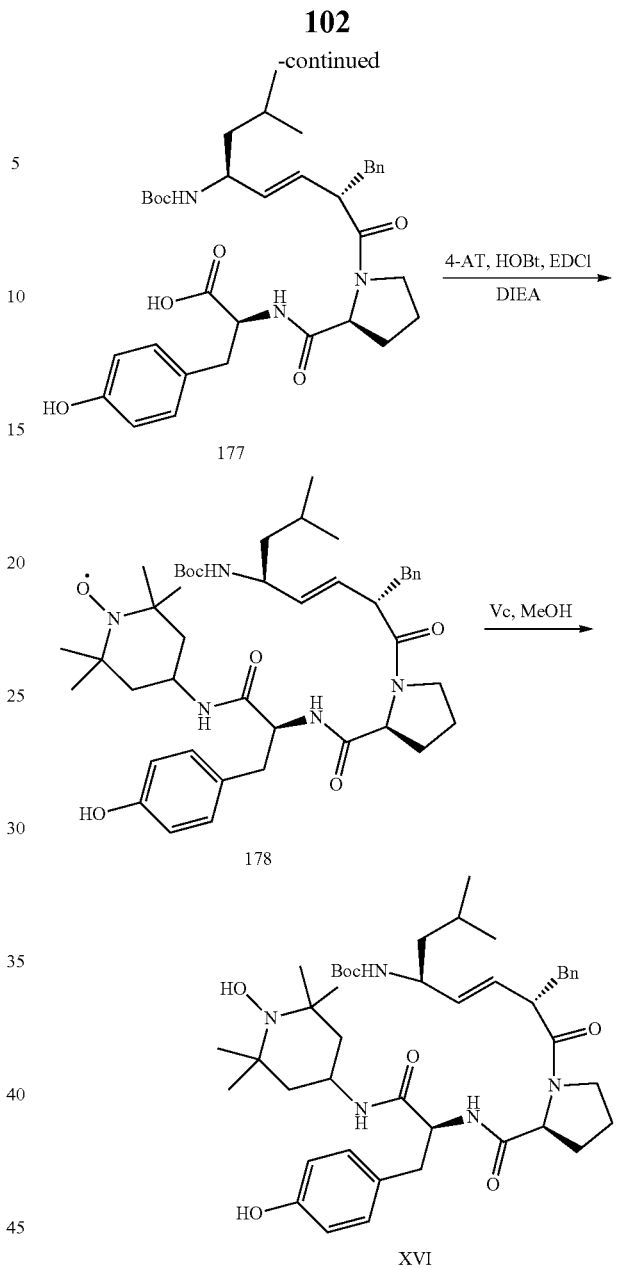

177 →(4-AT, HOBt, EDCl, DIEA)

178 →(Vc, MeOH)

XVI

Step 1: Synthesis of tert-butyl (2S)—2-{[(2S)-3-(4-hydroxyphenyl)-1-methoxy-1-oxopropan-2-yl]carbamoyl}pyrrolidine-1-carboxylate (173).

To a solution of compound 171 (1.7 g, 8.2 mmol) and compound 172 (1.8 g, 7.8 mmol) in CH₂Cl₂ (20 mL) at 0° C. was added T₃P (2.7 g, 8.6 mmol) and TEA (1.7 g, 17.2 mmol). The reaction mixture was allowed to warm to 25° C. and stirred for 16 h. The reaction mixture was washed with aqueous 5% NaHCO₃ (10 mL), aqueous HCl (10 mL, 1 M), and saturated aqueous brine solution (3×10 mL). The organic layer was dried over Na₂SO₄ and concentrated in vacuo. The residue was purified by column chromatography on silica gel (petroleum ether/EtOAc=5:1 to 1:1) to give product 173 (1.8 g, 60%) as a white foam. MS (ESI): [M+H⁺]=393.1.

Step 2: Synthesis of methyl (2S)-3-(4-hydroxyphenyl)-2-{[(2S)-pyrrolidin-2-yl]formamido}propanoate (174).

To a solution of compound 173 (1.8 g, 4.59 mmol) in CH₂Cl₂ (5 mL) was added HCl in MeOH (10 mL, 3 M) and stirred at 25° C. for 2 h and then the solvent was removed in vacuo to give product 174 (1.5 g, 100%) as a white foam. MS (ESI): [M+H$^+$]=293.1.

Step 3: Synthesis of methyl (2S)—2-{[(2S)-1-[(2S,3E,5S)-2-benzyl-5-{[(tert-butoxy)carbonyl]amino}-7-methyl-oct-3-enoyl]pyrrolidin-2-yl]formamido}-3-(4-hydroxyphenyl)propanoate (176).

To a solution of compound 174 (220 mg, 0.67 mmol) and compound 59 (220 mg, 0.61 mmol) in CH$_2$Cl$_2$ (5 mL) at 0° C. was added HOBt (100 mg, 0.73 mmol), EDCI (140 mg, 0.73 mmol) and DIPEA (200 mg, 1.53 mmol). The reaction mixture was allowed to warm to 25° C. and stirred for 16 h. The reaction mixture was quenched with saturated aqueous NH$_4$Cl solution (20 mL), washed with aqueous HCl (5 mL, 1 M), saturated aqueous brine solution (2×20 mL), dried over Na$_2$SO$_4$ and concentrated in vacuo. The residue was purified by column chromatography on silica gel (petroleum ether/EtOAc=3:1 to 1:1) to give product 176 (110 mg, 28%) as a white foam. MS (ESI): [M+H$^+$]=636.3.

Step 4: Synthesis of (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-3-(4-hydroxyphenyl)propanoic acid (177).

To a solution of the compound 176 (100 mg, 0.16 mmol) in THF/MeOH (4.0/1.0 mL) was treated with LiOH.H$_2$O (14 mg, 0.32 mmol in 0.2 mL water). The reaction mixture was stirred at 25° C. for 2 h, then the solvent was removed under vacuum. The resulting mixture was treated with EtOAc (10 mL) and aqueous HCl (1 M) until pH 2-3. The organic phase was separated from water phase. The water phase was extracted with EtOAc (2×20 mL), and the combined organic layers were washed with saturated aqueous brine solution (3×10 mL), dried over Na$_2$SO$_4$, and concentrated to afford compound 177 (91 mg, 92%), which was carried on crude for the next coupling reaction. MS (ESI): [M+H$^+$]=622.4.

Step 5: Synthesis of tert-butyl N-[(4S,5E,7S)-7-benzyl-8-[(2S)—2-{[(1S)-1-[(1-oxyl-2,2,6,6-tetramethylpiperidin-4-yl)carbamoyl]-2-(4-hydroxyphenyl)ethyl]carbamoyl}pyrrolidin-1-yl]-2-methyl-8-oxooct-5-en-4-yl]carbamate (178).

To a solution of the crude compound 177 (90 mg, 0.15 mmol) in dry CH$_2$Cl$_2$ (5 mL) at 0° C. was treated with HOBt (26 mg, 0.18 mmol), EDCI (38 mg, 0.2 mmol), DIPEA (39 mg, 0.3 mmol) and 4-AT (31 mg, 0.18 mmol). The reaction mixture was stirred at 25° C. for 16 h, then quenched with saturated aqueous NH$_4$Cl solution (20 mL). The aqueous phase was separated and extracted with CH$_2$Cl$_2$ (20 mL), and the combined organic layers were dried over MgSO$_4$ and concentrated in vacuo to give crude product 178 (105 mg, 90%) as a brownish red solid. MS (ESI): [M+H$^+$]=775.6.

Step 6: Synthesis of tert-butyl N-[(4S,5E,7S)-7-benzyl-8-[(2S)—2-{[(1S)-1-[(1-hydroxy-2,2,6,6-tetramethylpiperidin-4-yl)carbamoyl]-2-(4-hydroxyphenyl)ethyl]carbamoyl}pyrrolidin-1-yl]-2-methyl-8-oxooct-5-en-4-yl]carbamate (XVI).

To a solution of compound 178 (105 mg, 0.14 mmol) in dry MeOH (2 mL) was added Vc (27 mg, 0.16 mmol). After stirring at 25° C. for 30 min, the solvent was removed under vacuum. The residue was purified by prep-HPLC (Venusil XBP C18 (5 μm, 30×250 mm), 0.1% HCl in eluant) to give product XVI (42 mg, 34%) as a white solid. MS (ESI): [M+H$^+$]=776.6.

Example XVII

Benzyl N-[(4S)—4-{[(2R)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl]carbamate (XVII)

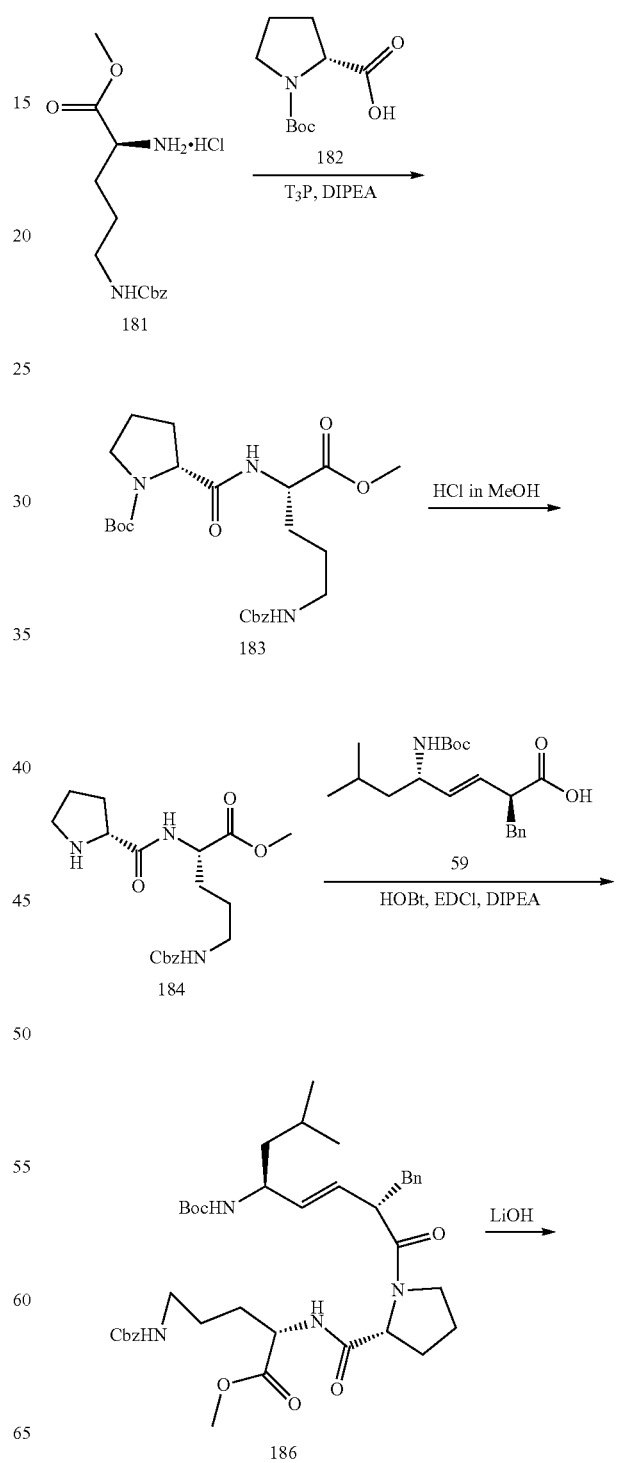

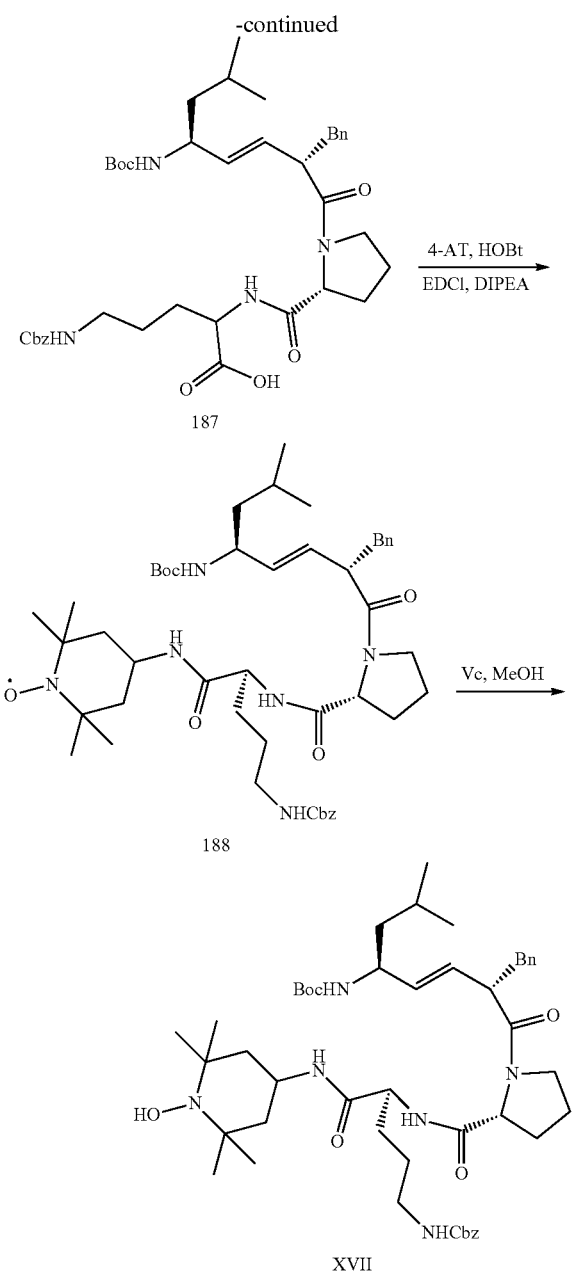

Step 1: Synthesis of tert-butyl 2-{[(2S)—5-{[(benzyloxy) carbonyl]amino}-1-methoxy-1-oxopentan-2-yl] carbamoyl}pyrrolidine-1-carboxylate (183).

To a solution of compound 181 (4.8 g, 15.22 mmol) and compound 182 (3.6 g, 16.74 mmol) in CH₂Cl₂ (50 mL) at 0° C. was added DIPEA (4.3 g, 33.48 mmol) and T₃P (5.8 g, 18.26 mmol). The reaction mixture was allowed to warm to 25° C. and stirred for 16 h. The reaction mixture was washed with aqueous 5% NaHCO₃ (10 mL), aqueous HCl (5 mL, 1 M) and saturated aqueous brine solution (2×20 mL). The organic layer was dried over Na₂SO₄ and concentrated in vacuo. The crude material was purified by column chromatography on silica gel (petroleum ether/EtOAc=5:1 to 1:1) to give product 183 (5.4 g, 75%) as a white solid.

Step 2: Synthesis of methyl (2S)—5-{[(benzyloxy)carbonyl]amino}-2-{[(2R)-pyrrolidin-2-yl] formamido}pentanoate (184).

To a solution of compound 183 (5.4 g, 11.31 mmol) in CH₂Cl₂ (10 mL) was added HCl in MeOH (5 mL, 3 M) and stirred at 25° C. for 2 h. The solvent was removed in vacuo to give product 184 (3.9 g, 93%) as a white solid. MS (ESI): [M+H⁺]=378.2.

Step 3: Synthesis of methyl (2S)—2-{[(2R)-1-[(2S,3E,5S)-2-benzyl-5-{[(tert-butoxy)carbonyl]amino}-7-methyl-oct-3-enoyl]pyrrolidin-2-yl]formamido}-5-{[(benzyloxy) carbonyl]amino}pentanoate (186).

To a solution of compound 184 (276 mg, 0.67 mmol) and compound 59 (220 mg, 0.61 mmol) in CH₂Cl₂ (5 mL) at 0° C. was added HOBt (99 mg, 0.73 mmol), DIPEA (197 mg, 1.53 mmol) and EDCI (139.0 mg, 0.73 mmol). The reaction mixture was washed with aqueous 5% NaHCO₃ (10 mL), aqueous HCl (5 mL, 1 M) and saturated aqueous brine solution (2×20 mL). The organic layer was dried over Na₂SO₄ and concentrated in vacuo. The crude material was purified by column chromatography on silica gel (petroleum ether/EtOAc=3:1 to 1:1) to give product 186 (140 mg, 32%) as a white solid. MS (ESI): [M+H⁻]=721.6.

Step 4: Synthesis of (2S)—2-{[(2R)-1-[(2S,3E,5S)-2-benzyl-5-{[(tert-butoxy)carbonyl]amino}-7-methyloct-3-enoyl]pyrrolidin-2-yl]formamido}-5-{[(benzyloxy)carbonyl]amino}pentanoic acid (187).

To a solution of compound 186 (140 mg, 0.19 mmol) in THF/MeOH=4/1 (4/1 mL) was treated with LiOH.H₂O (16 mg, 0.38 mmol, in 0.2 mL water). The reaction mixture was stirred at 25° C. for 2 h, then the solvent was removed under vacuum. The resulting mixture was treated with EtOAc (10 mL) and aqueous HCl (1 M) until pH=2-3. The organic phase was separated from water phase. The water phase was extracted with EtOAc (2×20 mL), and the combined organic layers were washed with saturated aqueous brine solution (3×10 mL), dried over Na₂SO₄, and concentrated to afford product 187 (118 mg, 88%), which was carried to the next coupling reaction. MS (ESI): [M+H⁺]=707.5.

Step 5: Synthesis of benzyl N-[(4S)—4-{[(2R)-1-[(2S,3E,5S)-2-benzyl-5-{[(tert-butoxy)carbonyl]amino}-7-methyl-oct-3-enoyl]pyrrolidin-2-yl]formamido}-4-[(1-oxyl-2,2,6,6-tetramethylpiperidin-4-yl)carbamoyl]butyl]carbamate (188).

To a solution of compound 187 (118 mg, 0.17 mmol) and 4-AT (34 mg, 0.20 mmol) in CH₂Cl₂ (5 mL) at 0° C. was added HOBt (30 mg, 0.22 mmol), DIPEA (44 mg, 0.34 mmol) and EDCI (42 mg, 0.22 mmol). The reaction mixture was washed with aqueous 5% NaHCO₃ (10 mL), aqueous HCl (5 mL, 1 M) and saturated aqueous brine solution (2×20 mL). The organic layer was dried over Na₂SO₄ and concentrated to give crude product 188 (160 mg) as a white solid. MS (ESI): [M+H⁺]=860.7.

Step 6: Synthesis of benzyl N-[(4S)—4-{[(2R)-1-[(2S,3E,5S)-2-benzyl-5-{[(tert-butoxy)carbonyl]amino}-7-methyl-oct-3-enoyl]pyrrolidin-2-yl]formamido}-4-[(1-hydroxy-2,2,6,6-tetramethylpiperidin-4-yl)carbamoyl]butyl]carbamate (XVII).

To a solution of compound 188 (160.0 mg, 0.18 mmol) in dry MeOH (2 mL) was added Vc (32 mg, 0.18 mmol). After stirring at 25° C. for 60 min, the solvent was removed under vacuum. The residue was purified by prep-HPLC (Venusil XBP C18 (5 μm, 30×250 mm), 0.1% HCl in eluant) to give product XVII (48 mg, 31%) as a white solid. MS (ESI): [M+H⁺]=861.8.

Example XVIII
(S)—Methyl 2-4S)-1-((2S,5S,E)-2-benzyl-5-((tert-butoxycarbonyl)amino)-7-methyloct-3-enoyl)pyrrolidine-2-carboxamido)-5-((((1-hydroxy-2,2,6,6-tetramethylpiperidin-4-yl)oxy)carbonyl)amino)pentanoate (XVIII)
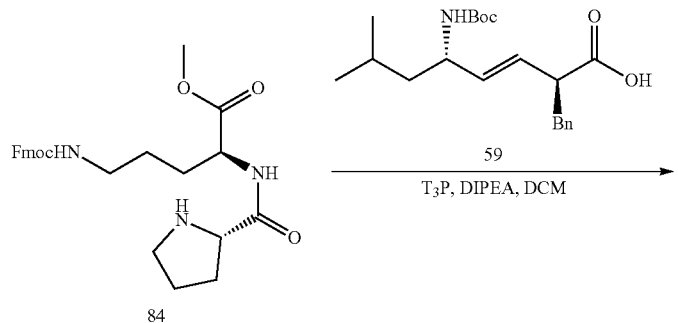
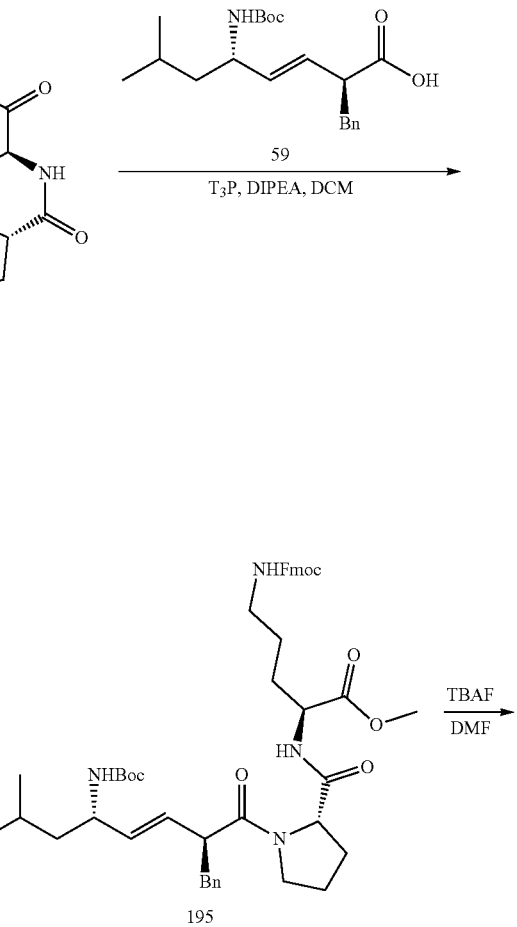
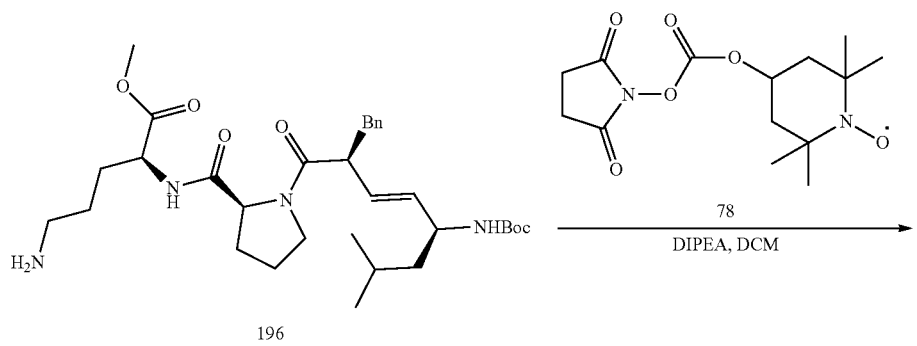

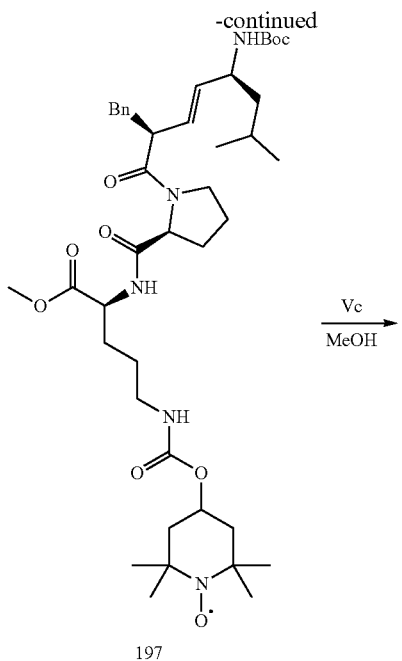

197

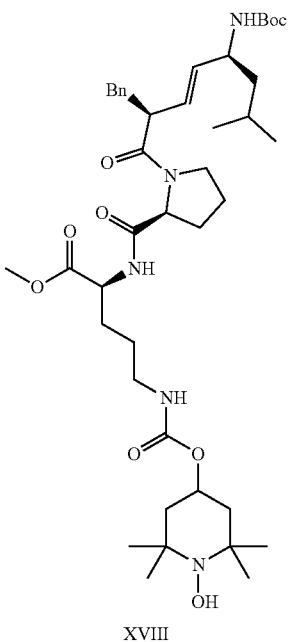

XVIII

Step 1: Synthesis of (S)-methyl 5-((((9H-fluoren-9-yl) methoxy)carbonyl)amino)-2-((S)-1-((2S,5S,E)-2-benzyl-5-((tert-butoxycarbonyl)amino)-7-methyloct-3-enoyl)pyrrolidine-2-carboxamido)pentanoate (195).

To a solution of compound 84 (0.5 mg, 1.0 mmol) and (2S,5S,E)-2-benzyl-5-((tert-butoxycarbonyl)amino)-7-methyloct-3-enoic acid (59, 433 mg, 1.2 mmol) in $CH_2Cl_2$ (5 mL) was added $T_3P$ (413 mg, 1.3 mmol) and DIPEA (284 mg, 2.2 mmol) at 0° C. The reaction mixture was allowed to warm to 25° C. and stirred for 16 h. The reaction mixture was quenched with saturated aqueous $NH_4Cl$ solution (20 mL), and the water layer extracted by EtOAc (3×10 mL). The combined organic layer was washed with aqueous 5% $NaHCO_3$ (10 mL), saturated aqueous brine solution (3×10 mL) and dried over $Na_2SO_4$. The residues were concentrated and purified by column chromatography on silica gel (petroleum ether/EtOAc=3:1 to 1:1) to give product 195 (380 mg, 47%) as a white solid. MS (ESI): [M+H$^-$]=809.6.

Step 2: Synthesis of (S)-methyl 5-amino-2-((S)-1-((2S,5S,E)-2-benzyl-5-((tert-butoxycarbonyl)amino)-7-methyloct-3-enoyl)pyrrolidine-2-carboxamido)pentanoate (196).

To a solution of compound 195 (380 mg, 0.47 mmol) in DMF (5 mL) at 0° C. was added a solution of TBAF (5% wt in THF, 6 mL). The reaction was stirred for 30 min. The mixture 196 (275 mg, 100%) was used for next step without a work up. MS (ESI): [M+H$^+$]=587.4.

Step 3: Synthesis of (S)-methyl 2-((S)-1-((2S,5S,E)-2-benzyl-5-((tert-butoxycarbonyl)amino)-7-methyloct-3-enoyl)pyrrolidine-2-carboxamido)-5-((((1-oxyl-2,2,6,6-tetramethylpiperidin-4-yl)oxy)carbonyl)amino)pentanoate (197).

To a solution of compound 196 (275 mg, 0.47 mmol) and 1,3-dioxoisoindolin-2-yl (1-oxyl-2,2,6,6-tetramethylpiperidin-4-yl)carbonate (78) (203 mg, 0.56 mmol) in $CH_2Cl_2$ (5 mL) at 0° C. was added DIPEA (121 mg, 0.94 mmol). The reaction mixture was allowed to warm to 25° C. and stirred for 2 h. The reaction mixture was quenched with saturated aqueous $NH_4Cl$ solution (20 mL), and water phase extracted by EtOAc (3×10 mL). The combined organic layer was washed with water (2×10 mL), saturated aqueous brine solution (3×20 mL) and dried over $Na_2SO_4$. The residue was concentrated under reduced pressure and purified by prep-HPLC (Venusil XBP C18 (5 μm, 30×250 mm), 0.1% HCl in eluant) to give product 197 (30 mg, 8%) as a pale red solid. MS (ESI): [M+H$^+$]=785.6.

Step 4: Synthesis of (S)-methyl 2-((S)-1-((2S,5S,E)-2-benzyl-5-((tert-butoxycarbonyl)amino)-7-methyloct-3-enoyl)pyrrolidine-2-carboxamido)-5-((((1-hydroxy-2,2,6,6-tetramethylpiperidin-4-yl)oxy)carbonyl)amino)pentanoate (XVIII).

To a solution of compound 197 (25 mg, 0.03 mmol) in dry MeOH (2 mL) was added Vc (5.3 mg, 0.03 mmol). After stirring at 25° C. for 30 min, the solvent was removed under vacuum. The resulting residue was purified by prep-HPLC (Venusil XBP C18 (5 μm, 30×250 mm), 0.1% HCl in eluant) to give product XVIII (7 mg, 28%) as a white solid. MS (ESI): [M+H$^+$]=787.4.

Example XX
tert-Butyl N-(4-{[(2S)-1-[(2R,3E,5S)-2-benzyl-5-{[(tert-butoxy)carbonyl]amino}-7-methyloct-3-enoyl]pyrrolidin-2-yl]formamido}-4-[(1-oxyl-2,2,6,6-tetramethylpiperidin-4-yl)carbamoyl]butyl)carbamate (XX)
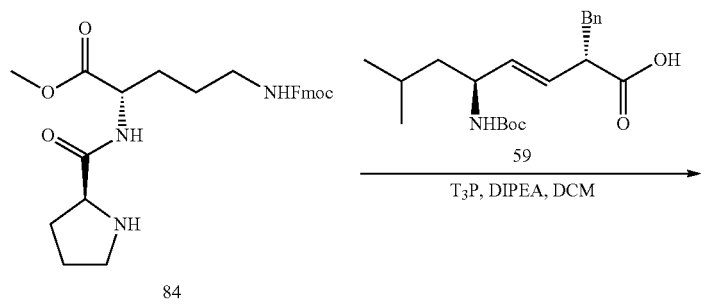
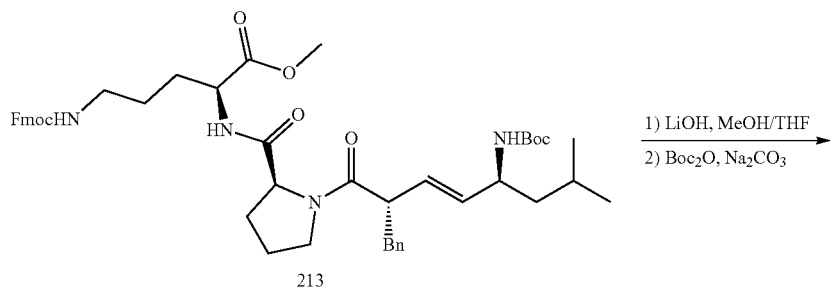
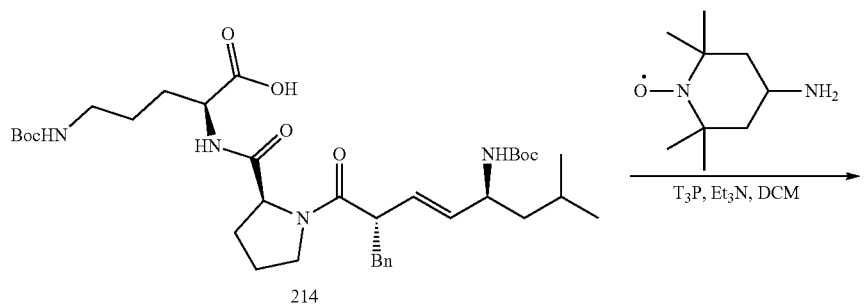
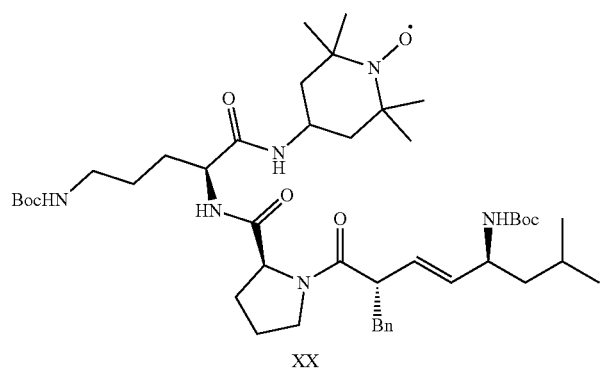

Step 1: Synthesis of methyl 2-{[(2S)-1-[(2R,3E,5S)-2-benzyl-5-{[(tert-butoxy)carbonyl]amino}-7-methyloct-3-enoyl]pyrrolidin-2-yl]formamido}-5-({[(9H-fluoren-9-yl)methoxy]carbonyl}amino)pentanoate (213).

To the solution of compound 84 (300 mg, 0.65 mmol) and intermediate 59 (0.2 g, 0.6 mmol) suspended in CH$_2$Cl$_2$ (20 mL) at 0° C. was added DIPEA (0.4 mL, 2 mmol). T$_3$P (50% in EtOAc, 0.9 mL, 1 mmol) was added slowly, and the reaction mixture was allowed to warm to 25° C. and stirred for 18 h. The reaction mixture was washed with 5% aqueous Na$_2$CO$_3$ solution (10 mL) and water (2×10 mL), and the organic layer was dried over MgSO$_4$ and concentrated in vacuo. The crude product was purified by column chromatography (silica gel with eluting solvent-petroleum ether/EtOAc=1:3), to obtain an oil product 213 (210 mg, 43%). MS (ESI): [M+H$^+$]=809.6.

Step 2: Synthesis of 2-{[(2S)-1-[(2R,3E,5S)-2-benzyl-5-{[(tert-butoxy)carbonyl]amino}-7-methyloct-3-enoyl]pyrrolidin-2-yl]formamido}-5-{[(tert-butoxy)carbonyl]amino}pentanoic acid (214).

To a solution of compound 213 (210 mg, 0.26 mmol) in THF/MeOH (4.0/1.0 mL) was treated with LiOH.H$_2$O (20 mg, 0.40 mmol in 0.2 mL water). The reaction mixture was stirred at 25° C. for 4 h, then the solvent was removed under vacuum. The resulting mixture was treated with EtOAc (20 mL) and aqueous HCl (1 M) until pH 3-4. The organic phase was separated from water phase. The water phase was extracted with EtOAc (2×20 mL), and the combined organic layers were washed with saturated aqueous brine solution (3×10 mL), dried over Na$_2$SO$_4$, and concentrated to afford the crude product 100 mg. The crude product was added into CH$_2$Cl$_2$ (10 mL), then Boc$_2$O (60 mg, 0.26 mmol) and DIPEA (20 mg, 0.26 mmol), the mixture was stirred at 25° C. for 16 h. The reaction was quenched by HCl (1 M) to pH 3-4, and extracted by EtOAc (2×20 mL). The combined organic phase was washed with water (2×10 mL), saturated aqueous brine solution (3×10 mL), dried over Na$_2$SO$_4$, and the solvent was removed under reduced pressure to give an oil product 214 (150 mg, 86%). MS (ESI): [M+H$^+$]=673.4.

Step 3: Synthesis of tert-butyl N-(4-{[(2S)-1-[(2R,3E,5S)-2-benzyl-5-{[(tert-butoxy)carbonyl]amino}-7-methyl-oct-3-enoyl]pyrrolidin-2-yl]formamido}-4-[(1-oxyl-2,2,6,6-tetramethylpiperidin-4-yl)carbamoyl]butyl)carbamate (XX).

To a solution of the compound of acid 214 (150 mg, 0.22 mmol) in CH$_2$Cl$_2$ (20 mL) at 0° C. was added 4-AT (75 mg, 0.44 mmol) and DIPEA (60 mg, 0.44 mmol). T$_3$P (50% in EtOAc, 0.2 mL, 0.4 mmol) was added slowly, and the reaction mixture was allowed to warm to 25° C. and stirred for 16 h. The reaction mixture was washed with 5% aqueous Na$_2$CO$_3$ solution, dried over MgSO$_4$, and concentrated in vacuo. The oil residue was purified by prep-HPLC (Venusil XBP C18 (5 μm, 30×250 mm), 0.1% HCl in eluant) to give product XX (6 mg, 3%). MS (ESI): [M+H$^+$]=826.7.

Example XXI tert-Butyl N-[(4S,5E,7S)-7-benzyl-8-[(2R)—2-{[(1S)—4-{[(tert-butoxy)carbonyl]amino}-1-[(1-hydroxy-2,2,6,6-tetramethylpiperidin-4-yl)carbamoyl]butyl]carbamoyl}pyrrolidin-1-yl]-2-methyl-8-oxooct-5-en-4-yl]carbamate (XXI)

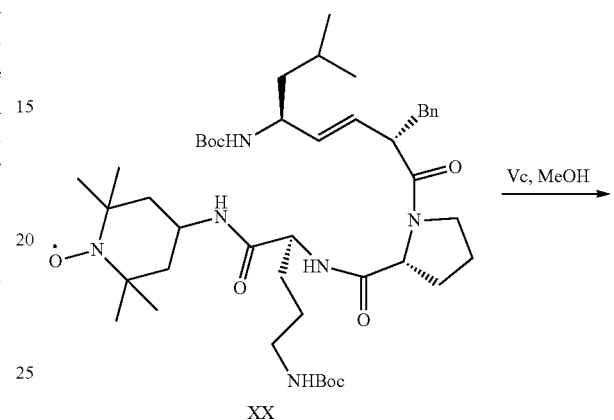

Step 1: Synthesis of tert-butyl N-[(4S,5E,7S)-7-benzyl-8-[(2R)—2-{[(1S)—4-{[(tert-butoxy)carbonyl]amino}-1-[(1-hydroxy-2,2,6,6-tetramethylpiperidin-4-yl)carbamoyl]butyl]carbamoyl}pyrrolidin-1-yl]-2-methyl-8-oxooct-5-en-4-yl]carbamate (216).

To a solution of compound XX (20 mg, 0.02 mmol) in MeOH (10 mL), was added Vc (10 mg, 0.10 mmol). After stirring at 25° C. for 60 min, the solvent was removed under vacuum. The residue was purified by prep-HPLC (Venusil XBP C18 (5 μm, 30×250 mm), 0.1% HCl in eluant) to give product XXI (15 mg, 75%) as a white solid. MS (ESI): [M+H$^+$]=827.7.

Example XXII
(2S)—2-{[(2S)-1-[(2S,3E,5S)-5-amino-2-benzyl-7-methyloct-3-enoyl]Pyrrolidin-2-yl]formamido}-5-carbamimidamido-N-(1-oxyl-2,2,6,6-tetramethylpiperidin-4-yl)pentanamide (XXII)
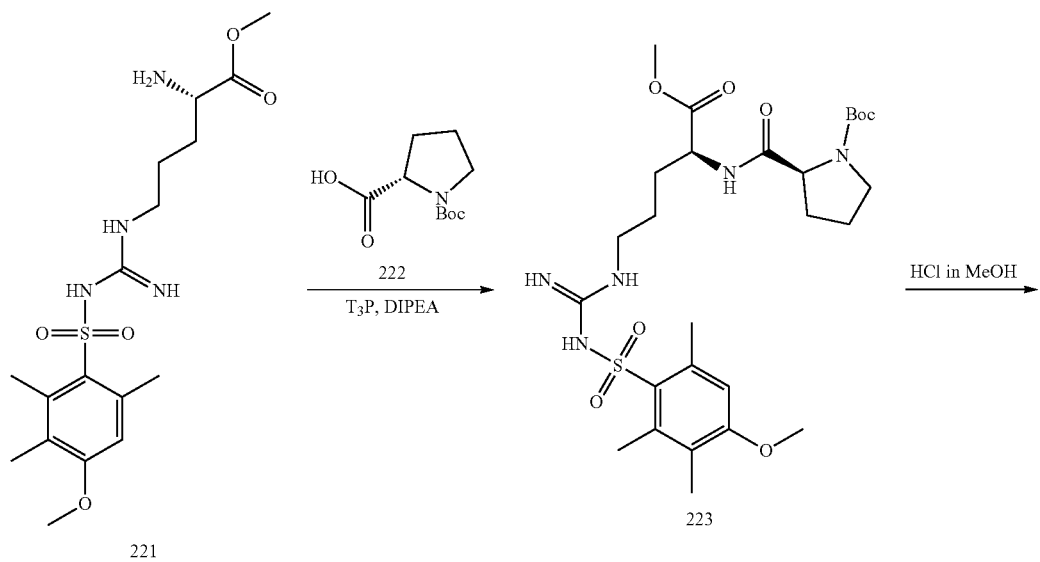
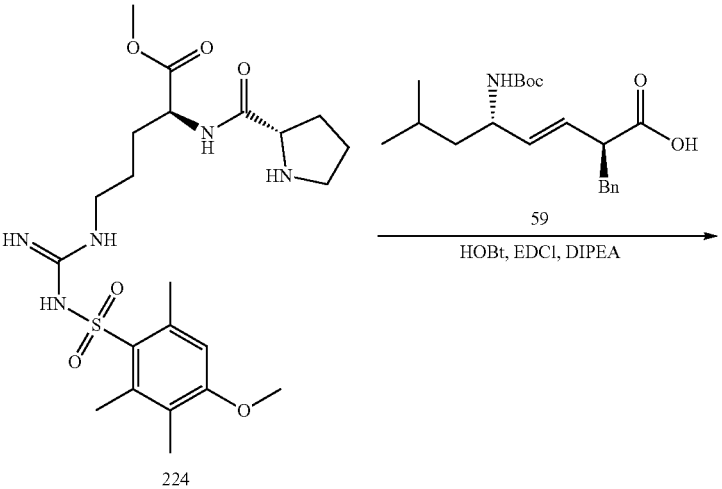
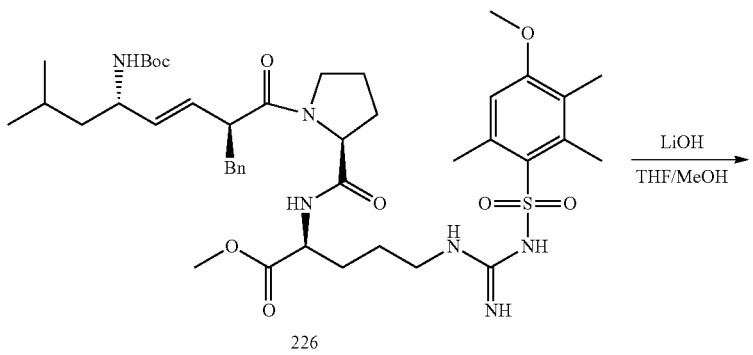

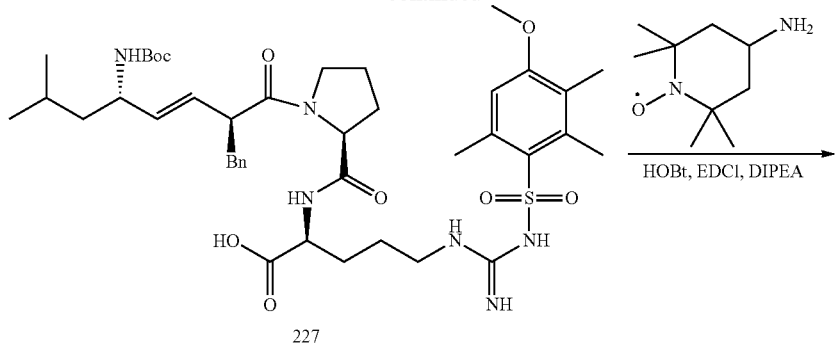

227

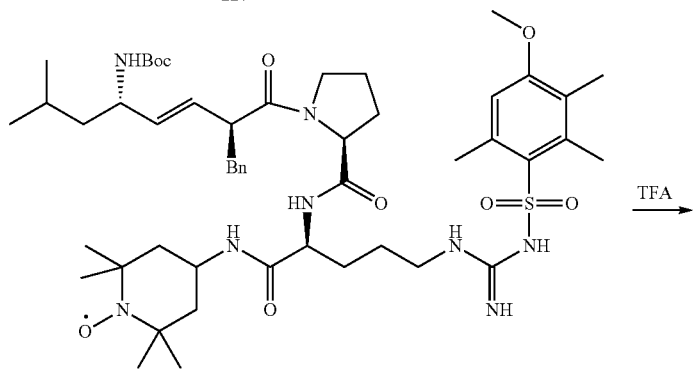

228

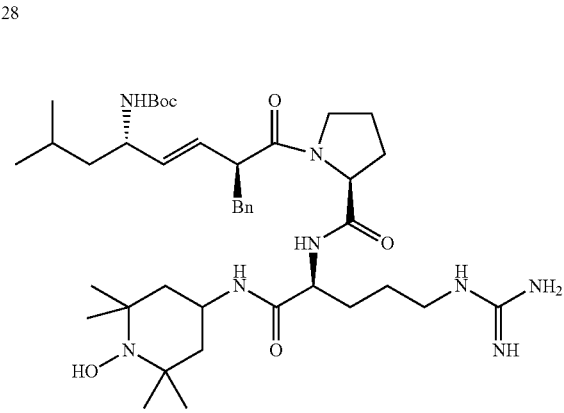

XXII

Step 1: Synthesis of tert-butyl (2S)—2-{[(2S)-1-methoxy-5-[N'-(4-methoxy-2,6-dimethyl-benzenesulfonyl)carbamimidamido]-1-oxopentan-2-yl]carbamoyl}pyrrolidine-1-carboxylate (223).

To a solution of compound 221 (360 mg, 0.9 mmol) and compound 222 (213 g, 0.99 mmol) in CH$_2$Cl$_2$ (3 mL) at 0° C. was added T$_3$P (343 mg, 1.1 mmol) and DIPEA (232 mg, 1.8 mmol). The reaction mixture was allowed to warm to 25° C. and stirred for 16 h. The reaction mixture was washed with aqueous 5% NaHCO$_3$, aqueous HCl (5 mL, 1 M), and saturated aqueous brine solution (3×10 mL). The organic layer was dried over Na$_2$SO$_4$ and concentrated to give product 223 (390 mg, 72%) as a white foam. MS (ESI): [M+H$^+$]=598.3.

Step 2: Synthesis of methyl (2S)-5-[N-(4-methoxy-2,3,6-trimethylbenzenesulfonyl)carbamimidamido]-2-{[(2S)-pyrrolidin-2-yl]formamido}pentanoate (224).

To a solution of compound 223 (390 mg, 0.65 mmol) in CH$_2$Cl$_2$ (10 mL) was added HCl in MeOH (10 mL, 3 M) was stirred at 25° C. for 2 h. Then the solvent was removed to give product 224 (323 mg, 100%) as a white foam. MS (ESI): [M+H$^+$]=498.2.

Step 3: Synthesis of methyl (2S)—2-{[(2S)-1-[(2S,3E,5S)-2-benzyl-5-{[(tert-butoxy)carbonyl]amino}-7-methyl-oct-3-enoyl]pyrrolidin-2-yl]formamido}-5-[N'-(4-methoxy-2,3,6-trimethylbenzenesulfonyl)carbamimidamido]pentanoate (226).

To a solution of compound 224 (200 mg, 0.4 mmol) and compound 59 (160 mg, 0.44 mmol) in CH$_2$Cl$_2$ (3 mL) at 0° C. was added HOBt (70 mg, 0.52 mmol), EDCI (100 mg, 0.52 mmol) and DIPEA (103 mg, 0.80 mmol). The reaction mixture was allowed to warm to 25° C. and stirred for 16 h. The reaction mixture was quenched with saturated NH$_4$Cl solution (20 mL), washed with aqueous HCl (10 mL, 1 M), saturated aqueous brine solution (2×20 mL), dried over Na$_2$SO$_4$ and concentrated. The residue was purified by column chromatography on silica gel (petroleum ether/EtOAc=3:1 to 1:1) to give product 226 (120 mg, 36%) as a white foam. MS (ESI): [M+H$^+$]=841.1.

Step 4: Synthesis of (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-5-[N'-(4-methoxy-2,3,6-trimethyl-benzenesulfonyl)carbamimidamido]pentanoic acid (227).

To a solution of the compound 226 (120 mg, 0.14 mmol) in THF/MeOH (4.0/2.0 mL) was treated with LiOH.H$_2$O (12 mg, 0.28 mmol in 0.2 mL water). The reaction mixture was stirred at 25° C. for 2 h, then the solvent was removed under vacuum and the resulting mixture treated with EtOAc (20 mL) and aqueous HCl (1 M) until pH 3. The organic phase was separated from water phase. The water phase was extracted with EtOAc (2×20 mL), and the combined organic layers were washed with saturated aqueous brine solution (2×20 mL), dried over Na$_2$SO$_4$, and concentrated to afford product 227 (100 mg, 86%), which was used for next step without purification. MS (ESI): [M+H+]=827.6.

Step 5: Synthesis of tert-butyl N-[(4S,5E,7S)-7-benzyl-8-[(2S)—2-{[(1S)-1-[(1-oxyL-2,2,6,6- tetramethylpiperidin-4-yl)carbamoyl]-4-[N'-(4-methoxy-2,3,6-trimethyl-benzenesulfonyl)carbamimidamido]butyl]carbamoyl pyrrolidin-1-yl]-2-methyl-8-oxooct-5-en-4-yl]carbamate (228).

To a solution of the crude compound 227 (100 mg, 0.12 mmol) in dry CH$_2$Cl$_2$ (3 mL) at 0° C. was treated with HOBt (22 mg, 0.16 mmol), EDCI (31 mg, 0.16 mmol) and DIPEA (31.0 mg, 0.24 mmol) and 4-AT (22.0 mg, 0.13 mmol). The reaction mixture was stirred at 25° C. for 3 h, then quenched with saturated aqueous NH$_4$Cl solution (20 mL). The aqueous phase was separated and extracted with CH$_2$Cl$_2$ (10 mL), and the combined organic layers were dried over MgSO$_4$ and concentrated to give product 228 (120 mg, crude) as an orange solid. MS (ESI): [M+H$^+$]=980.8.

Step 6: Synthesis of (2S)—2-{[(2S)-1-[(2S,3E,5S)-5-amino-2-benzyl-7-methyloct-3-enoyl]pyrrolidin-2-yl]formamido}-5-carbamimidamido-N-(1-oxyl-2,2,6,6-tetramethylpiperidin-4-yl)pentanamide (XXII).

A solution of compound 228 (20 mg, 0.02 mmol) in TFA (1 mL) was stirred at 25° C. for 4 h and then the solvent was removed. The residue was purified by prep-HPLC (Venusil XBP C18 (5 µm, 30×250 mm), 0.1% TFA in eluant) to give product XXII (4.2 mg, 31%) as a white foam. MS (ESI): [M+H$^-$]=699.5.

Example XXIII (2R)—2-{[(2S)-1-[(2S,3E,5S)-5-amino-2-benzyl-7-methyloct-3-enoyl]Pyrrolidin-2-yl]formamido}-N-(1- hydroxy-2,2,6,6-tetramethylpiperidin-4-yl)-3-methylbutanamide (XXIII)

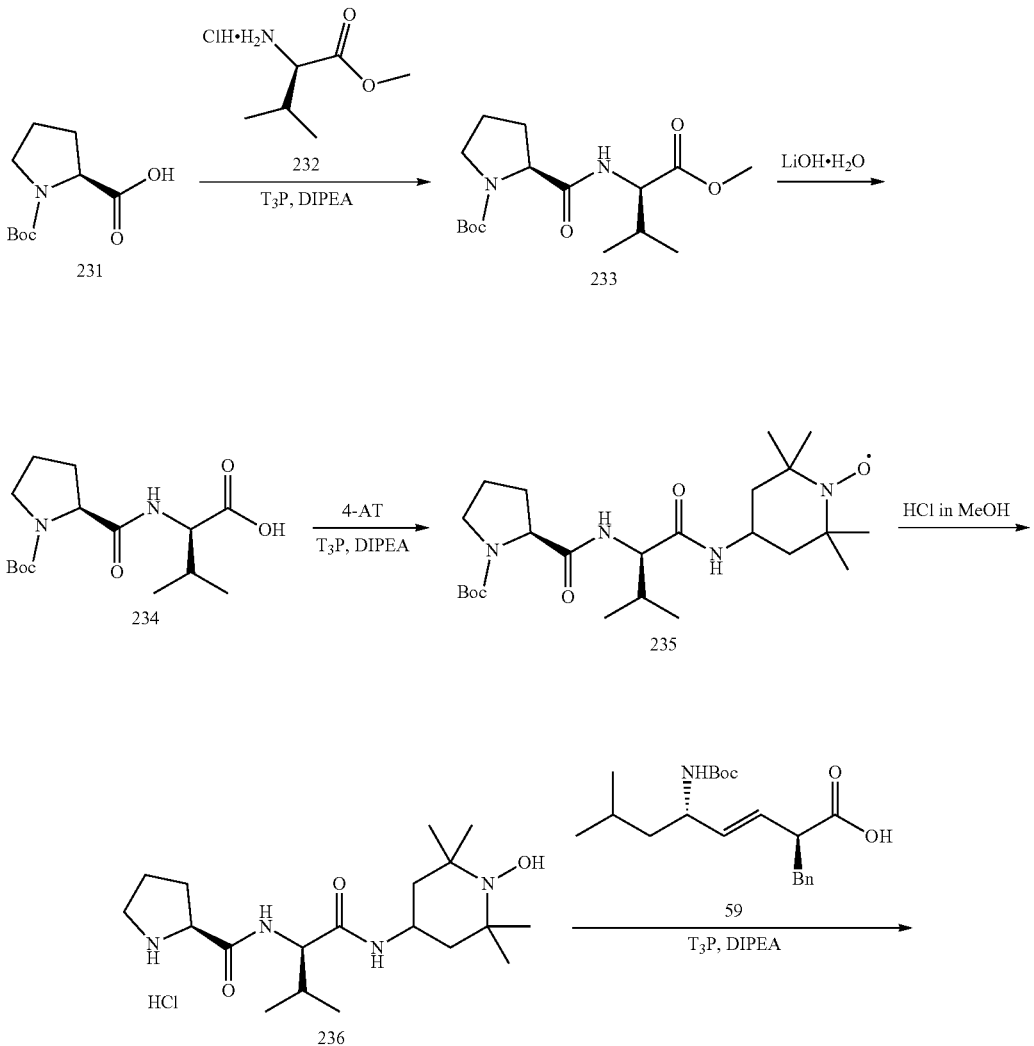

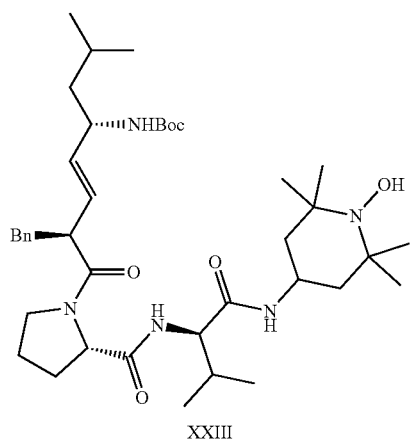

XXIII

Step 1: Synthesis of tert-butyl (2S)—2-{[(2R)-1-methoxy-3-methyl-1-oxobutan-2-yl]carbamoyl}pyrrolidine-1-carboxylate (233).

To a solution of compound 231 (2.0 g, 9.30 mmol) and compound 232 (1.7.0 g, 10.23 mmol) in $CH_2Cl_2$ (10 mL) at 0° C. was added $T_3P$ (3.5 g), and DIPEA (2.4 g, 18.6 mmol). The reaction mixture was allowed to warm to 25° C. and stirred for 3 h and then removed the solvent in vacuo. The mixture was dissolved in EtOAc (10 mL), washed with aqueous 5% $NaHCO_3$ (10 mL), and saturated aqueous brine solution (2×20 mL), dried over $Na_2SO_4$ and concentrated in vacuo to give crude product 233 (2.0 g, 67%) as a white foam. MS (ESI): [M+H$^+$]=329.0.

Step 2: Synthesis of (2R)—2-{[(2S)-1-[(tert-butoxy)carbonyl]pyrrolidin-2-yl]formamido}-3-methylbutanoic acid (234).

A solution of compound 233 (2.0 g, 6.1 mmol) in THF/MeOH (12.0/3.0 mL) was treated with $LiOH.H_2O$ (33.0 mg, 0.80 mmol in 0.2 mL water). The reaction mixture was stirred at 25° C. for 3 h, then the solvent was removed under vacuum and the resulting mixture treated with EtOAc (10 mL) and aqueous HCl (1 M) until pH 3-4. The organic phase was separated from water phase. The water phase was extracted with EtOAc (2×20 mL), and the combined organic layers were washed with saturated aqueous brine solution (2×20 mL), dried over $Na_2SO_4$, and concentrated in vacuo to afford product 234 (1.6 g, 84%) as a white foam, which was used for next step without purification. MS (ESI): [M+H$^-$]=315.0.

Step 3: Synthesis of tert-butyl (2S)—2-{[(1R)-1-[(1-oxyl-2,2,6,6-tetramethylpiperidin-4-yl)carbamoyl]-2-methylpropyl]carbamoyl}pyrrolidine-1-carboxylate (235).

A solution of the crude compound 234 (1.8 g, 5.73 mmol) in dry $CH_2Cl_2$ (5 mL) at 0° C. was treated with $T_3P$ (2.2 g, 6.88 mmol), DIPEA (1.5 g, 11.46 mmol), and 4-AT (1.1 g, 6.31 mmol). The reaction mixture was allowed to warm to 25° C. and stirred for 3 h and then removed the solvent in vacuo. The mixture was dissolved in EtOAc (20 mL), washed with aqueous 5% $NaHCO_3$(10 mL), and saturated aqueous brine solution (2×20 mL), dried over $Na_2SO_4$ and concentrated in vacuo to give crude product 235 (1.4 g, 54%) as a white foam. MS (ESI): [M+H$^+$]=468.3.

Step 4: Synthesis of (2R)—N-(1-hydroxy-2,2,6,6-tetramethylpiperidin-4-yl)-3-methyl-2-{[(2S)-pyrrolidin-2-yl]formamido}butanamide hydrochloride (236).

A solution of compound 235 (1.4 g, 3.0 mmol) in HCl in MeOH (10 mL, 3 M) was stirred at 25° C. for 3 h. The solvent as removed in vacuo to give product 236 (0.7 g, 64%) as a red oil. MS (ESI): [M+H$^-$]=368.3.

Step 5: Synthesis of (2R)—2-{[(2S)-1-[(2S,3E,5S)-5-amino-2-benzyl-7-methyloct-3-enoyl]pyrrolidin-2-yl]formamido}-N-(1-hydroxy-2,2,6,6-tetramethylpiperidin-4-yl)-3-methylbutanamide (XXIII).

To a solution of compound 236 (223 mg, 0.61 mmol) and intermediate 59 (200 mg, 0.55 mmol) in $CH_2Cl_2$ (5 mL) at 0° C. was added $T_3P$ (210 mg, 0.66 mmol), and DIPEA (142 mg, 1.1 mmol). The reaction mixture was allowed to warm to 25° C. and stirred for 3 h and then removed the solvent in vacuo. The mixture was dissolved in EtOAc (10 mL), washed with aqueous 5% $NaHCO_3$(10 mL), and saturated aqueous brine solution (2×10 mL), dried over $Na_2SO_4$ and concentrated in vacuo. The residue was purified by prep-HPLC (Venusil XBP C18 (5 μm, 30×250 mm), 0.1% HCl in eluant) to give product XXIII (6.4 mg, yield 4%) as white solid. MS (ESI): [M+H$^+$]=712.6.

Example XXIV
Benzyl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-{[(4-hydroxy-2,6-dimethylphenyl)methyl]carbamoyl}butyl]carbamate (XXIV)
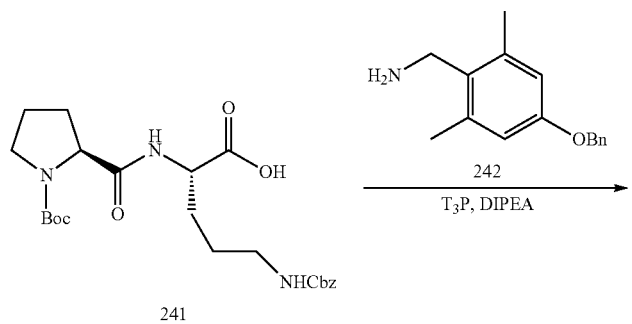
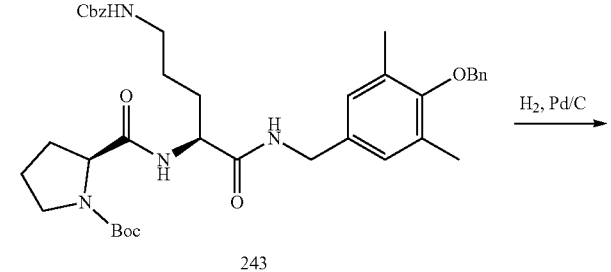
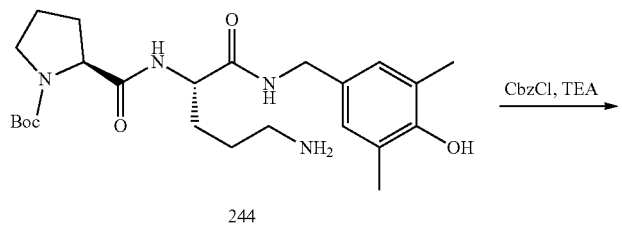
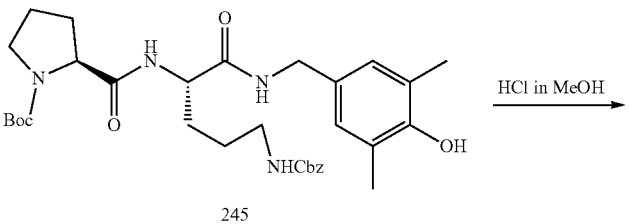
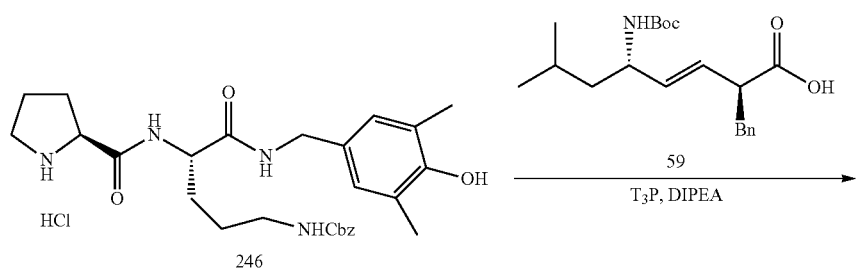

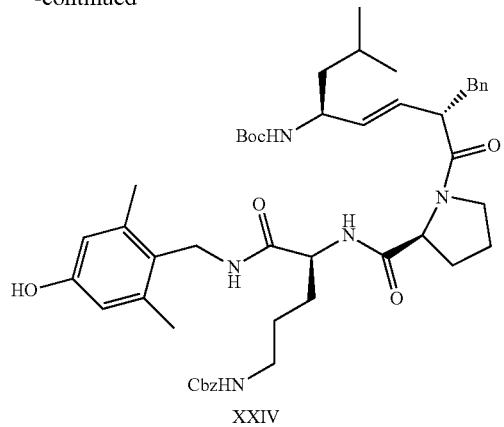

XXIV

Step 1: Synthesis of (S)-tert-butyl 2-(((S)-1-((4-(benzyloxy)-3,5-dimethylbenzyl)amino)-5-(((benzyloxy)carbonyl)amino)-1-oxopentan-2-yl)carbamoyl)pyrrolidine-1-carboxylate (243).

To a solution of compound 241 (1.5 g, 3.25 mmol this compound was syntheized from compound 193) and compound 242 (870 mg, 3.6 mmol) in $CH_2Cl_2$ (10 mL) at 0° C. was added $T_3P$ (1.3 g, 4.25 mmol), and DIPEA (840 mg, 6.5 mmol). The reaction mixture was allowed to warm to 25° C. and stirred for 3 h and then removed the solvent in vacuo. The mixture was dissolved in EtOAc (10 mL), washed with aqueous 5% $NaHCO_3$ (10 mL), and saturated aqueous brine solution (2×20 mL), dried over $Na_2SO_4$ and concentrated in vacuo to give crude product 243 (1.5 g, 85%) as a white foam. MS (ESI): [M+H$^+$]=687.4.

Step 2: Synthesis of (S)-tert-butyl 2-(((S)-5-amino-1-((4-hydroxy-3,5-dimethylbenzyl)amino)-1-oxopentan-2-yl)carbamoyl)pyrrolidine-1-carboxylate (244).

To a solution of compound 243 (1.5 g, 2.19 mmol) in MeOH (10 mL) was added Pd/C (0.1 g, 10%) at 25° C. under one atmosphere of hydrogen gas with balloon. The mixture was stirred at 25° C. for 16 h. Then the reaction was filtered and concentrated in vacuo to give product 244 (0.75 g, 75%) as a white solid. MS (ESI): [M+H$^+$]=463.2.

Step 3: Synthesis of (S)-tert-butyl 2-(((S)-5-(((benzyloxy)carbonyl)amino)-1-((4-hydroxy-3,5-dimethylbenzyl)amino)-1-oxopentan-2-yl)carbamoyl)pyrrolidine-1-carboxylate (245).

To a solution of compound 244 (750 mg, 1.62 mmol) in $CH_2Cl_2$ (5 mL) at 0° C. was added TEA (245 mg, 2.43 mmol) and CbzCl (290 mg, 1.7 mmol). The reaction mixture was allowed to warm to 25° C. and stirred for 3 h. The reaction was quenched with aqueous saturated $NH_4Cl$ solution (10 mL). The organic layer was washed with saturated aqueous brine solution (2×10 mL), dried over $Na_2SO_4$ and concentrated in vacuo. The residue was purified via column chromatography (silica gel, petroleum ether/EtOAc=3:1 to 1:1) to give product 245 (580 mg, 60%) as a white solid. MS (ESI): [M+H$^+$]=597.3.

Step 4: Synthesis of benzyl ((S)-5-((4-hydroxy-3,5-dimethylbenzypamino)-5-oxo-4-((S)-pyrrolidine-2-carboxamido)pentyl)carbamate (246).

A solution of compound 245 (0.4 g, 0.67 mmol) in HCl in MeOH (5 ml, 3 M) was stirred at 25° C. for 3 h. The solvent as removed in vacuo to give product 246 (350 mg, 98%) as a white solid. MS (ESI): [M+H$^+$]=497.3.

Step 5: Synthesis of benzyl N-[(4S)—4-{[(2S)-1-[(2S,3E,5S)-2-benzyl-5-{[(tert-butoxy)carbonyl]amino}-7-methyl-oct-3-enoyl]pyrrolidin-2-yl]formamido}-4-{[(4-hydroxy-2,6-dimethylphenyl)methyl]carbamoyl}butyl]carbamate (XXIV).

To a solution of compound 246 (350 mg, 0.66 mmol) and compound 59 (250 mg, 0.69 mmol) in $CH_2Cl_2$ (5 mL) at 0° C. was added $T_3P$ (251 mg, 0.79 mmol), and DIPEA (170 mg, 1.32 mmol). The reaction mixture was allowed to warm to 25° C., stirred for 3 h and then removed the solvent in vacuo. The mixture was dissolved in EtOAc (20 mL), washed with aqueous 5% $NaHCO_3$(10 mL), and saturated aqueous brine solution (3×10 mL), dried over $Na_2SO_4$ and concentrated. The residue was purified by prep-HPLC (Venusil XBP C18 (5 µm, 30×250 mm), 0.1% HCl in eluant) to give product XXIV (110 mg, yield 20%) as white solid. MS (ESI): [M+H$^+$]=840.7.

Example XXV

1-Hydroxy-2,2,6,6-tetramethylpiperidin-4-yl N-[(4S,5E,7S)-7-benzyl-8-[(2S)—2-{[(1S)—1-{[(1S)—4-{[(benzyloxy)carbonyl]amino}-1-[(1-hydroxy-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl]carbamate dihydrochloride (XXV)

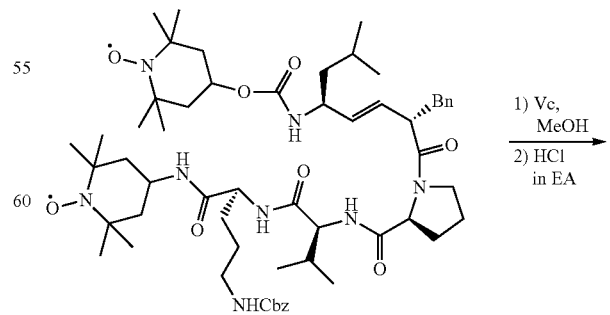

VIII

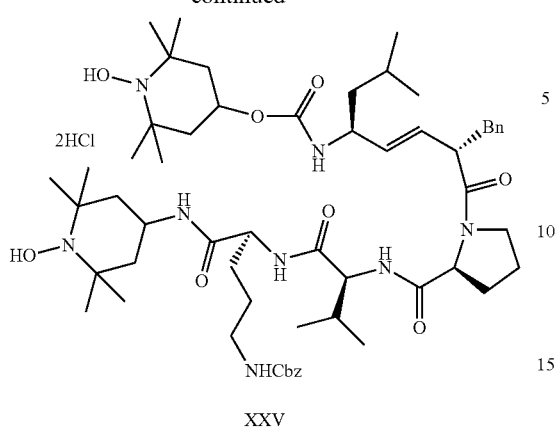

XXV

Step 1: Synthesis of 1-hydroxy-2,2,6,6-tetramethylpiperidin-4-yl N-[(4S,5E,7S)-7-benzyl-8-[(2S)—2-{[(1S)—1-{[(1S)—4-{[(benzyloxy)carbonyl]amino}-1-[(1-hydroxy-2,2,6,6-tetramethylpiperidin-4-yl)carbamoyl]butyl]carbamoyl}-2-methylpropyl]carbamoyl}pyrrolidin-1-yl]-2-methyl-8-oxooct-5-en-4-yl]carbamate dihydrochloride (XXV).

To a solution of compound VIII (30 mg, 0.028 mmol) in dry MeOH (3 mL) was added Vc (5 mg, 0.028 mmol). After stirring at 25° C. for 1 h, the solvent was removed under vacuum. The residue was purified by prep-HPLC (Venusil XBP C18 (5 μm, 30×250 mm), 0.1% HCl in eluant) to give product XXV (27 mg, 84%) as a white solid. MS (ESI): [M+H⁺]=1060.0.

Example XXVI and XXVII

Benzyl N—[(5 S)—5-{[(2S)-1-[(2S,3E,5S)-2-benzyl-5-{[(tert-butoxy)carbonyl]amino}-7-methyloct-3-enoyl]pyrrolidin-2-yl]formamido}-5-[(1-oxyl-2,2,6,6-tetramethylpiperidin-4-yl)carbamoyl]pentyl]carbamate (XXVI) and Benzyl N-[(5S)—5-{[(2S)-1-[(2S,3E,5S)-2-benzyl-5-{[(tertbutoxy)carbonyl]amino}-7-methyloct-3-enoyl]pyrrolidin-2-yl]formamido}-5-[(1-hydroxy-2,2,6,6-tetramethylpiperidin-4-yl)carbamoyl]pentyl]carbamate (XXVII)

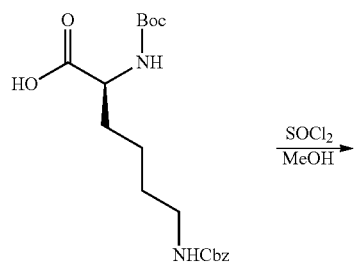

251

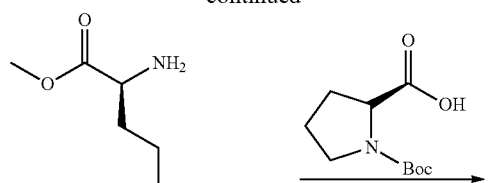

252

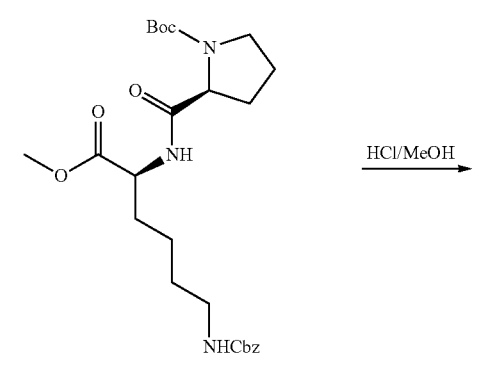

253

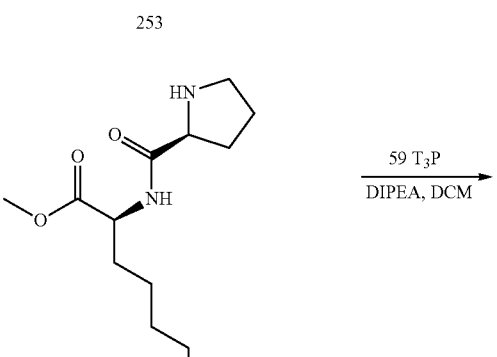

254

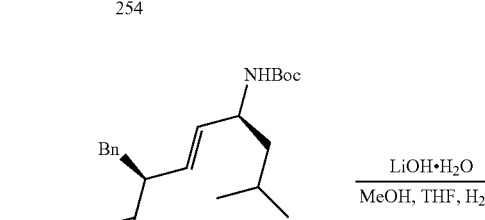

255

129

-continued

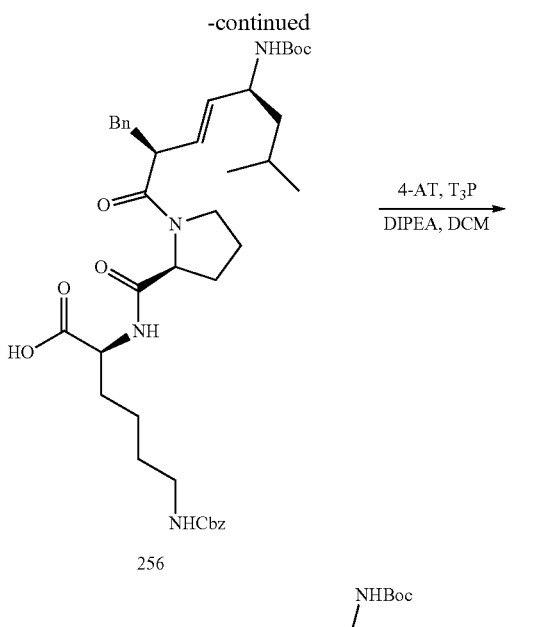

256

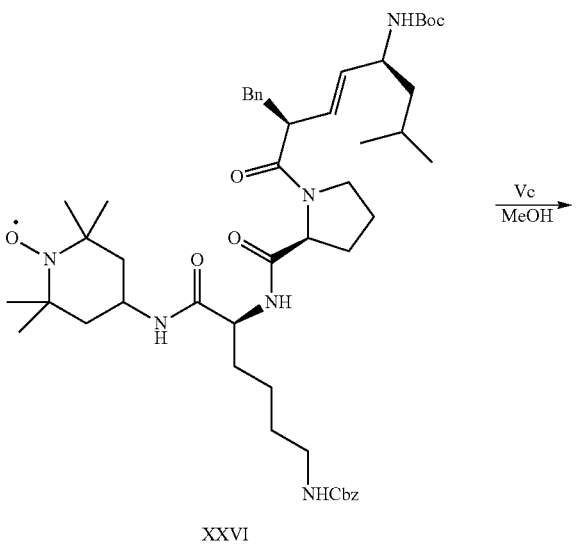

XXVI

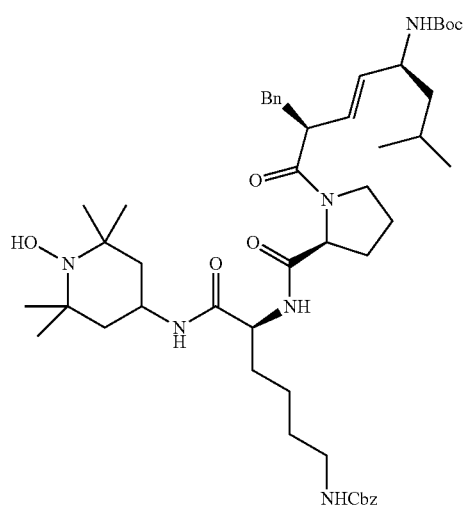

XXVII

130

Step 1: synthesis of (S)-methyl 2-amino-6-(((benzyloxy) carbonyl)amino)hexanoate (252)

To a solution of 251 (2 g, 5.26 mmol) in MeOH (20 mL) was added $SOCl_2$ (6.21 g, 52.6 mmol). The mixture was stirred at 25° C. for 12 h and concentrated in vacuo to obtain the titled compound 252 (1.74 g, 100%) as a white solid. MS (ESI): $[M+H^+]$=294.9.

Step 2: synthesis of (S)-tert-butyl 2-(((S)-6-(((benzyloxy) carbonyl)amino)-1-methoxy-1-oxohexan-2-yl)carbamoyl) pyrrolidine-1-carboxylate (253).

To a solution of compound 252 (1.74 g, 5.26 mmol), (S)-1-(tert-butoxycarbonyl)pyrrolidine-2-carboxylic acid (1.7 g, 7.89 mmol) in $CH_2Cl_2$ (20 mL) was added DIPEA (2.04 g, 15.78 mmol) and $T_3P$ (4.35 g, 6.84 mmol, 50% in EtOAc). The mixture was stirred at 25° C. for 10 h, then the organic solution was concentrated in vacuo. To the residue was added EtOAc (100 mL) and washed with $H_2O$ (3×20 mL). The organic phase was collected and concentrated to obtain the titled compound 253 (2.6 g, 100%) as a white solid. MS (ESI): $[M+H^+]$=492.2.

Step 3: synthesis of (S)-methyl 6-(((benzyloxy)carbonyl) amino)-2-((5)—pyrrolidine-2-carboxa-mido)hexanoate (254).

To a 50-mL single-neck flask was added compound 253 (2.6 g, 5.26 mmol) and HCl in MeOH (40 mL, 3 M), then the mixture was stirred at 25° C. for 1 h. The organic solution was concentrated and dried under vacuum pump to obtain the titled compound 254 (2.25 g, 100%) as a white solid. MS (ESI): $[M+H^+]$=392.1.

Step 4: synthesis of (S)-methyl 2-((S)-1-((2S,5S,E)-2-benzyl-5-((tert-butoxycarbonyl)amino)-7-methyloct-3-enoyl)pyrrolidine-2-carboxamido)-6-(((benzyloxy)carbo-nyl)amino)hexanoate (255).

To a solution of compound 254 (270 mg, 0.63 mmol), (2S,5S,E)-2-benzyl-5-((tert-butoxycarbonyl)amino)-7-methyloct-3-enoic acid (250 mg, 0.69 mmol), and DIPEA (244 mg, 1.89 mmol) in $CH_2Cl_2$ (20 mL) was added. After adding $T_3P$ (521 mg, 0.82 mmol, 50% in EtOAc) at 0° C., the mixture was stirred at 25° C. for 12 h and then the organic solution was concentrated in vacuo. To the residue was added EtOAc (100 mL) and washed with $H_2O$ (3×50 mL). The organic phase was collected, dried over $Na_2SO_4$ and concentrated in vacuo. The residues were purified by column chromatography on silica gel (petroleum ether/ EtOAc=3:1 to 1:1) to obtain the titled compound 255 (463 mg, 100%) as a white solid. MS (ESI): $[M+H^+]$=735.5.

Step 5: Synthesis of (S)-2-((S)-1-((2S,5S,E)-2-benzyl-5-((tert-butoxycarbonyl)amino)-7-methyloct-3-enoyl)pyrroli-dine-2-carboxamido)-6-(((benzyloxy)carbonyl)amino) hexanoic acid (256).

To a solution of compound 255 (463 mg, 0.63 mmol) in MeOH/THF/$H_2O$ (5 mL/5 mL/5 mL) was added LiOH.$H_2O$ (132 mg, 3.15 mmol). The mixture was stirred at 25° C. for 4 h was concentrated in vacuo. The residue was acidified to pH 3 with aqueous HCl (1 M), diluted with EtOAc (50 mL) and organic layer was washed with $H_2O$ (3×25 mL). The organic phase was concentrated in vacuo to obtain the titled compound 256 (454 mg, 100%) as a white solid. MS (ESI): $[M+H^+]$=721.5.

Step 6: Synthesis of Benzyl N-[(5S)—5-{[(2S)-1-[(2S, 3E,5S)-2-benzyl-5-{[(tert-butoxy)carbonyl]amino}-7-meth-yloct-3-enoyl]pyrrolidin-2-yl]formamido}-5-[(1-oxyl-2,2,6, 6-tetramethylpiperidin-4-yl)carbamoyl]pentyl]carbamate (XXVI).

To a solution of compound 256 (454 mg, 0.63 mmol), 4-AT (129 mg, 0.76 mmol), DIPEA (244 mg, 1.89 mmol) in $CH_2Cl_2$(10 mL) was added $T_3P$ (521 mg, 0.82 mmol, 50% in EtOAc). The mixture was stirred at 25° C. for 12 h, then the organic solution was concentrated in vacuo. After adding EtOAc (100 mL), the organic layer washed with H₂O (3×50 mL), and concentrated in vacuo. The residue was purified by prep-HPLC (Venusil XBP C18 (5 μm, 30×250 mm), 0.5% NH₃.H₂O in eluant) to obtain the titled compound XXVI (103 mg, 19%) as a pink solid. MS (ESI): [M+H⁺]=874.7.

Step 7: Synthesis of benzyl N-[(5S)—5-{[(2S)-1-[(2S,3E,5S)-2-benzyl-5-{[(tert-butoxy)carbonyl]amino}-7-methyl-oct-3-enoyl]pyrrolidin-2-yl]formamido}-5-[(1-hydroxy-2,2,6,6-tetramethylpipe-ridin-4-yl)carbamoyl]pentyl]carbamate (XXVII).

To a solution of compound XXVI (73 mg, 0.08 mmol) in MeOH (5 mL) was added Vc (14 mg, 0.08 mmol). The mixture was stirred at 25° C. for 30 min, then the organic solution was concentrated in vacuo and the residue was purified by prep-HPLC (Venusil XBP C18 (5 μm, 30×250 mm), 0.5% HCl in eluant) to obtain the titled compound XXVII (73 mg, 100%) as a white solid. MS (ESI): [M+H⁺]= 875.8.

Example XXVIII tert-Butyl N-[(4S,5E,7S)-7-benzyl-8-[(2S)—2-{[(1S)-1-carbamoyl-4-({[(1-oxyl-2,2,6,6-tetramethylpiperidin-4-yl)oxy]carbonyl}amino-)butyl]carbamoyl}pyrrolidin-1-yl]-2-methyl-8-oxooct-5-en-4-yl]carbamate (XXVIII)

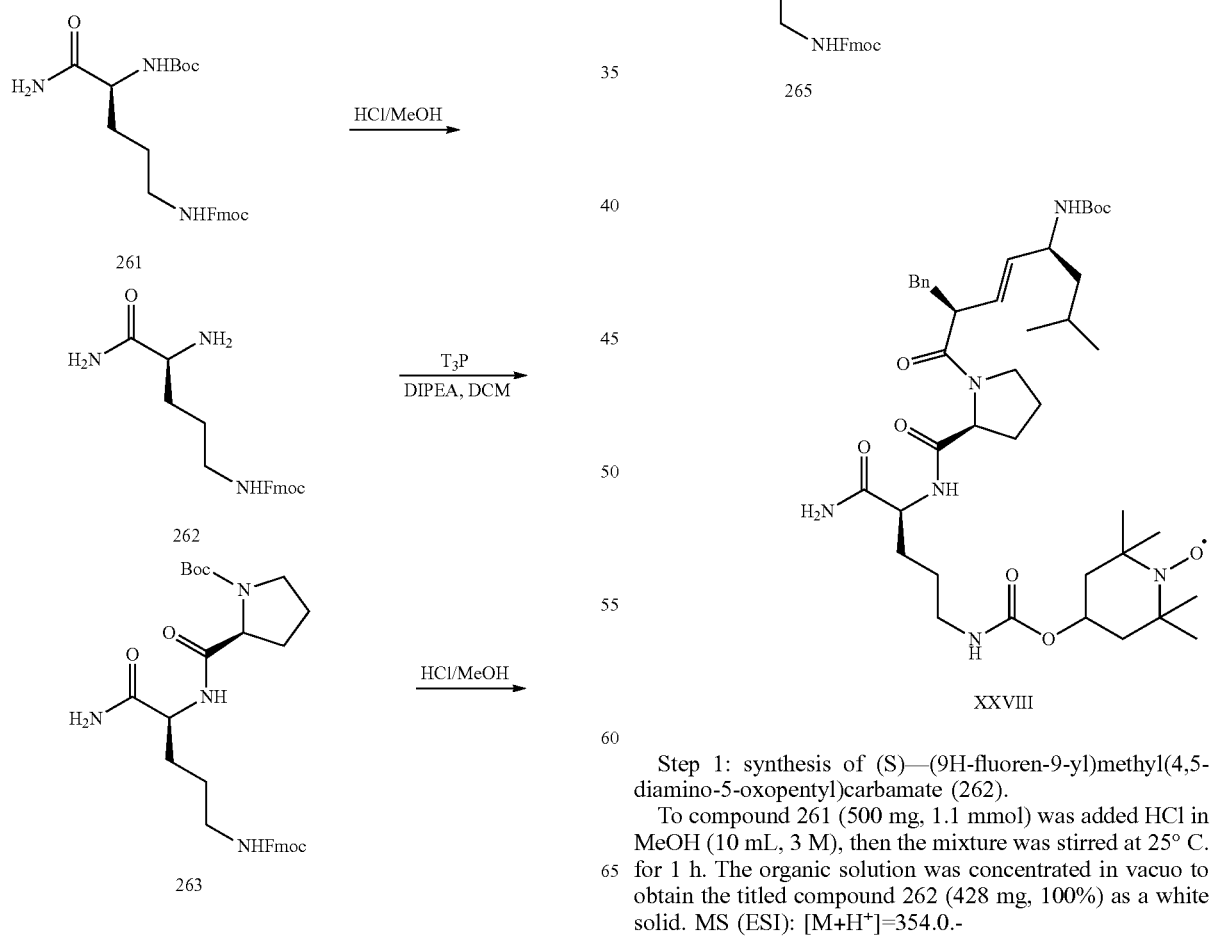

Step 1: synthesis of (S)—(9H-fluoren-9-yl)methyl(4,5-diamino-5-oxopentyl)carbamate (262).

To compound 261 (500 mg, 1.1 mmol) was added HCl in MeOH (10 mL, 3 M), then the mixture was stirred at 25° C. for 1 h. The organic solution was concentrated in vacuo to obtain the titled compound 262 (428 mg, 100%) as a white solid. MS (ESI): [M+H⁺]=354.0.-

Step 2: Synthesis of (S)-tert-butyl 2-(((S)-5-((((9H-fluoren-9-yl)methoxy)carbonyl)amino)-1-amino-1-oxopentan-2-yl)carbamoyl)pyrrolidine-1-carboxylate (263).

To a solution of compound 262 (428 mg, 1.1 mmol), (S)-1-(tert-butoxycarbonyl)pyrrolidine-2-carboxylic acid (355 mg, 1.5 mmol) in CH$_2$Cl$_2$ (20 mL) was added DIPEA (426 mg, 3.3 mmol) and T$_3$P (910 mg, 1.43 mmol, 50% in EtOAc) at 0° C. The mixture was stirred at 25° C. for 12 h, then the organic solution was concentrated in vacuo. To the residue was added EtOAc (100 mL) and the organic layer washed with H$_2$O (3×50 mL). The organic phase was collected and dried with Na$_2$SO$_4$ and then concentrated in vacuo to obtain the titled compound 263 (605 mg, 100%) as a white solid. MS (ESI): [M+H$^+$]=551.2.

Step 3: Synthesis of (9H-fluoren-9-yl)methyl ((S)-5-amino-5-oxo-(((S)-pyrrolidine-2-carboxamido)pentyl)carbamate (264).

To a 50 mL single-neck flask was added compound 263 (135 mg, 0.25 mmol) and HCl in MeOH (5 mL, 3 M), then the mixture was stirred at 25° C. for 1 h. The organic solution was concentrated under vacuum to obtain the titled compound 264 (110 mg, 100%) as a white solid. MS (ESI): [M+H$^+$]=451.1.

Step 4: Synthesis of (9H-fluoren-9-yl)methyl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-carba-moylbutyl]carbamate (265).

To a solution of compound 264 (110 mg, 0.25 mmol), (2S,5S,E)-2-benzyl-5-((tert-butoxycarbonyl)amino)-7-methyloct-3-enoic acid (91 mg, 0.25 mmol) in CH$_2$Cl$_2$ (15 mL) was added DIPEA (97 mg, 0.75 mmol) and T$_3$P (207 mg, 0.33 mmol, 50% in EtOAc) at 0° C. The mixture was stirred at 25° C. for 12 h, then the organic solution was concentrated in vacuo. To the residue was added EtOAc (100 mL) and the organic layer washed with H$_2$O (3×20 mL). The organic phase was collected and dried with Na$_2$SO$_4$ and then concentrated in vacuo. The residue was purified by column chromatography on silica gel (petroleum ether/EtOAc=3:1 to 1:1) to obtain the titled compound 265 (153 mg, 77%) as a white solid. MS (ESI): [M+H$^+$]=794.5.

Step 5: Synthesis of tert-butyl N-[(4S,5E,7S)-7-benzyl-8-[(2S)—2-{[(1S)-1-carbamoyl-4-({[(1-oxyl-2,2,6,6-tetramethylpiperidin-4-yl)oxy]carbonyl}amino+butyl] carbamoyl}pyrrolidin-1-yl]-2-methyl-8-oxooct-5-en-4-yl] carbamate (XXVIII).

To a solution of compound 265 (150 mg, 0.18 mmol) in CH$_2$Cl$_2$ (15 mL) was added DBU (144 mg, 0.94 mmol). The mixture was stirred at 25° C. for 20 min. To the mixture was added DMAP (44 mg, 0.36 mmol) and compound 266 (130 mg, 0.36 mmol, the procedure for 266 was according to Acs Central Science, 2016, 2 (9): 653-659). The mixture was stirred at 25° C. for 40 min, diluted with CH$_2$Cl$_2$ (50 mL) and the organic phase washed with H$_2$O (3×20 mL). The organic phase was concentrated in vacuo and purified by prep-HPLC (Venusil XBP C18 (5 μm, 30×250 mm), 0.1% HCl in eluant) to obtain the titled compound XXVIII (12 mg, 9%) as a pink solid. MS (ESI): [M+H$^-$]=770.6.

Example XXIX and XXX

Propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-5-({[(1-oxyl-2,2,6,6-tetramethylpiperidin-4-yl)oxy]carbonyl}amino) pentanoate (XXIX) and Propan-2-yl (2S)—2-{[(2S)-1-[(2S,3E,5S)-2-benzyl-5-{[(tert-butoxy) carbonyl]amino}-7-methyloct-3-enoyl]pyrrolidin-2-yl]formamido}-5-({[(1-hydroxy-2,2,6,6-tetramethylpiperidin-4-yl)oxy]carbonyl}amino)pentanoate (XXX)

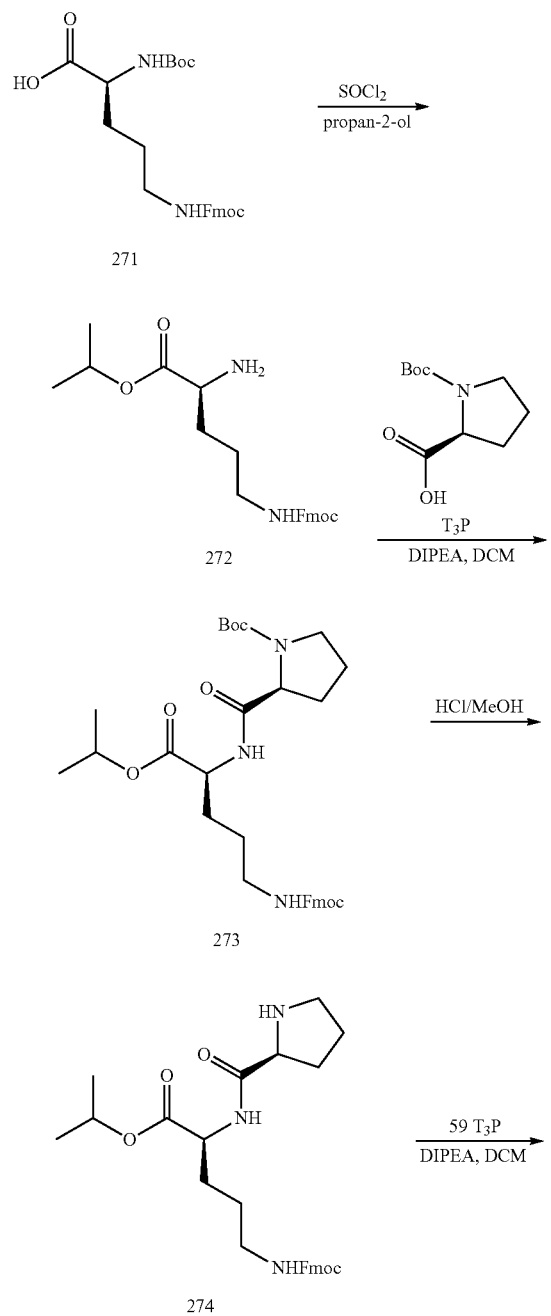

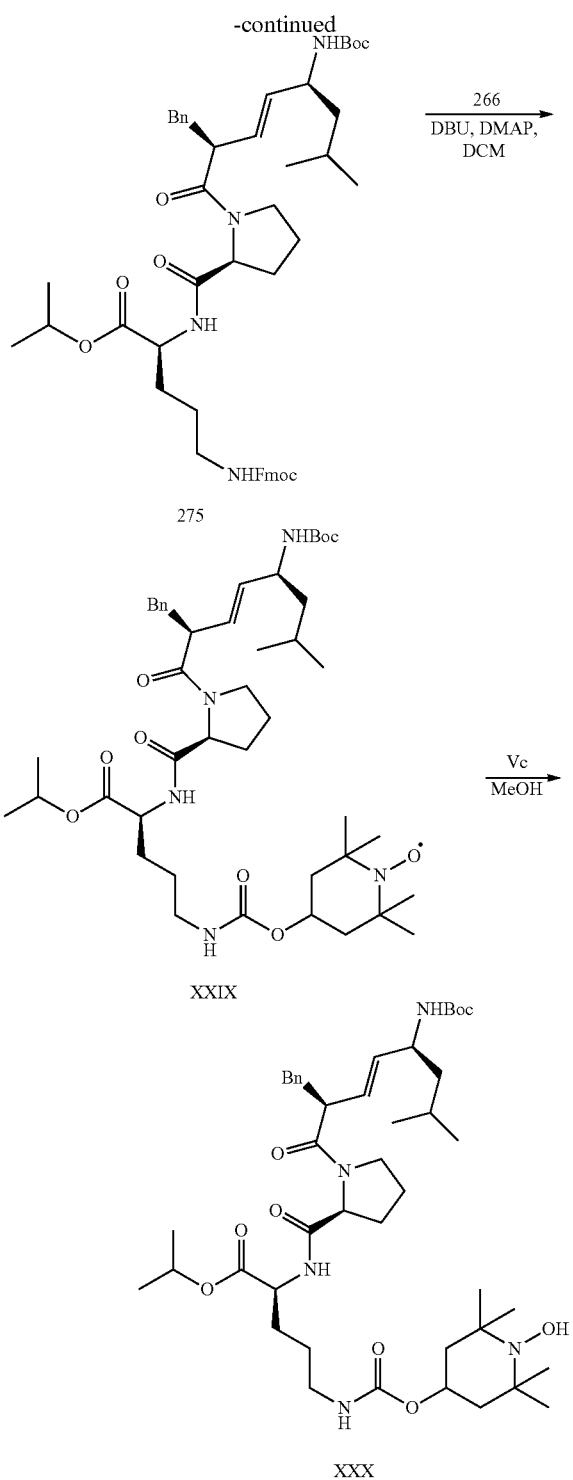

To a solution of compound 272 (476 mg, 1.1 mmol), (S)-1-(tert-butoxycarbonyl)pyrrolidine-2-carboxylic acid (355 mg, 1.65 mmol) in CH$_2$Cl$_2$ (20 mL) was added DIPEA (426 mg, 3.3 mmol) and T$_3$P (910 mg, 1.43 mmol, 50% in EtOAc). The mixture was stirred at 25° C. for 12 h, then the organic solution was concentrated in vacuo. To the residue was added EtOAc (100 mL) and the organic layer washed with H$_2$O (3×20 mL). The organic phase was collected after dried with Na$_2$SO$_4$ and concentrated to obtain the titled compound 273 (653 mg, 100%) as a white solid. MS (ESI): [M+H$^-$]=594.4.

Step 3: Synthesis of (S)—isopropyl 5-((((9H-fluoren-9-yl)methoxy)carbonyl)amino)-2-((S)-pyrrolidine-2-carboxamido)pentanoate (274).

To 273 (653 mg, 1.1 mmol) was added HCl in MeOH (10 mL, 3 M), then the mixture was stirred at 25° C. for 1 h. The organic solution was concentrated under vacuum pump to obtain the titled compound 274 (543 mg, 100%) as a white solid. MS (ESI): [M+H$^+$]=494.2.

Step 4: synthesis of (S)—isopropyl 5-((((9H-fluoren-9-yl)methoxy)carbonyl)amino)-2-((S)-1-((2S, 5S, E)-2-benzyl-5-((tert-butoxycarbonyl)amino)-7-methyloct-3-enoyl)pyrrolidine-2-carboxamido)pentanoate (275).

To a solution of compound 274 (543 mg, 1.1 mmol), (2S,5S,E)-2-benzyl-5-((tert-butoxycarbonyl)amino)-7-methyloct-3-enoic acid (397 mg, 1.1 mmol), DIPEA (426 mg, 3.3 mmol) in CH$_2$Cl$_2$ (10 mL) was added and T$_3$P (910 mg, 1.43 mmol, 50% in EtOAc) at 0° C. The mixture was stirred at 25° C. for 12 h, then the organic solution was concentrated in vacuo. To the residue was added EtOAc (100 mL) and the organic layer washed with H$_2$O (3×20 mL). The organic phase was dried with Na$_2$SO$_4$ and concentrated in vacuo and purified by column chromatography on silica gel eluting with EtOAc to obtain the titled compound 275 (513 mg, 56%) as a white solid. MS (ESI): [M+H$^+$]=837.6.

Step 5: Synthesis of propan-2-yl (2S)—2-{[(2S)-1-[(2S, 3E,5S)-2-benzyl-5-{[(tert-butoxy)carbonyl]amino}-7-methyloct-3-enoyl]pyrrolidin-2-yl]formamido}-5-({[(1-oxyl-2, 2,6,6-tetramethylpiperidin-4-yl)oxy]carbonyl}amino)pentanoate (XXIX).

To a solution of compound 275 (250 mg, 0.3 mmol) in CH$_2$Cl$_2$ (15 mL) was added DBU (227 mg, 1.5 mmol). The mixture was stirred at 25° C. for 20 min. To the mixture was added DMAP (73 mg, 0.6 mmol) and compound 266 (217 mg, 0.6 mmol). The mixture was stirred at 25° C. for 40 min, then the mixture was added CH$_2$Cl$_2$ (50 mL) and the organic layer washed with H$_2$O (3×20 mL). The organic phase was dried with Na$_2$SO$_4$ and concentrated in vacuo and purified by prep-HPLC (Venusil XBP C18 (5 μm, 30×250 mm), 0.1% HCl in eluant) to obtain the titled compound XXIX (72 mg, 29%) as a pink solid. MS (ESI): [M+H$^+$]=813.6.

Step 6: Synthesis of propan-2-yl (2S)—2-{[(2S)-1-[(2S, 3E,5S)-2-benzyl-5-{[(tert-butoxy)carbonyl]amino}-7-methyloct-3-enoyl]pyrrolidin-2-yl]formamido}-5-({[(1-hydroxy-2,2,6,6-tetramethylpiperidin-4-yl)oxy]carbonyl}amino)pentanoate (XXX).

To a solution of compound XXIX (50 mg, 0.06 mmol) in MeOH (5 mL) was added Vc (11 mg, 0.06 mmol). The mixture was stirred at 25° C. for 30 min, was concentrated in vacuo and the residue was purified by prep-HPLC (Venusil XBP C18 (5 μm, 33×250 mm), 0.5% NH$_3$.H$_2$O in eluant) to obtain the titled compound XXIX (13 mg, 27%) as a white solid. MS (ESI): [M+H$^+$]=814.7.

Step 1: Synthesis of (S)—isopropyl 5-((((9H-fluoren-9-yl)methoxy)carbonyl)amino)-2-amino-pentanoate (272).

To a solution of compound 271 (500 mg, 1.1 mmol) in propan-2-ol (10 mL) was added SOCl$_2$ (1 mL). The mixture was stirred at 100° C. for 24 h, then concentrated under vacuum to obtain the titled compound 272 (476 mg, 100%) as a white solid. MS (ESI): [M+H$^+$]=397.1.

Step 2: Synthesis of (S)-tert-butyl 2-(((S)-5-((((9H-fluoren-9-yl)methoxy)carbonyl)amino)-1-isopropoxy-1-oxopentan-2-yl)carbamoyl)pyrrolidine-1-carboxylate (273).

Example XXXI and XXXII

Propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate (XXXI) and Propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-6-[(1-oxyl-2,2,5,5-tetramethylpyrrolidin-3-yl)formamido]-hexanoate (XXXII)

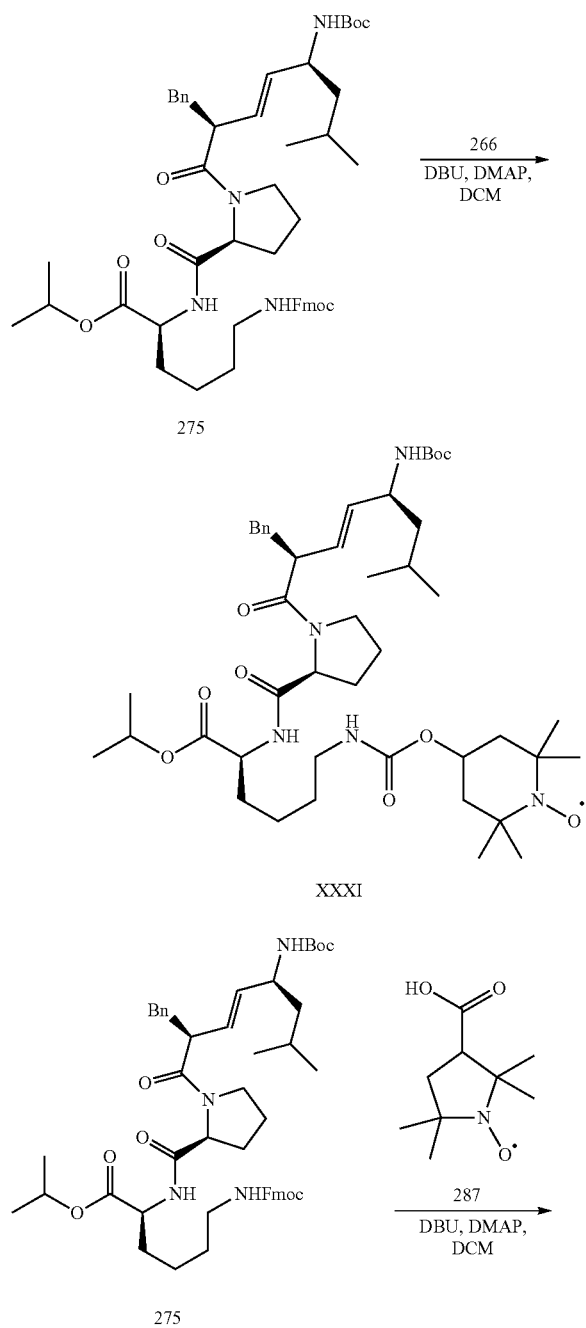

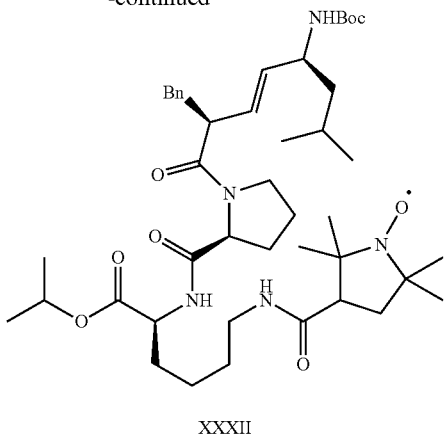

Step 1: Synthesis of propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate (XXXI).

To a solution of compound 275 (350 mg, 0.41 mmol) in $CH_2Cl_2$ (15 mL) was added DBU (313 mg, 2.1 mmol). The mixture was stirred at 25° C. for 20 min. To the mixture was added DMAP (100 mg, 0.82 mmol) and compound 266 (296 mg, 0.82 mmol). After stirring at 25° C. for 1 h, the mixture was diluted with $CH_2Cl_2$ (50 mL) and washed with $H_2O$ (3×20 mL). The organic phase was dried with $Na_2SO_4$ and then concentrated in vacuo and purified by prep-HPLC (Venusil XBP C18 (5 μm, 30×250 mm), 0.1% HCl in eluant) to obtain the titled compound (80 mg, 22%) as a pink solid. MS (ESI): [M+H$^-$]=827.7.

Step 2: Synthesis of propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-6-[(1-oxyl-2,2,5,5-tetramethylpyrrolidin-3-yl)formamido]-hexanoate (XXXII).

To a solution of compound 275 (225 mg, 0.26 mmol) in $CH_2Cl_2$ (15 mL) was added DBU (395 mg, 2.6 mmol). The mixture was stirred at 25° C. for 20 min. To the mixture was added 287 (45 mg, 0.26 mmol) and $T_3P$ (215 mg, 0.34 mmol, 50% in EtOAc). The mixture was stirred at 25° C. for 10 h, was diluted with $CH_2Cl_2$ (50 mL) and washed with $H_2O$ (3×20 mL). The organic phase was dried with $Na_2SO_4$ and then concentrated in vacuo and purified by prep-HPLC (Venusil XBP C18 (5 μm, 30×250 mm), 0.1% HCl in eluant) to obtain the titled compound XXXII (10 mg, 5%) as an off-white solid. MS (ESI): [M+H$^+$]=797.7.

Example XXXIII and XXXIV
Propan-2-yl (2R)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate (XXXIII) and (2R)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoic acid (XXXIV)
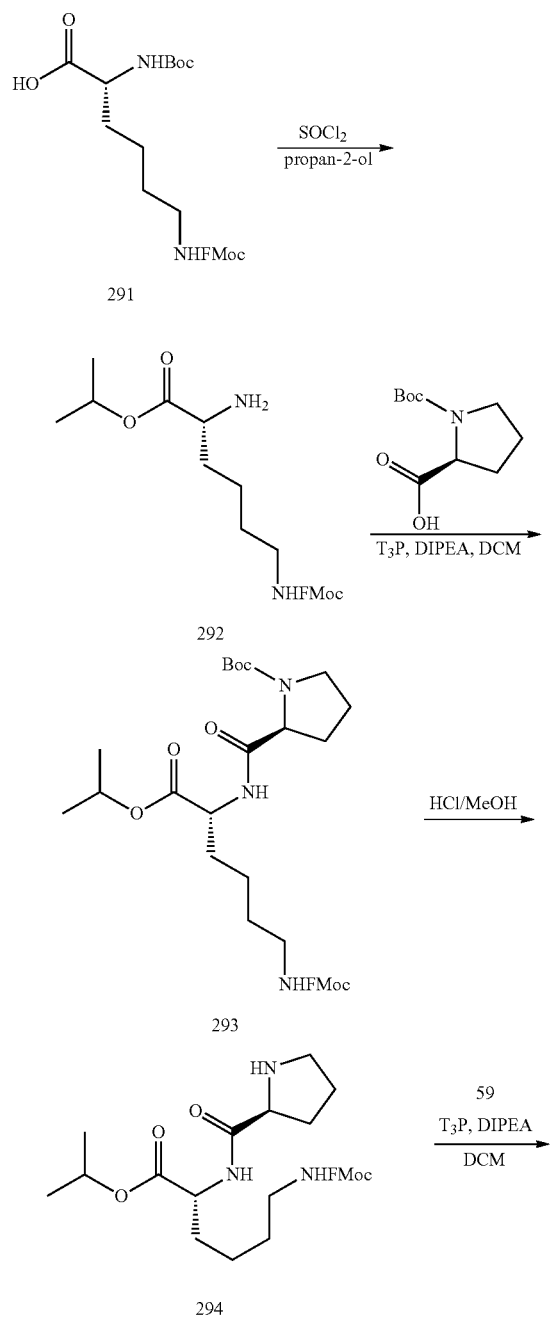
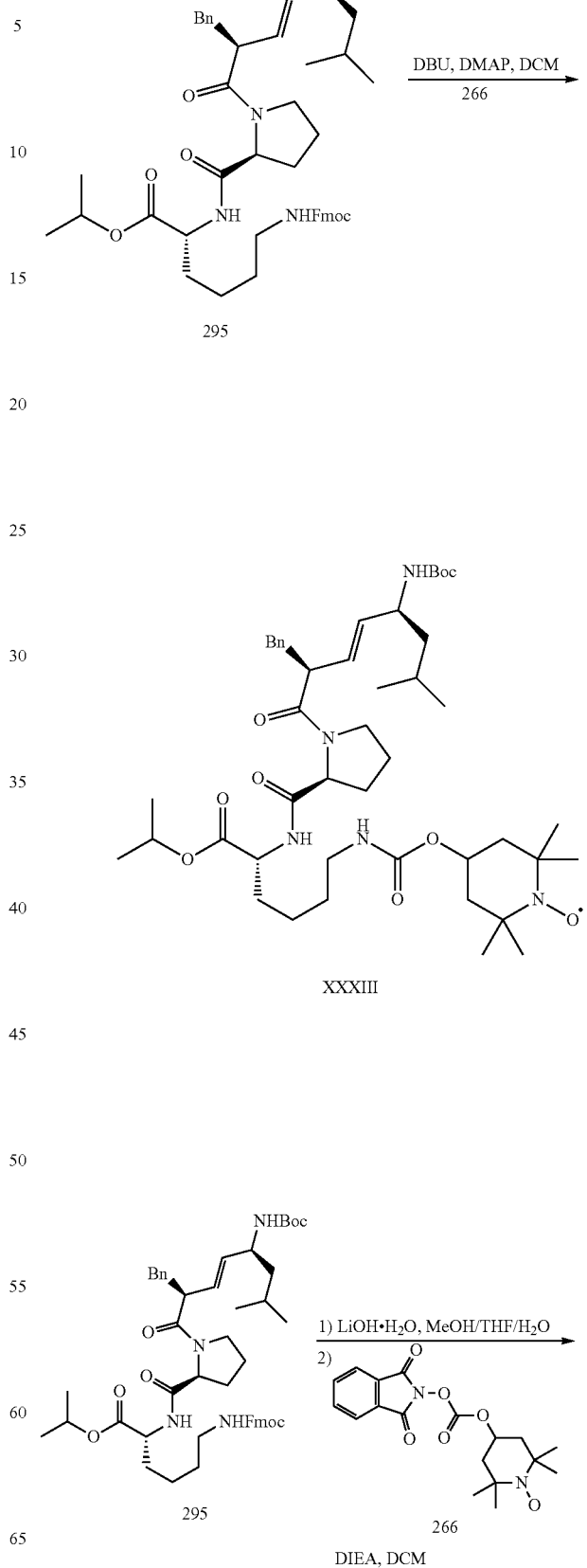

-continued

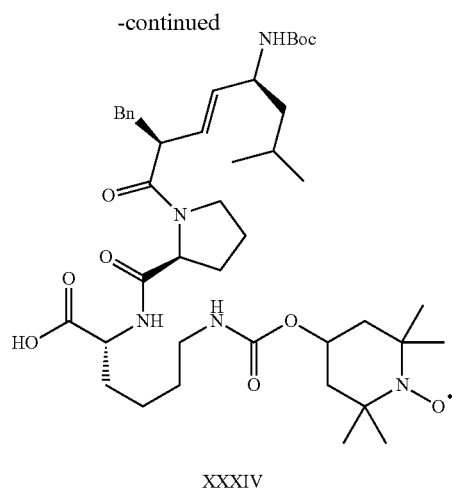

XXXIV

Step 1: Synthesis of (R)—isopropyl 6-((((9H-fluoren-9-yl)methoxy)carbonyl)amino)-2-aminohexanoate (292).

To a solution of compound 291 (500 mg, 1.07 mmol) in propan-2-ol (10 mL) was added SOCl$_2$ (0.5 mL). The mixture was stirred at 100° C. for 10 h, then concentrated under vacuum to obtain the titled compound 292 (439 mg, 100%) as a white solid. MS (ESI): [M+H$^+$]=411.1.

Step 2: Synthesis of (S)-tert-butyl 2-(((R)-6-((((9H-fluoren-9-yl)methoxy)carbonyl)amino)-1-isopropoxy-1-oxohexan-2-yl)carbamoyl)pyrrolidine-1-carboxylate (293).

To a solution of compound 292 (439 mg, 1.07 mmol), (S)-1-(tert-butoxycarbonyl)pyrrolidine-2-carboxylic acid (345 mg, 1.61 mmol) in CH$_2$Cl$_2$(15 mL) was added DIPEA (414 mg, 3.21 mmol) and T$_3$P (885 mg, 1.39 mmol, 50% in EtOAc) at 0° C. The mixture was stirred at 25° C. for 12 h, then was concentrated. To the residue was added EtOAc (100 mL) and the organic layer washed with H$_2$O (3×20 mL). The organic phase was collected and dried with Na$_2$SO$_4$ and then concentrated in vacuo to obtain the titled compound 293 (650 mg, 100%) as a white solid. MS (ESI): [M+H$^+$]=608.3.

Step 3: Synthesis of (R)—isopropyl 6-((((9H-fluoren-9-yl)methoxy)carbonyl)amino)-2-((S)—pyrrolidine-2-carboxamido)hexanoate (294).

To compound 293 (650 mg, 1.07 mmol) was added HCl in MeOH (5 mL, 3 M). After stirring at 25° C. for 1 h, the organic solution was concentrated under vacuum to obtain the titled compound 294 (544 mg, 100%) as a white solid. nMS (ESI): [M+H$^+$]=508.2.

Step 4: Synthesis of (R)—isopropyl 6-((((9H-fluoren-9-yl)methoxy)carbonyl)amino)-2-((S)-1-((2S,5S,E)-2-benzyl-5-((tert-butoxycarbonyl)amino)-7-methyloct-3-enoyl)pyrrolidine-2-carboxamido)hexanoate (295).

To a solution of compound 294 (544 mg, 1.07 mmol) in CH$_2$Cl$_2$(10 mL) were added (2S,5S, E)-2-benzyl-5-((tert-butoxycarbonyl)amino)-7-methyloct-3-enoic acid (59, 386 mg, 1.07 mmol), DIPEA (414 mg, 3.21 mmol) and T$_3$P (884 mg, 1.4 mmol, 50% in EtOAc) at 0° C. The mixture was stirred at 25° C. for 12 h, then was concentrated. To the residue was added EtOAc (100 mL) and the organic layer washed with H$_2$O (3×20 mL). The organic phase was collected and dried with Na$_2$SO$_4$ and then concentrated in vacuo. The residue was purified by column chromatography on silica gel (petroleum ether/EtOAc=3:1 to 1:1) to obtain the titled compound 295 (911 mg, 100%) as a white solid. MS (ESI): [M+H$^-$]=851.6.

Step 5: Synthesis of propan-2-yl (2R)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate (XXXIII).

To a solution of compound 295 (250 mg, 0.3 mmol) in CH$_2$Cl$_2$ (15 mL) was added DBU (277 mg, 1.5 mmol). The mixture was stirred at 25° C. for 20 min. To the mixture was added DMAP (73 mg, 0.6 mmol) and compound 266 (217 mg, 0.6 mmol). The mixture was stirred at 25° C. for 1 h, diluted with CH$_2$Cl$_2$ (50 mL) and washed with H$_2$O (3×20 mL). The organic phase was dried with Na$_2$SO$_4$ and concentrated in vacuo and purified by prep-HPLC (Venusil XBP C18 (5 μm, 30×250 mm), 0.1% HCl in eluant) to obtain the titled compound XXXIII (100 mg, 40%) as a pink solid. MS (ESI): [M+H$^+$]=827.7.

Step 6: Synthesis of (2R)—2-{[(2S)-1-[(2S,3E,5S)-2-benzyl-5-{[tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoic acid (XXXIV).

To a solution of compound 295 (280 mg, 0.33 mmol) in THF/MeOH/H$_2$O (10 mL/10 mL/5 mL) was added LiOH.H$_2$O (69 mg, 1.65 mmol). The mixture was stirred at 25° C. for 10 h, then the organic solution was concentrated in vacuo. The residue was diluted with EtOAc (20 mL) and acidified to pH 3 with aqueous HCl (1 M), then the inorganic solid was filtered and the filtrate was concentrated in vacuo to obtain a light-yellow solid. To a solution of the yellow solid in CH$_2$C$_2$ (15 mL) was added DIPEA (426 mg, 3.3 mmol) and compound 266 (238 mg, 0.66 mmol). The mixture was stirred at 25° C. for 1 h, then concentrated and purified by prep-HPLC (Venusil XBP C18(5 μm, 30×250 mm), 0.1% HCl in eluant) to obtain the titled compound XXXIV (12 mg, 5%) as a pink solid. MS (ESI): [M+H$^+$] =785.6.

Example XXXV tert-Butyl N-[(4S,5E,7S)-7-benzyl-8-[(2S)—2-{[(1S)-1-(diethylcarbamoyl)-4-({[(1-oxyl-2,2,6,6-tetramethylpiperidin-4-yl)oxy]carbonyl}amino)-butyl]carbamoyl}pyrrolidin-1-yl]-2-methyl-8-oxooct-5-en-4-yl]carbamate (XXXV)

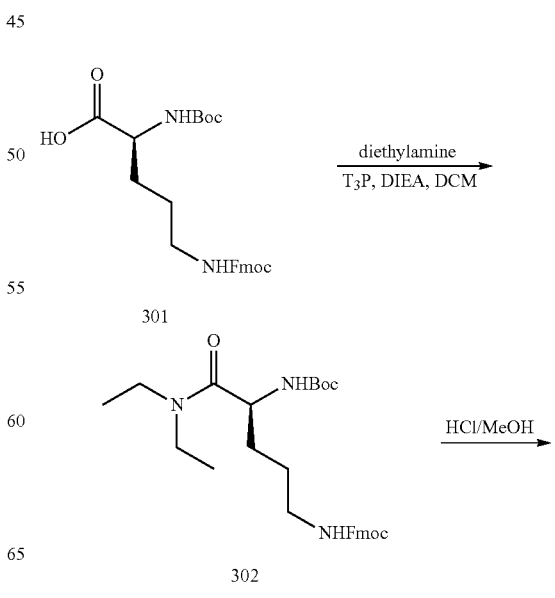

-continued

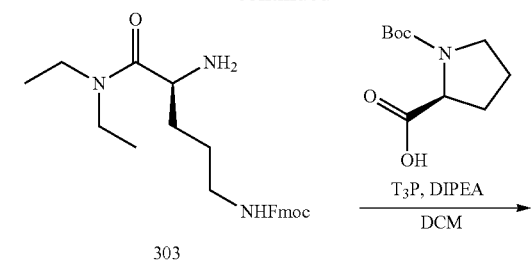

303

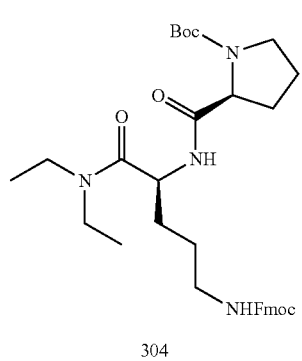

304

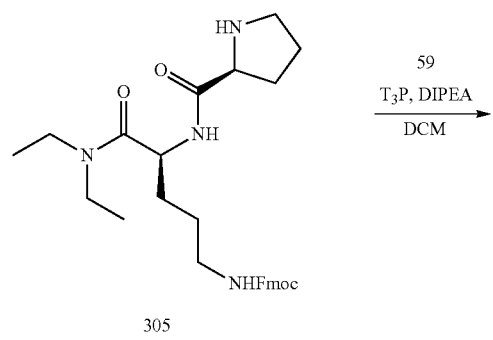

305

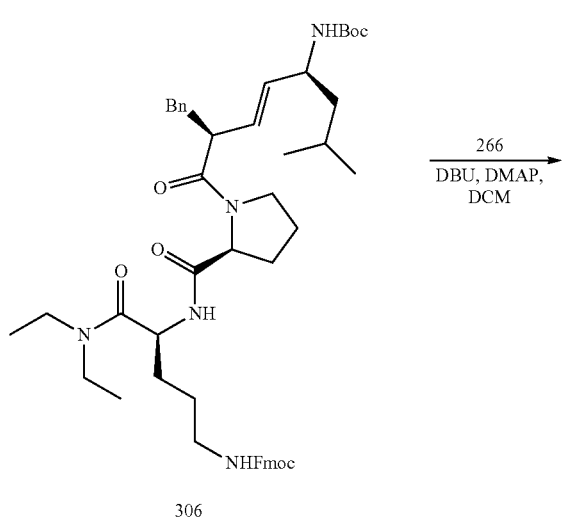

306

-continued

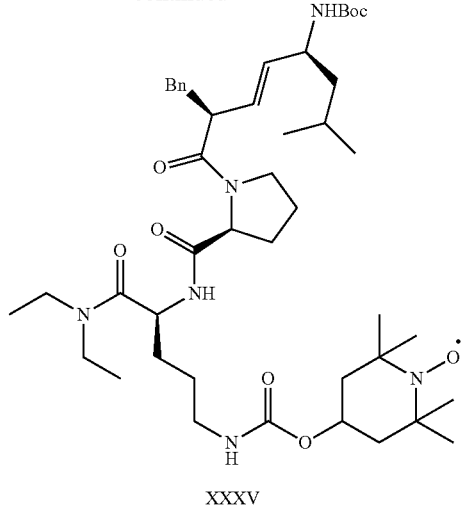

XXXV

Step 1: Synthesis of (S)—(9H-fluoren-9-yl)methyl tert-butyl (5-(diethylamino)-5-oxopentane-1,4-diyl)dicarbamate (302).

To a solution of compound 301 (500 mg, 1.1 mmol), diethylamine (241 mg, 3.3 mmol), DIPEA (426 mg, 3.3 mmol) in $CH_2Cl_2$ (15 mL) was added and $T_3P$ (910 mg, 1.43 mmol, 50% in EtOAc). The mixture was stirred at 25° C. for 2 h, then concentrated in vacuo. To the residue was added EtOAc (100 mL) and the organic layer washed with $H_2O$ (3×20 mL). The organic phase was collected and dried with $Na_2SO_4$ and then concentrated to obtain the titled compound 302 (560 mg, 100%) as a white solid. MS (ESI): [M+H$^+$]=510.2.

Step 2: Synthesis of (S)—(9H-fluoren-9-yl)methyl (4-amino-5-(diethylamino)-5-oxopentyl)carbamate (303).

To compound 302 (560 mg, 1.1 mmol) was added HCl in MeOH (5 mL, 3 M) and EtOAc (5 mL). After stirring at 25° C. for 1 h, the organic solution was concentrated under vacuum to obtain the titled compound 303 (450 mg, 100%) as a white solid. MS (ESI): [M+H$^+$]=410.1.

Step 3: Synthesis of (S)-tert-butyl 2-(((S)-5-((((9H-fluoren-9-yl)methoxy)carbonyl)amino)-1-(diethylamino)—1-oxopentan-2-yl)carbamoyl)pyrrolidine-1-carboxylate (304).

To a solution of compound 303 (450 mg, 1.1 mmol), (S)-1-(tert-butoxycarbonyl)pyrrolidine-2-carboxylic acid (355 mg, 1.65 mmol) in $CH_2Cl_2$ (15 mL) was added DIPEA (426 mg, 3.3 mmol) and $T_3P$ (910 mg, 1.43 mmol, 50% in EtOAc). The mixture was stirred at 25° C. for 12 h, then concentrated in vacuo. To the residue was added EtOAc (100 mL) and the organic layer washed with $H_2O$ (3×20 mL). The organic phase was collected and dried with $Na_2SO_4$ and then concentrated in vacuo to obtain the titled compound 304 (667 mg, 100%) as a white solid. MS (ESI): [M+H$^+$]=607.4.

Step 4: Synthesis of (9H-fluoren-9-yl)methyl ((S)-5-(diethylamino)—5-oxo-4-((S)-pyrrolidine-2-carboxamido) pentyl)carbamate (305).

To compound 304 (667 mg, 1.1 mmol) was added HCl in MeOH (10 mL, 3 M). The mixture was stirred at 25° C. for 30 min, and concentrated under vacuum to obtain the titled compound 305 (557 mg, 100%) as a white solid. MS (ESI): [M+H$^+$]=507.2.

Step 5: Synthesis of (9H-fluoren-9-yl)methyl N-[(4S)—4-{[(2S)-1-[(2S,3E,5S)-2-benzyl-5-{[(tert- butoxy)carbonyl]amino}-7-methyloct-3-enoyl]pyrrolidin-2-yl]formamido}-4-(diethylcarbamoyl)butyl]carbamate (306).

To a solution of compound 305 (557 mg, 1.1 mmol) in $CH_2Cl_2$ (15 mL), (2S,5S, E)-2-benzyl-5-((tert-butoxycarbonyl)amino)-7-methyloct-3-enoic acid (59) (397 mg, 1.1 mmol), DIPEA (426 mg, 3.3 mmol) and $T_3P$ (910 mg, 1.43 mmol, 50% in EtOAc) were added at 0° C. The mixture was stirred at 25° C. for 12 h, then was concentrated in vacuo. To the residue was added EtOAc (100 mL) and the organic layer washed with $H_2O$ (3×20 mL). The organic phase was collected and dried with $Na_2SO_4$ and then concentrated in vacuo. The residue was purified by column chromatography on silica gel (petroleum ether/EtOAc=3:1 to 1:1) to obtain the titled compound 306 (935 mg, 100%) as a white solid. MS (ESI): [M+H$^+$]=850.6.

Step 6: Synthesis of tert-butyl N-[(4S,5E,7S)-7-benzyl-8-[(2S)—2-{[(1S)-1-(diethylcarbamoyl)-4-({[(1-oxyl-2,2,6,6-tetramethylpiperidin-4-yl)oxy]carbonyl}amino)-butyl]carbamoyl}pyrrolidin-1-yl]-2-methyl-8-oxooct-5-en-4-yl]carbamate (XXXV).

To a solution of compound 306 (350 mg, 0.41 mmol) in $CH_2Cl_2$ (15 mL) was added DBU (313 mg, 2.1 mmol). The mixture was stirred at 25° C. for 20 min. To the mixture was added DMAP (100 mg, 0.82 mmol) and 266 (296 mg, 0.82 mmol). The mixture was stirred at 25° C. for 1 h, then the mixture was diluted with $CH_2Cl_2$ (50 mL) and the organic layer washed with $H_2O$ (3×20 mL). The organic phase was dried with $Na_2SO_4$ and concentrated in vacuo and purified by prep-HPLC (Venusil XBP C18 (5 μm, 30×250 mm), 0.1% HCl in eluant) to obtain the titled compound XXXV (42 mg, 12%) as a pink solid. MS (ESI): [M+H$^+$]=826.9.

Example XXXVI tert-Butyl N-[(4S,5E,7S)-7-benzyl-8-[(2S)—2-{[(1S)-1-(tert-butylcarbamoyl)-5-({[(1-oxyl-2,2,6,6-tetramethylpiperidin-4-yl)oxy]carbonyl}amino)pentyl]-carbamoyl}pyrrolidin-1-yl]-2-methyl-8-oxooct-5-en-4-yl]carbamate (XXXVI)

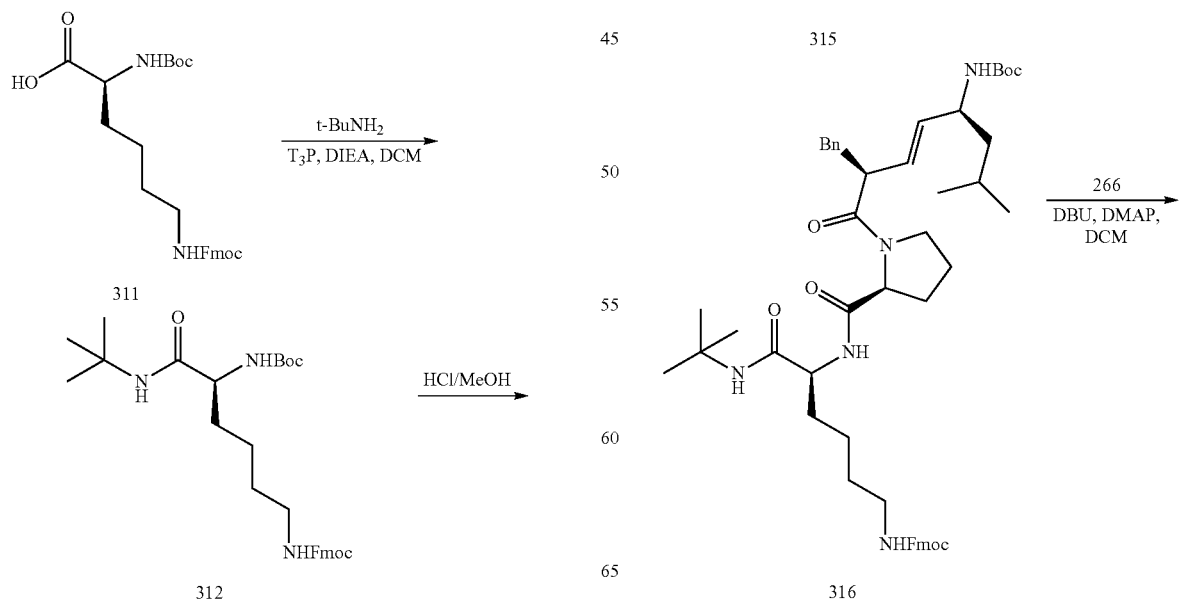

147

-continued

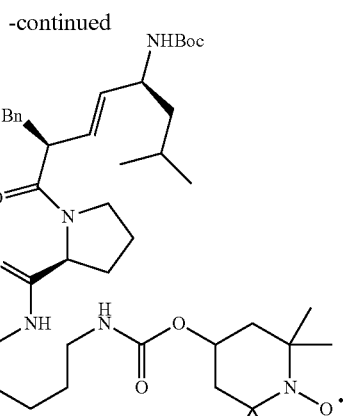

XXXVI

Step 1: Synthesis of (S)—(9H-fluoren-9-yl)methyl tert-butyl (6-(tert-butylamino)-6-oxohexane-1,5-diyl)dicarbamate (312).

To a solution of compound 311 (500 mg, 1.07 mmol), t-BuNH$_2$ (234 mg, 3.21 mmol), DIPEA (414 mg, 3.21 mmol) in CH$_2$Cl$_2$ (20 mL) was added and T$_3$P (885 mg, 1.39 mmol, 50% in EtOAc) at 0° C. The mixture was stirred at 25° C. for 12 h, then concentrated in vacuo. To the residue was added EtOAc (100 mL) and the organic layer washed with H$_2$O (3×20 mL). The organic phase was dried with Na$_2$SO$_4$ and concentrated in vacuo and purified by prep-TLC (petroleum ether/EtOAc=1:1) to obtain the titled compound 312 (427 mg, 76%) as a white solid. MS (ESI): [M+H$^+$]=524.2.

Step 2: Synthesis of (S)—(9H-fluoren-9-yl)methyl (5-amino-6-(tert-butylamino)-6-oxohexyl)carbamate (313).

To compound 312 (427 mg, 0.81 mmol) was added HCl in MeOH (10 mL, 3 M). After stirring at 25° C. for 0.5 h, the organic solution was concentrated under vacuum to obtain the titled compound 313 (343 mg, 100%) as a white solid. MS (ESI): [M+H$^+$]=424.1.

Step 3: Synthesis of (S)-tert-butyl 2-4(S)-6-4((9H-fluoren-9-yl)methoxy)carbonyl)amino)-1-(tert-butylamino)-1-oxohexan-2-yl)carbamoyl)pyrrolidine-1-carboxylate (314).

To a solution of compound 313 (343 mg, 0.81 mmol) and (S)-1-(tert-butoxycarbonyl)pyrrolidine-2-carboxylic acid (261 mg, 1.21 mmol) in CH$_2$Cl$_2$ (15 mL) was added DIPEA (314 mg, 2.43 mmol) and T$_3$P (670 mg, 1.1 mmol, 50% in EtOAc) at 0° C. The mixture was stirred at 25° C. for 12 h, then concentrated in vacuo. To the residue was added EtOAc (100 mL) and the organic layer washed with H$_2$O (3×20 mL). The organic phase was collected and dried with Na$_2$SO$_4$ and then concentrated to obtain the titled compound 314 (503 mg, 100%) as a white solid. MS (ESI): [M+H$^+$]= 621.3.

Step 4: Synthesis of (9H-fluoren-9-yl)methyl ((S)-6-(tert-butylamino)-6-oxo-54(S)-pyrrolidine-2-carboxamido)hexyl)carbamate (315).

To compound 314 (503 mg, 0.81 mmol) was added HCl in MeOH (10 mL, 3 M). After stirring at 25° C. for 30 min, the organic solution was concentrated under vacuum to obtain the titled compound 315 (422 mg, 100%) as a white solid. MS (ESI): [M+H$^+$]=521.2.

Step 5: Synthesis of (9H-fluoren-9-yl)methyl N-[(5S)—5-{[(2S)-1-[(2S,3E,5S)-2-benzyl-5-{[(tert- butoxy)carbonyl]amino}-7-methyloct-3-enoyl]pyrrolidin-2-yl]formamido}-5-(tert-butylcarbamoyl)pentyl]carbamate (316).

To a solution of compound 315 (422 mg, 0.81 mmol), (2S,5S,E)-2-benzyl-5-((tert-butoxycarbonyl)amino)-7-methyloct-3-enoic acid (293 mg, 0.81 mmol), DIPEA (313 mg, 2.43 mmol) in CH$_2$Cl$_2$ (15 mL) was added T$_3$P (670 mg, 1.05 mmol, 50% in EtOAc) at 0° C. After stirring at 25° C. for 12 h, the organic solution was concentrated in vacuo. To the residue was added EtOAc (100 mL) and the organic layer was washed with H$_2$O (3×20 mL). The organic phase was concentrated in vacuo. The residue was purified by column chromatography on silica gel (petroleum ether/EtOAc=3:1 to 1:1) to obtain the titled compound 316 (700 mg, 100%) as a white solid. MS (ESI): [M+H$^+$]=864.6.

Step 6: Synthesis of tert-butyl N-[(4S,5E,7S)-7-benzyl-8-[(2S)—2-{[(1S)-1-(tert-butylcarbamoyl)—({[(1-oxyl-2,2,6,6-tetramethylpiperidin-4-yl)oxy]carbonyl}amino)pentyl]carbamoyl}pyrrolidin-1-yl]-2-methyl-8-oxooct-5-en-4-yl]carbamate (XXXVI).

To a solution of compound 316 (350 mg, 0.41 mmol) in CH$_2$Cl$_2$ (15 mL) was added DBU (313 mg, 2.1 mmol). The mixture was stirred at 25° C. for 20 min. To the mixture was added DMAP (100 mg, 0.82 mmol) and compound 266 (296 mg, 0.82 mmol). The mixture was stirred at 25° C. for 1 h, diluted with CH$_2$Cl$_2$ (50 mL) and washed with H$_2$O (3×20 mL). The organic phase was concentrated in vacuo and purified by prep-HPLC (Venusil XBP C18 (5 μm, 30×250 mm), 0.1% HCl in eluant) to obtain the titled compound XXXVI (84 mg, 24%) as a pink solid. MS (ESI): [M+H$^+$]=840.6.

Example XXXVII tert-Butyl N-[(4S,5E,7S)-7-benzyl-8-[(2S)—2-{[(1S)-5-({[(1-oxyl-2,2,6,6-tetramethylpiperidin-4-yl)oxy]carbonyl}amino)-1-[(propan-2-yl)carbamoyl]pentyl]carbamoyl}pyrrolidin-1-yl]-2-methyl-8-oxooct-5-en-4-yl]carbamate (XXXVII)

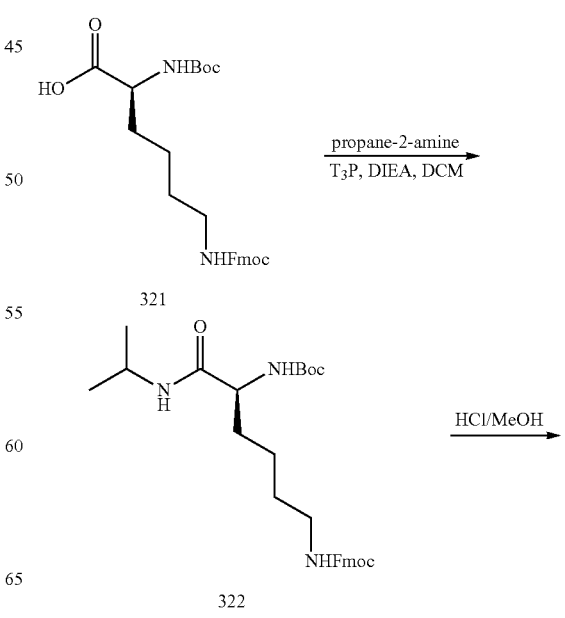

-continued

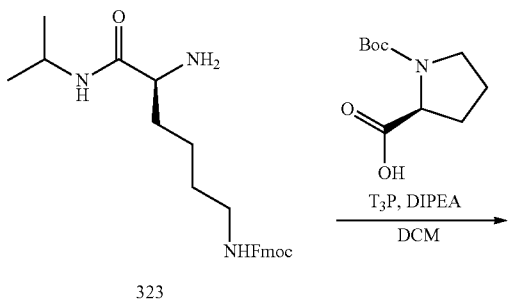
323

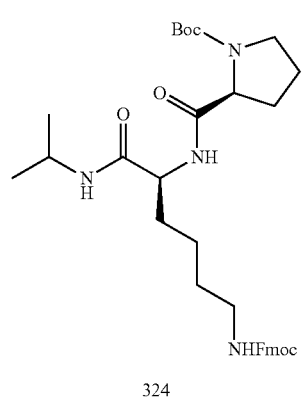
324

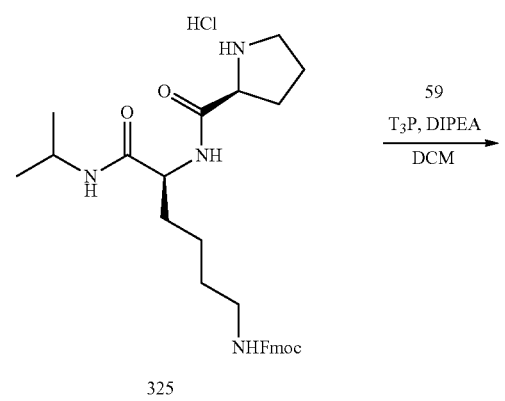
325

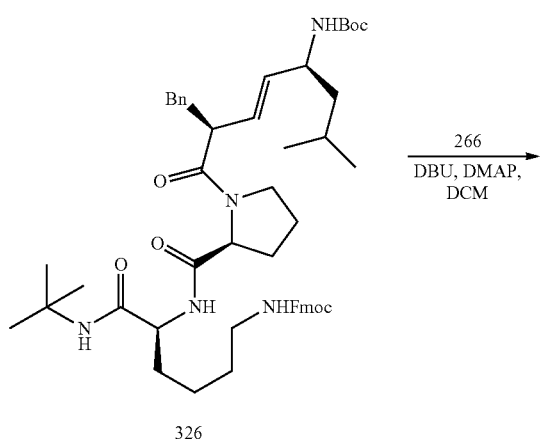
326

-continued

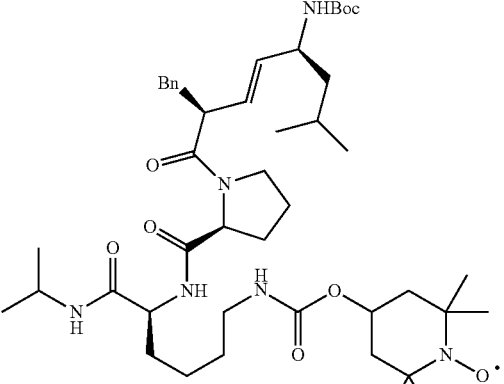
XXXVII

Step 1: Synthesis of (S)—(9H-fluoren-9-yl)methyl tert-butyl (6-(isopropylamino)-6-oxohexane-1,5-diyl)dicarbamate (322).

To a solution of compound 321 (500 mg, 1.07 mmol), propan-2-amine (190 mg, 3.21 mmol), DIPEA (414 mg, 3.21 mmol) in $CH_2Cl_2$ (20 mL) was added $T_3P$ (885 mg, 1.39 mmol, 50% in EtOAc) at 0° C. After stirring at 25° C. for 12 h, the organic solution was concentrated in vacuo. To the residue was added EtOAc (100 mL) and the organic layer washed with $H_2O$ (3×20 mL). The organic phase was dried with $Na_2SO_4$ and then concentrated in vacuo and purified by prep-TLC (1.5 mm thick silica gel plate, petroleum ether/EtOAc=1:1) to obtain the titled compound 322 (341 mg, 63%) as a white solid. MS (ESI): [M+H$^+$]=510.15.

Step 2: Synthesis of (S)—(9H-fluoren-9-yl)methyl (5-amino-6-(isopropylamino)-6-oxohexyl)carbamate (323).

To compound 322 (341 mg, 0.67 mmol) was added HCl in MeOH (10 mL, 3 M). After stirring at 25° C. for 0.5 h, the organic solution was concentrated in vacuo under vacuum to obtain the titled compound 323 (274 mg, 100%) as a white solid. MS (ESI): [M+H$^+$]=410.0.

Step 3: Synthesis of (S)-tert-butyl 2-(((S)-6-((((9H-fluoren-9-yl)methoxy)carbonyl)amino)-1-(isopropylamino)—1-oxohexan-2-yl)carbamoyl)pyrrolidine-1-carboxylate (324).

To a solution of compound 323 (274 mg, 0.67 mmol), (S)-1-(tert-butoxycarbonyl)pyrrolidine-2-carboxylic acid (216 mg, 1.01 mmol) in $CH_2Cl_2$ (15 mL) was added DIPEA (260 mg, 2.01 mmol) and $T_3P$ (554 mg, 0.87 mmol, 50% in EtOAc). The mixture was stirred at 25° C. for 12 h, then the organic solution was concentrated in vacuo. To the residue was added EtOAc (100 mL) and the organic layer washed with $H_2O$ (3×20 mL). The organic phase was collected and dried with $Na_2SO_4$ and then concentrated in vacuo to obtain the titled compound 324 (407 mg, 100%) as a white solid. MS (ESI): [M+H$^+$]=607.3.

Step 4: Synthesis of (9H-fluoren-9-yl)methyl ((S)-6-(isopropylamino)—6-oxo-5-((S)-pyrrolidine-2-carboxamido) hexyl)carbamate hydrochloride (325).

To compound 325 (407 mg, 0.67 mmol) was added HCl in MeOH (10 mL, 3 M). After stirring at 25° C. for 30 min, the organic solution was concentrated in vacuo under vacuum to obtain the titled compound 325 (340 mg, 100%) as a white solid. MS (ESI): [M+H$^+$]=507.2.

Step 5: Synthesis of (9H-fluoren-9-yl)methyl N-[(5S)—5-{[(2S)-1-[(2S,3E,5S)-2-benzyl-5-{[(tert-butoxy)carbonyl]amino}-7-methyloct-3-enoyl]pyrrolidin-2-yl]formamido}-5-[(pro-pan-2-yl)carbamoyl]pentyl]carbamate (326).

To a solution of compound 325 (340 mg, 0.67 mmol), (2S,5S,E)-2-benzyl-5-((tert-butoxycarbonyl)amino)-7-methyloct-3-enoic acid (59, 242 mg, 0.67 mmol), DIPEA (259 mg, 2.01 mmol) in CH$_2$Cl$_2$ (15 mL) was added T$_3$P (554 mg, 0.87 mmol, 50% in EtOAc). The mixture was stirred at 25° C. for 12 h, then the organic solution was concentrated in vacuo. To the residue was added EtOAc (100 mL) and the organic layer washed with H$_2$O (3×20 mL). The organic phase was collected and dried with Na$_2$SO$_4$ and concentrated in vacuo. The residue was purified by column chromatography on silica gel (petroleum ether/EtOAc=3:1 to 1:1) to obtain the titled compound 326 (570 mg, 100%) as a white solid. MS (ESI): [M+H$^+$]=850.5. $^1$H NMR: (400 MHz, CDC$_3$) δ 7.76-7.69 (m, 2H), 7.61-7.59 (m, 2H), 7.40-7.36 (m, 2H), 7.32-7.30 (m, 2H), 7.25-7.22 (m, 2H), 7.19-7.12 (m, 3H), 5.59 (dd, 1H, J=15.0, 8.5 Hz), 5.42 (dd, 1H, J=15.0, 5.0 Hz), 4.42-4.41 (m, 1H), 4.35-4.34 (m, 2H), 4.20-4.18 (m, 1H), 4.12-4.03 (m, 2H), 3.54-3.47 (m, 1H), 3.38-3.34 (m, 1H), 3.18-3.10 (m, 3H), 2.79-2.74 (m, 1H), 1.90-1.62 (m, 9H), 1.45-1.07 (m, 25H), 0.89-0.85 (m, 6H).

Step 6: Synthesis of tert-butyl N-[(4S,5E,7S)-7-benzyl-8-[(2S)—2-{[(1S)-5-({[(1-oxyl-2,2,6,6-tetramethylpiperidin-4-yl)oxy]carbonyl}amino)-1-[(propan-2-yl)carbamoyl]pentyl]carbamoyl}pyrrolidin-1-yl]-2-methyl-8-oxooct-5-en-4-yl]carbamate (XXXVII).

To a solution of compound 326 (350 mg, 0.41 mmol) in CH$_2$Cl$_2$ (15 mL) was added DBU (313 mg, 2.1 mmol). The mixture was stirred at 25° C. for 20 min. To the mixture was added DMAP (100 mg, 0.82 mmol) and compound 266 (296 mg, 0.82 mmol). The mixture was stirred at 25° C. for 1 h, diluted with CH$_2$Cl$_2$ (50 mL) and washed with H$_2$O (3×20 mL). The organic phase was dried with Na$_2$SO$_4$ and concentrated in vacuo and purified by prep-HPLC (Venusil XBP C18 (5 μm, 30×250 mm), 0.1% HCl in eluant) to obtain the titled compound XXXVII (75 mg, 22%) as a pink solid. MS (ESI): [M+H$^+$]=826.7.

Example XXXVIII and XXXIX (S)—Methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-oxyl-2,2,6,6-tetramethylpiperidin-4-yl)oxy)carbonyl)amino)pentanoate (XXXVIII) and (S)-methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-hydroxy-2,2,6,6-tetramethylpiperidin-4-yl)oxy)carbonyl)amino)pentanoate (XXXIX)

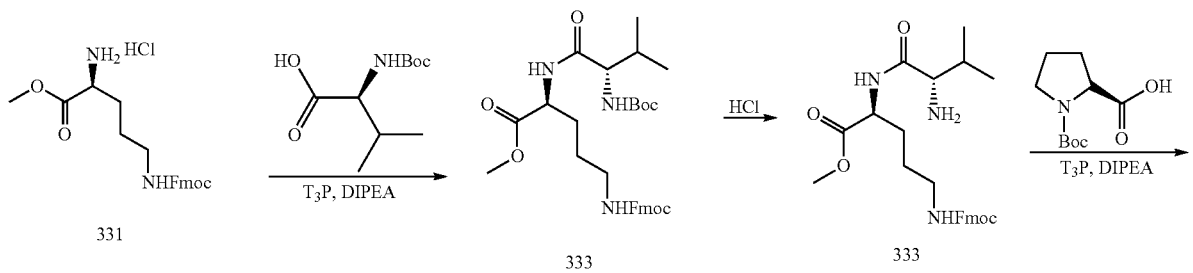

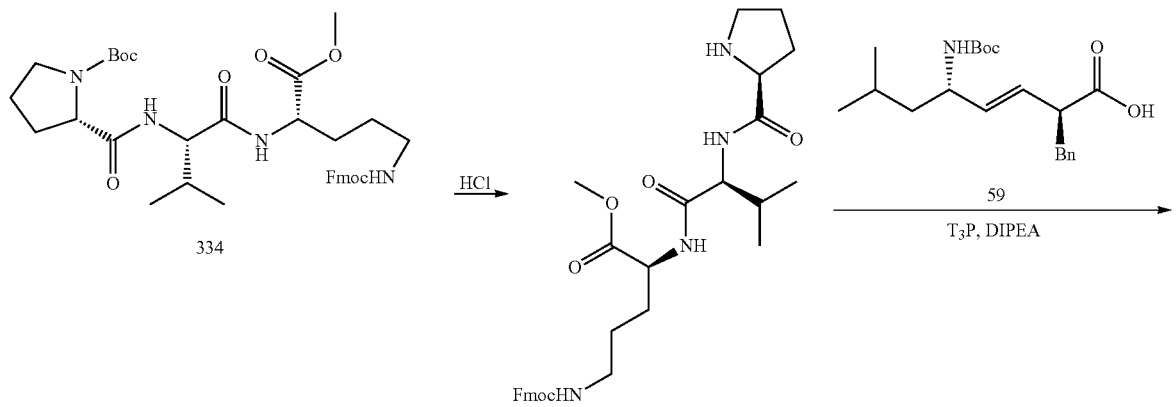

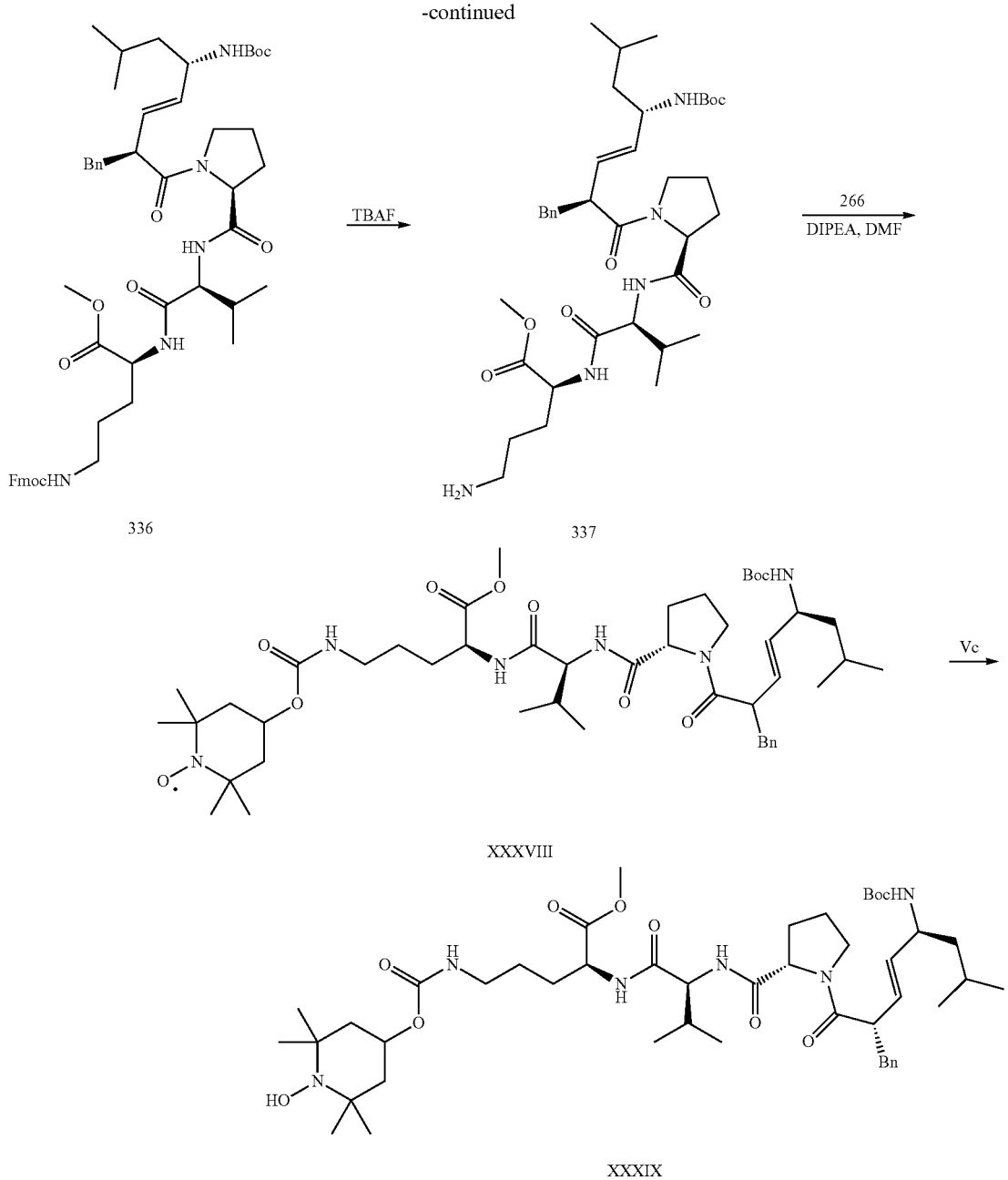

Step 1: Synthesis of (S)-methyl 5-((((9H-fluoren-9-yl)methoxy)carbonyl)amino)-2-((S)-2-((tert-butoxycarbonyl)amino)-3-methylbutanamido)pentanoate (332).

To a solution of (S)-methyl 5-((((9H-fluoren-9-yl)methoxy)carbonyl)amino)-2-aminopentanoate (331, 1.0 g, 2.5 mmol) and (S)-2-((tert-butoxycarbonyl)amino)-3-methylbutanoic acid (705 mg, 3.3 mmol) in CH$_2$Cl$_2$ (5 mL) was added T$_3$P (2.2 g, 3.3 mmol) and DIPEA (645 g, 5.0 mmol) at 0° C. The reaction mixture was allowed to warm to 25° C. and stirred for 16 h. The reaction mixture was extracted by CH$_2$Cl$_2$ (3×10 mL). The organic layer was washed with aqueous 5% NaHCO$_3$ (10 mL), aqueous HCl (5 mL, 1 M), and saturated aqueous brine solution (3×20 mL). The organic layer was dried over Na$_2$SO$_4$ and concentrated in vacuo. The residue was purified by column chromatography on silica gel (petroleum ether/EtOAc=5:1-1:1) to give product 332 (1.0 g, 91%) as a white solid. MS (ESI): [M+H$^+$]= 568.4.

Step 2: Synthesis of (S)-methyl 5-((((9H-fluoren-9-yl)methoxy)carbonyl)amino)-2-((5)—2-amino-3-methylbutanamido)pentanoate (333).

A solution of compound 332 (1.0 g, 1.8 mmol) in HCl in MeOH (20 mL, 3 M) was stirred at 25° C. for 3 h and then the solvent was removed in vacuo to give product 333 (841 mg, 100%) as a white foam. MS (ESI): [M+H$^+$]=468.2.

Step 3: Synthesis of (S)-tert-butyl 2-(((S)-1-(((S)-5-((((9H-fluoren-9-yl)methoxy)carbonyl)amino)-1-methoxy-1-oxopentan-2-yl)amino)-3-methyl-1-oxobutan-2-yl)carbamoyl)pyrrolidine-1-carboxylate (334).

To a solution of compound 333 (905 mg, 1.8 mmol) and (S)-1-(tert-butoxycarbonyl)pyrrolidine-2-carboxylic acid (464.0 mg, 2.2 mmol) in CH$_2$Cl$_2$ (10 mL) was added T$_3$P (731 mg, 2.3 mmol) and DIPEA (510 g, 4.0 mmol) at 0° C. The reaction mixture was allowed to warm to 25° C. and stirred for 16 h. The reaction mixture was quenched with saturated aqueous NH$_4$Cl solution (20 mL), and extracted by EtOAc (3×10 mL). The organic phase was washed with aqueous HCl (10 mL, 1 M), saturated aqueous brine solution (3×20 mL), and dried over Na$_2$SO$_4$. The organic phase was concentrated under reduced pressure to give product 334 (110 mg, 28%) as a white foam. MS (ESI): [M+H$^+$]=665.5.

Step 4: Synthesis of (S)-methyl 5-((((9H-fluoren-9-yl)methoxy)carbonyl)amino)-2-((S)-3-methyl-2-((S)-pyrrolidine-2-carboxamido)butanamido)pentanoate (335).

A solution of compound 334 (0.96 g, 1.4 mmol) in HCl in MeOH (20 mL, 3 M) was stirred at 25° C. for 3 h and then the solvent was removed in vacuo to give product 335 (840 mg, 100%) as a white foam. MS (ESI): [M+H$^+$]=565.3.

Step 5: Synthesis of (S)-methyl 5-((((9H-fluoren-9-yl)methoxy)carbonyl)amino)—2((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)pentanoate (336).

To a solution of compound 335 (0.84 g, 1.4 mmol) and (2S,5S,E)-2-benzyl-5-((tert-butoxycarbonyl)amino)-7-methyloct-3-enoic acid (59, 606 mg, 1.7 mmol) in CH$_2$Cl$_2$ (10 mL) was added T$_3$P (572 g, 1.8 mmol) and DIPEA (400 mg, 3.1 mmol) at 0° C. The reaction mixture was allowed to warm to 25° C. and stirred for 16 h. The reaction mixture was quenched with saturated aqueous NH$_4$Cl solution (20 mL), and extracted by EtOAc (3×10 mL). The organic phase was washed with aqueous 5% NaHCO$_3$ (10 mL), saturated aqueous brine solution (3×20 mL), and dried over Na$_2$SO$_4$. The organic phase was concentrated and purified by column chromatography on silica gel (petroleum ether/EtOAc=3:1 to 1:1) to give product 336 (810 mg, 90%) as a white solid. MS (ESI): [M+H$^+$]=908.7.

Step 6: Synthesis of (S)-methyl 5-amino-2-((S)-2-((S)-1-42S,5S,E)-2-benzyl-5-((tert-butoxycarbonyl)amino)-7-methyloct-3-enoyl)pyrrolidine-2-carboxamido)-3-methylbutanamido)pentanoate (337).

To a solution of compound 336 (680 mg, 0.75 mmol) in DMF (8 mL) was added a solution of TBAF (5% wt in THF, 6 mL) at 0° C. The reaction was stirred for 30 min. The mixture compound 337 (514 mg, 100%) was used for next step without a work up. MS (ESI): [M+H$^+$]=686.5.

Step 7: Synthesis of (S)-methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-oxyl-2,2,6,6-tetramethylpiperidin-4-yl)oxy)carbonyl)amino)pentanoate (XXXVIII).

To a solution of compound 337 (514 mg, 0.75 mmol) and 1,3-dioxoisoindolin-2-yl (1-oxyl-2,2,6,6-tetramethylpiperidin-2-yl)carbonate (266) (325 mg, 0.9 mmol) in CH$_2$Cl$_2$ (8 mL) at 0° C. was added DIPEA (194 mg, 1.5 mmol). The reaction mixture was allowed to warm to 25° C. and stirred for 2 h. The reaction mixture was quenched with saturated aqueous NH$_4$Cl solution (20 mL), and the water phase extracted by EtOAc (3×10 mL). The combined organic layer was dried over Na$_2$SO$_4$ and concentrated in vacuo. The residue was purified by prep-HPLC (Venusil XBP C18 (5 μm, 30×250 mm), 0.1% HCl in eluant) to give product XXXVIII (75 mg, 11%) as a red solid. MS (ESI): [M+H$^+$]= 884.7

Step 8: (S)-methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-hydroxy-2,2,6,6-tetramethylpiperidin-4-yl)oxy)carbonyl)amino)pentanoate (XXXIX).

To a solution of compound XXXVIII (40 mg, 0.05 mmol) in dry MeOH (2 mL) was added Vc (8.0 mg, 0.05 mmol). After stirring at 25° C. for 30 min, the solvent was removed in vacuo. The resulting residue was purified by prep-HPLC (Venusil XBP C18 (5 μm, 30×250 mm), 0.1% HCl in eluant) to give product XXXIX (25 mg, 63%) as a white solid. MS (ESI): [M+H$^+$]=885.8.

Example XXXX and XXXXI (S)-1-Oxyl-2,2,6,6-tetramethylpiperidin-4-yl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (XXXX) and (S)-1-hydroxy-2,2,6,6-tetramethylpiperidin-4-yl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (XXXXI)

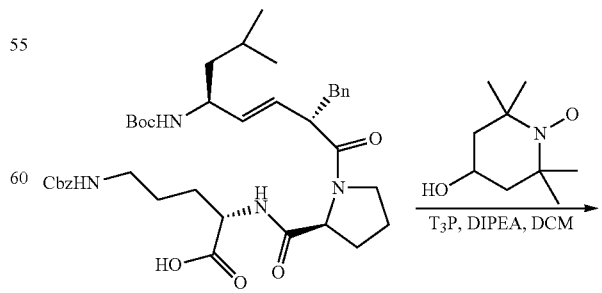

64

-continued

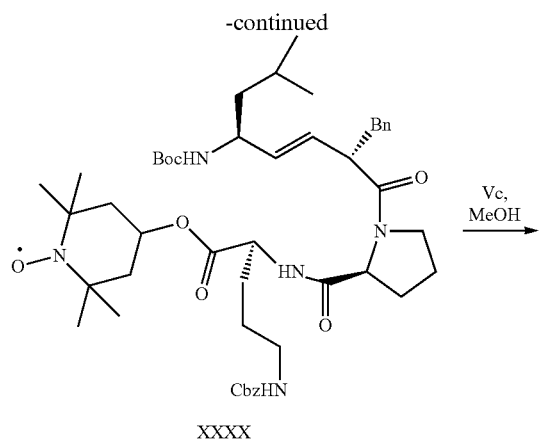

XXXX

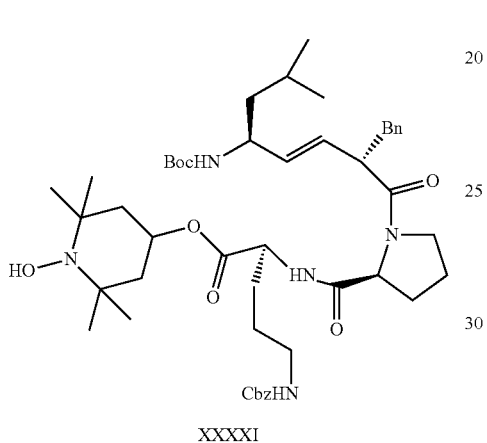

XXXXI

Step 1: Synthesis of (S)-1-oxyl-2,2,6,6-tetramethylpiperidin-4-yl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (XXXX).

To a solution of compound 64 (380 mg, 0.54 mmol) and 4-hydroxy-TEMPO (112 mg, 0.65 mmol) in $CH_2Cl_2$ (5 mL) at 0° C. was added $T_3P$ (446 mg, 1.4 mmol), and DIPEA (153 mg, 1.2 mmol). The reaction mixture was allowed to warm to 25° C. and stirred for 3 h. The mixture was diluted with $CH_2Cl_2$ (5 mL) and washed with aqueous 5% $NaHCO_3$ (10 mL), saturated aqueous brine solution (3×20 mL), and dried over $Na_2SO_4$. The solvent was removed under reduced pressure and the residue was purified by prep-HPLC (Venusil XBP C18 (5 μm, 30×250 mm), 0.1% HCl in eluant) to give product XXXX (90 mg, 19%) as a red solid. MS (ESI): $[M+H^+]=861.7$.

Step 2: Synthesis of (S)-1-hydroxy-2,2,6,6-tetramethylpiperidin-4-yl 2-((S)-1-((2S,5S,E)-2-benzyl-5-((tert-butoxycarbonyl)amino)-7-methyloct-3-enoyl)pyrrolidine-2-carboxamido)-5-(((benzyloxy)carbonyl)amino)pentanoate (XXXXI).

To a solution of compound XXXX (60 mg, 0.07 mmol) in dry MeOH (2 mL) was added Vc (13 mg, 0.07 mmol). After stirring at 25° C. for 30 min, the solvent was removed under vacuum. The resulting residue was purified by prep-HPLC (Venusil XBP C18 (5 μm, 30×250 mm), 0.1% HCl in eluant) to give product XXXXI (36 mg, 60%) as a white solid. MS (ESI): $[M+H^+]=862.7$.

Example XXXXII and XXXXIII

1-Oxyl-2,2,6,6-tetramethylpiperidin-4-yl-N-[(4S)—4-{[(2S)-1-[(2S,3E,5S)-2-benzyl-5-{[(tert- butoxy)carbonyl]amino}-7-methyloct-3-enoyl]pyrrolidin-2-yl]formamido}-4-[(1-oxyl-2,2,6,6-tetramethylpiperidin-4-yl)carbamoyl]butyl]carbamate (XXXXII) and 1-Hydroxy-2,2,6,6-tetramethylpiperidin-4-yl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl]carbamate (XXXXIII)

341

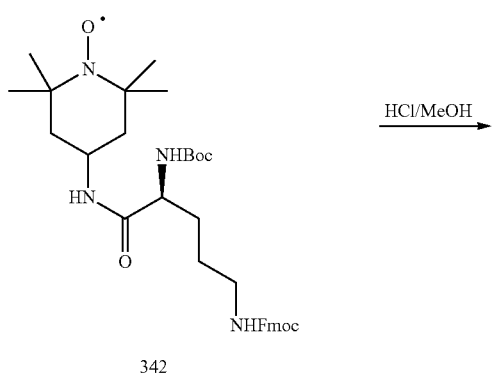

342

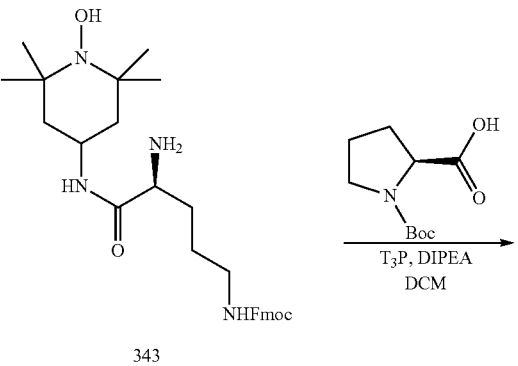

343

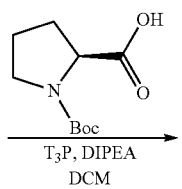

159 -continued

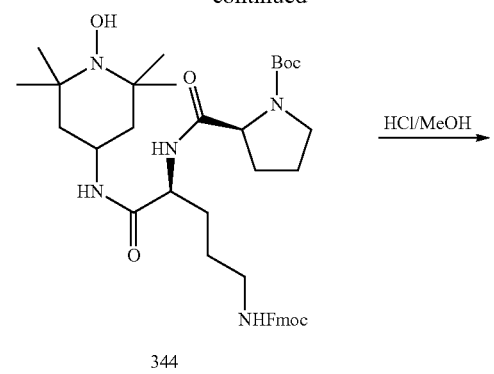

344

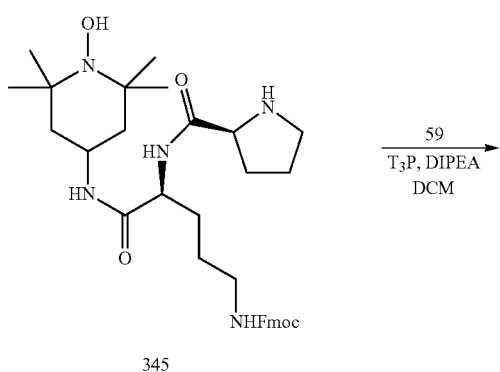

345

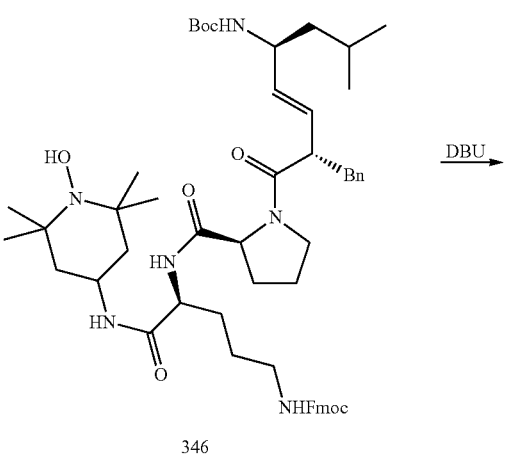

346

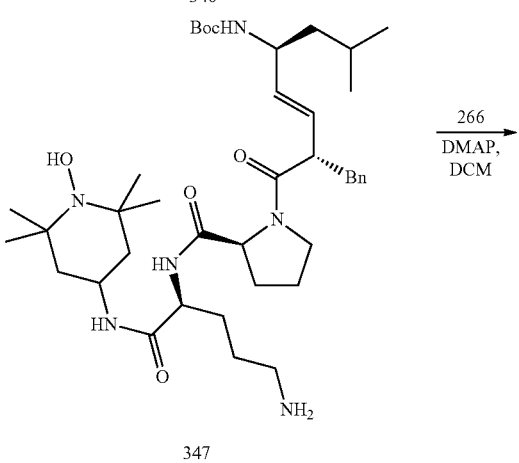

347

160 -continued

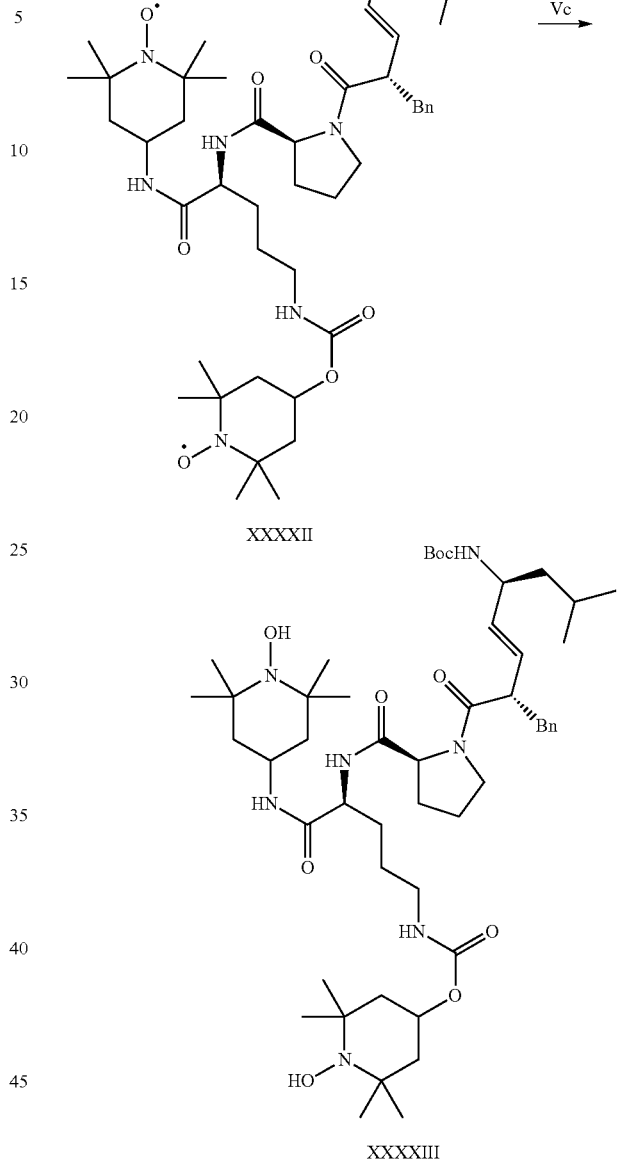

XXXXII

XXXXIII

Step 1: Synthesis of (S)—(9H-fluoren-9-yl)methyl tert-butyl (5-((1-oxyl-2,2,6,6-tetramethylpiperidin-4-yl)amino)-5-oxopentane-1,4-diyl)dicarbamate (342).

To a solution of compound 341 (1.0 g, 2.2 mmol) and 4-AT (451 mg, 2.64 mmol) in $CH_2Cl_2$ (10 mL) was added $T_3P$ (909 mg, 2.86 mmol), and DIPEA (369 mg, 2.86 mmol) at 0° C. The reaction mixture was allowed to warm to 25° C. and stirred for 3 h. The mixture was diluted with $CH_2Cl_2$ (10 mL), washed with aqueous 5% $NaHCO_3$ (10 mL), saturated aqueous brine solution (3×20 mL), dried over $Na_2SO_4$. The solvent was removed under reduced pressure to give crude product 2 (0.8 g, 62%) as a red solid. MS (ESI): [M+H$^+$]=608.3.

Step 2: Synthesis of (S)—(9H-fluoren-9-yl)methyl (4-amino-5-((1-hydroxy-2,2,6,6-tetramethylpiperidin-4-yl) amino)-5-oxopentyl)carbamate (343).

A solution of compound 342 (0.8 g, 1.3 mmol) in HCl in MeOH (10 mL, 3 M) was stirred at 25° C. for 3 h. The solvent as removed in vacuo to give product 343 (654 mg, 100%) as a white solid. MS (ESI): [M+H⁺]=509.2.

Step 3: Synthesis of (S)-tert-butyl 2-4(S)-5-4((9H-fluoren-9-yl)methoxy)carbonyl)amino)-1-((1-hydroxy-2,2,6,6-tetramethylpiperidin-4-yl)amino)-1-oxopentan-2-yl)carbamoyl)pyrrolidine-1-carboxylate (344).

To a solution of compound 343 (654 mg, 1.29 mmol) and (S)-1-(tert-butoxycarbonyl)pyrrolidine-2-carboxylic acid (333 mg, 1.55 mmol) in CH₂Cl₂ (5 mL) was added T₃P (1.1 g, 1.68 mmol), and DIPEA (366 mg, 2.84 mmol) at 0° C. The reaction mixture was allowed to warm to 25° C. and stirred for 3 h. The mixture was diluted with CH₂Cl₂ (5 mL), washed with aqueous 5% NaHCO₃ (5 mL), saturated aqueous brine solution (3×20 mL), dried over Na₂SO₄. The solvent was removed under reduced pressure to give crude product 344 (630 mg, 69%) as a yellow solid. MS (ESI): [M+H⁺]=706.3

Step 4: Synthesis of (9H-fluoren-9-yl)methyl ((S)-5-((1-hydroxy-2,2,6,6-tetramethylpiperidin-4-yl)amino)-5-oxo-4-((S)-pyrrolidine-2-carboxamido)pentyl)carbamate (345).

A solution of compound 344 (630 mg, 0.89 mmol) in HCl in MeOH (10 mL, 3 M) was stirred at 25° C. for 2 h. The solvent was removed in vacuo to give product 345 (538 mg, 100%) as a yellow solid. MS (ESI): [M+H⁺]=606.4.

Step 5: Synthesis of (9H-fluoren-9-yl)methyl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl]carbamate (346).

To a solution of compound 345 (0.3 g, 0.5 mmol) and (2S,5S,E)-2-benzyl-5-((tert-butoxycarbonyl)amino)-7-methyloct-3-enoic acid (59) (217 mg, 0.6 mmol) in CH₂Cl₂ (5 mL) at 0° C. was added T₃P (420 mg, 0.65 mmol, 50% in EtOAc) and DIPEA (142 mg, 1.1 mmol). The reaction mixture was allowed to warm to 25° C. and stirred for 3 h. The mixture was diluted with CH₂Cl₂ (10 mL), washed with aqueous NaHCO₃, saturated aqueous brine solution (3×20 mL), and dried over Na₂SO₄. The solvent was removed under reduced pressure to give crude product 346 (220 mg, 46%) as a yellow solid. MS (ESI): [M+H⁺]=949.8.

Step 6: Synthesis of tert-butyl ((4S,7S,E)-8-((S)-2-(((S)-5-amino-1-((1-hydroxy-2,2,6,6-tetramethylpiperidin-4-yl)amino)-1-oxopentan-2-yl)carbamoyl)pyrrolidin-1-yl)-7-benzyl-2-methyl-8-oxooct-5-en-4-yl)carbamate (347).

A solution of compound 346 (220 mg, 0.23 mmol) in CH₂Cl₂ (5 mL) was added DBU (70 mg, 0.46 mmol) at 25° C. The reaction was stirred at 25° C. for 30 min. The solvent was removed in vacuo to give product 347 (167 mg, 100%) as a red oil without purification to use for next step. MS (ESI): [M+H⁺]=727.6.

Step 7: Synthesis of 1-oxyl-2,2,6,6-tetramethylpiperidin-4-yl N-((4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-oxyl-2,2,6,6-tetramethylpiperidin-4-yl)carbamoyl]butyl carbamate (XXXXII).

To a solution of compound 347 (167 mg, 0.23 mmol) and 1,3-dioxoisoindolin-2-yl (1-oxyl-2,2,6,6-tetramethylpiperidin-4-yl)carbonate (266) (159 mg, 0.46 mmol) in CH₂Cl₂ (5 mL) at 0° C. was added DIPEA (60 mg, 0.46 mmol). The reaction mixture was allowed to warm to 25° C. and stirred for 3 h. After adding CH₂Cl₂ (10 mL), the organic phase was washed with aqueous 5% NaHCO₃ (10 mL), saturated aqueous brine solution (3×20 mL), and dried over Na₂SO₄. The solvent was removed under reduced pressure and the residue was purified by prep-HPLC (Venusil XBP C18 (5 µm, 3250 mm), 0.1% HCl in eluant) to give product XXXXII (80 mg, yield 38%) as red solid. MS (ESI): [M+H⁺]=924.8.

Step 8: Synthesis of 1-hydroxy-2,2,6,6-tetramethylpiperidin-4-yl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(1-hydroxy-2,2,6,6-tetramethylpiperidin-4-yl)carbamoyl]butyl]carbamate (XXXXIII).

To a solution of compound XXXXII (70 mg, 0.08 mmol) in dry MeOH (2 mL) was added Vc (13 mg, 0.08 mmol). After stirring at 25° C. for 30 min, the solvent was removed under vacuum. The resulting residue was purified by prep-HPLC (Venusil XBP C18 (5 µm, 30x250 mm), 0.1% HCl in eluant) to give product XXXXIII (28 mg, 38%) as a white solid. MS (ESI): [M+H⁺]=925.8.

Example XXXXIV and XXXXV tert-Butyl N-[(4S,5E,7S)-7-benzyl-8-[(2S)—2-{[(1S)-4-({[(1-oxyl-2,2,6,6-tetramethylpiperidin-4-yl)oxy]carbonyl}amino)-1-[(propan-2-yl)carbamoyl]butyl]carbamoyl}pyrrolidin-1-yl]-2-methyl-8-oxooct-5-en-4-yl]carbamate (XXXXIV) and tert-butyl N-[4S,5E,7S]-7-benzyl-8-[(2S)—2-{[(1S)-4-({[(1-hydroxy-2,2,6,6-tetramethylpiperidin-4-yl)oxy]carbonyl}amino)-1-[(propan-2-yl)carbamoyl]butyl]carbamoyl}pyrrolidin-1-yl]-2-methyl-8-oxooct-5-en-4-yl]carbamate (XXXXV)

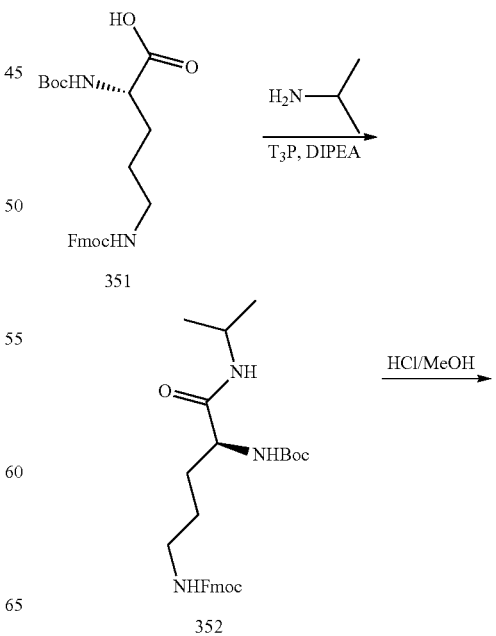

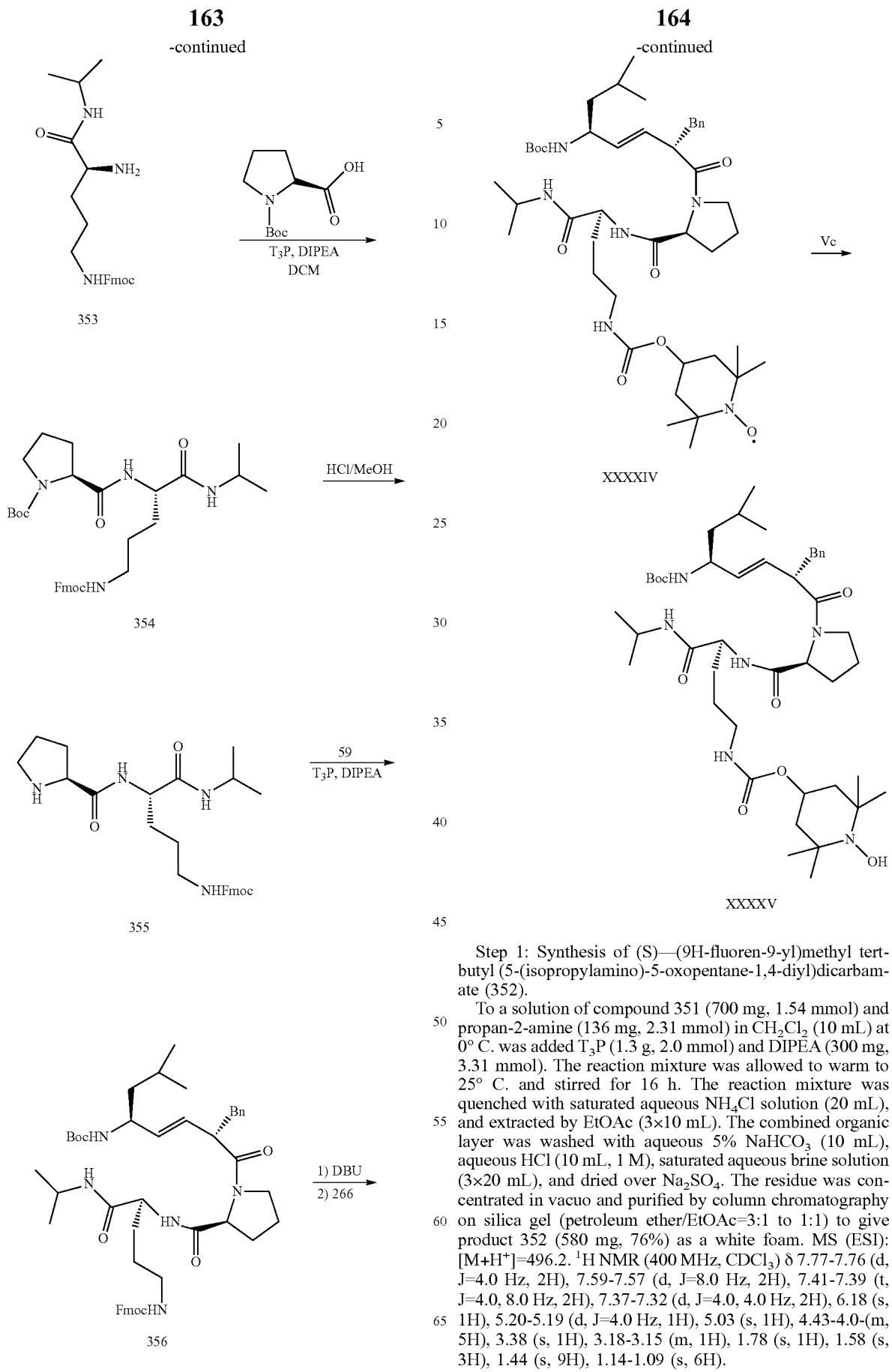

Step 1: Synthesis of (S)—(9H-fluoren-9-yl)methyl tert-butyl (5-(isopropylamino)-5-oxopentane-1,4-diyl)dicarbamate (352).

To a solution of compound 351 (700 mg, 1.54 mmol) and propan-2-amine (136 mg, 2.31 mmol) in CH$_2$Cl$_2$ (10 mL) at 0° C. was added T$_3$P (1.3 g, 2.0 mmol) and DIPEA (300 mg, 3.31 mmol). The reaction mixture was allowed to warm to 25° C. and stirred for 16 h. The reaction mixture was quenched with saturated aqueous NH$_4$Cl solution (20 mL), and extracted by EtOAc (3×10 mL). The combined organic layer was washed with aqueous 5% NaHCO$_3$ (10 mL), aqueous HCl (10 mL, 1 M), saturated aqueous brine solution (3×20 mL), and dried over Na$_2$SO$_4$. The residue was concentrated in vacuo and purified by column chromatography on silica gel (petroleum ether/EtOAc=3:1 to 1:1) to give product 352 (580 mg, 76%) as a white foam. MS (ESI): [M+H$^+$]=496.2. $^1$H NMR (400 MHz, CDCl$_3$) δ 7.77-7.76 (d, J=4.0 Hz, 2H), 7.59-7.57 (d, J=8.0 Hz, 2H), 7.41-7.39 (t, J=4.0, 8.0 Hz, 2H), 7.37-7.32 (d, J=4.0, 4.0 Hz, 2H), 6.18 (s, 1H), 5.20-5.19 (d, J=4.0 Hz, 1H), 5.03 (s, 1H), 4.43-4.0-(m, 5H), 3.38 (s, 1H), 3.18-3.15 (m, 1H), 1.78 (s, 1H), 1.58 (s, 3H), 1.44 (s, 9H), 1.14-1.09 (s, 6H).

Step 2: Synthesis of (S)—(9H-fluoren-9-yl)methyl (4-amino-5-(isopropylamino)-5-oxopentyl)carbamate (353).

A solution of compound 352 (580 mg, 1.17 mmol) in HCl in MeOH (10 mL, 3 M) was stirred at 25° C. for 2 h and then the solvent was removed in vacuo to give product 353 (462 mg, 100%) as a white foam. MS (ESI): [M+H$^+$]=396.1.

Step 3: Synthesis of (S)-tert-butyl 2-(((S)-5-((((9H-fluoren-9-yl)methoxy)carbonyl)amino)-1-(isopropylamino)—1-oxopentan-2-yl)carbamoyl)pyrrolidine-1-carboxylate (354).

To a solution of compound 353 (462 mg, 1.17 mmol) and (S)-1-(tert-butoxycarbonyl)pyrrolidine-2-carboxylic acid (302 mg, 1.4 mmol) in CH$_2$Cl$_2$ (10 mL) at 0° C. was added T$_3$P (484 mg, 1.5 mmol) and DIPEA (302 mg, 2.34 mmol). The reaction mixture was allowed to warm to 25° C. and stirred for 16 h. The reaction mixture was quenched with saturated aqueous NH$_4$Cl solution (20 mL), and extracted by EtOAc (3×10 mL). The combined organic layer was washed with aqueous 5% NaHCO$_3$ (10 mL), aqueous HCl (10 mL, 1 M), saturated aqueous brine solution (3×20 mL), and dried over Na$_2$SO$_4$. The solvent was removed in vacuo and residue purified by column chromatography on silica gel (petroleum ether/EtOAc=3:1 to 1:1) to give product 354 (490 mg, 85%) as a white foam. MS (ESI): [M+H$^+$]=593.4. $^1$H NMR: (400 MHz, CDCl$_3$) δ 7.76-7.74 (d, J=8.0 Hz, 2H), 7.58-7.57 (d, J=4.0 Hz, 2H), 7.40-7.37 (t, J=4.0, 8.0 Hz, 2H), 7.30-7.28 (t, J=4.0, 4.0 Hz, 2H), 6.97 (s, 1H), 6.71 (s, 1H), 5.25 (s, 1H), 4.45-4.18 (m, 5H), 4.0 (s, 1H), 3.46-3.14 (m, 4H), 2.11 (s, 3H), 1.93-1.73 (s, 3H), 1.62-1.55 (m, 3H), 1.43 (s, 9H), 1.12-1.11 (d, J=4.0 Hz, 6H).

Step 4: Synthesis of (9H-fluoren-9-yl)methyl ((S)-5-(isopropylamino)—5-oxo-4-((5)—pyrrolidine-2-carboxamido) pentyl)carbamate (355).

A solution of compound 354 (490 mg, 1.0 mmol) in HCl in MeOH (10 mL, 3 M) was stirred at 25° C. for 2 h and then the solvent was removed in vacuo to give product 355 (392 mg, 100%) as a white foam. MS (ESI): [M+H$^+$]=493.3.

Step 5: Synthesis of (9H-fluoren-9-yl)methyl N-[(4S)—4-{[(2S)-1-[(2S,3E,5S)-2-benzyl-5-{[(tert-butoxy)carbonyl]amino}-7-methyloct-3-enoyl]pyrrolidin-2-yl]formamido}-4-[(propan-2-yl)carbamoyl]butyl]carbamate (356).

To a solution of compound 355 (392 mg, 0.80 mmol) and (2S,5S,E)-2-benzyl-5-((tert-butoxycarbonyl)amino)-7-methyloct-3-enoic acid (59, 346 mg, 0.96 mmol) in CH$_2$Cl$_2$ (5 mL) at 0° C. was added T$_3$P (318 mg, 1.0 mmol) and DIPEA (220 g, 1.7 mmol). The reaction mixture was allowed to warm to 25° C. and stirred for 16 h. The reaction mixture was quenched with saturated aqueous NH$_4$Cl solution (20 mL), and extracted by EtOAc (3×10 mL). The combined organic layer was washed with aqueous HCl (10 mL, 1 M), saturated aqueous brine solution (3×20 mL), and dried over Na$_2$SO$_4$. The residue was after concentrated in vacuo was purified by column chromatography on silica gel (petroleum ether/EtOAc=3:1 to 1:1) to give product 356 (320 mg, 48%) as a white foam. MS (ESI): [M+H$^+$]=836.5. $^1$H NMR: (400 MHz, CDCl$_3$) δ 7.76-7.75 (d, J=4.0 Hz, 2H), 7.59-7.58 (d, J=4.0 Hz, 2H), 7.40-7.38 (t, J=4.0, 4.0 Hz, 2H), 7.31-7.29 (t, J=4.0, 4.0 Hz, 2H), 7.24-7.23 (d, J=4.0 Hz, 2H), 7.19-7.17 (t, J=4.0, 4.0 Hz, 1H), 7.14-7.13 (d, J=4.0 Hz, 2H), 6.86-6.84 (d, J=8.0 Hz, 1H), 6.49-6.48 (d, J=4.0 Hz, 1H), 5.61-5.57 (m, 1H), 5.39-5.34 (m, 1H), 5.15-5.13 (m, 1H), 4.43-4.32 (m, 3H), 4.21-4.19 (t, J=4.0, 4.0 Hz, 1H), 4.07-4.03 (m, 1H), 3.53 (s, 1H), 3.38-3.32 (m, 1H), 3.19-3.12 (m, 2H), 2.78-2.75 (m, 1H), 2.07-1.18 (m, 4H), 1.79-1.63 (m, 6H), 1.54-1.41 (m, 12H), 1.28-1.14 (m, 9H), 0.87-0.82 (m, 6H).

Step 6: Synthesis of tert-butyl N-[(4S,5E,7S)-7-benzyl-8-[(2S)—2-{[(1S)-4-({[(1-oxyl-2,2,6,6- tetramethylpiperidin-4-yl)oxy]carbonyl}amino)-1-[(propan-2-yl)carbamoyl]butyl]carbamoyl}pyrrolidin-1-yl]-2-methyl-8-oxooct-5-en-4-yl]carbamate (XXXXIV).

To a solution of compound 356 (320 mg, 0.38 mmol) in CH$_2$Cl$_2$ (5 mL) was added DBU (289 mg, 1.9 mmol) at 25° C. The reaction mixture was stirred at 25° C. for 30 min and used to next step without purification. The mixture was treated with 1,3-dioxoisoindolin-2-yl (1-oxyl-2,2,6,6-tetramethylpiperidin-4-yl)carbonate (266) (262 mg, 0.76 mmol) and DIPEA (98 mg, 0.76 mmol). The reaction mixture was stirred at 25° C. for 30 min, then quenched with saturated aqueous NH$_4$Cl solution (20 mL). The aqueous phase was separated and extracted with CH$_2$Cl$_2$ (3×20 mL), and the combined organic layers were dried over Na$_2$SO$_4$ and concentrated in vacuo. The residue was purified by pre-HPLC (Venusil XBP C18 (5 μm, 30×250 mm), 0.1% HCl in eluant) to give product XXXXVI (150 mg, 49%) as a red solid. MS (ESI): [M+H$^+$]=812.6.

Step 7: Synthesis of tert-butyl N-[(4S,5E,7S)-7-benzyl-8-[(2S)—2-{[(1S)-4-({[(1-hydroxy-2,2,6,6- tetramethylpiperidin-4-yl)oxy]carbonyl}amino)-1-[(propan-2-yl) carbamoyl}butyl]carbamoyl}-pyrrolidin-1-yl]-2-methyl-8-oxooct-5-en-4-yl]carbamate (XXXXV).

To a solution of compound XXXXIV (70 mg, 0.09 mmol) in dry MeOH (2 mL) was added Vc (16.0 mg, 0.09 mmol). After stirring at 25° C. for 30 min, the solvent was removed under vacuum. The resulting residue was purified by prep-HPLC (Venusil XBP C18 (5 μm, 30x250 mm), 0.1% HCl in eluant) to give product XXXXV (50 mg, 68%) as a white solid. MS (ESI): [M+H$^+$]=813.6.

Example XXXXVI (S)—Cyclohexyl 2-((R)-1-((2S,5S,E)-2-benzyl-5-((tert-butoxycarbonyl)amino)-7-methyloct-3-enoyl) pyrrolidine-2-carboxamido)-6-((((1-hydroxy-2,2,6,6-tetramethylpiperidin-4-yl)oxy)carbonyl)amino) hexanoate (XXXXVI)

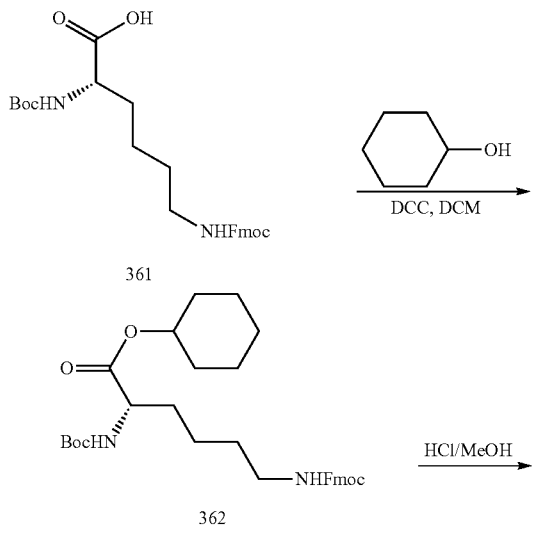

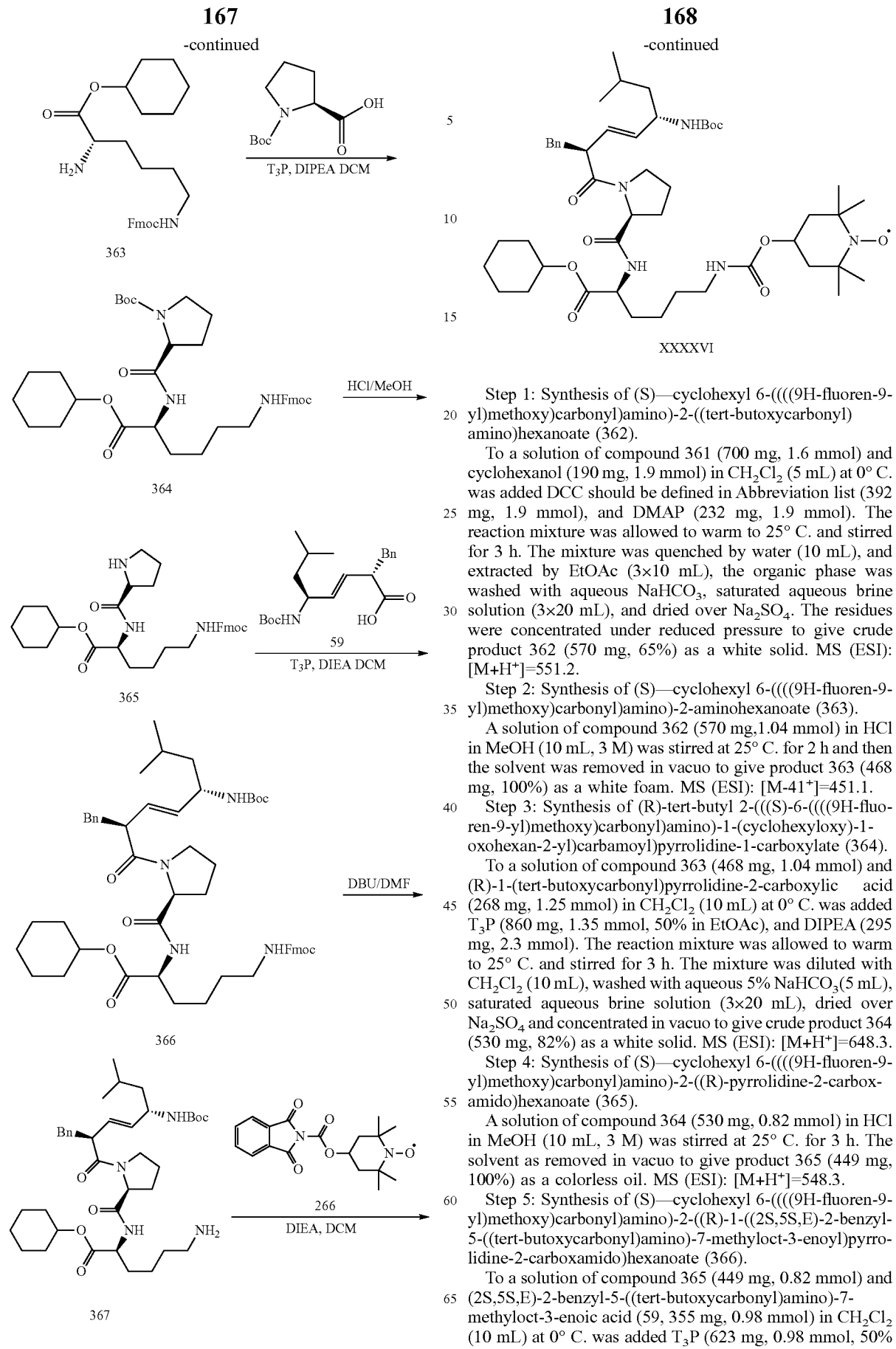

Step 1: Synthesis of (S)—cyclohexyl 6-((((9H-fluoren-9-yl)methoxy)carbonyl)amino)-2-((tert-butoxycarbonyl)amino)hexanoate (362).

To a solution of compound 361 (700 mg, 1.6 mmol) and cyclohexanol (190 mg, 1.9 mmol) in $CH_2Cl_2$ (5 mL) at 0° C. was added DCC should be defined in Abbreviation list (392 mg, 1.9 mmol), and DMAP (232 mg, 1.9 mmol). The reaction mixture was allowed to warm to 25° C. and stirred for 3 h. The mixture was quenched by water (10 mL), and extracted by EtOAc (3×10 mL), the organic phase was washed with aqueous $NaHCO_3$, saturated aqueous brine solution (3×20 mL), and dried over $Na_2SO_4$. The residues were concentrated under reduced pressure to give crude product 362 (570 mg, 65%) as a white solid. MS (ESI): $[M+H^+]=551.2$.

Step 2: Synthesis of (S)—cyclohexyl 6-((((9H-fluoren-9-yl)methoxy)carbonyl)amino)-2-aminohexanoate (363).

A solution of compound 362 (570 mg, 1.04 mmol) in HCl in MeOH (10 mL, 3 M) was stirred at 25° C. for 2 h and then the solvent was removed in vacuo to give product 363 (468 mg, 100%) as a white foam. MS (ESI): $[M-41^+]=451.1$.

Step 3: Synthesis of (R)-tert-butyl 2-(((S)-6-((((9H-fluoren-9-yl)methoxy)carbonyl)amino)-1-(cyclohexyloxy)-1-oxohexan-2-yl)carbamoyl)pyrrolidine-1-carboxylate (364).

To a solution of compound 363 (468 mg, 1.04 mmol) and (R)-1-(tert-butoxycarbonyl)pyrrolidine-2-carboxylic acid (268 mg, 1.25 mmol) in $CH_2Cl_2$ (10 mL) at 0° C. was added $T_3P$ (860 mg, 1.35 mmol, 50% in EtOAc), and DIPEA (295 mg, 2.3 mmol). The reaction mixture was allowed to warm to 25° C. and stirred for 3 h. The mixture was diluted with $CH_2Cl_2$ (10 mL), washed with aqueous 5% $NaHCO_3$ (5 mL), saturated aqueous brine solution (3×20 mL), dried over $Na_2SO_4$ and concentrated in vacuo to give crude product 364 (530 mg, 82%) as a white solid. MS (ESI): $[M+H^+]=648.3$.

Step 4: Synthesis of (S)—cyclohexyl 6-((((9H-fluoren-9-yl)methoxy)carbonyl)amino)-2-((R)-pyrrolidine-2-carboxamido)hexanoate (365).

A solution of compound 364 (530 mg, 0.82 mmol) in HCl in MeOH (10 mL, 3 M) was stirred at 25° C. for 3 h. The solvent as removed in vacuo to give product 365 (449 mg, 100%) as a colorless oil. MS (ESI): $[M+H^+]=548.3$.

Step 5: Synthesis of (S)—cyclohexyl 6-((((9H-fluoren-9-yl)methoxy)carbonyl)amino)-2-((R)-1-((2S,5S,E)-2-benzyl-5-((tert-butoxycarbonyl)amino)-7-methyloct-3-enoyl)pyrrolidine-2-carboxamido)hexanoate (366).

To a solution of compound 365 (449 mg, 0.82 mmol) and (2S,5S,E)-2-benzyl-5-((tert-butoxycarbonyl)amino)-7-methyloct-3-enoic acid (59, 355 mg, 0.98 mmol) in $CH_2Cl_2$ (10 mL) at 0° C. was added $T_3P$ (623 mg, 0.98 mmol, 50% in EtOAc), and DIPEA (233 mg, 1.8 mmol). The reaction mixture was allowed to warm to 25° C. and stirred for 3 h. The mixture was quenched by water (10 mL), and extracted by EtOAc (3×10 mL). The combined organic phase was washed with aqueous 5% NaHCO₃ (10 mL), saturated aqueous brine solution (3×20 mL), and dried over Na₂SO₄. The residues after concentrated in vacuo were purified by column chromatography on silica gel (petroleum ether/EtOAc=3:1 to 1:1) to give product 366 (380 mg, 52%) as a white solid. MS (ESI): [M+H⁺]=891.8.

Step 6: Synthesis of (S)—cyclohexyl 6-amino-2-((R)-1-((2S,5S,E)-2-benzyl-5-((tert-butoxycarbonyl)amino)-7-methyloct-3-enoyl)pyrrolidine-2-carboxamido)hexanoate (367).

A solution of compound 366 (380 mg, 0.43 mmol) in CH₂Cl₂ (5 mL) was added DBU (327 mg, 2.15 mmol) at 25° C., and the reaction was stirred at 25° C. for 30 min. The solvent was removed to give product 367 (293 mg, 100%) as a yellow oil, which was used to next step without purification. MS (ESI): [M+H⁺]=669.9.

Step 7: Synthesis of (S)—cyclohexyl 2-((R)-1-((2S,5S,E)-2-benzyl-5-((tert-butoxycarbonyl)amino)-7-methyloct-3-enoyl)pyrrolidine-2-carboxamido)-6-((((1-hydroxy-2,2,6,6-tetramethylpiperidin-4-yl)oxy)carbonyl)amino)hexanoate (XXXXVI).

A solution of the crude compound 367 (293 mg, 0.43 mmol) in dry CH₂Cl₂ (5 mL) at 0° C. was treated with 1,3-dioxoisoindolin-2-yl (1-oxyl-2,2,6,6-tetramethylpiperidin-4-yl)carbonate (266) (178 mg, 0.52 mmol) and DIPEA (67 mg, 0.52 mmol). The reaction mixture was stirred at 25° C. for 30 min, diluted with CH₂Cl₂ (10 mL) and then quenched with saturated aqueous NH₄Cl solution (20 mL). The aqueous phase was separated and extracted with CH₂Cl₂ (10 mL), and the combined organic layers were dried over Na₂SO₄ and concentrated in vacuo. The residue was purified by prep-HPLC (Venusil XBP C18 (5 μm, 30×250 mm), 0.1% HCl in eluant) to give product XXXXVI (35 mg, 10%) as a red solid. MS (ESI): [M+H⁺]=867.6.

Example XXXXVII tert-Butyl N-[(4S,5E,7S)-7-benzyl-8-[(2S)—2-{[(1S)—1-{[(1S)-4-({[(1-oxyl-2,2,6,6- tetramethylpiperidin-4-yl)oxy]carbonyl}amino)-1-[(propan-2-yl)carbamoyl]butyl]carbamoyl}-2-methylpropyl]carbamoyl}pyrrolidin-1-yl]-2-methyl-8-oxooct-5-en-4-yl]carbamate (XXXXVII)

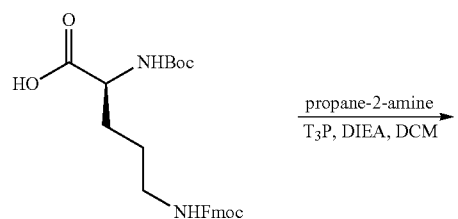

371

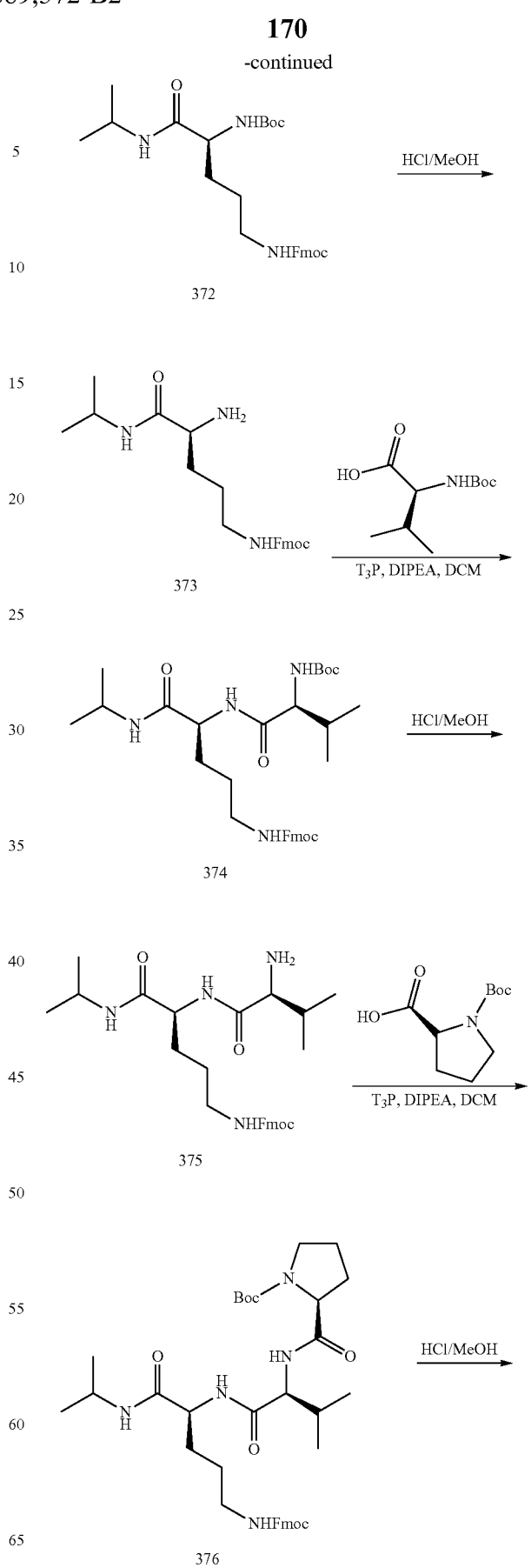

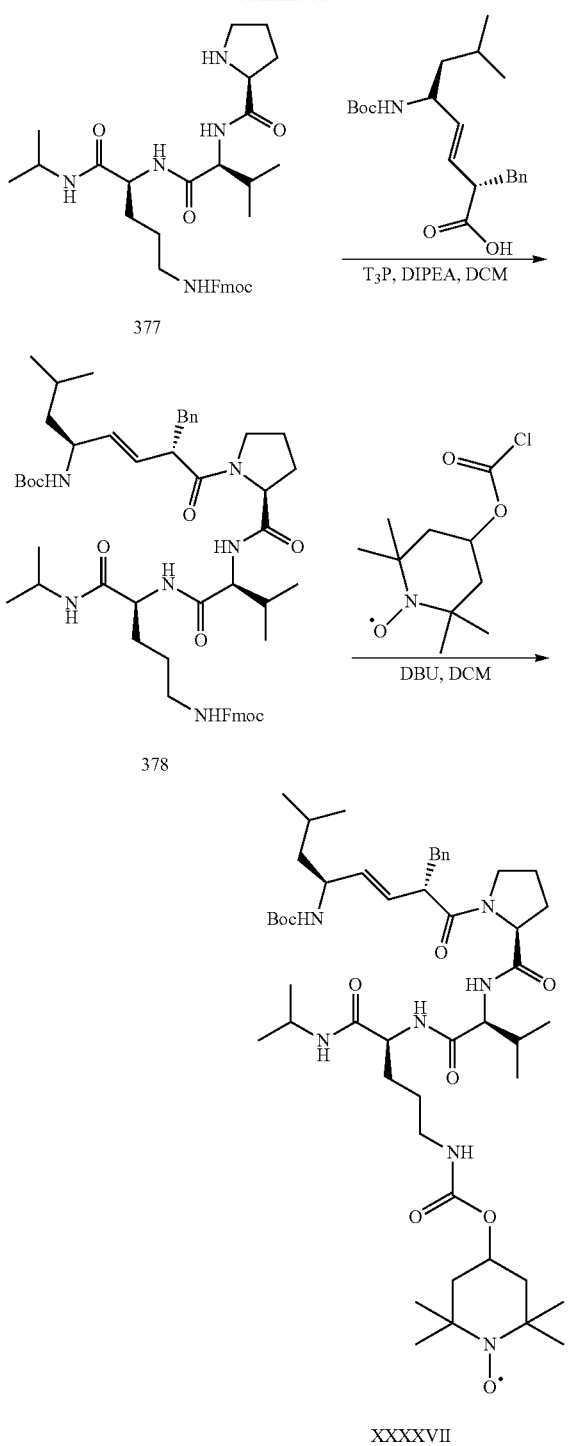

Step 1: Synthesis of (S)—(9H-fluoren-9-yl)methyl tert-butyl (5-(isopropylamino)-5-oxopentane-1,4-diyl)dicarbamate (372).

To a solution of 371 (1 g, 2.2 mmol), propan-2-amine (389 mg, 6.6 mmol), DIPEA (851 mg, 6.6 mmol) in DCM (30 mL) was added T₃P (1.82 g, 2.9 mmol) at 0° C. The mixture was stirred at 25° C. for 10 h, and concentrated in vacuum. EA (100 mL) was added to the residue and washed with H₂O (3×50 mL). The organic phase was collected after dried with Na₂SO₄ and concentrated in vacuum to obtain the titled compound 372 (1.09 g, 100%) as a yellow solid. MS (ESI): [M+H⁺]=496.1.

Step 2: Synthesis of (S)—(9H-fluoren-9-yl)methyl (4-amino-5-(isopropylamino)-5-oxopentyl)carbamate (373).

To compound 372 (1.09 g, 2.2 mmol) was added HCl in MeOH (15 mL, 3M) and EA (15 mL), then the mixture was stirred at 25° C. for 0.5 h. The organic solution was concentrated under vacuum to obtain the titled compound 373 (870 mg, 100%) as a yellow solid. MS (ESI): [M+H⁺]=396.2.

Step 3: Synthesis of (9H-fluoren-9-yl)methyl N-[(4S)-4-[(2S)—2-{[(tert-butoxy)carbonyl]amino}-3-methylbutanamido]-4-[(propan-2-yl)carbamoyl]butyl]carbamate (374)

To a solution of 373 (870 mg, 2.2 mmol), (S)-2-((tert-butoxycarbonyl)amino)-3-methylbutanoic acid (477 mg, 2.2 mmol), DIPEA (851 mg, 6.6 mmol) in DCM (30 mL) was added T₃P (1.82 g, 2.9 mmol) at 0° C. The mixture was stirred at 25° C. for 2 h and concentrated in vacuo. To the residue was added EA (100 mL) and the organic layer washed with H₂O (3×50 mL). The organic phase was collected after dried with Na₂SO₄ and concentrated in vacuo to obtain the titled compound 374 (1.31 g, 100%) as a yellow solid. MS (ESI): [M+H⁺]=595.3.

Step 4: Synthesis of (9H-fluoren-9-yl)methyl N-[(4S)-4-[(2S)-2-amino-3-methylbutanamido]-4-[(propan-2-yl)carbamoyl]butyl]carbamate (375).

To a 50-mL single-neck flask was added 374 (1.31 g, 2.2 mmol) and HCl in MeOH (20 mL, 3M), then the mixture was stirred at 25° C. for 1 h. The organic solution was concentrated under vacuum to obtain the titled compound 5 (1.09 g, 100%) as a yellow solid. MS (ESI): [M+H⁺]=495.3.

Step 5: Synthesis of (S)-tert-butyl 2-(((S)-1-(((S)-5-((((9H-fluoren-9-yl)methoxy)carbonyl)amino)-1-(isopropylamino)—1-oxopentan-2-yl)amino)-3-methyl-1-oxobutan-2-yl)carbamoyl)pyrrolidine-1-carboxylate (376).

To a solution of 375 (1.09 g, 2.2 mmol), (S)-1-(tert-butoxycarbonyl)pyrrolidine-2-carboxylic acid (710 mg, 3.3 mmol), DIPEA (851 mg, 6.6 mmol) in DCM (30 mL) was added T₃P (1.82 mg, 2.8 mmol) at 0° C.

The mixture was stirred at 25° C. for 2 h and concentrated in vacuum. EA (100 mL) was added to the residue and the organic layer washed with H₂O (3×50 mL). The organic phase was collected after dried with Na₂SO₄ and concentrated in vacuum to obtain the titled compound 376 (1.52 g, 100%) as a yellow solid. MS (ESI): [M+H⁺]=692.4.

Step 6: Synthesis of (9H-fluoren-9-yl)methyl ((S)-5-(isopropylamino)—4-((S)-3-methyl-2-((S)-pyrrolidine-2-carboxamido)butanamido)-5-oxopentyl)carbamate (377).

To EA (10 mL) solution of 376 (800 mg, 1.16 mmol) was added HCl in MeOH (10 mL, 3M) and the mixture was stirred at 25° C. for 0.5 h. The organic solution was concentrated under vacuum to obtain the titled compound 377 (684 mg, 100%) as a yellow solid. MS (ESI): [M+H⁺]=592.2.

Step 7: Synthesis of (9H-fluoren-9-yl)methyl N-[(4S)-4-[(2S)—2-{[2S)-1-[(2S,3E,5S)-2-benzyl-5-{[(tert-butoxy)carbonyl]amino}-7-methyloct-3-enoyl]pyrrolidin-2-yl]formamido}-3-methylbutanamido]-4-[(propan-2-yl)carbamoyl]butyl]carbamate (378).

To a solution of 377 (592 mg, 1 mmol), (2S, 5S, E)-2-benzyl-5-((tert-butoxycarbonyl)amino)-7-methyloct-3-enoic acid (59, 453 mg, 1.25 mmol), DIPEA (387 mg, 3 mmol) in DCM (30 mL) was added T₃P (827 mg, 1.3 mmol) at 0° C. The mixture was stirred at 25° C. for 10 h, then concentrated in vacuo. To the residue was added EA (50 mL) and the organic layer washed with H₂O (3×50 mL). The organic phase was dried with $Na_2SO_4$ and concentrated in vacuo and purified by column chromatography on silica gel (PE/EA=1:1) to obtain the titled compound 378 (580 mg, 62%) as a yellow solid. MS (ESI): [M+H$^+$]=935.6. $^1$H NMR (400 MHz, CDCl$_3$) δ 7.76-7.75 (m, 2H), 7.59-7.57 (m, 2H), 7.41-7.37 (m, 2H), 7.32-7.28 (m, 2H), 7.24-7.11 (m, 5H), 5.65-5.30 (m, 2H), 4.53-3.99 (m, 8H), 3.74-3.09 (m, 6H), 2.77-2.75 (m, 1H), 2.29-1.84 (m, 8H), 1.52-0.79 (m, 36H).

Step 8: Synthesis of tert-butyl N-[(4S,5E,7S)-7-benzyl-8-[(2S)—2-{[(1S)—1-{[(1S)-4-({[(1- oxyl-2,2,6,6-tetramethylpiperidin-4-yl)oxy]carbonyl}amino)-1-[(propan-2-yl)carbamoyl]butyl]carbamoyl}-2-methylpropyl]carbamoyl}pyrrolidin-1-yl]-2-methyl-8-oxooct-5-en-4-yl]carbamate (XXXXVII).

To a solution of 378 (200 mg, 0.21 mmol) in DCM (5 mL) was added DBU (163 mg, 1.07 mmol). After stirring at 25° C. for 0.5 h, 1-oxyl-2,2,6,6-tetramethylpiperidin-4-yl carbonochloridate (56 mg, 0.25 mmol) was added. The mixture was stirred for 4 h at 25° C. To the residue was added DCM (50 mL) and the organic layer was washed with H$_2$O (3×50 mL). The organic phase was dried with Na$_2$SO$_4$ and concentrated and purified by prep-HPLC (Venusil XBP C18 (5 μm, 30×250 mm), 0.5% NH$_3$H$_2$O in eluant) to obtain the titled compound XXXXVII (0.4 mg, 0.2%) as a pink solid. MS (ESI): [M+H$^+$]=911.6.

Example XXXXVIII

Primary Screening by Ferroptosis Assay

Cell Lines and Media: HT-1080 (fibrosarcoma) cells were obtained from American Type Culture Collection. Cells were grown in EMEM media, 10% Heat-Inactivated FBS, and penicillin-streptomycin mix (Invitrogen). Cells were maintained at 37° C. and 5% CO$_2$ in a tissue culture incubator.

Cell Viability Assay: Seed 10,000 cell/well of HT-1080 cells with 195 μL growth media in black and clear bottom 96-well plates (Cat #Corning 3904) and allow cells to adhere overnight. The next day, dilute test compound by 2-fold dilution into 12 points with medium containing 400 μM Erastin. Transfer 5 μL of compounds solution into growth medium in triplicated wells. 30 hours later, add Cell Titer-Glo® Luminescent cell viability assay reagent (Cat #, Promega G8081) to measure HT-1080 cell viability according to the manufacture protocol. Briefly, aspirate 100 μL medium, and add 50 μL CellTiter-Glo® Luminescent reagent to each well and incubated for 30 minutes at room temperature to stabilize the Luminescent signal. Seal the plates and centrifuged for 1 minute at 1,000 rpm to remove bubbles. Shake the plates for 1 minute on an orbital shaker. Read the plate to detect Luminescent signal with EnSpire Multimode Plate Reader (PerkinElmer). The remaining activity % is used to evaluate Erastin induced ferroptosis in HT-1080 cells and expressed as the following formula:

% Remaining Activity=100×[(Sample−Background$_{avg}$)/(Vehicle−Background $_{avg}$)]

Sample: Readout from the test compound
Vehicle: Readout from the vehicle sample
Background: Readout from the Erastin only treatment Dose response curve is graphed by using the non-linear regression analysis (formula equation 201) in XLFit (Excel add-in software) for the average % remaining activity from triplicates, and the EC50 values is then calculated. In this anti-ferroptosis assay, ferrostatin-1, and XJB-5-131 are included as reference. The acceptance criteria were set based on historical result, mean±2.58*SD in logarithmic scale, meanwhile Z'>0.5.

TABLE 1

Summary of Example Compounds Inhibition for Ferroptosis in HT-1080 Cell

| Example No. | EC50/nM | Example No. | EC50/nM |
|---|---|---|---|
| I | 260 | XXV | 254.9 |
| II | 289.2 | XXVI | 140 |
| III | 90.5 | XXVII | 141 |
| IV | 563.9 | XXVIII | 251 |
| V | 141 | XXIX | 73 |
| VI | 1022 | XXX | 46 |
| VII | 341.7 | XXXI | 36 |
| VIII | 265.9 | XXXII | 573 |
| IX | 260.9 | XXXIII | 291 |
| X | 285 | XXXIV | >4000 |
| XI | 526 | XXXV | 192 |
| XII | 480.7 | XXXVI | 141.8 |
| XIII | 262.2 | XXXVII | 201.05 |
| XIV | 515.29 | XXXVIII | 76 |
| XV | 2233.26 | XXXIX | 141.8 |
| XVI | 535.67 | XXXX | 140 |
| XVII | 284.27 | XXXXI | 139 |
| XVIII | 86 | XXXXII | 274 |
| XX | 532 | XXXXIII | 123 |
| XXI | 257 | XXXXIV | 140 |
| XXII | >4000 | XXXXV | 144 |
| XXIII | 546 | XXXXVI | 66.27 |
| XXIV | >4000 | XXXXVII | 143.08 |

Compound of formula (I) preferably have IC50 of less than 1 μM, more preferable less than 200 nM.

Example XXXXIX

Apoptosis Assay

Cell Lines and Media. 3T$_3$-L1 cells were obtained from American Type Culture Collection. Cells were grown in DMEM completed media, 10% FBS, and penicillin-streptomycin mix (Invitrogen). Cells were maintained at 37° C. and 5% CO$_2$ in a tissue culture incubator.

Apoptosis Assay. Promega's Caspase-Glo®3/7 assay uses a luminogenic substrate containing the DEVD sequence, which has been shown to be selective for caspase-3 and -7. We used this assay to screen our compounds for apoptosis inhibition. Briefly, 40 μL of 3000 3T$_3$-L1 cells were seeded per well in 384 well plates, cells were allowed to adhere overnight. In the next day, prepare the Actinomycin D as the apoptosis inducing agent into 100 μM DMSO stock. Prepare the test compounds into 10 mM DMSO stock. Serial dilute the compound into 10 points by 3-fold dilution with DMSO. Pre-treat the 3T$_3$-L1 cells with test compound by transfer 40 nL of stock of serial concentration in triplicate wells using acoustic fluid transfer, incubate for 2 hours. Then transfer 40 nL of 100 μM of Actinomycin D (final concentration is 100 nM) into designated wells using acoustic fluid transfer. Incubate the assay plates at 37° C., 5% CO$_2$, 95% humidity incubator for 48 hours. For caspase assay, add 20 μL/well of Caspase-Glo>3/7 reagent (Promega) into test wells. Incubate for 30 minutes at room temperature to stabilize the luminescence signal. Read the plate with EnSpire Multimode Plate Reader (PerkinElmer). Calculate the EC50 value using formula equation 201: y=(A+((B−A)/(1+((x/C)^D)))) from the XLFit (Excel add-in software), where A: Average mean of vehicle samples
B: Average mean of cells treated with 100 nM AcD
C: EC50
D: HillSlope Z' factor was used to describe the screening assay performance. The Z' factor value was >0.5 in all the test plates which indicated the assay was qualified and the IC50 value was reliable for all tested compounds.

TABLE 2

Summary of Example Compounds Inhibition for Apoptosis in 3T3-L1 Cell induced by Actinomycin D.

| Example No. | EC50/µM | Example No. | EC50/µM |
|---|---|---|---|
| I | 1.575 | XXVI | 0.683 |
| II | 3.036 | XXVIII | 3.930 |
| IV | 1.269 | XXIX | 4.322 |
| V | 1.308 | XXXI | 4.080 |
| VII | 4.638 | XXXVIII | 2.652 |
| IX | 1.368 | XXXXIV | 0.628 |
| X | 1.381 | XXXXII | 0.708 |

Compound of formula (I) preferably have IC50 of less than 10 µM, more preferable less than 1 µM.

Example XXXXXI

Ischemia Reperfusion (IR) Induced Acute Kidney Injury (AKI) Animal Model

Mice were anesthetized with a 5% chloral hydrate (400 mg/kg 5% chloral hydrate). Bilateral renal ischemia was induced by the application of non-traumatic micro-vascular clamps around both left and right renal pedicles. Ischemia was confirmed by blanching of the kidneys. After 30-minute ischemia, the clamps were removed and reperfusion was confirmed visually. Sham-operated animals were not subjected to ischemia. During the ischemic interval, the animals were kept hydrated with normal saline instilled intraperitoneally and were kept on warm heating pads to maintain body temperature.

Animals were randomly assigned to the following groups: Sham control, IR with saline, or IR with test article (5.0 mg/kg, 15 mg/kg). Treatment was administered subcutaneously 2 h before onset of ischemia, at the onset of reperfusion, and at 2 hours after reperfusion. Serum and urine samples were collected at 24 hours and stored at −20° C. until analysis. Kidneys were harvested at different times after onset of reperfusion 24 hours for assessment of oxidative markers, and histopathology by light and electron microscopy.

The effect of example compounds not onity decrease the creatinine and BUN to normal function level, but also shown protection on the kidney histological damage in renal IR.

Finally, it should be noted that there are other ways to practice the invention. Accordingly, embodiments of the present invention is to be described as examples, but the present invention is not limited to the contents described, further modifications may be made within the scope of the present invention or the equivalents added in the claims.

All publications or patents cited herein are incorporated by reference in this invention.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example", "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound selected from:

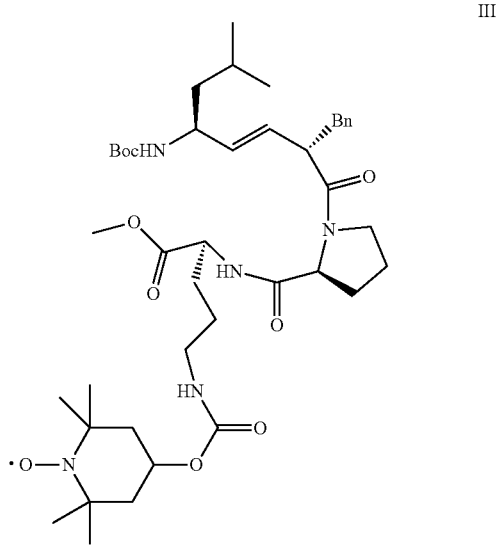

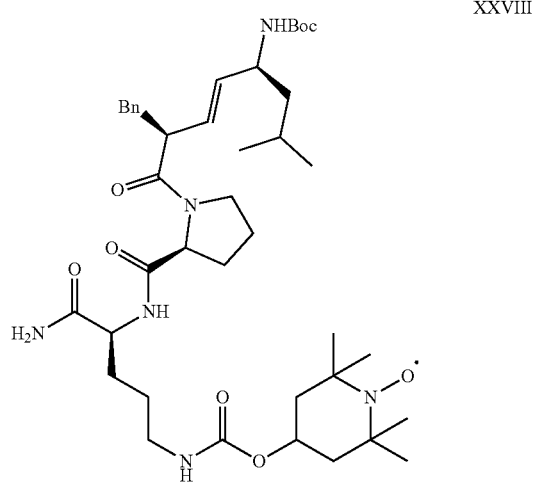

-continued
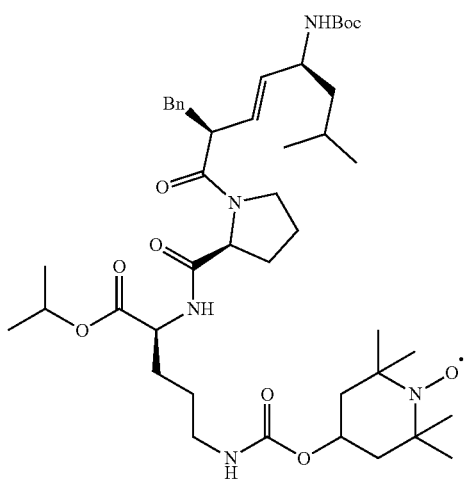
XXIX
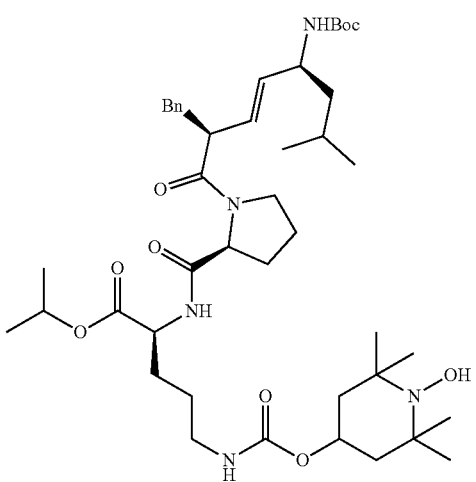
XXX
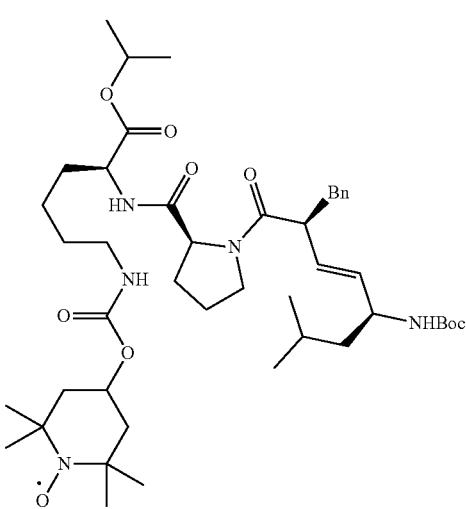
XXXI
-continued
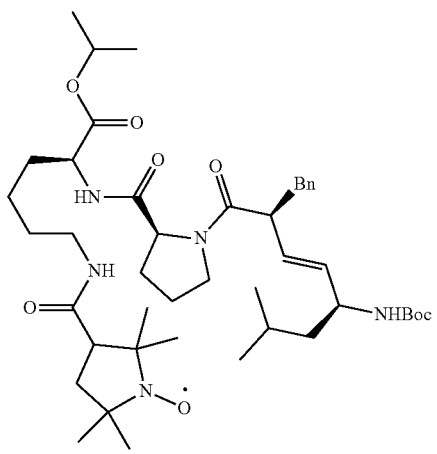
XXXII
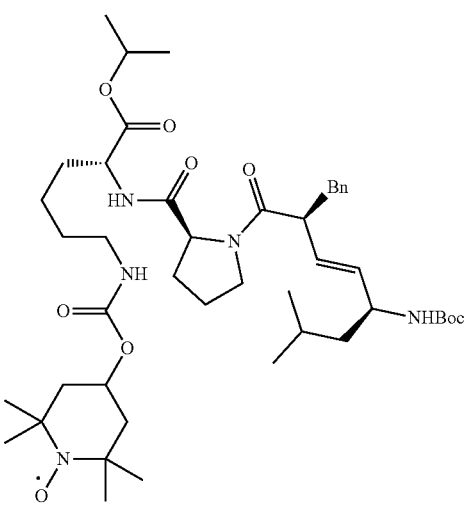
XXXIII
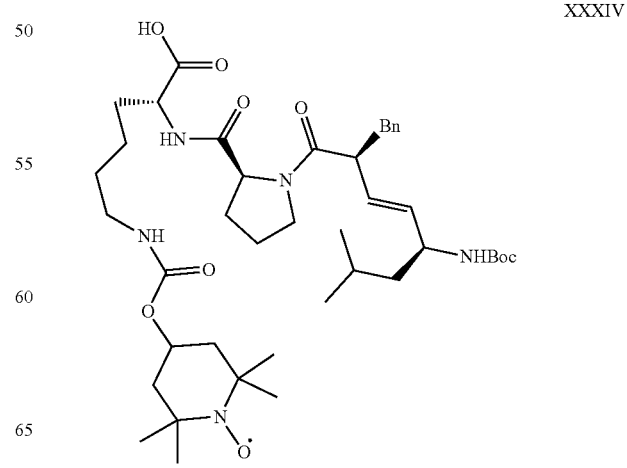
XXXIV -continued
XXXV
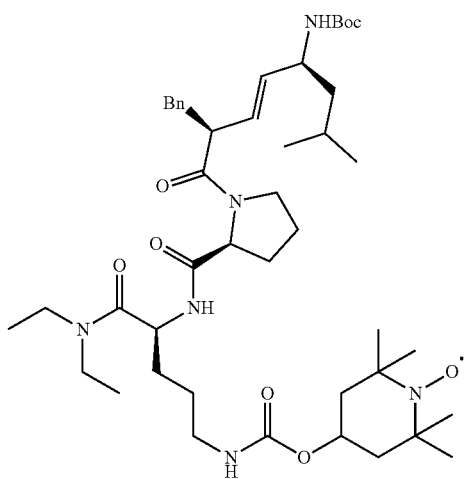
XXXVI
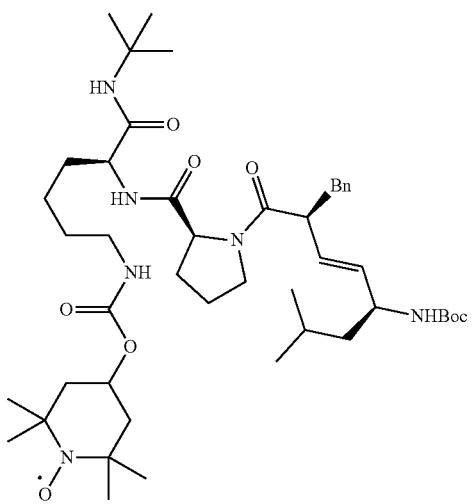
XXXVII
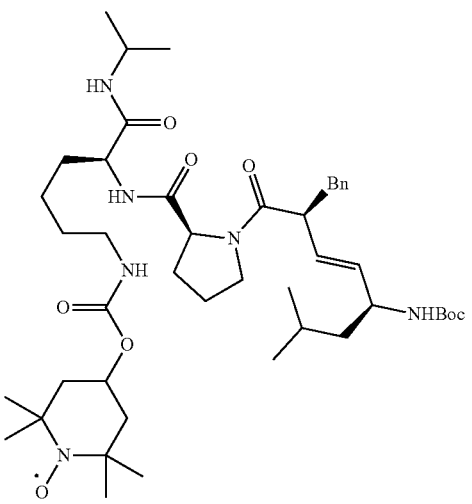
-continued
XXXVIII
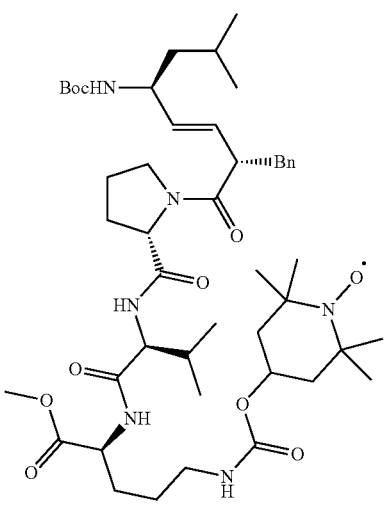
XXXIX
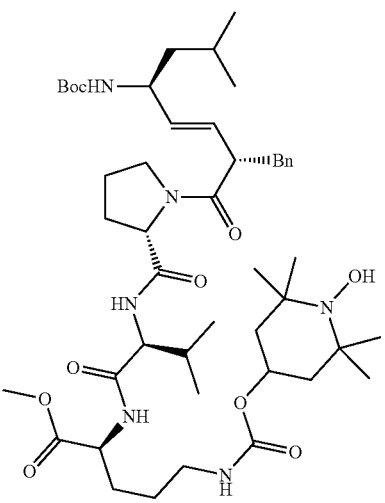
XXXXIV
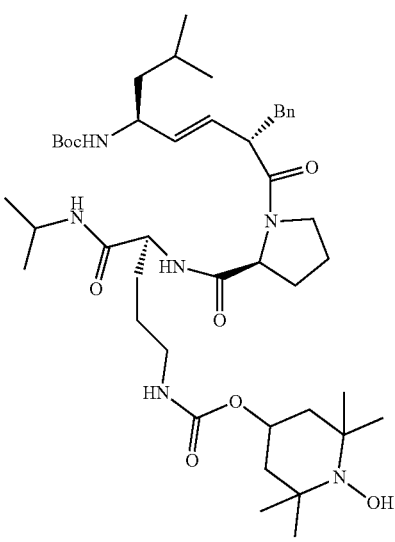

-continued

XXXXV

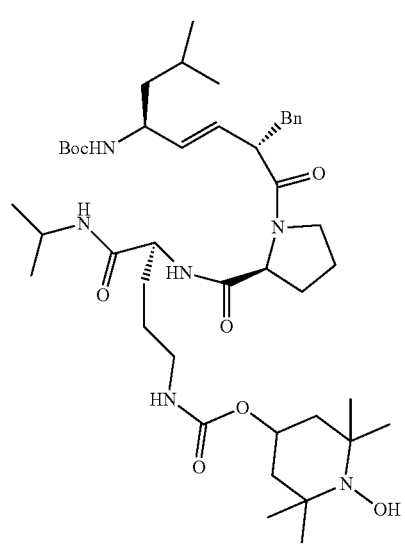

XXXXVI

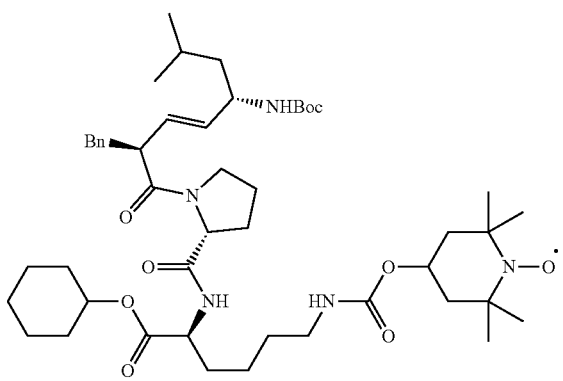

XXXXVII

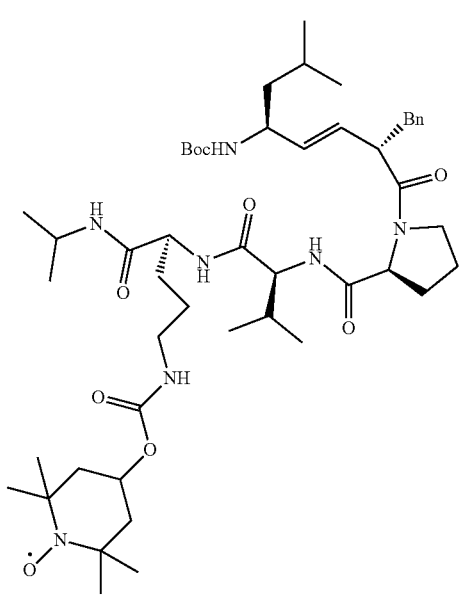

or a pharmaceutically acceptable salt of any of the foregoing.

2. The compound of claim 1, wherein the compound has the structure of Formula (III) (methyl (2S)—2-{[(2S)-1-1-[(2S,3E,5S)-2-benzyl-5-{[(tert-butoxy) carbonyl]amino}-7-methyloct-3-enoyl]pyrrolidin-2-yl]formamido}-5-({[(1-oxyl-2,2,6,6-tetramethylpiperidin-4-yl)oxy]carbonyl}amino)pentanoate):

(III)

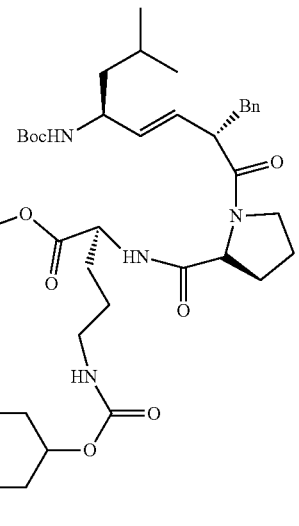

or a pharmaceutically acceptable salt thereof.

3. The compound of claim 1, wherein the compound has the structure of Formula (XXVIII) (tert-butyl N—[(4S,5E,7S)-7-benzyl-8-[(2S)—2-{[(1S)-1-carbamoyl-4-({[(1-oxyl-2,2,6,6-tetramethylpiperidin-4-yl)oxy]carbonyl}amino-)butyl]carbamoyl}pyrrolidin-1-yl]-2-methyl-8-oxooct-5-en-4-yl]carbamate);

(XXVIII)

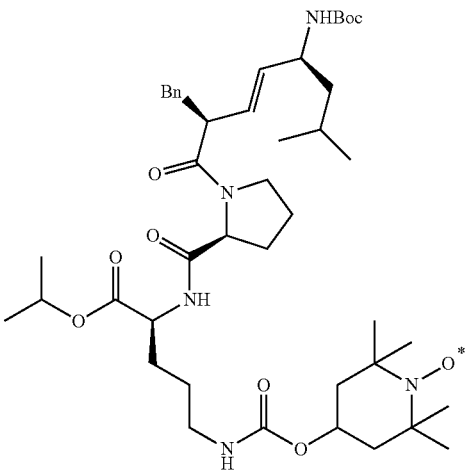

or a pharmaceutically acceptable salt thereof.

4. The compound of claim 1, wherein the compound has the structure of Formula (XXIX) ((2S)—2-{[(2S)—1-[(2S,3E,5S)-2-benzyl-5-{[(tert-butoxy)carbonyl]amino}-7-methyloct-3-enoyl]pyrrolidin-2-yl]formamido}-5-({[(1-oxyl-2,2,6,6-tetramethylpiperidin-4-yl)oxy]carbonyl}amino)pentanoate):

(XXIX)

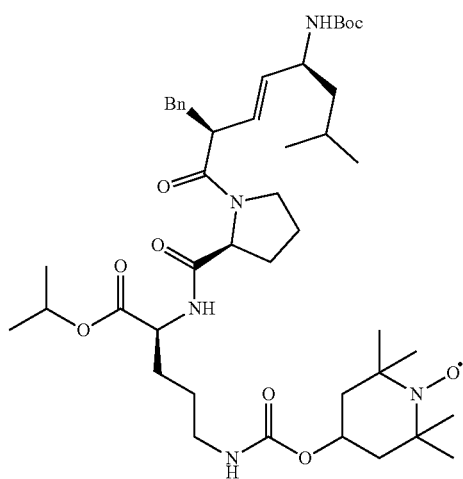

or a pharmaceutically acceptable salt thereof.

5. The compound of claim 1, wherein the compound has the structure of Formula (XXX) (propan-2-yl (2S)—2-{[(2S)-1-[(2S,3E,5S)-2-benzyl-5-{[(tert-butoxy)carbonyl]amino}-7-methyloct-3-enoyl]pyrrolidin-2-yl]formamido}-5-({[(1-hydroxy-2,2,6,6-tetramethylpiperidin-4-yl)oxy]carbonyl}amino)pentanoate):

(XXXI)

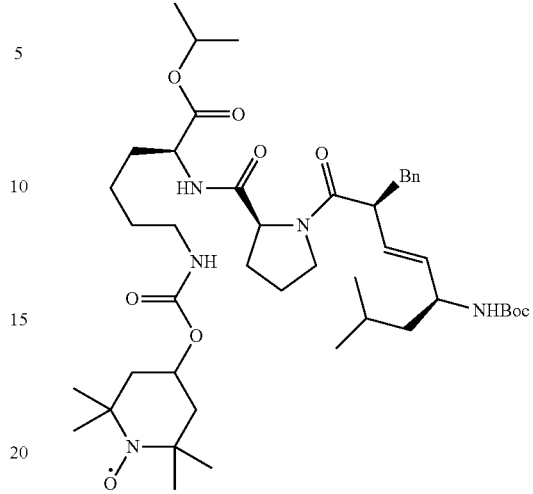

or a pharmaceutically acceptable salt thereof.

7. The compound of claim 1, wherein the compound has the structure of Formula (XXXII) (propan-2-yl (2S)-2-1 [(2S)-1-[(2S,3E,5S)-2-benzyl-5-{[(tert-butoxy) carbonyl] amino 1-7-methyloct-3-enoyl]pyrrolidin-2-yl]formamido}-6-[(1-oxyl-2,2,5,5-tetramethylpyrrolidin-3-yl)formamido]-hexanoate):

(XXX)

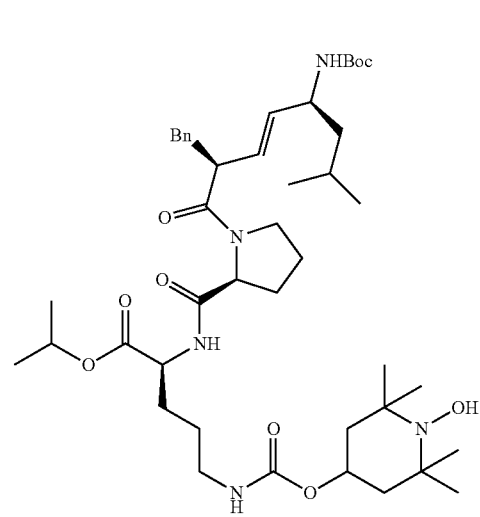

or a pharmaceutically acceptable salt thereof.

6. The compound of claim 1, wherein the compound has the structure of Formula (XXXI) (propan-2-yl (2S)—2-{[(2S)-1-[(2S,3E,5S)-2-benzyl-5-{[(tert-butoxy) carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate):

(XXXII)

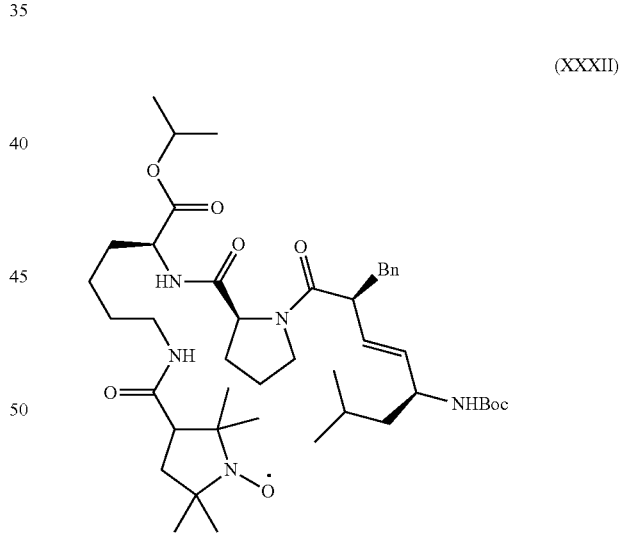

or a pharmaceutically acceptable salt thereof.

8. The compound of claim 1, wherein the compound has the structure of Formula (XXXIII) ((2R)—2-{[(2S)—1-[(2S,3E,5S)-2-benzyl-5{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoate):

(XXXIII)

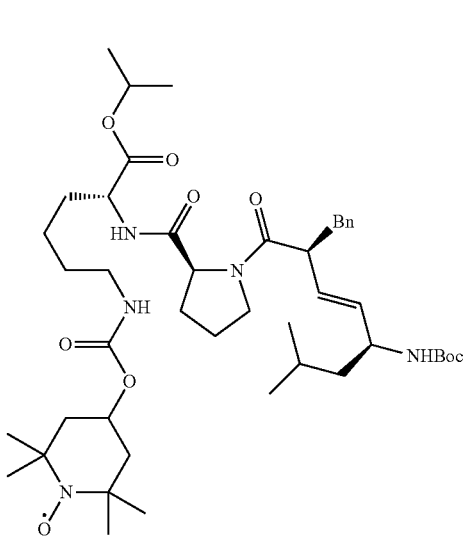

or a pharmaceutically acceptable salt thereof.

9. The compound of claim 1, wherein the compound has the structure of Formula (XXXIV) ((2R)—2-{[(2S)-1-[(2S,3E,5S)-2-benzyl-5-{[(tert-butoxy)carbonyl]amino}-7-methyloct-3-enoyl]pyrrolidin-2-yl]formamido}-6-({[(1-oxyl-2,2,6,6-tetramethylpiperidin-4-yl)oxy]carbonyl}amino)hexanoic acid):

(XXXIV)

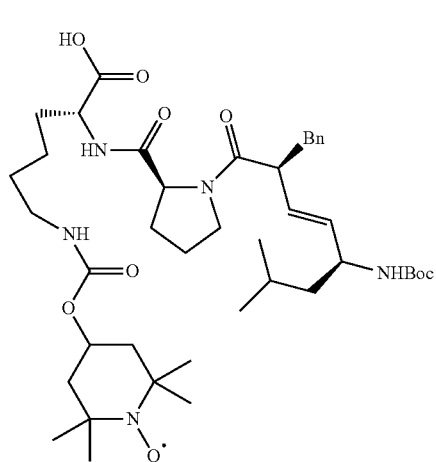

or a pharmaceutically acceptable salt thereof.

10. The compound of claim 1, wherein the compound has the structure of Formula (XXXV) (tert-butyl N—[(4S,5E,7S)-7-benzyl-8-[(2S)-2-{[(1S)-1-(diethylcarbamoyl)-4-({[(1-oxyl-2,2,6,6-tetramethylpiperidin-4-yl)oxy]carbonyl}amino)-butyl]carbamoyl}pyrrolidin-1-yl]-2-methyl-8-oxooct-5-en-4-yl]carbamate):

(XXXV)

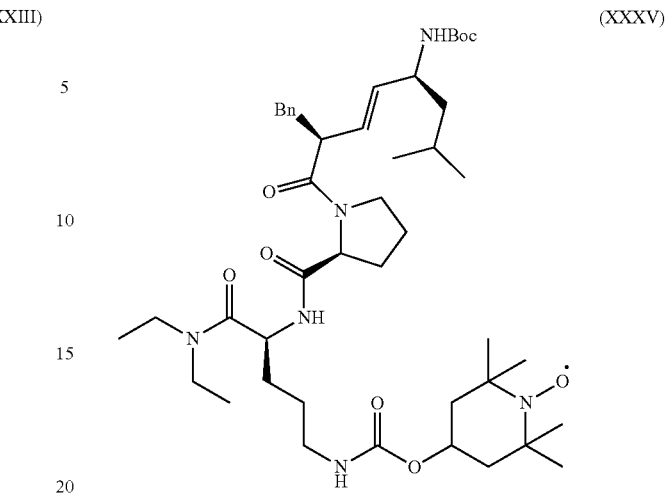

or a pharmaceutically acceptable salt thereof.

11. The compound of claim 1, wherein the compound has the structure of Formula (XXXVI) (tert-butyl N-{(4S,5E,7S)-7-benzyl-8-[(2S)—2-{[(1 S)-1-(tert-butylcarbamoyl)-5-({[(1-oxyl-2,2,6,6-tetramethylpiperidin-4-yl)oxy]carbonyl}amino)pentyl]-carbamoyl}pyrrolidin-1-yl]-2-methyl-8-oxooct-5-en-4-yl carbamate):

(XXXVI)

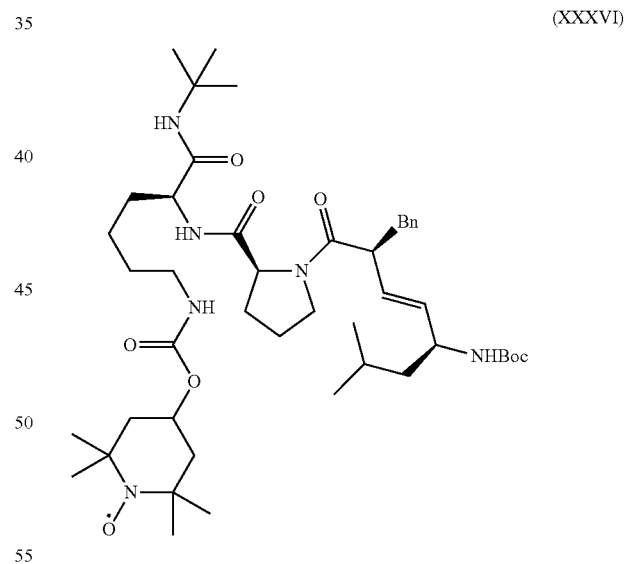

or a pharmaceutically acceptable salt thereof.

12. The compound of claim 1, wherein the compound has the structure of Formula (XXXVII) (tert-butyl N—[(4S,5E,7S)-7-benzyl-8-[(2S)-2-{[1S)-5-({[(1-oxyl-2,2,6,6-tetramethylpiperidin-4-yl)oxy]carbonyl}amino)-1-[(propan-2-yl)carbamoyl]pentyl]carbamoyl}pyrrolidin-1-yl]-2-methyl-8-oxooct-5-en-4-yl]carbamate):

(XXXVII)

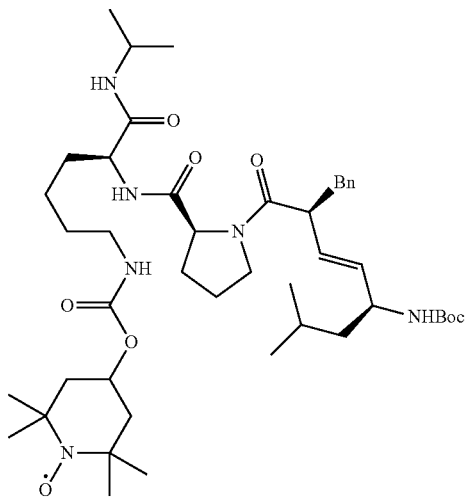

or a pharmaceutically acceptable salt thereof.

13. The compound of claim 1, wherein the compound has the structure of Formula (XXXVIII) ((S)-methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-oxyl-2,2,6,6-tetramethylpiperidin-4-yl)oxy)carbonyl)amino)pentanoate):

(XXXVIII)

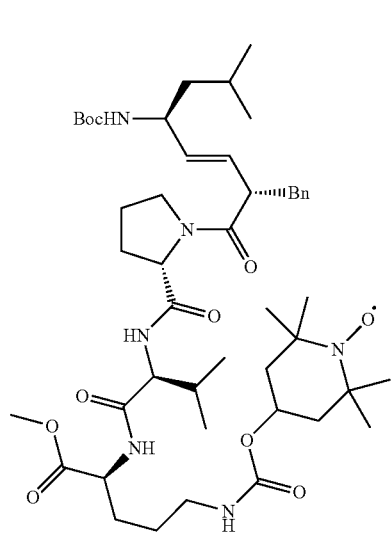

or a pharmaceutically acceptable salt thereof.

14. The compound of claim 1, wherein the compound has the structure of Formula (XXXIX) ((S)-methyl 2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)—5-((((1-hydroxy-2,2,6,6-tetramethylpiperidin-4-yl)oxy)carbonyl)amino)pentanoate):

(XXXIX)

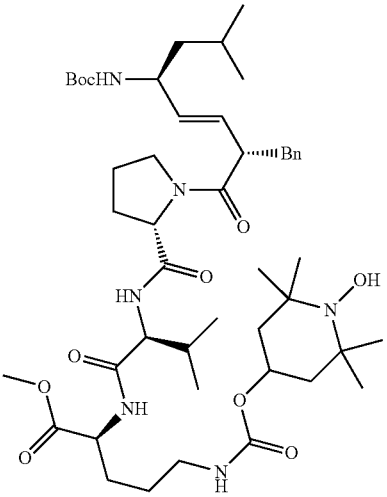

or a pharmaceutically acceptable salt thereof.

15. The compound of claim 1, wherein the compound has the structure of Formula (XXXXIV) (tert-butyl N—[(4S,5E,7S)-7-benzyl-8-[(2S)-2-{[(1S)-4-({[(1-oxyl-2,2,6,6-tetramethylpiperidin-4-yl)oxy]carbonyl}amino)-1-[(propan-2-yl)carbamoyl]butyl]carbamoyl}pyrrolidin-1-yl]-2-methyl-8-oxooct-5-en-4-yl]carbamate):

(XXXXIV)

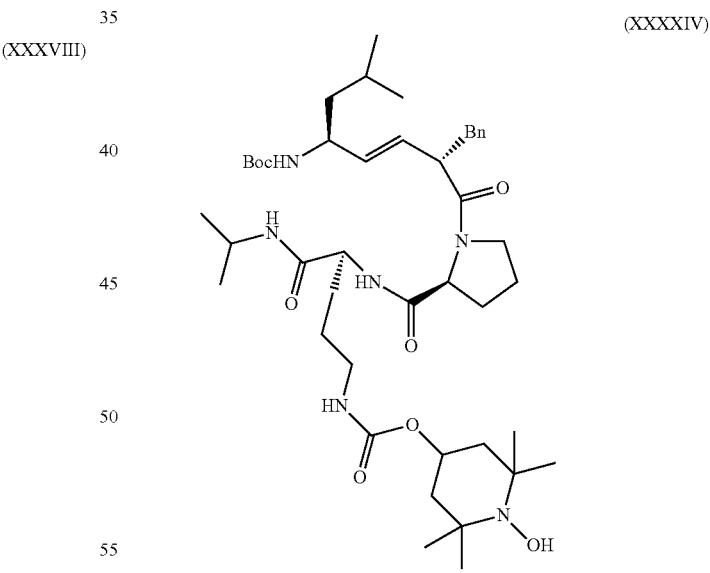

or a pharmaceutically acceptable salt thereof.

16. The compound of claim 1, wherein the compound has the structure of Formula (XXXXV) (tert-butyl N—[(4S,5E,7S)-7-benzyl-8-[(2S)-2-{[(1S)-4-({[(1-hydroxy-2,2,6,6-tetramethylpiperidin-4-yl)oxy]carbonyl}amino)-1-[(propan-2-yl)carbamoyl]butyl]carbamoyl}pyrrolidin-1-yl]-2-methyl-8-oxooct-5-en-4-yl]carbamate):

(XXXXV)

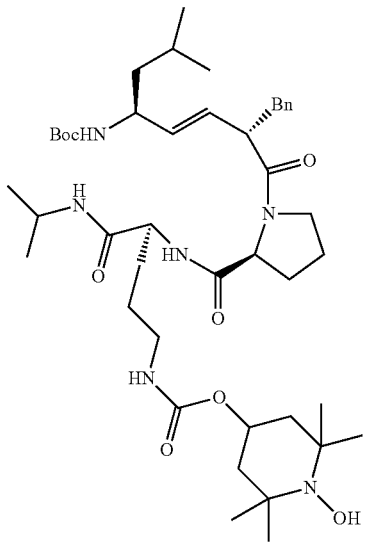

or a pharmaceutically acceptable salt thereof.

17. The compound of claim 1, wherein the compound has the structure of Formula (XXXXVI) ((S)—cyclohexyl 2-((R)-1-((2S,5S,E)-2-benzyl-5-((tert-butoxycarbonyl) amino)-7-methyloct-3-enoyl)pyrrolidine-2-carboxamido)-6-((((1-hydroxy-2,2,6,6-tetramethylpiperidin-4-yl)oxy)carbonyl)amino)hexanoate):

(XXXXVI)

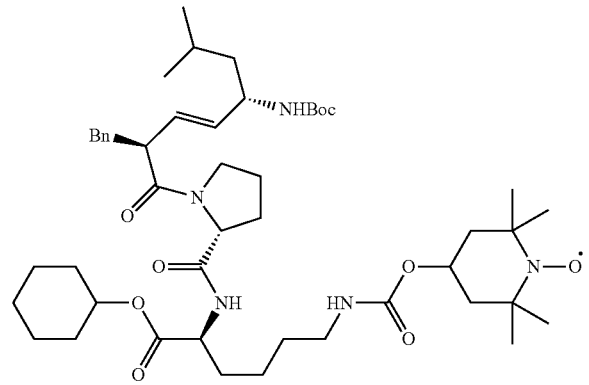

or a pharmaceutically acceptable salt thereof.

18. The compound of claim 1, wherein the compound has the structure of Formula (XXXXVII) (tert-butyl N—[(4S, 5E,7S)-7-benzyl-8-[(2S)—2-{[(1S)—1-{[(1S)-4-({[(1-oxyl- 2,2,6,6-tetramethylpiperidin-4-yl)oxy] carbonyl}amino)-1-[(propan-2-yl)carbamoyl] butyl}carbamoyl]-2-methylpropyl]carbamoyl}pyrrolidin-1-yl]-2-methyl-8-oxooct-5-en-4-yl]carbamate):

(XXXXVII)

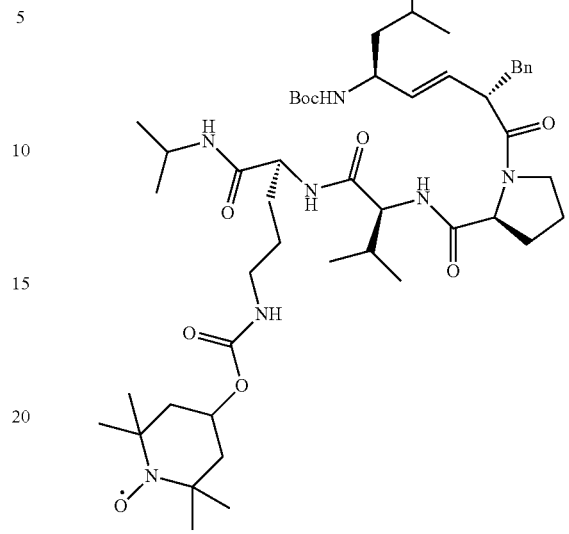

or a pharmaceutically acceptable salt thereof.

19. A pharmaceutical composition comprising the compound of claim 1 or a pharmaceutically acceptable salt thereof.

20. A method of treating acute kidney injury in a patient comprising administering to a patient in need thereof a therapeutically effective amount of the compound of claim 1 or a pharmaceutically acceptable salt thereof.

21. A method of treating acute kidney injury in a patient comprising administering to a patient in need thereof a therapeutically effective amount of the pharmaceutical composition of claim 19.

22. A compound selected from:

I

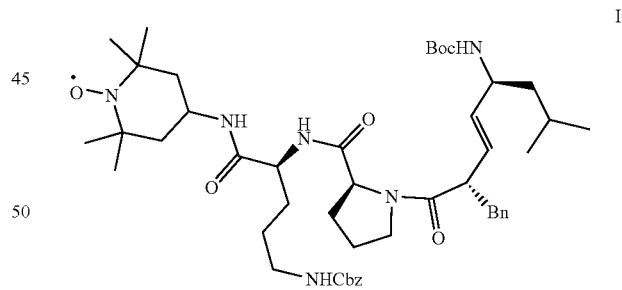

II

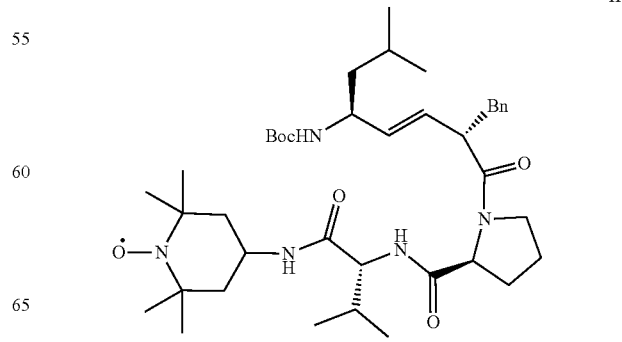

-continued
V
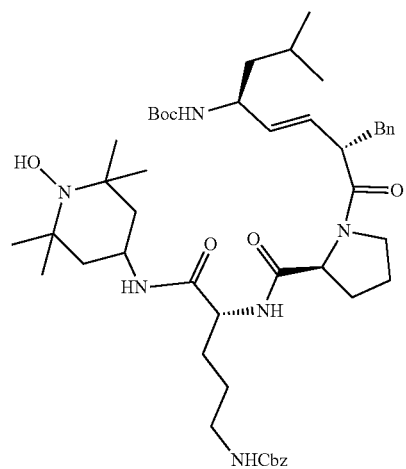
VI
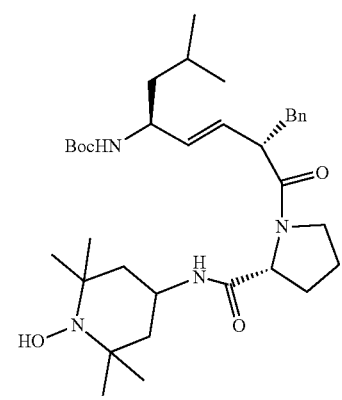
VII
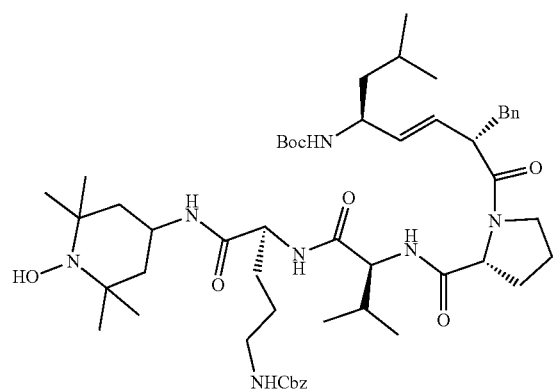
-continued
VIII
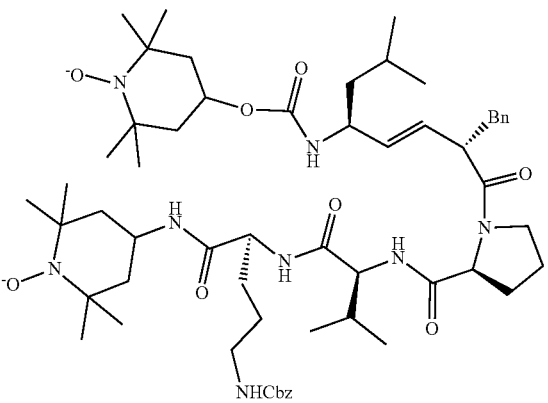
IX
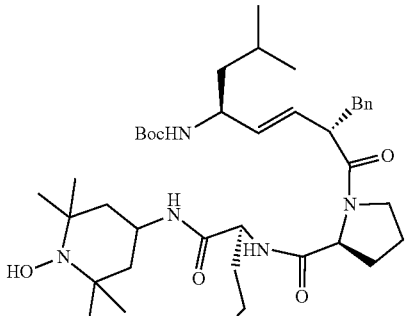
X
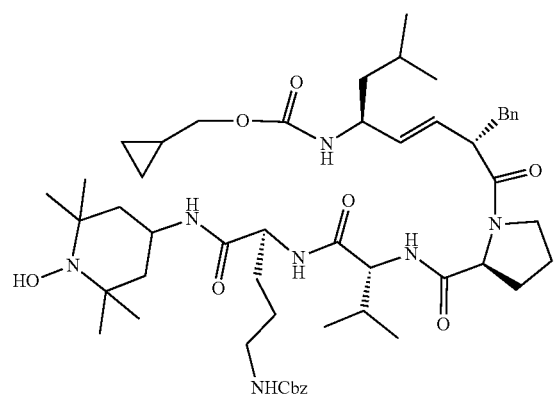
XI
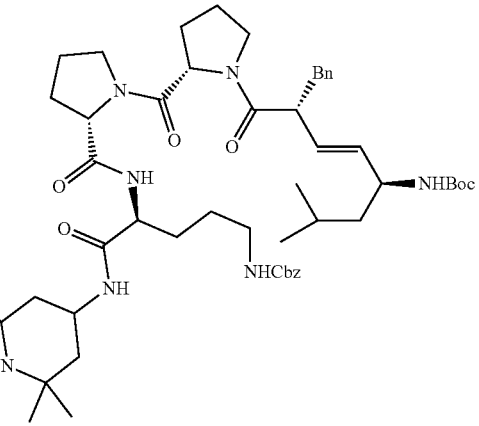

XII
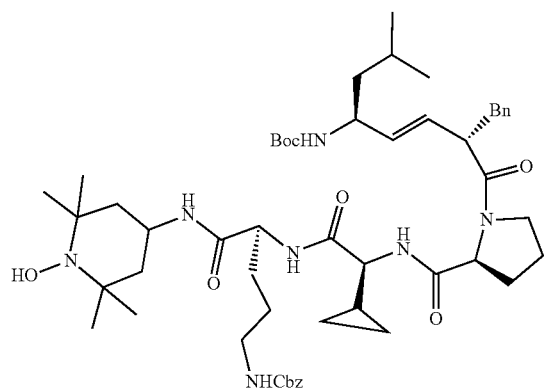
XIII
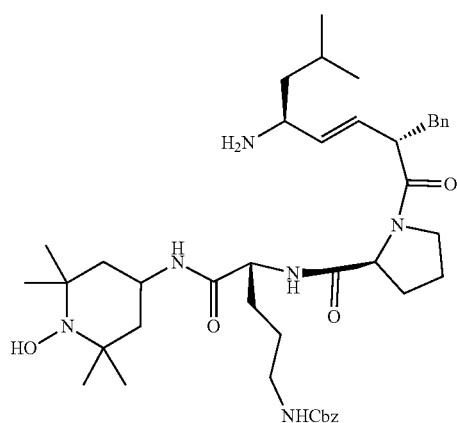
XIV
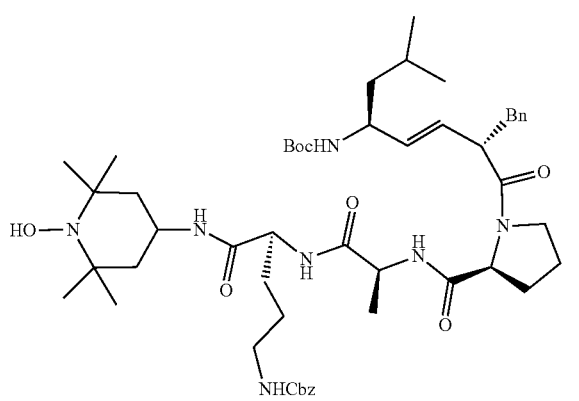
XV
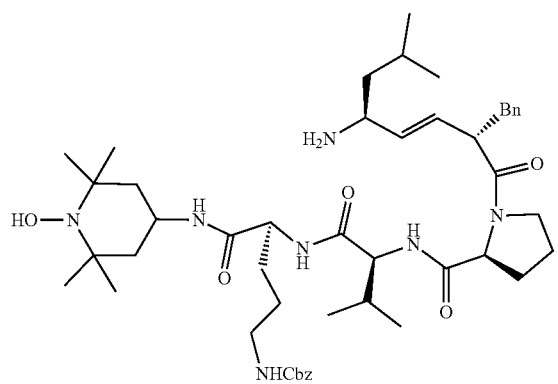
XVI
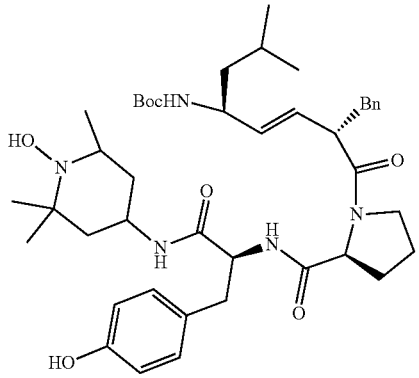
XVII
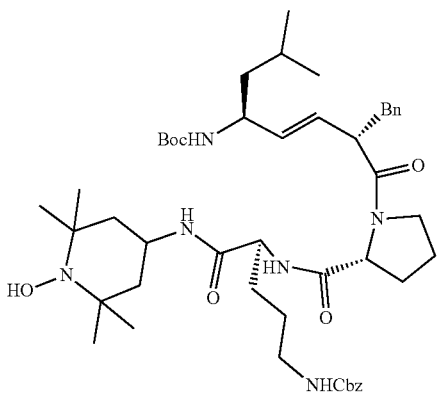
XVIII
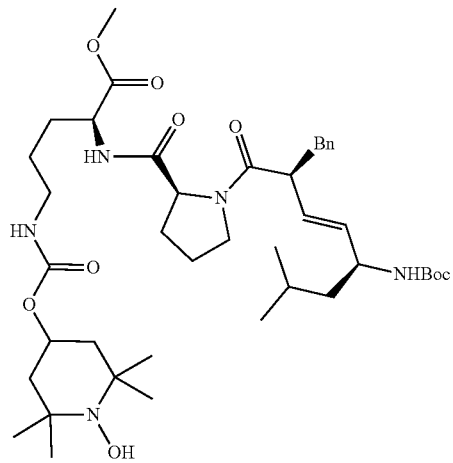
XX
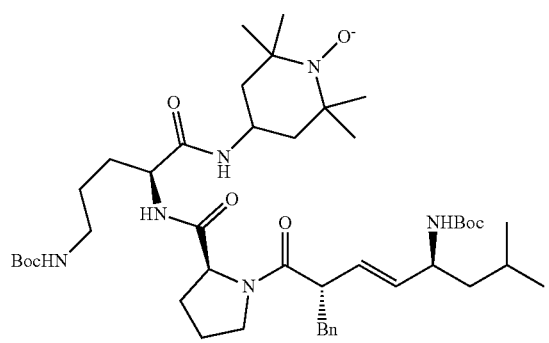

-continued
XXI
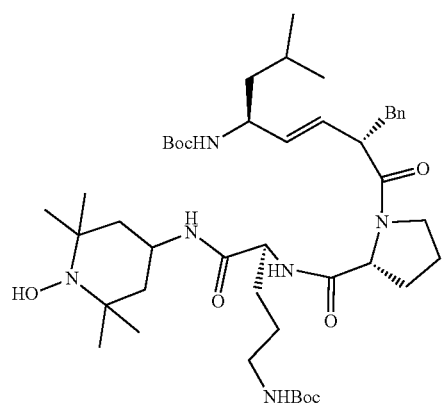
XXII
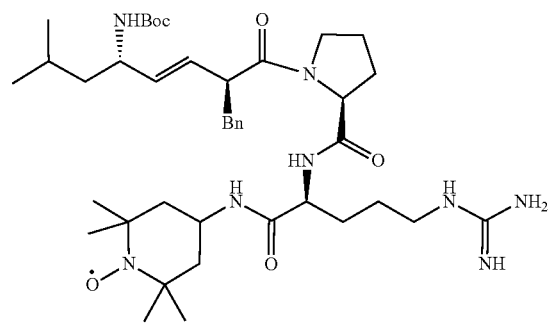
XXIII
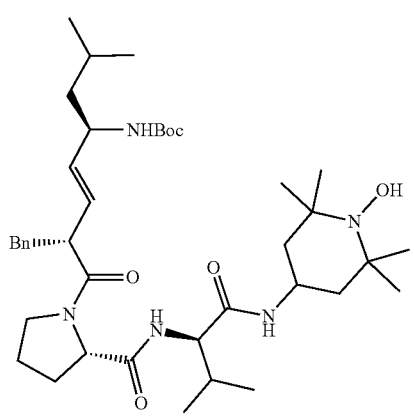
-continued
XXIV
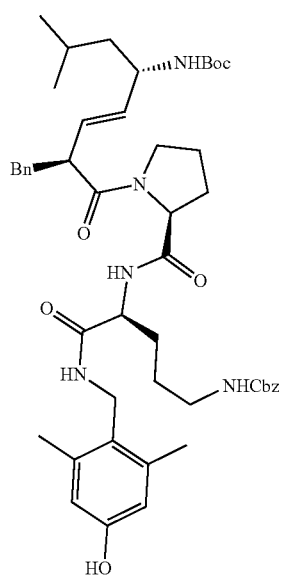
XXV
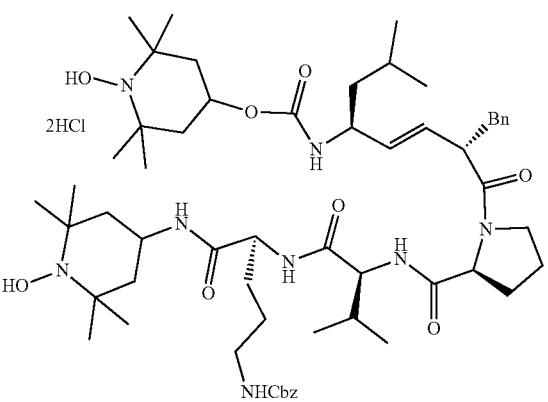
XXVI
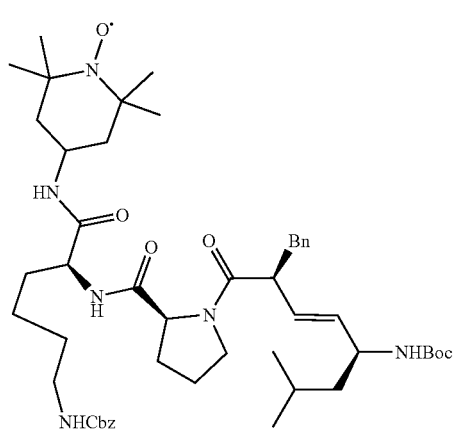

XXVII

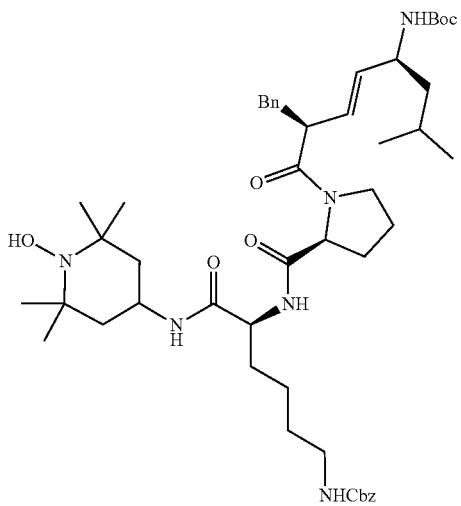

XXXX

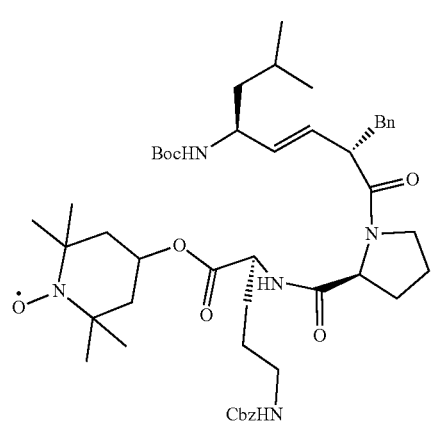

XXXXI

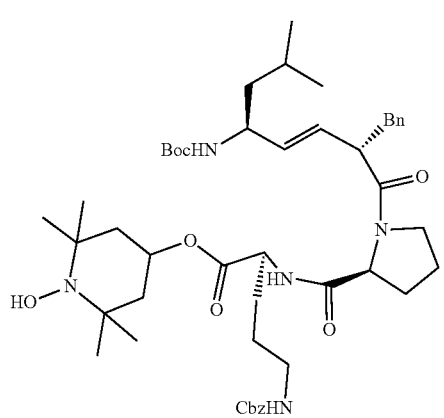

XXXXII

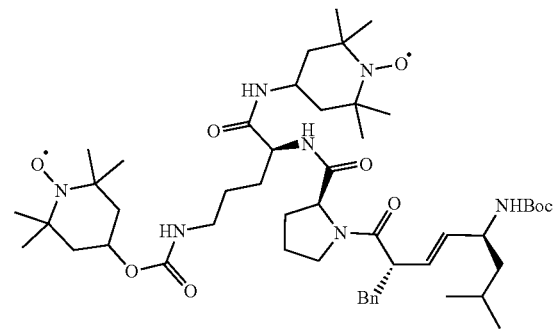

XXXXIII or a pharmaceutically acceptable salt of any of the foregoing.

23. A pharmaceutical composition comprising the compound of claim 22 or a pharmaceutically acceptable salt thereof.

24. A method of treating acute kidney injury in a patient comprising administering to a patient in need thereof a therapeutically effective amount of the compound of claim 22 or a pharmaceutically acceptable salt thereof.

25. A method of treating acute kidney injury in a patient comprising administering to a patient in need thereof a therapeutically effective amount of the pharmaceutical composition of claim 23.

* * * * *

UNITED STATES PATENT AND TRADEMARK OFFICE
CERTIFICATE OF CORRECTION

PATENT NO. : 10,889,572 B2  
APPLICATION NO. : 16/801286  
DATED : January 12, 2021  
INVENTOR(S) : Jia-Ning Xiang et al.

Page 1 of 2

It is certified that error appears in the above-identified patent and that said Letters Patent is hereby corrected as shown below:

In the Claims

Column 182, Claim 3, Line 40 that reads:

"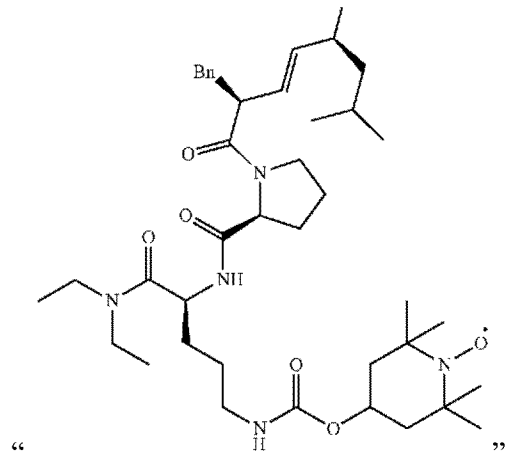"

Should read:

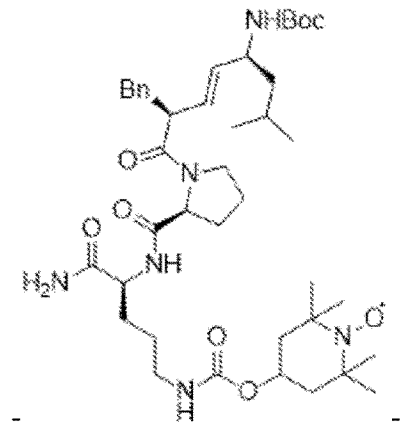

Signed and Sealed this  
Thirteenth Day of April, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,889,572 B2

Page 2 of 2

Column 186, Claim 11, Line 25 that reads:
"(tert-butyl N-{(4S,5E,7S)-7-benzyl-8-[(2S)-2-{[(1S)-1-(tert-butylcarbamoyl)-5-({[(1-oxyl-2,2,6,6-tetramethylpiperidin-4-yl)oxy]carbonyl}amino)pentyl]-carbamoyl}pyrrolidin-1-yl]-2-methyl-8-oxooct-5-en-4-yl carbamate):"
Should read:
-tert-butyl N-[(4S,5E,7S)-7-benzyl-8-[(2S)-2-{[(1S)-1-(tert-butylcarbamoyl)-5-({[(1-oxyl-2,2,6,6-tetramethylpiperidin-4-yl)oxy] carbonyl}amino)pentyl]-carbamoyl}pyrrolidin-1-yl]-2-methyl-8-oxooct-5-en-4-yl]carbamate-